US008173639B2

(12) United States Patent
Simonsen et al.

(10) Patent No.: US 8,173,639 B2
(45) Date of Patent: May 8, 2012

(54) ISOQUINOLINONE DERIVATIVES AS NK3 ANTAGONISTS

(75) Inventors: Klaus Baek Simonsen, Odense (DK); Jan Kehler, Lyngby (DK); Karsten Juhl, Greve (DK); Nikolay Khanzhin, Humlebaek (DK); Soren Moller Nielsen, Hillerod (DK)

(73) Assignee: H. Lundbeck A/S, Valby (DK)

( * ) Notice: Subject to any disclaimer, the term of this patent is extended or adjusted under 35 U.S.C. 154(b) by 990 days.

(21) Appl. No.: 12/101,592

(22) Filed: Apr. 11, 2008

(65) Prior Publication Data

US 2009/0143402 A1  Jun. 4, 2009

Related U.S. Application Data

(60) Provisional application No. 60/914,159, filed on Apr. 26, 2007.

(51) Int. Cl.
*C07D 217/26* (2006.01)
*C07D 401/02* (2006.01)
*A61K 31/47* (2006.01)

(52) U.S. Cl. ............... 514/218; 514/253.05; 514/309; 544/363; 546/141; 540/575

(58) Field of Classification Search .................. None
See application file for complete search history.

(56) References Cited

FOREIGN PATENT DOCUMENTS

| WO | WO-95/32948 | 12/1995 |
|----|----|----|
| WO | WO-2005/014575 | 2/2005 |
| WO | WO-2006/050991 | 5/2006 |
| WO | WO-2006/050992 | 5/2006 |
| WO | WO-2006/130080 | 12/2006 |

OTHER PUBLICATIONS

J. Albert, "Neurokinin antagonists and their potential role in treating depression and other stress disorders," Expert Opinion Ther. Patents, 14:1421-1433 (2004).
Spooren et al., "NK$_3$ receptor antagonists: the next generation of antipsychotics?," Nature Reviews, 4:967-975 (2005).
Meltzer et al., "Placebo-Controlled Evaluation of Four Novel Compounds for the Treatment of Schizophrenia and Schizoaffective Disorder," Am J Psychiatry, 161:975-984 (2004).
S. Evangelista, "Talnetant," Current Opinion in Investigational Drugs, 6:7 717-721, (2005).
Modi et al, "Isoquinolones: Part IV—Synthesis of $_3$-Methyl, $_3$-Formyl & Other $_3$-Substituted N-Arylisoquinolones," Indian Journal of Chemistry, 18B:304-306, (1979).
Berge et al., "Pharmaceutical Salts," Journal of Pharmaceutical Sciences, 66:1 1-19 (1977).
Langlois et al., "Use of the beta-Imager for Rapid ex Vivo Autoradiography Exemplified with Central Nervous System Penetrating Neurokinin 3 Antagonists," The Journal of Pharmacology and Experimental Therapeutics, 299:2 712-717 (2001).

Yip et al., "Localization of Fos-like immunoreactivity induced by the NK$_3$ tachykinin receptor agonist, senktide, in the guinea-pig brain," British Journal of Pharmacology, 122:715-722 (1997).
Fioramonti et al., "Intestinal anti-nociceptive behavoir of NK$_3$ receptor antagonism in conscious rats: evidence to support a peripheral mechanism of action," Neurogastroenterol Motil, 15:363-369 (2003).
Mazelin et al., "Comparative Effects of Nonpeptide Tachykinin Receptor Antagonists on Experimental Gut Inflammation in Rats and Guinea-Pigs," Life Sciences, 63:4 293-304 (1998).
Daoui et al., "Involvement of Tachykinin NK$_3$ Receptors in Citric Acid-induced Cough and Bronchial Responses in Guinea Pigs," American Journal of Respiratory and Critical Care Medicine, 158:42-48 (1998).
Maubach et al., "Tachykinins May Modify Spontaneous Epileptiform Activity in the Rat Entorhinal Cortex in Vitro by Activating Gabaergic Inhibition," Neuroscience, 83:4 1047-1062 (1998).
Kernel et al., "Facilitation by Endogenous Tachykinins of the Nmda-Evoked Release of Acetylcholine after Acute and Chronic Suppression of Dopaminergic Transmission in the Matrix of the Rat Striatum," J. Neurosci., 22(5):1929-1936 (2002).
Dai et al., "Efficient Rhodium-Catalyzed Asymmetric Hydrogenation for the Synthesis of a New Class of N-Aryl beta-Amino Acid Derivatives," Org. Lett., 7:23 5343-5345 (2005).
Liu et al., "Synthesis of Enantiomerically Pure N-tert-Butanesulfinyl (mines (tort-Butanesulfinimines) by the Direct Condensation of tert-Butanesulfinamide with Aldehydes and Ketones," J. Org. Chem., 64:1278-1284 (1999).

(Continued)

*Primary Examiner* — Zinna Northington Davis
(74) *Attorney, Agent, or Firm* — Stephen G. Kalinchak; Margaret M. Buck; Mary Catherine Di Nunzio

(57) ABSTRACT

Isoquinolone derivatives of the general formula

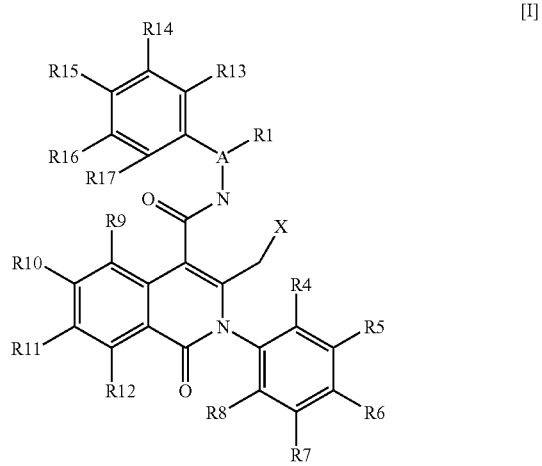

[I]

are provided. The compounds are NK3 antagonists and useful for the treatment of e.g. psychosis and schizophrenia.

48 Claims, No Drawings

OTHER PUBLICATIONS

Cogan et al., "Asymmetric Synthesis of Chiral Amines by Highly Diastereoselective 1,2-Additions of Organometallic Reagents to N-tert-Butanesulfinyl (mines," Tetrahedron, 55:88838904 (1999).

Amato et al., "Synthesis of 1-tert-Butyl-4-chloropiperidine: Generaton of an N-tert-Butyl Group by the Reaction of a Dimethyliminium Salt with Methylmagnesium Chloride," J. Org. Chem., 70:1930-1933 (2005).

S. Glossop, "A Microwave-Assisted Alternative Synthesis of 8-Amino-2-methyl-3,4-dihydroisoguinolin-1-one," Synthesis, 7:0981-0983 (2007).

Sugaya et al., "Synthesis of a 6H-Pyrazolo[4,5,1-de]acridin-6-one Derivative: a Useful Intermediate of Anti-tumour Agents," Synthesis, 73-76 (Jan. 1994).

ISOQUINOLINONE DERIVATIVES AS NK3 ANTAGONISTS

CROSS REFERENCE TO RELATED APPLICATIONS

This application claims the benefit of priority under 35 U.S.C. 119(e) of provisional application 60/914,159, filed Apr. 26, 2007.

FIELD OF THE INVENTION

The present invention relates to compounds useful in therapy, in particular in the treatment of psychosis, to compositions comprising said compounds, and to methods of treating diseases comprising the administration of said compounds.

BACKGROUND OF THE INVENTION

The currently approved antipsychotic drugs share the common feature of reducing the dopamine signalling in the brain. This is achieved through either a dopamine D2 receptor antagonistic or partial agonistic effect. The first generation antipsychotics (also referred to as "typical") are often associated with extra-pyrimidal side effects wherefore the use of these agents have diminished. Second generation or "atypical" antipsychotics in addition to the D2 receptor affinity have affinity to the serotonin receptor 2A (5-$HT_{2A}$). Some atypical antipsychotics in addition have affinity for the 5-$HT_{2C}$, 5-$HT_6$, or 5-$HT_7$ receptors. Atypical antipsychotics give rise to fewer extra-pyrimidal side effects, but are still hampered by weight gain and $QT_C$ effects. Examples of atypicals are clozapine, olanzapine and risperidone.

More recently, neurokinin receptors have been suggested as targets for CNS diseases [Albert, *Expert Opin. Ther. Patents*, 14, 1421-1433, 2004]. Neurokinins (or tachykinins) are a family of neuropeptides, which include substance P (SP), neurokinin A (NKA), and neurokinin B (NKB). The biological effects of these substances are primarily effected through binding to and activation of the three neurokinin receptors NK1, NK2, and NK3. Although some cross reactivity probably exists, SP has the highest affinity and is believed to be the endogenous ligand for NK1, and likewise for NKA and NK2, and for NKB and NK3.

NK3 is primarily expressed centrally in regions including cortical regions, such as frontal, parietal and cingulated cortex; nuclei of the amygdale, such as the basal, central and lateral nuclei; the hippocampus; and mesencephalon structures, such as ventral tegmental area, substantia nigra pars compacta, and dorsal raphe nuclei [Spooren et al, *Nature Reviews*, 4, 967-975, 2005]. The NK3 receptor is expressed on dopaminergic neurons, and Spooren et al has suggested that the antipsychotic effects of NK3 antagonists are mediated by an inhibition of the dopamine tone, particularly at the D2 receptor combined with a reduction of the serotonergic tone, particularly at the 5-$HT_{2A}$ receptor.

Two structurally distinct NK3 antagonists, namely talnetant and osanetant, have been clinically tested for antipsychotic, and in particular antischizophrenic effects.

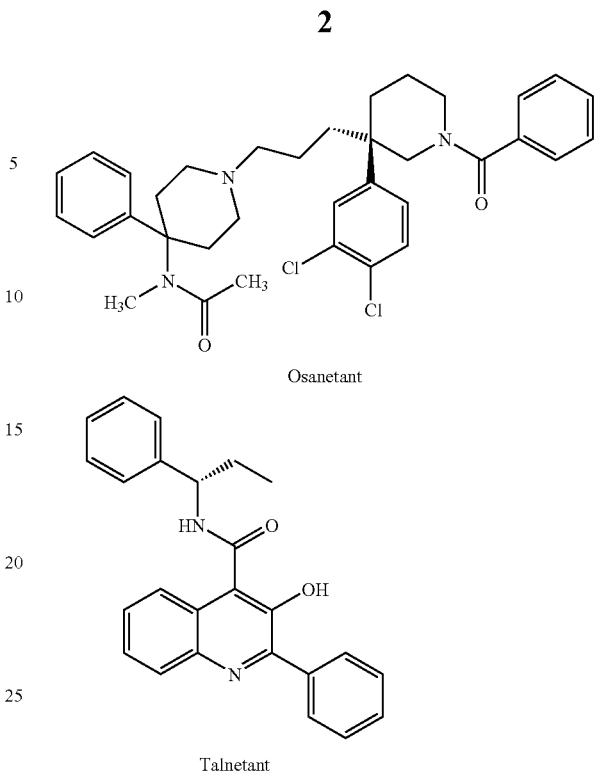

Osanetant

Talnetant

Osanetant proved superior to placebo in clinical trials, in particular on positive symptoms of psychosis, i.e. delusions, hallucinations and paranoia [*Am. J. Psychiatry*, 161, 2004, 975-984]. Similarly, talnetant has been shown in clinical trials to ameliorate the cognitive behaviour of schizophrenics [*Curr. Opion. Invest. Drug*, 6, 717-721, 2005]. Nevertheless, both compounds are hampered by poor pharmacokinetic and pharmacodynamic properties including poor solubility, poor bioavailability, relatively high clearance, and poor blood-brain barrier penetration [*Nature reviews*, 4, 967-975, 2005]. These results lend support to the notion that the NK3 receptor is a promising target for the treatment of e.g. psychosis, however emphasising the need for identifying compounds with adequate pharmacokinetic and pharmacodynamic properties.

WO95/32948 discloses a range of quinoline derivatives, including talnetant as NK3 antagonists.

More recently, WO 2006/130080 discloses compounds having the core structure

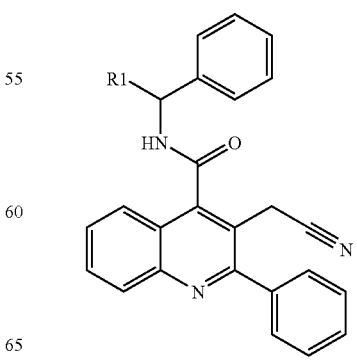

which compounds are said to be NK3 antagonists; and WO 2006/050991 and WO 2006/050992 disclose further quinolinecarboxamides derivatives, which derivatives are said to be NK3 antagonists.

WO 2005/014575 discloses compounds of the formula

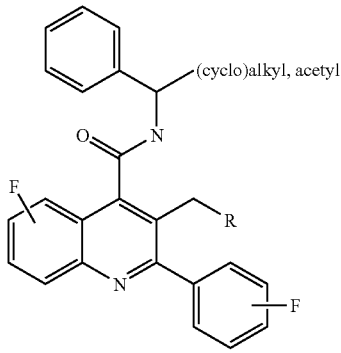

wherein R represents N-containing heterocycles, i.e. pyrazolyl, triazolyl and tetrazolyl.

Finally, *Ind. J. Chem. Section B*, 18B, 304-306, 1979 discloses a study on the synthesis of compounds with the following core structure

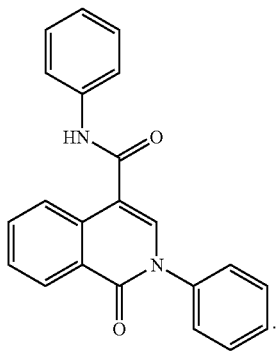

SUMMARY OF THE INVENTION

The present inventors have surprisingly found that certain isoquinolinone derivatives are potent NK3 antagonists, which may as such be used in the treatment of e.g. psychosis. Accordingly, in one embodiment the invention relates to compounds of formula I

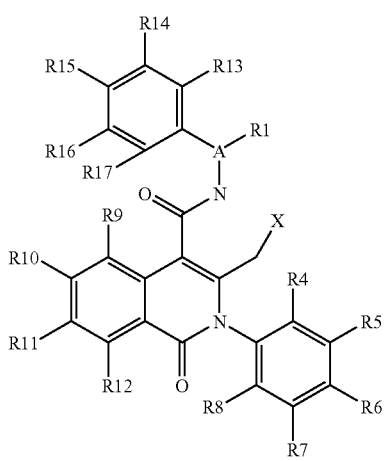

wherein A represents N, CH or $CR^1$;

wherein each $R^1$ independently represents hydrogen, $C_{1-6}$alkyl, $C_{2-6}$alkenyl, $C_{2-6}$alkynyl, —C(O)—$C_{1-6}$alkyl, —C(O)—$C_{2-6}$alkenyl, —C(O)—$C_{2-6}$alkynyl, —C(O)—O—$C_{1-6}$alkyl, —C(O)—O—$C_{2-6}$alkenyl, —C(O)—O—$C_{2-6}$alkynyl or phenyl, wherein said phenyl, $C_{1-6}$alkyl, $C_{2-6}$alkenyl or $C_{2-6}$alkynyl is optionally substituted with one or more substituents selected from halogen, hydroxyl, halo$C_{1-6}$alkyl, nitro, $C_{1-6}$alkoxy, and $NR^2R^3$;

wherein X represents hydrogen, $C_{1-6}$alkyl, $C_{2-6}$alkenyl, $C_{2-6}$alkynyl, cyano, —$OR^2$, —O—C(O)$R^2$, —OC(O)$NR^2R^3$, —C(O)—$NR^2R^3$, —N($R^2$)C(O)$R^3$, —N($R^2$)—C(O)$NR^2R^3$ or $NR^2R^3$, or X represents a mono-cyclic, bi-cyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{2-6}$alkenyl, $C_{2-6}$alkynyl, $C_{1-6}$alkoxy, —C(O)—$C_{1-6}$alkyl, —C(O)—$C_{2-6}$alkenyl, —C(O)—$C_{2-6}$alkynyl, —C(O)—O—$C_{1-6}$alkyl, —C(O)—O—$C_{2-6}$alkenyl, —C(O)—O—$C_{2-6}$alkynyl, —O—C(O)—$C_{1-6}$alkyl, —O—C(O)—$C_{2-6}$alkenyl, —O—C(O)—$C_{2-6}$alkynyl, —C(O)H, COOH; or wherein W represents a moiety of the formula —$(CH_2)_a$—Y—$(CH_2)_b$—Z;

wherein a and b independently represent an integer selected from 0, 1, 2 and 3;

wherein Y represents a bond, C(O), O, S, —O—C(O), —C(O)—O—, —$NR^2$—, —$NR^2$—C(O)—, —C(O)—NH—, or $S(O)_2$;

wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;

wherein each of $R^4$-$R^8$, $R^9$-$R^{12}$, and $R^{13}$-$R^{17}$ independently represent hydrogen, $C_{1-6}$alkyl, $C_{2-6}$alkenyl, $C_{2-6}$alkynyl, halogen, $NR^2R^3$, hydroxy, cyano, nitro, $C_{1-6}$alkoxy, halo$C_{1-6}$alkyl or hydroxy$C_{1-6}$alkyl;

wherein $R^2$ and $R^3$ independently represent hydrogen, $C_{1-6}$alkyl, $C_{2-6}$alkenyl, $C_{2-6}$alkynyl, hydroxy$C_{1-6}$alkyl, halo$C_{1-6}$alkyl or phenyl;

and pharmaceutically acceptable salts thereof.

In one embodiment, the invention relates to compounds of formula I and pharmaceutically acceptable salts thereof for use in therapy.

In one embodiment, the invention relates to pharmaceutical compositions comprising compounds of formula I and pharmaceutically acceptable salts thereof.

In one embodiment, the invention relates to methods of treatment, which methods comprise the administration of therapeutically effective amounts of a compound of formula I and pharmaceutically acceptable salts thereof to a patient in need thereof.

In one embodiment, the invention relates to the use of a compound of formula I and pharmaceutically acceptable salts thereof in the manufacture of a medicament.

In one embodiment, the invention relates to compounds of formula I and pharmaceutically acceptable salts thereof for use in the treatment of diseases.

DEFINITIONS

In the present context, "alkyl" is intended to indicate a straight, branched and/or cyclic saturated hydrocarbon. In particular "$C_{1-6}$alkyl" is intended to indicate such hydrocarbon having 1, 2, 3, 4, 5, or 6 carbon atoms. Examples of $C_{1-6}$alkyl include methyl, ethyl, propyl, butyl, pentyl, hexyl, cyclopropyl, cyclobutyl, cyclopentyl, cyclohexyl, 2-methylpropyl, tert.-butyl, and cyclopropylmethyl.

In the present context, "alkenyl" is intended to indicate a straight, branched and/or cyclic hydrocarbon comprising at least one carbon-carbon double bond. In particular "$C_{2-6}$alkenyl" is intended to indicate such hydrocarbon having 2, 3, 4, 5, or 6 carbon atoms. Examples of $C_{2-6}$alkenyl include ethenyl, 1-propenyl, 2-propenyl, 1-butenyl, 2-butenyl, 3-butenyl, and cyclohexenyl.

In the present context, "alkynyl" is intended to indicate a straight, branched and/or cyclic hydrocarbon comprising at least one carbon-carbon triple bond and optionally also one or more carbon-carbon double bonds. In particular "$C_{2-6}$alkynyl" is intended to indicate such hydrocarbon having 2, 3, 4, 5, or 6 carbon atoms. Examples of $C_{2-6}$alkynyl include ethynyl, 1-propynyl, 2-propynyl, 1-butynyl, 2-butynyl, 3-butynyl and 5-but-1-en-3-ynyl.

In the present context "halogen" is intended to indicate members of the $7^{th}$ group of the periodic system, e.g. fluoro, chloro, bromo, and iodo.

In the present context, "alkoxy" is intended to indicate a moiety of the formula —OR', wherein R' indicates alkyl as defined above. In particular "$C_{1-6}$alkoxy" is intended to indicate such moiety wherein the alkyl part has 1, 2, 3, 4 5, or 6 carbon atoms.

In the present context, haloalkyl is intended to indicate an alkyl as defined above substituted with one or more halogens. In particular, halo$C_{1-6}$alkyl is intended to indicate a moiety wherein the alkyl part has 1, 2, 3, 4, 5 or 6 carbon atoms. One example of haloalkyl is trifluoromethyl.

In the present context, pharmaceutically acceptable salts include pharmaceutical acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

In the present context, a "ring atom" is intended to indicate the atoms constituting a ring, and ring atoms are selected from C, N, O and S. As an example, benzene and toluene both have 6 carbons as ring atoms whereas pyridine has 5 carbons and 1 nitrogen as ring atoms.

In the present context, a "mono-cyclic moiety" is intended to indicate a ring formed structure comprising only one ring. Similarly, a "bi-cyclic moiety" is intended to indicate a structure comprised of two joined rings. The two rings may be joined at two adjacent ring atoms in each ring in which case said bi-cyclic moiety is said to be fused. Naphthalene is an example of a fused bi-cyclic ring moiety. Alternatively, the two rings are joined at a single ring atom in which case said bi-cyclic moiety is said to be spiro. 1,4-Dioxa-8-aza-spiro[4.5]decane is an example of a bi-cyclic ring moiety in spiro form. Alternatively, the two rings may be joined at two non-adjacent ring atoms in each ring in which case said bi-cyclic ring moiety is said to be caged. 3-Aza-bicyclo[3.2.2]nonane is an example of a caged bi-cyclic moiety. A "tri-cyclic moiety" is intended to indicate a structure comprised of three joined rings. As discussed for the bi-cyclic moieties above, tri-cyclic moieties may be fused, spiro or caged, or in deed, a combination thereof.

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

DETAILED DESCRIPTION OF THE INVENTION

The compounds of the present invention are defined by formula I below

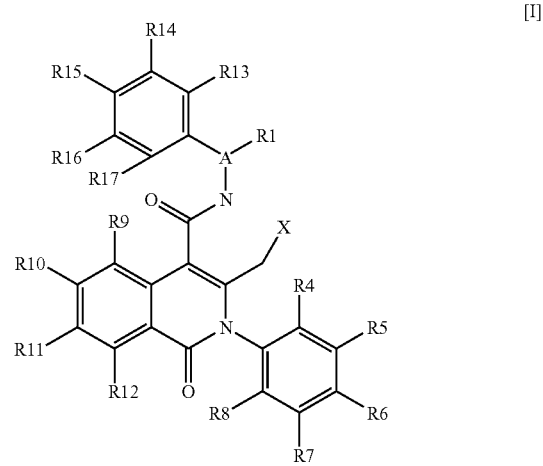

[I]

wherein A represents N, CH or CR$^1$;
wherein each R$^1$ independently represents hydrogen, C$_{1-6}$alkyl, C$_{2-6}$alkenyl, C$_{2-6}$alkynyl, —C(O)—C$_{1-6}$alkyl, —C(O)—C$_{2-6}$alkenyl, —C(O)—C$_{2-6}$alkynyl, —C(O)—O—C$_{1-6}$alkyl, —C(O)—O—C$_{2-6}$alkenyl, —C(O)—O—C$_{2-6}$alkynyl or phenyl, wherein said phenyl, C$_{1-6}$alkyl, C$_{2-6}$alkenyl or C$_{2-6}$alkynyl is optionally substituted with one or more substituents selected from halogen, hydroxyl, haloC$_{1-6}$alkyl, nitro, C$_{1-6}$alkoxy, and NR$^2$R$^3$; wherein X represents hydrogen, C$_{1-6}$alkyl, C$_{2-6}$alkenyl, C$_{2-6}$alkynyl, cyano, —OR$^2$, —O—C(O)R$^2$, —OC(O)NR$^2$R$^3$, —C(O)—NR$^2$R$^3$, —N(R$^2$)C(O)R$^3$, —N(R$^2$)—C(O)NR$^2$R$^3$ or NR$^2$R$^3$, or X represents a mono-cyclic, bi-cyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{2-6}$alkenyl, C$_{2-6}$alkynyl, C$_{1-6}$alkoxy, —C(O)—C$_{1-6}$alkyl, —C(O)—C$_{2-6}$alkenyl, —C(O)—C$_{2-6}$alkynyl, —C(O)—O—C$_{1-6}$alkyl, —C(O)—O—C$_{2-6}$alkenyl, —C(O)—O—C$_{2-6}$alkynyl, —O—C(O)—C$_{1-6}$alkyl, —O—C(O)—C$_{2-6}$alkenyl, —O—C(O)—C$_{2-6}$alkynyl, —C(O)H, COOH; or wherein W represents a moiety of the formula —(CH$_2$)$_a$—Y—(CH$_2$)$_b$—Z;
wherein a and b independently represent an integer selected from 0, 1, 2 and 3;
wherein Y represents a bond, C(O), O, S, —O—C(O), —C(O)—O—, —NR$^2$—, —NR$^2$—C(O)—, —C(O)—NH—, or S(O)$_2$;
wherein Z represents hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;
wherein each of R$^4$-R$^8$, R$^9$-R$^{12}$, and R$^{13}$-R$^{17}$ independently represent hydrogen, C$_{1-6}$alkyl, C$_{2-6}$alkenyl, C$_{2-6}$alkynyl, halogen, NR$^2$R$^3$, hydroxy, cyano, nitro, C$_{1-6}$alkoxy, haloC$_{1-6}$alkyl or hydroxyC$_{1-6}$alkyl;
wherein R$^2$ and R$^3$ independently represent hydrogen, C$_{1-6}$alkyl, C$_{2-6}$alkenyl, C$_{2-6}$alkynyl, hydroxyC$_{1-6}$alkyl, haloC$_{1-6}$alkyl or phenyl;
and pharmaceutically acceptable salts thereof.

In one embodiment, R$^4$-R$^8$ represent hydrogen.
In one embodiment, R$^9$-R$^{12}$ represent hydrogen.
In one embodiment, R$^{13}$-R$^{17}$ represent hydrogen.
In one embodiment, the compounds of the present invention are defined by formula I$_a$

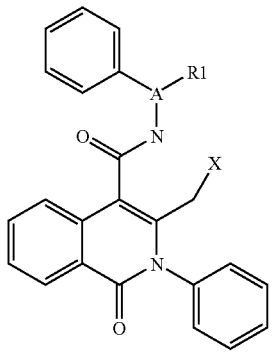

[Ia]

wherein A represents N, CH or CR$^1$;
wherein each R$^1$ independently represents hydrogen, C$_{1-6}$alkyl, —C(O)—C$_{1-6}$alkyl, —C(O)—O—C$_{1-6}$alkyl, or phenyl, wherein said phenyl or C$_{1-6}$alkyl, is optionally substituted with one or more substituents selected from halogen, hydroxyl, haloC$_{1-6}$alkyl, nitro, C$_{1-6}$alkoxy, and NR$^2$R$^3$;
wherein X represents hydrogen, C$_{1-6}$alkyl, cyano, —OR$^2$, —O—C(O)R$^2$, —OC(O)NR$^2$R$^3$, —C(O)—NR$^2$R$^3$, —N(R$^2$)C(O)R$^3$, —N(R$^2$)—C(O)NR$^2$R$^3$ or NR$^2$R$^3$, or X represents a mono-cyclic, bicyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{1-6}$alkoxy, —C(O)—C$_{1-6}$alkyl, —C(O)—O—C$_{1-6}$alkyl, —O—C(O)—C$_{1-6}$alkyl, —C(O)H, COOH; or wherein W represents a moiety of the formula —(CH$_2$)$_a$—Y—(CH$_2$)$_b$—Z;
wherein a and b independently represent an integer selected from 0, 1, 2 and 3;
wherein Y represents a bond, C(O), O, S, —O—C(O), —C(O)—O—, —NR$^2$—, —NR$^2$—C(O)—, —C(O)—NH—, or S(O)$_2$;
wherein Z represents hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;
wherein each of R$^4$-R$^8$, R$^9$-R$^{12}$, and R$^{13}$-R$^{17}$ independently represent hydrogen, C$_{1-6}$alkyl, C$_{2-6}$alkenyl, C$_{2-6}$alkynyl, halogen, NR$^2$R$^3$, hydroxy, cyano, nitro, C$_{1-6}$alkoxy, haloC$_{1-6}$alkyl or hydroxyC$_{1-6}$alkyl;
wherein R$^2$ and R$^3$ independently represent hydrogen, C$_{1-6}$alkyl, C$_{2-6}$alkenyl, C$_{2-6}$alkynyl, hydroxyC$_{1-6}$alkyl, haloC$_{1-6}$alkyl or phenyl; and pharmaceutically acceptable salts thereof. In particular, A represents CH and R$^1$ represents C$_{1-6}$alkyl, such as ethyl or cyclopropyl.

In one embodiment wherein the compounds of the present invention are defined by formula I$_a$, X represents hydrogen, C$_{1-6}$alkyl, cyano, —OR$^2$, —O—C(O)R$^2$, —OC(O)NR$^2$R$^3$, —C(O)—NR$^2$R$^3$—, —N(R$^2$)C(O)R$^3$, —N(R$^2$)—C(O)NR$^2$R$^3$ or NR$^2$R$^3$, wherein R$^2$ and R$^3$ independently represent hydrogen, C$_{1-6}$alkyl, hydroxyC$_{1-6}$alkyl, haloC$_{1-6}$alkyl or phenyl. In particular, X represents hydrogen, methyl, or NR$^2$R$^3$, wherein R$^2$ and R$^3$ independently represent hydrogen, C$_{1-6}$alkyl, or hydroxyC$_{1-6}$alkyl, and particular mentioning is made of R$^2$ and R$^3$ independently representing hydrogen, cyclopropylmethyl, methyl, ethyl or cyclopropyl.

In one embodiment wherein the compounds of the present invention are defined by formula $I_a$, X represents a mono-cyclic, bi-cyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —O—C(O)—, —C(O)H, COOH; or wherein W represents a moiety of the formula —$(CH_2)_a$—Y—$(CH_2)_b$—Z;
wherein a and b independently represent an integer selected from 0, 1, 2 and 3;
wherein Y represents a bond, C(O), O, S, —O—C(O), —C(O)—O—, —$NR^2$—, —$NR^2$—C(O)—, —C(O)—NH—, or $S(O)_2$;
wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein $R^2$ and $R^3$ independently represent hydrogen, $C_{1-6}$alkyl, hydroxy$C_{1-6}$alkyl, halo$C_{1-6}$alkyl or phenyl.

In one embodiment wherein the compounds of the present invention are defined by formula $I_a$, X represents a mono-cyclic moiety having 5 ring atoms one of which is nitrogen, and wherein one, two or three additional ring atoms may be a hetero atom selected from N, O and S, and wherein said mono-cyclic moiety may optionally be substituted with one or more substituents W, wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —O—C(O)—, —C(O)H, COOH; or wherein W represents a moiety of the formula —$(CH_2)_a$—Y—$(CH_2)_b$—Z;
wherein a and b independently represent an integer selected from 0, 1, 2 and 3;
wherein Y represents a bond, C(O), O, S, —O—C(O), —C(O)—O—, —$NR^2$—, —$NR^2$—C(O)—, —C(O)—NH—, or $S(O)_2$;
wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein $R^2$ and $R^3$ independently represent hydrogen, $C_{1-6}$alkyl, hydroxy$C_{1-6}$alkyl, halo$C_{1-6}$alkyl or phenyl.
Examples of such mono-cyclic moiety having 5 ring atoms include pyrrole, 2H-pyrrole, pyrazole, isothiazole, pyrrolidine, pyrroline, tetrazole, imidazolidine, imidazoline, pyrazolidine and pyrazoline.

In one embodiment wherein the compounds of the present invention are defined by formula $I_a$, X represents a mono-cyclic moiety having 6 ring atoms one of which is nitrogen, and wherein one, two or three additional ring atoms may be a hetero atom selected from N, O and S, and wherein said mono-cyclic moiety may optionally be substituted with one or more substituents W, wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —O—C(O)—, —C(O)H, COOH; or wherein W represents a moiety of the formula —$(CH_2)_a$—Y—$(CH_2)_b$—Z;
wherein a and b independently represent an integer selected from 0, 1, 2 and 3;
wherein Y represents a bond, C(O), O, S, —O—C(O), —C(O)—O—, —$NR^2$—, —$NR^2$—C(O)—, —C(O)—NH—, or $S(O)_2$;
wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein $R^2$ and $R^3$ independently represent hydrogen, $C_{1-6}$alkyl, hydroxy$C_{1-6}$alkyl, halo$C_{1-6}$alkyl or phenyl.
Examples of such mono-cyclic moiety having 6 ring atoms include pyridine, pyrazine, pyrimidine, pyridazine, piperidine, piperazine dihydropyridine, tetrahydropyridine, and morpholine.

In one embodiment, wherein the compounds of the present invention are defined by formula $I_a$, X represents a mono-cyclic moiety having 7 ring atoms one of which is nitrogen, and wherein one, two or three additional ring atoms may be a hetero atom selected from N, O and S, and wherein said mono-cyclic moiety may optionally be substituted with one or more substituents W, wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{2-6}$alkenyl, $C_{2-6}$alkynyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W represents a moiety of the formula —$(CH_2)_a$—Y—$(CH_2)_b$—Z;
wherein a and b independently represent an integer selected from 0, 1, 2 and 3;
wherein Y represents a bond, C(O), O, S, —O—C(O), —C(O)—O—, —$NR^2$—, —$NR^2$—C(O)—, —C(O)—NH—, or $S(O)_2$;
wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein $R^2$ and $R^3$ independently represent hydrogen, $C_{1-6}$alkyl, hydroxy$C_{1-6}$alkyl, halo$C_{1-6}$alkyl or phenyl.
Examples of such mono-cyclic moiety having 7 ring atoms include azepane, [1,4]diazepane and 2,3,4,5-tetrahydro-1H-[1,4]diazepane.

In one embodiment wherein compounds of the present invention are defined by formula $I_a$, X represents a mono-cyclic or bi-cyclic moiety having 8 ring atoms one of which is nitrogen, and wherein one, two or three additional ring atoms may be a hetero atom selected from N, O and S, and wherein said cyclic or bicyclic moiety may optionally be substituted with one or more substituents W, wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—C$_{1-6}$alkyl, —O—C(O)—C$_{1-6}$alkyl, —C(O)H, COOH; or wherein W represents a moiety of the formula —(CH$_2$)$_a$—Y—(CH$_2$)$_b$—Z;

wherein a and b independently represent an integer selected from 0, 1, 2 and 3;

wherein Y represents a bond, C(O), O, S, —O—C(O), —C(O)—O—, —NR$^2$—, —NR$^2$—C(O)—, —C(O)—NH—, or S(O)$_2$;

wherein Z represents hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;

wherein R$^2$ and R$^3$ independently represent hydrogen, C$_{1-6}$alkyl, hydroxyC$_{1-6}$alkyl, haloC$_{1-6}$alkyl or phenyl. Examples of such mono-cyclic or bi-cyclic moiety having 8 ring atoms include quinnuclidine, 8-aza-bicyclo[3.2.1]octane and 2-aza-bicyclo[2.2.2]octane.

In one embodiment wherein the compounds of the present invention are defined by formula I$_a$, X represents a mono-cyclic or bi-cyclic moiety having 9 ring atoms one of which is nitrogen, and wherein one, two or three additional ring atoms may be a hetero atom selected from N, O and S, and wherein said mono-cyclic or bi-cyclic moiety may optionally be substituted with one or more substituents W, wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{1-6}$alkoxy, —C(O)—C$_{1-6}$alkyl, —C(O)—O—C$_{1-6}$alkyl, —O—C(O)—C$_{1-6}$alkyl, —C(O)H, COOH; or wherein W represents a moiety of the formula —(CH$_2$)$_a$—Y—(CH$_2$)$_b$—Z;

wherein a and b independently represent an integer selected from 0, 1, 2 and 3;

wherein Y represents a bond, C(O), O, S, —O—C(O), —C(O)—O—, —NR$^2$—, —NR$^2$—C(O)—, —C(O)—NH—, or S(O)$_2$;

wherein Z represents hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;

wherein R$^2$ and R$^3$ independently represent hydrogen, C$_{1-6}$alkyl, C$_{2-6}$alkenyl, C$_{2-6}$alkynyl, hydroxyC$_{1-6}$alkyl, haloC$_{1-6}$alkyl or phenyl. Examples of such mono-cyclic or bi-cyclic moiety having 9 ring atoms include indolizine, isoindole, 3H-indole, indole, 1H-indazole, purine, indoline, and isoindoline.

In one embodiment wherein the compounds of the present invention are defined by formula I$_a$, X represents a mono-cyclic or bi-cyclic moiety having 10 ring atoms one of which is nitrogen, and wherein one, two or three additional ring atoms may be a hetero atom selected from N, O and S, and wherein said mono-cyclic or bi-cyclic moiety may optionally be substituted with one or more substituents W, wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{1-6}$alkoxy, —C(O)—C$_{1-6}$alkyl, —C(O)—O—C$_{1-6}$alkyl, —O—C(O)—C$_{1-6}$alkyl, —C(O)H, COOH; or wherein W represents a moiety of the formula —(CH$_2$)$_a$—Y—(CH$_2$)$_b$—Z;

wherein a and b independently represent an integer selected from 0, 1, 2 and 3;

wherein Y represents a bond, C(O), O, S, —O—C(O), —C(O)—O—, —NR$^2$—, —NR$^2$—C(O)—, —C(O)—NH—, or S(O)$_2$;

wherein Z represents hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;

wherein R$^2$ and R$^3$ independently represent hydrogen, C$_{1-6}$alkyl, hydroxyC$_{1-6}$alkyl, haloC$_{1-6}$alkyl or phenyl. Examples of such mono-cyclic or bi-cyclic moiety having 10 ring atoms include 4H-quinolizine, isoquinoline, quinoline, phthalazine, naphthyridine, quinoxaline, cinnoline, pterridine, 1,2,3,4-tetrahydro-isoquinolone, 1,4,8-triaza-spiro[4.5]decane and 1,2,3,4-tetrahydro-quinoline.

In one embodiment, the compounds of the present invention are defined by formula I$_b$

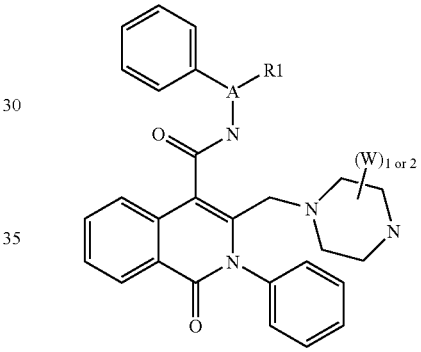

[Ib]

wherein A represents N, CH or CR$^1$;

wherein each R$^1$ independently represents hydrogen, C$_{1-6}$alkyl, —C(O)—C$_{1-6}$alkyl, C(O)—O—C$_{1-6}$alkyl, or phenyl, wherein said phenyl, or C$_{1-6}$alkyl is optionally substituted with one or more substituents selected from halogen, hydroxyl, haloC$_{1-6}$alkyl, nitro, C$_{1-6}$alkoxy, and NR$^2$R$^3$;

wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{1-6}$alkoxy, —C(O)—C$_{1-6}$alkyl, —C(O)—O—C$_{1-6}$alkyl, —O—C(O)—C$_{1-6}$alkyl, —C(O)H, COOH; or wherein W represents a moiety of the formula —(CH$_2$)$_a$—Y—(CH$_2$)$_b$—Z;

wherein a and b independently represent an integer selected from 0, 1, 2 and 3;

wherein Y represents a bond, C(O), O, S, —O—C(O), —C(O)—O—, —NR$^2$—, —NR$^2$—C(O)—, —C(O)—NH—, or S(O)$_2$;

wherein Z represents hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;

wherein $R^2$ and $R^3$ independently represent hydrogen, $C_{1-6}$alkyl, hydroxy$C_{1-6}$alkyl, halo$C_{1-6}$alkyl or phenyl; and pharmaceutically acceptable salts thereof. In particular, A represent CH, and $R^1$ represents $C_{1-6}$alkyl, such as ethyl or cyclopropyl.

In one embodiment wherein the compounds of the present invention are defined by formula $I_b$, W represents a moiety of the formula —$(CH_2)_a$—Y—$(CH_2)_b$—Z;
wherein a and b independently represent an integer selected from 0, 1, 2 and 3;
wherein Y represents a bond, C(O), O, S, —O—C(O), —C(O)—O—, —$NR^2$—, —$NR^2$—C(O)—, —C(O)—NH—, or $S(O)_2$;
wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein $R^2$ and $R^3$ independently represent hydrogen, $C_{1-6}$alkyl, hydroxy$C_{1-6}$alkyl, halo$C_{1-6}$alkyl or phenyl. In a further embodiment, Y represents a bond, C(O) or $S(O)_2$;
wherein a+b is 0, 1, 2, 3, or 4; and wherein Z represents mono-cyclic or fused bi-cyclic moiety comprising 5 to 12 carbon ring atoms and optionally one, two or three hetero atoms selected from amongst N, O, and S, and wherein said cyclic or bicyclic moiety is optionally substituted with one or more substituents selected from the group consisting of halogen, cyano, $C_{1-6}$alkyl, hydroxyl, and $C_{1-6}$alkoxy, phenyl, pyrazinyl, pyridyl, and halogen substituted phenyl. Particular mentioning is made of the embodiment, wherein Y represents a bond or C(O), and a+b is 0, 1, 2, or 3. In particular, Z comprises 5-9 ring atoms, such as e.g. 5, 6, or 9 ring atoms. Examples of Z with 5 ring atoms include pyrrolide and cyclopentyl; examples of Z with 6 ring atoms include phenyl, pyrimidinyl, morpholinyl and pyridyl; examples of Z with 9 ring atoms include furo [3.2-c]pyridyl. A particular example of Z is morpholinyl, e.g. attached to the rest of the W moiety via the nitrogen, and optionally substituted with one or more substituents selected from the group consisting of halogen, cyano, $C_{1-6}$alkyl, hydroxyl, and $C_{1-6}$alkoxy, phenyl, pyrazinyl, pyridyl, and halogen substituted phenyl. Another particular example of Z is piperidyl, e.g. attached to the rest of the W moiety via the nitrogen, and optionally substituted with one or more substituents selected from the group consisting of halogen, cyano, $C_{1-6}$alkyl, hydroxyl, and $C_{1-6}$alkoxy, phenyl, pyrazinyl, pyridyl, and halogen substituted phenyl. Another particular example of Z is pyridyl, e.g. attached to the rest of the W moiety via the nitrogen. Another particular example of Z is pyridyl, e.g. attached to the rest of the W moiety at the 2, 3 or 4 position, and optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl. Another particular example of Z is phenyl, optionally substituted with one or more substituents selected from the group consisting of halogen, cyano, $C_{1-6}$alkyl, hydroxyl, and $C_{1-6}$alkoxy, phenyl, pyrazinyl, pyridyl, and halogen substituted phenyl. Another particular example of Z is pyrrolidinyl, optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl. Another particular example of Z is indolyl, e.g. attached to the rest of the W moiety at the 4, 5, 6, or 7 position, and optionally substituted with one or more substituents selected from the group consisting of halogen, cyano, $C_{1-6}$alkyl, hydroxyl, and $C_{1-6}$alkoxy, phenyl, pyrazinyl, pyridyl, and halogen substituted phenyl. Other particular examples of Z include cyclopentyl, furopyridyl, tetrahydrofuranyl, benzo[1.4]oxazinyl, benzo[1.4]dioxinyl, benzo[1.2.5]thiadiazol, and quinazolinyl.

In one embodiment wherein the compounds of the present invention are defined by formula $I_b$, Y represents a bond, C(O), —C(O)—O—, C(O)—NH—, —O—, or $S(O)_2$; a+b is 0, 1, 2, 3 or 4; and wherein Z represents hydrogen, $C_{1-6}$alkyl, such as methyl, iso-propyl, iso-butyl, or tert.-butyl, $NR^2R^3$ or cyano.

In one embodiment wherein the compounds of the present invention are defined by formula $I_b$, A represents CH; $R^1$ represents $C_{1-6}$alkyl, such as ethyl or cyclopropyl, W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH.

In one embodiment the compounds of the present invention are defined by formula $I_c$

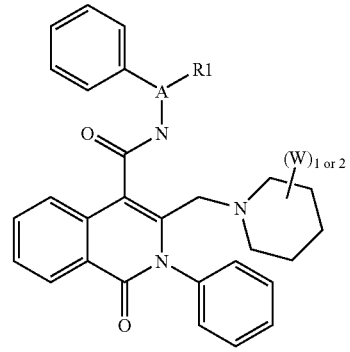

[Ic]

wherein A represents N, CH or $CR^1$;
wherein each $R^1$ independently represents hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from halogen, hydroxyl, halo$C_{1-6}$alkyl, nitro, $C_{1-6}$alkoxy, and $NR^2R^3$;
wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W represents a moiety of the formula —$(CH_2)_a$—Y—$(CH_2)_b$—Z;
wherein a and b independently represent an integer selected from 0, 1, 2 and 3;
wherein Y represents a bond, C(O), O, S, —O—C(O), —C(O)—O—, —$NR^2$—, —$NR^2$—C(O)—, —C(O)—NH—, or $S(O)_2$;
wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;

wherein $R^2$ and $R^3$ independently represent hydrogen, $C_{1-6}$alkyl, hydroxy$C_{1-6}$alkyl, halo$C_{1-6}$alkyl or phenyl; and pharmaceutically acceptable salts thereof. In particular, A represent CH, and $R^1$ represents $C_{1-6}$alkyl, such as ethyl or cyclopropyl.

In one embodiment wherein the compounds of the present invention are defined by formula $I_c$, W independently represents hydrogen, hydroxyl, phenyl, phenyl substituted with $C_{1-6}$alkoxy, piperidyl, pyridyl, —O—(CH$_2$)$_c$—O—, wherein c is 2 or 3 (spiro), N(CH$_3$)$_2$, $C_{1-6}$alkyl, —(CH$_2$)$_a$—C(O)—O—(CH$_2$)$_b$—H, wherein a+b is 1, 2, or 3, or

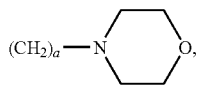

wherein a represents 1, 2, or 3.

In one embodiment, the compounds of the present invention are defined by formula $I_d$

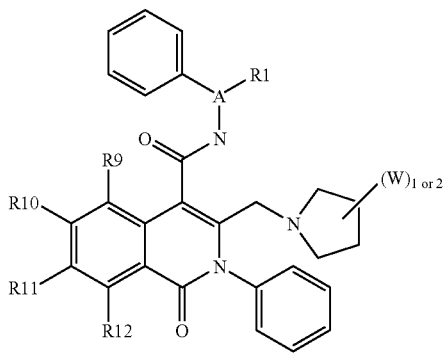

[Id]

wherein A represents N, CH or CR$^1$;

wherein each $R^1$ independently represents hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from halogen, hydroxyl, halo$C_{1-6}$alkyl, nitro, $C_{1-6}$alkoxy, and NR$^2$R$^3$;

wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH;

wherein $R^2$ and $R^3$ independently represent hydrogen, $C_{1-6}$alkyl, hydroxy$C_{1-6}$alkyl, halo$C_{1-6}$alkyl or phenyl; wherein $R^9$-$R^{12}$ independently represent hydrogen or halogen; and pharmaceutically acceptable salts thereof. In particular, A is CH; $R^1$ represents $C_{1-6}$alkyl, such as ethyl or cyclopropyl; and each of $R^9$-$R^{12}$ independently represent hydrogen or halogen.

In one embodiment, the compounds of the present invention are defined by formula $I_e$

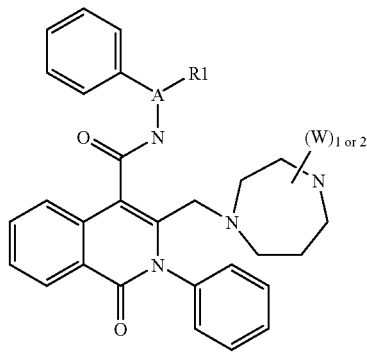

[Ie]

wherein A represents N, CH or CR$^1$;

wherein each $R^1$ independently represents hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from halogen, hydroxyl, halo$C_{1-6}$alkyl, nitro, $C_{1-6}$alkoxy, and NR$^2$R$^3$;

wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W represents a moiety of the formula —(CH$_2$)$_a$—Y—(CH$_2$)$_b$—Z;

wherein a and b independently represent an integer selected from 0, 1, 2 and 3;

wherein Y represents a bond, C(O), O, S, —O—C(O), —C(O)—O—, NR$^2$, —NR$^2$—C(O)—, —C(O)—NH—, or S(O)$_2$;

wherein Z represents hydrogen, $C_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl; wherein $R^2$ and $R^3$ independently represent hydrogen, $C_{1-6}$alkyl, hydroxy$C_{1-6}$alkyl, halo$C_{1-6}$alkyl or phenyl; and pharmaceutically acceptable salts thereof. In particular, A is CH, and $R^1$ represents $C_{1-6}$alkyl, such as ethyl or cyclopropyl. In particular, Z comprises 5-9 ring atoms, such as e.g. 5, 6, or 9 ring atoms. Examples of Z with 5 ring atoms include pyrrolide and cyclopentyl; examples of Z with 6 ring atoms include phenyl, pyrimidinyl, morpholinyl and pyridyl; examples of Z with 9 ring atoms include furo [3.2-c]pyridyl.

In one embodiment, the compounds of the present invention are defined by formula $I_f$

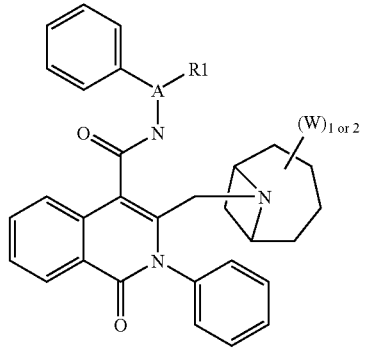

[If]

wherein A represents N, CH or CR¹;
wherein each R¹ independently represents hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from halogen, hydroxyl, halo$C_{1-6}$alkyl, nitro, $C_{1-6}$alkoxy, and NR²R³;
wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W represents a moiety of the formula —(CH$_2$)$_a$—Y—(CH$_2$)$_b$—Z;
wherein a and b independently represent an integer selected from 0, 1, 2 and 3;
wherein Y represents a bond, C(O), O, S, —O—C(O), —C(O)—O—, NR², —NR²—C(O)—, —C(O)—NH—, or S(O)$_2$;
wherein Z represents hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein R² and R³ independently represent hydrogen, $C_{1-6}$alkyl, hydroxy$C_{1-6}$alkyl, halo$C_{1-6}$alkyl or phenyl; and pharmaceutically acceptable salts thereof. In particular, A is CH, and R¹ represents $C_{1-6}$alkyl, such as ethyl or cyclopropyl. In particular, Z comprises 5-9 ring atoms, such as e.g. 5, 6, or 9 ring atoms. Examples of Z with 5 ring atoms include pyrrolide and cyclopentyl; examples of Z with 6 ring atoms include phenyl, pyrimidinyl, morpholinyl and pyridyl; examples of Z with 9 ring atoms include furo [3.2-c]pyridyl.

In one embodiment, the compounds of the present invention are defined by formula $I_g$

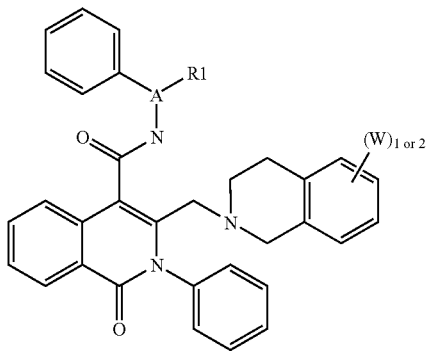

[Ig]

wherein A represents N, CH or CR¹;
wherein each R¹ independently represents hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from halogen, hydroxyl, halo$C_{1-6}$alkyl, nitro, $C_{1-6}$alkoxy, and NR²R³;
wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —N(R²)—C(O)—R³, —C(O)H, COOH; or wherein W represents a moiety of the formula —(CH$_2$)$_a$—Y—(CH$_2$)$_b$—Z;
wherein a and b independently represent an integer selected from 0, 1, 2 and 3;
wherein Y represents a bond, C(O), O, S, —O—C(O), —C(O)—O—, NR², —NR²—C(O)—, —C(O)—NH—, or S(O)$_2$;
wherein Z represents hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein R² and R³ independently represent hydrogen, $C_{1-6}$alkyl, hydroxy$C_{1-6}$alkyl, halo$C_{1-6}$alkyl or phenyl; and pharmaceutically acceptable salts thereof. In particular, A is CH, and R¹ represents $C_{1-6}$alkyl, such as ethyl or cyclopropyl. In particular, Z comprises 5-9 ring atoms, such as e.g. 5, 6, or 9 ring atoms. Examples of Z with 5 ring atoms include pyrrolide and cyclopentyl; examples of Z with 6 ring atoms include phenyl, pyrimidinyl, morpholinyl and pyridyl; examples of Z with 9 ring atoms include furo [3.2-c]pyridyl.

In one embodiment, the compounds of the present invention are defined by formula $I_h$

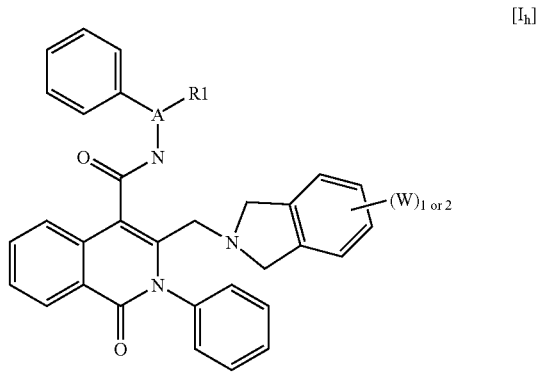

[$I_h$]

wherein A represents N, CH or CR¹;
wherein each R¹ independently represents hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from halogen, hydroxyl, halo$C_{1-6}$alkyl, nitro, $C_{1-6}$alkoxy, and NR²R³;
wherein W is selected from hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W represents a moiety of the formula —(CH$_2$)$_a$—Y—(CH$_2$)$_b$—Z;
wherein a and b independently represent an integer selected from 0, 1, 2 and 3;
wherein Y represents a bond, C(O), O, S, —O—C(O), —C(O)—O—, NR², —NR²—C(O)—, —C(O)—NH—, or S(O)$_2$;
wherein Z represents hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl; wherein $R^2$ and $R^3$ independently represent hydrogen, $C_{1-6}$alkyl, hydroxy$C_{1-6}$alkyl, halo$C_{1-6}$alkyl or phenyl; and pharmaceutically acceptable salts thereof. In particular, A is CH, and $R^1$ represents $C_{1-6}$alkyl, such as ethyl or cyclopropyl. In particular, Z comprises 5-9 ring atoms, such as e.g. 5, 6, or 9 ring atoms. Examples of Z with 5 ring atoms include pyrrolide and cyclopentyl; examples of Z with 6 ring atoms include phenyl, pyrimidinyl, morpholinyl and pyridyl; examples of Z with 9 ring atoms include furo [3.2-c]pyridyl.

In one embodiment, the compounds of the present invention are defined by formula $I_i$

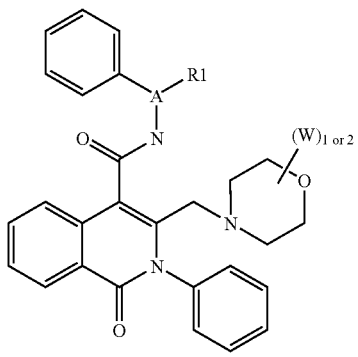

[Ii]

wherein A represents N, CH or $CR^1$;
wherein each $R^1$ independently represents hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from halogen, hydroxyl, halo$C_{1-6}$alkyl, nitro, $C_{1-6}$alkoxy, and $NR^2R^3$;
wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein X represents a moiety of the formula —$(CH_2)_a$—Y—$(CH_2)_b$—Z;
wherein a and b independently represent an integer selected from 0, 1, 2 and 3;
wherein Y represents a bond, C(O), O, S, —O—C(O), —C(O)—O—, $NR^2$, —$NR^2$—C(O)—, —C(O)—NH—, or $S(O)_2$;
wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl; wherein $R^2$ and $R^3$ independently represent hydrogen, $C_{1-6}$alkyl, hydroxy$C_{1-6}$alkyl, halo$C_{1-6}$alkyl or phenyl; and pharmaceutically acceptable salts thereof. In particular, A is CH, and $R^1$ represents $C_{1-6}$alkyl, such as ethyl or cyclopropyl. In particular, Z comprises 5-9 ring atoms, such as e.g. 5, 6, or 9 ring atoms. Examples of Z with 5 ring atoms include pyrrolide and cyclopentyl; examples of Z with 6 ring atoms include phenyl, pyrimidinyl, morpholinyl and pyridyl; examples of Z with 9 ring atoms include furo [3.2-c]pyridyl.

In one embodiment, the compounds of the present invention are defined by formula $I_j$

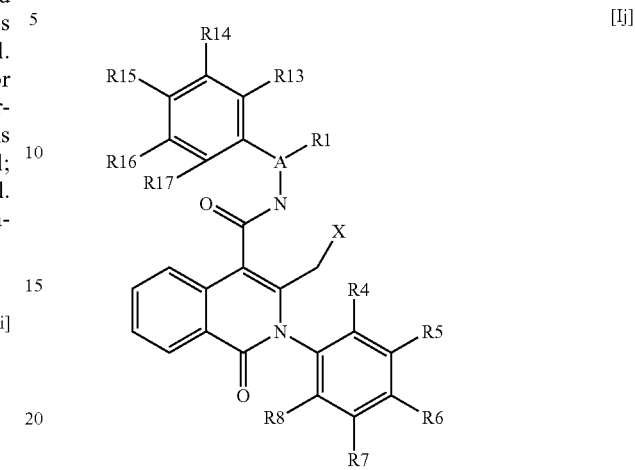

[Ij]

wherein A represents N, CH or $CR^1$;
wherein each $R^1$ independently represents hydrogen, $C_{1-6}$alkyl, —C(O)—$C_{1-6}$alkyl, —C(O)—O—$C_{1-6}$alkyl, or phenyl, wherein said phenyl or $C_{1-6}$alkyl is optionally substituted with one or more substituents selected from halogen, hydroxyl, halo$C_{1-6}$alkyl, nitro, $C_{1-6}$alkoxy, and $NR^2R^3$;
wherein X represents hydrogen, $C_{1-6}$alkyl, cyano, —$OR^2$, —O—$C(O)R^2$, —$OC(O)NR^2R^3$, —$C(O)$—$NR^2R^3$, —$N(R^2)C(O)R^3$, —$N(R^2)$—$C(O)NR^2R^3$ or $NR^2R^3$, or X represents a mono-cyclic, bicyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W represents a moiety of the formula —$(CH_2)_a$—Y—$(CH_2)_b$—Z;
wherein a and b independently represent an integer selected from 0, 1, 2 and 3;
wherein Y represents a bond, C(O), O, S, —O—C(O), —C(O)—O—, —$NR^2$—, —$NR^2$—C(O)—, —C(O)—NH—, or $S(O)_2$;
wherein Z represents hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, phenyl, pyridyl, and halogen substituted phenyl;
wherein one of $R^4$-$R^8$ represents halogen and the other represent hydrogen; wherein one of $R^{13}$-$R^{17}$ represents halogen and the other represent hydrogen;
wherein $R^2$ and $R^3$ independently represent hydrogen, $C_{1-6}$alkyl, hydroxy$C_{1-6}$alkyl, halo$C_{1-6}$alkyl or phenyl; and pharmaceutically acceptable salts thereof. In particular, A represents CH; $R^1$ represents $C_{1-6}$alkyl, such as ethyl or cyclopropyl; $R^{14}$ represents halogen; and $R^5$ or $R^8$ represents halogen. Particular mentioning is made of the embodiment wherein X represents piperazinyl or 1-piperidyl substituted with one or two substituents W, wherein said W is a moiety of the formula —$(CH_2)_a$—Y—$(CH_2)_b$—Z, wherein a and b independently represent 0, 1, 2 or 3; Y represents a bond, O, —$NR^2$—C(O)—; and wherein Z represents hydrogen, $C_{1-6}$alkyl, piperidyl, morpholinyl, pyridyl, phenyl, phenyl substituted with $C_{1-6}$alkoxy, or pyrrolidinyl.

In one embodiment, the compounds of the invention are defined by formula $I_k$

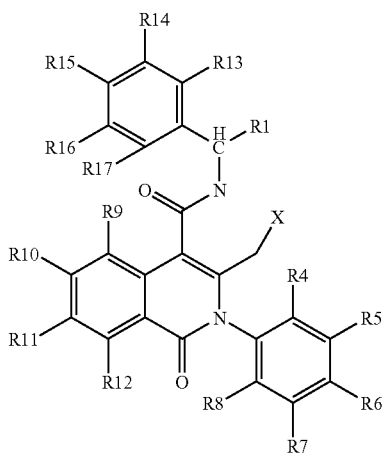

[Ik]

wherein $R^1$ represents hydrogen, $C_{1-6}$alkyl, $C_{2-6}$alkenyl or $C_{2-6}$alkynyl;
wherein X represents hydrogen, $C_{1-6}$alkyl, $C_{2-6}$alkenyl, $C_{2-6}$alkynyl or $NR^2R^3$, or X represents a mono-cyclic or bi-cyclic moiety having 5-9 ring atoms one of which is nitrogen, and wherein one, two or three additional ring atoms may be a hetero atom selected from N, O and S, and wherein said mono-cyclic or bi-cyclic moiety may optionally be substituted with one or more substituents W, wherein W is selected from hydrogen, halogen, hydroxy, (=O), $C_{1-6}$alkyl, $C_{2-6}$alkenyl, $C_{2-6}$alkynyl, $C_{1-6}$alkoxy, or wherein W represents a moiety of the formula —$(CH_2)_a$—Y—$(CH_2)_b$—Z;
wherein a and b independently represent an integer selected from 0, 1, 2 and 3;
wherein Y represents a bond, and wherein Z represents a mono-cyclic moiety comprising 5 to 6 ring atoms of which optionally one, two or three are hetero atoms selected from amongst N, O, and S, and wherein said mono-cyclic moiety is optionally substituted with one or more substituents selected from the group consisting of halogen, $C_{1-6}$alkyl, hydroxyl, and $C_{1-6}$alkoxy;
wherein each of $R^4$-$R^8$ independently represents hydrogen or halogen;
wherein each of $R^9$-$R^{12}$ independently represents hydrogen or halogen provided that at least one of $R^9$-$R^{12}$ represents halogen;
wherein each of $R^{13}$-$R^{17}$ independently represent hydrogen or halogen;
wherein $R^2$ and $R^3$ independently represent hydrogen, $C_{1-6}$alkyl, $C_{2-6}$alkenyl, $C_{2-6}$alkynyl; and pharmaceutically acceptable salts thereof. In particular, the compounds defined by formula $I_k$ may be further defined by formula $I_k'$

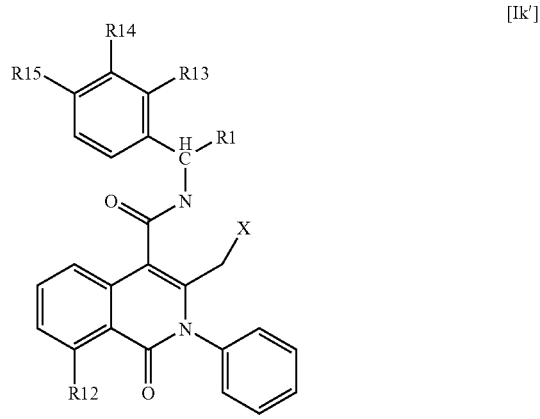

[Ik']

wherein $R^1$ is selected from $C_{1-6}$alkyl;
wherein X is selected from hydrogen, $C_{1-6}$alkyl or $NR^2R^3$, or X represents a mono-cyclic or bi-cyclic moiety having 5-9 ring atoms one of which is nitrogen, and wherein one additional ring atoms may be a hetero atom selected from N, and wherein said mono-cyclic or bi-cyclic moiety may optionally be substituted with one or more substituents W, wherein W is selected from hydrogen, hydroxy, (=O), $C_{1-6}$alkyl or wherein W represents a moiety of the formula —$(CH_2)_a$—Y—$(CH_2)_b$—Z;
wherein a and b independently represent an integer selected from 0, 1, 2 and 3;
wherein Y represents a bond, and wherein Z represents a mono-cyclic moiety comprising 5 to 6 ring atoms of which optionally one is a hetero atom selected from amongst N, O, and S, and wherein said mono-cyclic moiety is optionally substituted with one or more substituents selected from the group consisting of halogen, $C_{1-6}$alkyl, hydroxyl, and $C_{1-6}$alkoxy;
wherein $R^{12}$ represents halogen;
$R^{13}$-$R^{15}$ each independently represents hydrogen or halogen;
and pharmaceutically acceptable salts thereof. In particular, $R^1$ represents methyl, ethyl, cyclopropyl, cyclobutyl, cyclopentyl or cyclohexyl, and X represents

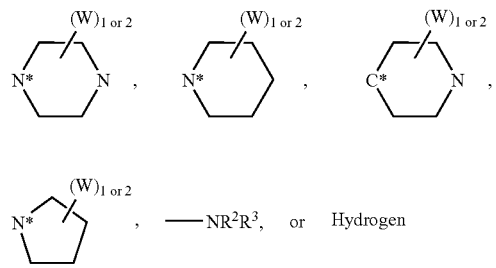

* indicates the point of attachment

In one embodiment, wherein the compounds of the invention are defined by formula $I_k{'}$ and $R^1$ represents methyl, ethyl, cyclopropyl, cyclobutyl, cyclopentyl or cyclohexyl, X represents

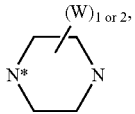

and wherein W represents hydrogen, (=O), $C_{1-6}$-alkyl, or —$(CH_2)_a$—Y—$(CH_2)_b$—Z. In particular, W represents hydrogen, methyl, cyclopropylmethyl, isopropyl, isobutyl, tert-butyl, (=O), or —$(CH_2)_a$—Y—$(CH_2)_a$—Z, wherein a+b is 2 and Z is selected from 4-morpholinyl, phenyl, 1-piperidine or 1-pyrrolidinyl.

In one embodiment, wherein the compounds of the invention are defined by formula $I_k{'}$ and $R^1$ represents methyl, ethyl, cyclopropyl, cyclobutyl, cyclopentyl or cyclohexyl, X represents

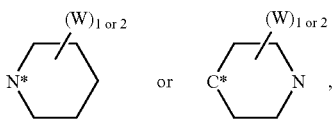

wherein W represents hydrogen, hydroxyl, $C_{1-6}$-alkyl or —$(CH_2)_a$—Y—$(CH_2)_a$—Z. In particular, W represents hydrogen, hydroxyl, tert-butyl, or a+b is 0 or 2 and Z represents 4-morpholinyl, phenyl, optionally substituted with $C_{1-6}$alkoxy, or 4-piperidyl.

In one embodiment, wherein the compounds of the invention are defined by formula $I_k{'}$ and $R^1$ represents methyl, ethyl, cyclopropyl, cyclobutyl, cyclopentyl or cyclohexyl, X represent

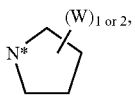

and W represents (=O), and in particular, X represents

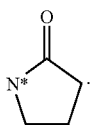

In one embodiment, wherein the compounds of the invention are defined by formula $I_k{'}$ and $R^1$ represents methyl, ethyl, cyclopropyl, cyclobutyl, cyclopentyl or cyclohexyl, X represents —$NR^2R^3$. In particular, $R^2$ and $R^3$ independently represents hydrogen or $C_{1-6}$-alkyl, and special mention is made of the compounds wherein $R^2$ represents hydrogen, and $R^3$ represents cyclopropyl, isobutyl or tert-butyl.

In one embodiment, wherein the compounds of the invention are defined by formula $I_k{'}$ and $R^1$ represents methyl, ethyl, cyclopropyl, cyclobutyl, cyclopentyl or cyclohexyl, X is hydrogen.

In one embodiment, the compounds of the invention are defined by formula $I_k{''}$

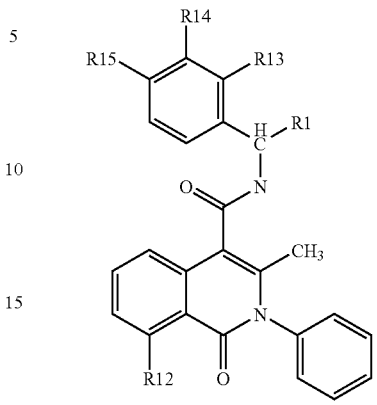

wherein $R^1$ represents ethyl, cylopropyl or cyclobutyl;
wherein $R^{12}$ represents fluoro or chloro; and
$R^{13}$, $R^{14}$ and $R^{15}$ each individually represent hydrogen, fluoro or chloro, wherein two of $R^{13}$, $R^{14}$ and $R^{15}$ represent hydrogen, and pharmaceutically acceptable salts thereof. In particular, said compound is essentially the S enantiomers as depicted in formula $I_k{'''}$

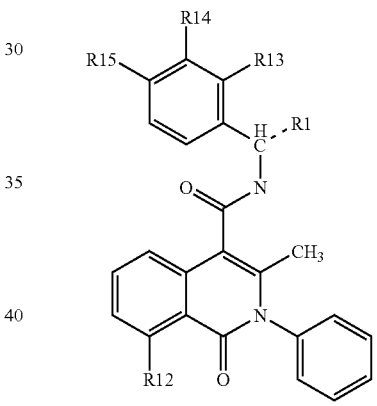

wherein $R^1$ represents ethyl or cylopropyl;
wherein $R^{12}$ represents fluoro or chloro; and
$R^{13}$, $R^{14}$ and $R^{15}$ each individually represent hydrogen, fluoro or chloro, wherein two of $R^{13}$, $R^{14}$ and $R^{15}$ represent hydrogen.

In one embodiment, the compounds of the inventions are defined by formula $I_d{'}$

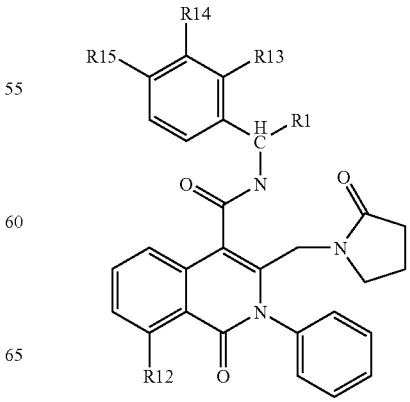

wherein R¹ represents ethyl or cyclopropyl;
R¹² represent halogen;
R¹³, R¹⁴ and R15 each independently represents hydrogen, or halogen;
and pharmaceutically acceptable salts thereof.

In one embodiment, the compounds of the invention are defined by formula $I_d''$

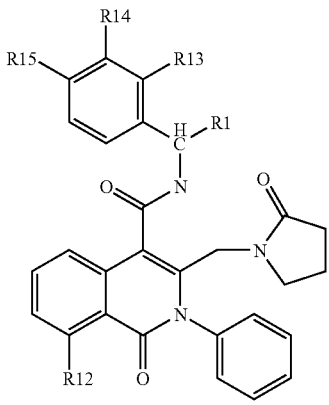

[Id'']

wherein R¹ represents ethyl or cyclopropyl;
R¹² represent chloro or fluoro;
R¹², R¹⁴ and R¹⁵ each independently represent hydrogen, chloro or fluoro, wherein two of R¹², R¹⁴ and R¹⁵ represent hydrogen;
and pharmaceutically acceptable salts thereof. In particular, said compound is essentially the S enantiomer as depicted in formula Id'''

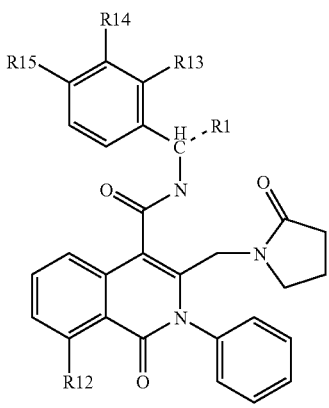

[Id''']

wherein R¹ represents ethyl or cyclopropyl;
R¹² represent chloro or fluoro;
R¹², R¹⁴ and R¹⁵ each independently represent hydrogen, chloro or fluoro, wherein two of R¹², R¹⁴ and R¹⁵ represent hydrogen;
and pharmaceutically acceptable salts thereof.

In one embodiment the compounds of the present invention are selected from the below list. For convenience, the number indicated in bold in front of the compound name refers to the corresponding example number.

1a 3-Methyl-1-oxo-2-phenyl-1,2-dihydro-isoquinoline-4-carboxylic acid ((S)-1-phenyl-propyl)-amide
1b 3,6-Dimethyl-1-oxo-2-phenyl-1,2-dihydro-isoquinoline-4-carboxylic acid ((S)-1-phenyl-propyl)-amide
1c 7-Chloro-3-methyl-1-oxo-2-phenyl-1,2-dihydro-isoquinoline-4-carboxylic acid ((S)-1-phenyl-propyl)-amide
1d 7-Bromo-3-methyl-1-oxo-2-phenyl-1,2-dihydro-isoquinoline-4-carboxylic acid ((S)-1-phenyl-propyl)-amide
1e 6-Fluoro-3-methyl-1-oxo-2-phenyl-1,2-dihydro-isoquinoline-4-carboxylic acid ((S)-1-phenyl-propyl)-amide
1f 3,5-Dimethyl-1-oxo-2-phenyl-1,2-dihydro-isoquinoline-4-carboxylic acid ((S)-1-phenyl-propyl)-amide
1g 7-Fluoro-3-methyl-1-oxo-2-phenyl-1,2-dihydro-isoquinoline-4-carboxylic acid ((S)-1-phenyl-propyl)-amide
1h 3,7-Dimethyl-1-oxo-2-phenyl-1,2-dihydro-isoquinoline-4-carboxylic acid ((S)-1-phenyl-propyl)-amide
1i 8-Chloro-3-methyl-1-oxo-2-phenyl-1,2-dihydro-isoquinoline-4-carboxylic acid ((S)-1-phenyl-propyl)-amide
1r 3-Methyl-1-oxo-2-phenyl-1,2-dihydro-isoquinoline-4-carboxylic acid ((S)-cyclopropyl-phenyl-methyl)-amide
1s 3-Methyl-1-oxo-2-phenyl-1,2-dihydro-isoquinoline-4-carboxylic acid [(S)-cyclopropyl-(3-fluoro-phenyl)-methyl]-amide
1j 3,8-Dimethyl-1-oxo-2-phenyl-1,2-dihydro-isoquinoline-4-carboxylic acid ((S)-1-phenyl-propyl)-amide
1k 2-(2-Fluoro-phenyl)-3-methyl-1-oxo-1,2-dihydro-isoquinoline-4-carboxylic acid ((S)-1-phenyl-propyl)-amide
1l 3-Methyl-1-oxo-2-o-tolyl-1,2-dihydro-isoquinoline-4-carboxylic acid ((S)-1-phenyl-propyl)-amide
1m 2-(2-Chloro-phenyl)-3-methyl-1-oxo-1,2-dihydro-isoquinoline-4-carboxylic acid ((S)-1-phenyl-propyl)-amide
1n 2-(2,6-Difluoro-phenyl)-3-methyl-1-oxo-1,2-dihydro-isoquinoline-4-carboxylic acid ((S)-1-phenyl-propyl)-amide
1o 2-(3-Fluoro-phenyl)-3-methyl-1-oxo-1,2-dihydro-isoquinoline-4-carboxylic acid ((S)-1-phenyl-propyl)-amide
1p 3-Methyl-1-oxo-2-m-tolyl-1,2-dihydro-isoquinoline-4-carboxylic acid ((S)-1-phenyl-propyl)-amide
1q 2-(3-Chloro-phenyl)-3-methyl-1-oxo-1,2-dihydro-isoquinoline-4-carboxylic acid ((S)-1-phenyl-propyl)-amide
1t 8-Chloro-3-methyl-1-oxo-2-phenyl-1,2-dihydro-isoquinoline-4-carboxylic acid [(S)-cyclopropyl-(3-fluoro-phenyl)-methyl]-amide
2a 3-Dimethylaminomethyl-1-oxo-2-phenyl-1,2-dihydro-isoquinoline-4-carboxylic acid ((S)-1-phenyl-propyl)-amide
2b 3-Methylaminomethyl-1-oxo-2-phenyl-1,2-dihydro-isoquinoline-4-carboxylic acid ((S)-1-phenyl-propyl)-amide
2c 3-Ethylaminomethyl-1-oxo-2-phenyl-1,2-dihydro-isoquinoline-4-carboxylic acid ((S)-1-phenyl-propyl)-amide
2d 3-Cyclopropylaminomethyl-1-oxo-2-phenyl-1,2-dihydro-isoquinoline-4-carboxylic acid ((S)-1-phenyl-propyl)-amide
2e 3-[(Cyclopropylmethyl-amino)-methyl]-1-oxo-2-phenyl-1,2-dihydro-isoquinoline-4-carboxylic acid ((S)-1-phenyl-propyl)-amide
2f 3-(3,6-Dihydro-2H-pyridin-1-ylmethyl)-1-oxo-2-phenyl-1,2-dihydro-isoquinoline-4-carboxylic acid ((S)-1-phenyl-propyl)-amide
2g 3-[4-(2-Methoxy-phenyl)-piperazin-1-ylmethyl]-1-oxo-2-phenyl-1,2-dihydro-isoquinoline-4-carboxylic acid ((S)-1-phenyl-propyl)-amide
2h 3-[4-(4-Fluoro-phenyl)-piperazin-1-ylmethyl]-1-oxo-2-phenyl-1,2-dihydro-isoquinoline-4-carboxylic acid ((S)-1-phenyl-propyl)-amide
2i 3-(4-Formyl-piperazin-1-ylmethyl)-1-oxo-2-phenyl-1,2-dihydro-isoquinoline-4-carboxylic acid ((S)-1-phenyl-propyl)-amide
2j 4-[1-Oxo-2-phenyl-4-(1-phenyl-propylcarbamoyl)-1,2-dihydro-isoquinolin-3-ylmethyl]-piperazine-1-carboxylic acid ethyl ester 2k 3-(4-Methyl-piperazin-1-ylmethyl)-1-oxo-2-phenyl-1,2-dihydro-isoquinoline-4-carboxylic acid ((S)-1-phenyl-propyl)-amide 2l 1-Oxo-2-phenyl-3-(1,3,4,9-tetrahydro-beta-carbolin-2-ylmethyl)-1,2-dihydro-isoquinoline-4-carboxylic acid ((S)-1-phenyl-propyl)-amide 2m 1-Oxo-2-phenyl-3-piperazin-1-ylmethyl-1,2-dihydro-isoquinoline-4-carboxylic acid ((S)-1-phenyl-propyl)-amide 2n 3-(3-Methyl-piperazin-1-ylmethyl)-1-oxo-2-phenyl-1,2-dihydro-isoquinoline-4-carboxylic acid ((S)-1-phenyl-propyl)-amide 2o 3-(3,5-Dimethyl-piperazin-1-ylmethyl)-1-oxo-2-phenyl-1,2-dihydro-isoquinoline-4-carboxylic acid ((S)-1-phenyl-propyl)-amide 2p 3-(4-Benzyl-piperazin-1-ylmethyl)-1-oxo-2-phenyl-1,2-dihydro-isoquinoline-4-carboxylic acid ((S)-1-phenyl-propyl)-amide 2q 1-Oxo-3-[4-(2-oxo-2-pyrrolidin-1-yl-ethyl)-piperazin-1-ylmethyl]-2-phenyl-1,2-dihydro-isoquinoline-4-carboxylic acid ((S)-1-phenyl-propyl)-amide 2r 3-Morpholin-4-ylmethyl-1-oxo-2-phenyl-1,2-dihydro-isoquinoline-4-carboxylic acid ((S)-1-phenyl-propyl)-amide 2s 3-(2,6-Dimethyl-morpholin-4-ylmethyl)-1-oxo-2-phenyl-1,2-dihydro-isoquinoline-4-carboxylic acid ((S)-1-phenyl-propyl)-amide 2t 1-Oxo-2-phenyl-3-thiomorpholin-4-ylmethyl-1,2-dihydro-isoquinoline-4-carboxylic acid ((S)-1-phenyl-propyl)-amide 2u 3-(1,4-Dioxa-8-aza-spiro[4.5]dec-8-ylmethyl)-1-oxo-2-phenyl-1,2-dihydro-isoquinoline-4-carboxylic acid ((S)-1-phenyl-propyl)-amide 2v 1-Oxo-2-phenyl-3-piperidin-1-ylmethyl-1,2-dihydro-isoquinoline-4-carboxylic acid ((S)-1-phenyl-propyl)-amide 2w 3-(2-Methyl-piperidin-1-ylmethyl)-1-oxo-2-phenyl-1,2-dihydro-isoquinoline-4-carboxylic acid ((S)-1-phenyl-propyl)-amide 2x 3-(2,6-Dimethyl-piperidin-1-ylmethyl)-1-oxo-2-phenyl-1,2-dihydro-isoquinoline-4-carboxylic acid ((S)-1-phenyl-propyl)-amide 2y 3-(2-Hydroxymethyl-piperidin-1-ylmethyl)-1-oxo-2-phenyl-1,2-dihydro-isoquinoline-4-carboxylic acid ((S)-1-phenyl-propyl)-amide 2z 1-[1-Oxo-2-phenyl-4-(1-phenyl-propylcarbamoyl)-1,2-dihydro-isoquinolin-3-ylmethyl]-piperidine-3-carboxylic acid ethyl ester 2aa 3-(3-Methyl-piperidin-1-ylmethyl)-1-oxo-2-phenyl-1,2-dihydro-isoquinoline-4-carboxylic acid ((S)-1-phenyl-propyl)-amide 2ab 3-(4-Hydroxy-piperidin-1-ylmethyl)-1-oxo-2-phenyl-1,2-dihydro-isoquinoline-4-carboxylic acid ((S)-1-phenyl-propyl)-amide 2ac 1-Oxo-2-phenyl-3-(4-phenyl-piperidin-1-ylmethyl)-1,2-dihydro-isoquinoline-4-carboxylic acid ((S)-1-phenyl-propyl)-amide 2ad 1-[1-Oxo-2-phenyl-4-(1-phenyl-propylcarbamoyl)-1,2-dihydro-isoquinolin-3-ylmethyl]-piperidine-4-carboxylic acid ethyl ester 2ae 3-(4-Methyl-piperidin-1-ylmethyl)-1-oxo-2-phenyl-1,2-dihydro-isoquinoline-4-carboxylic acid ((S)-1-phenyl-propyl)-amide 2af 1-Oxo-2-phenyl-3-(4-pyridin-2-yl-piperazin-1-ylmethyl)-1,2-dihydro-isoquinoline-4-carboxylic acid ((S)-1-phenyl-propyl)-amide 2ag 3-(Octahydro-quinolin-1-ylmethyl)-1-oxo-2-phenyl-1,2-dihydro-isoquinoline-4-carboxylic acid ((S)-1-phenyl-propyl)-amide 2ah 3-Azepan-1-ylmethyl-1-oxo-2-phenyl-1,2-dihydro-isoquinoline-4-carboxylic acid ((S)-1-phenyl-propyl)-amide 2ai 3-(3-Hydroxy-piperidin-1-ylmethyl)-1-oxo-2-phenyl-1,2-dihydro-isoquinoline-4-carboxylic acid ((S)-1-phenyl-propyl)-amide 2aj 3-[4-(2,4-Dimethyl-phenyl)-piperazin-1-ylmethyl]-1-oxo-2-phenyl-1,2-dihydro-isoquinoline-4-carboxylic acid ((S)-1-phenyl-propyl)-amide 2ak 3-[4-(3,4-Dimethyl-phenyl)-piperazin-1-ylmethyl]-1-oxo-2-phenyl-1,2-dihydro-isoquinoline-4-carboxylic acid ((S)-1-phenyl-propyl)-amide 2al 3-(4-Dimethylamino-piperidin-1-ylmethyl)-1-oxo-2-phenyl-1,2-dihydro-isoquinoline-4-carboxylic acid ((S)-1-phenyl-propyl)-amide 2am 3-[4-(2,5-Dimethyl-phenyl)-piperazin-1-ylmethyl]-1-oxo-2-phenyl-1,2-dihydro-isoquinoline-4-carboxylic acid ((S)-1-phenyl-propyl)-amide 2an 3-[4-(2-Fluoro-phenyl)-piperazin-1-ylmethyl]-1-oxo-2-phenyl-1,2-dihydro-isoquinoline-4-carboxylic acid ((S)-1-phenyl-propyl)-amide 2ao 3-[4-(3-Methoxy-phenyl)-piperazin-1-ylmethyl]-1-oxo-2-phenyl-1,2-dihydro-isoquinoline-4-carboxylic acid ((S)-1-phenyl-propyl)-amide 2ap 1-Oxo-2-phenyl-3-(4-m-tolyl-piperazin-1-ylmethyl)-1,2-dihydro-isoquinoline-4-carboxylic acid ((S)-1-phenyl-propyl)-amide 2aq 3-[4-(4-Methoxy-phenyl)-piperazin-1-ylmethyl]-1-oxo-2-phenyl-1,2-dihydro-isoquinoline-4-carboxylic acid ((S)-1-phenyl-propyl)-amide 2ar 1-Oxo-3-(4-phenethyl-piperazin-1-ylmethyl)-2-phenyl-1,2-dihydro-isoquinoline-4-carboxylic acid ((S)-1-phenyl-propyl)-amide 2as 1-Oxo-2-phenyl-3-(4-pyrimidin-2-yl-piperazin-1-ylmethyl)-1,2-dihydro-isoquinoline-4-carboxylic acid ((S)-1-phenyl-propyl)-amide 2at 3-[4-(2-Cyano-phenyl)-piperazin-1-ylmethyl]-1-oxo-2-phenyl-1,2-dihydro-isoquinoline-4-carboxylic acid ((S)-1-phenyl-propyl)-amide 2au 3-[4-(4-Chloro-phenyl)-piperazin-1-ylmethyl]-1-oxo-2-phenyl-1,2-dihydro-isoquinoline-4-carboxylic acid ((S)-1-phenyl-propyl)-amide 2av 3-((1S,3R,5R)-3-Hydroxy-8-aza-bicyclo[3.2.1]oct-8-ylmethyl)-1-oxo-2-phenyl-1,2-dihydro-isoquinoline-4-carboxylic acid ((S)-1-phenyl-propyl)-amide 2aw 3-(4-Acetyl-piperazin-1-ylmethyl)-1-oxo-2-phenyl-1,2-dihydro-isoquinoline-4-carboxylic acid ((S)-1-phenyl-propyl)-amide 2ax 3-(4-Methyl-[1,4]diazepan-1-ylmethyl)-1-oxo-2-phenyl-1,2-dihydro-isoquinoline-4-carboxylic acid ((S)-1-phenyl-propyl)-amide 2ay 3-(4-Ethyl-piperazin-1-ylmethyl)-1-oxo-2-phenyl-1,2-dihydro-isoquinoline-4-carboxylic acid ((S)-1-phenyl-propyl)-amide 2az 3-((2S,6R)-2,6-Dimethyl-morpholin-4-ylmethyl)-1-oxo-2-phenyl-1,2-dihydro-isoquinoline-4-carboxylic acid ((S)-1-phenyl-propyl)-amide 2ba 3-[4-(2,4-Difluoro-phenyl)-piperazin-1-ylmethyl]-1-oxo-2-phenyl-1,2-dihydro-isoquinoline-4-carboxylic acid ((S)-1-phenyl-propyl)-amide 2bb 3-[4-(3-Dimethylamino-propyl)-piperazin-1-ylmethyl]-1-oxo-2-phenyl-1,2-dihydro-isoquinoline-4-carboxylic acid ((S)-1-phenyl-propyl)-amide 2bc 3-(4-Isopropyl-piperazin-1-ylmethyl)-1-oxo-2-phenyl-1,2-dihydro-isoquinoline-4-carboxylic acid ((S)-1-phenyl-propyl)-amide 2bd 3-(3-Aza-bicyclo[3.2.2]non-3-ylmethyl)-1-oxo-2-phenyl-1,2-dihydro-isoquinoline-4-carboxylic acid ((S)-1-phenyl-propyl)-amide 2be 3-(4-Cyclopentyl-piperazin-1-ylmethyl)-1-oxo-2-phenyl-1,2-dihydro-isoquinoline-4-carboxylic acid ((S)-1-phenyl-propyl)-amide 2bf 3-[1,4']Bipiperidinyl-1'-ylmethyl-1-oxo-2-phenyl-1,2-dihydro-isoquinoline-4-carboxylic acid ((S)-1-phenyl-propyl)-amide 2bg 3-(3,4-Dihydro-1H-isoquinolin-2-ylmethyl)-1-oxo-2-phenyl-1,2-dihydro-isoquinoline-4-carboxylic acid ((S)-1-phenyl-propyl)-amide 2bh 3-[4-(2-Dimethylamino-ethyl)-piperazin-1-ylmethyl]-1-oxo-2-phenyl-1,2-dihydro-isoquinoline-4-carboxylic acid ((S)-1-phenyl-propyl)-amide 2bi 3-(4-Hydroxymethyl-piperidin-1-ylmethyl)-1-oxo-2-phenyl-1,2-dihydro-isoquinoline-4-carboxylic acid ((S)-1-phenyl-propyl)-amide 2bj 1-Oxo-2-phenyl-3-[4-(tetrahydro-furan-2-carbonyl)-piperazin-1-ylmethyl]-1,2-dihydro-isoquinoline-4-carboxylic acid ((S)-1-phenyl-propyl)-amide 2bk 3-(4-Isobutyl-piperazin-1-ylmethyl)-1-oxo-2-phenyl-1,2-dihydro-isoquinoline-4-carboxylic acid ((S)-1-phenyl-propyl)-amide 2bl 3-[4-(2-Methoxy-ethyl)-piperazin-1-ylmethyl]-1-oxo-2-phenyl-1,2-dihydro-isoquinoline-4-carboxylic acid ((S)-1-phenyl-propyl)-amide 2bm 3-[4-(2-Morpholin-4-yl-ethyl)-piperazin-1-ylmethyl]-1-oxo-2-phenyl-1,2-dihydro-isoquinoline-4-carboxylic acid ((S)-1-phenyl-propyl)-amide 2bn 3-(1,3-Dihydro-isoindol-2-ylmethyl)-1-oxo-2-phenyl-1,2-dihydro-isoquinoline-4-carboxylic acid ((S)-1-phenyl-propyl)-amide 2bo 3-[4-(1-Methyl-piperidin-4-yl)-piperazin-1-ylmethyl]-1-oxo-2-phenyl-1,2-dihydro-isoquinoline-4-carboxylic acid ((S)-1-phenyl-propyl)-amide 2bp 1-Oxo-2-phenyl-3-[4-(2-piperidin-1-yl-ethyl)-piperazin-1-ylmethyl]-1,2-dihydro-isoquinoline-4-carboxylic acid ((S)-1-phenyl-propyl)-amide 2bq 1-Oxo-2-phenyl-3-[4-(2-pyrrolidin-1-yl-ethyl)-piperazin-1-ylmethyl]-1,2-dihydro-isoquinoline-4-carboxylic acid ((S)-1-phenyl-propyl)-amide 2br 3-(4-Dimethylcarbamoylmethyl-piperazin-1-ylmethyl)-1-oxo-2-phenyl-1,2-dihydro-isoquinoline-4-carboxylic acid ((S)-1-phenyl-propyl)-amide 2bs 3-(Octahydro-pyrido[1,2-a]pyrazin-2-ylmethyl)-1-oxo-2-phenyl-1,2-dihydro-isoquinoline-4-carboxylic acid ((S)-1-phenyl-propyl)-amide 2bt 3-(4-Formyl-[1,4]diazepan-1-ylmethyl)-1-oxo-2-phenyl-1,2-dihydro-isoquinoline-4-carboxylic acid ((S)-1-phenyl-propyl)-amide 2bu 3-[4-(4-Cyano-phenyl)-piperazin-1-ylmethyl]-1-oxo-2-phenyl-1,2-dihydro-isoquinoline-4-carboxylic acid ((S)-1-phenyl-propyl)-amide 2by 1-Oxo-2-phenyl-3-(4-pyridin-4-ylmethyl-piperazin-1-ylmethyl)-1,2-dihydro-isoquinoline-4-carboxylic acid ((S)-1-phenyl-propyl)-amide 2bw 1-Oxo-2-phenyl-3-[4-(3-pyrrolidin-1-yl-propyl)-piperazin-1-ylmethyl]-1,2-dihydro-isoquinoline-4-carboxylic acid ((S)-1-phenyl-propyl)-amide 2bx 1-Oxo-2-phenyl-3-(4-pyridin-2-ylmethyl-piperazin-1-ylmethyl)-1,2-dihydro-isoquinoline-4-carboxylic acid ((S)-1-phenyl-propyl)-amide 2by 3-(4-Ethanesulfonyl-piperazin-1-ylmethyl)-1-oxo-2-phenyl-1,2-dihydro-isoquinoline-4-carboxylic acid ((S)-1-phenyl-propyl)-amide 2bz 3-(4-sec-Butyl-piperazin-1-ylmethyl)-1-oxo-2-phenyl-1,2-dihydro-isoquinoline-4-carboxylic acid ((S)-1-phenyl-propyl)-amide 2ca 3-[4-(1-Ethyl-propyl)-piperazin-1-ylmethyl]-1-oxo-2-phenyl-1,2-dihydro-isoquinoline-4-carboxylic acid ((S)-1-phenyl-propyl)-amide 2cb 3-[4-(2-Cyano-ethyl)-piperazin-1-ylmethyl]-1-oxo-2-phenyl-1,2-dihydro-isoquinoline-4-carboxylic acid ((S)-1-phenyl-propyl)-amide 2cc 3-(4-Methanesulfonyl-piperazin-1-ylmethyl)-1-oxo-2-phenyl-1,2-dihydro-isoquinoline-4-carboxylic acid ((S)-1-phenyl-propyl)-amide 2cd {1-[1-Oxo-2-phenyl-4-(1-phenyl-propylcarbamoyl)-1,2-dihydro-isoquinolin-3-ylmethyl]-piperidin-4-yl}-acetic acid ethyl ester 2ce 3-[4-(3-Fluoro-phenyl)-piperazin-1-ylmethyl]-1-oxo-2-phenyl-1,2-dihydro-isoquinoline-4-carboxylic acid ((S)-1-phenyl-propyl)-amide 2cf 1-Oxo-2-phenyl-3-((S)-3-phenyl-piperidin-1-ylmethyl)-1,2-dihydro-isoquinoline-4-carboxylic acid ((S)-1-phenyl-propyl)-amide 2cg 1-Oxo-2-phenyl-3-[4-(pyrrolidine-1-carbonyl)-piperazin-1-ylmethyl]-1,2-dihydro-isoquinoline-4-carboxylic acid ((S)-1-phenyl-propyl)-amide 2ch 3-[4-(Morpholine-4-carbonyl)-piperazin-1-ylmethyl]-1-oxo-2-phenyl-1,2-dihydro-isoquinoline-4-carboxylic acid ((S)-1-phenyl-propyl)-amide 2ci 3-(4-Methoxy-piperidin-1-ylmethyl)-1-oxo-2-phenyl-1,2-dihydro-isoquinoline-4-carboxylic acid ((S)-1-phenyl-propyl)-amide 2cj 3-(4'-Hydroxy-3',4',5',6'-tetrahydro-2'H-[3,4']bipyridinyl-1'-ylmethyl)-1-oxo-2-phenyl-1,2-dihydro-isoquinoline-4-carboxylic acid ((S)-1-phenyl-propyl)-amide 2ck 3-(4-Hydroxy-3,4,5,6-tetrahydro-2H-[4,4']bipyridinyl-1-ylmethyl)-1-oxo-2-phenyl-1,2-dihydro-isoquinoline-4-carboxylic acid ((S)-1-phenyl-propyl)-amide 2cl 3-(3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide 2cm 3-(4-Hydroxy-4-methyl-piperidin-1-ylmethyl)-1-oxo-2-phenyl-1,2-dihydro-isoquinoline-4-carboxylic acid ((S)-1-phenyl-propyl)-amide 2cn 3-(hexahydro-spiro[benzo[1,3]dioxole-2,4'-piperidin]-1'-ylmethyl)-1-oxo-2-phenyl-1,2-dihydro-isoquinoline-4-carboxylic acid ((S)-1-phenyl-propyl)-amide 2co 1-Oxo-2-phenyl-3-(3,4,5,6-tetrahydro-2H-[4,4']bipyridinyl-1-ylmethyl)-1,2-dihydro-isoquinoline-4-carboxylic acid ((S)-1-phenyl-propyl)-amide 2cp 3-[4-(2-Dimethylamino-ethyl)-piperidin-1-ylmethyl]-1-oxo-2-phenyl-1,2-dihydro-isoquinoline-4-carboxylic acid ((S)-1-phenyl-propyl)-amide 2cq 3-(4-Dimethylsulfamoyl-piperazin-1-ylmethyl)-1-oxo-2-phenyl-1,2-dihydro-isoquinoline-4-carboxylic acid ((S)-1-phenyl-propyl)-amide 2cr 3-(1,1-Dioxo-thiomorpholin-4-ylmethyl)-1-oxo-2-phenyl-1,2-dihydro-isoquinoline-4-carboxylic acid ((S)-1-phenyl-propyl)-amide 2cs 1-Oxo-2-phenyl-3-(2-pyridin-2-ylmethyl-piperidin-1-ylmethyl)-1,2-dihydro-isoquinoline-4-carboxylic acid ((S)-1-phenyl-propyl)-amide 2ct 3-(2-Morpholin-4-ylmethyl-piperidin-1-ylmethyl)-1-oxo-2-phenyl-1,2-dihydro-isoquinoline-4-carboxylic acid ((S)-1-phenyl-propyl)-amide 2cu 3-(4-Furo[3,2-c]pyridin-4-yl-piperazin-1-ylmethyl)-1-oxo-2-phenyl-1,2-dihydro-isoquinoline-4-carboxylic acid ((S)-1-phenyl-propyl)-amide 2cv 3-(4-Cyclopropylmethyl-piperazin-1-ylmethyl)-1-oxo-2-phenyl-1,2-dihydro-isoquinoline-4-carboxylic acid ((S)-1-phenyl-propyl)-amide 2cw 3-[4-(2-Morpholin-4-yl-ethyl)-piperidin-1-ylmethyl]-1-oxo-2-phenyl-1,2-dihydro-isoquinoline-4-carboxylic acid ((S)-1-phenyl-propyl)-amide 2cx 1-Oxo-2-phenyl-3-(4-pyrimidin-2-yl-[1,4]diazepan-1-ylmethyl)-1,2-dihydro-isoquinoline-4-carboxylic acid ((S)-1-phenyl-propyl)-amide 2cy 3-(4-Methyl-6,7-dihydro-4H-thieno[3,2-c]pyridin-5-ylmethyl)-1-oxo-2-phenyl-1,2-dihydro-isoquinoline-4-carboxylic acid ((S)-1-phenyl-propyl)-amide 2cz 3-[1,4]Diazepan-1-ylmethyl-1-oxo-2-phenyl-1,2-dihydro-isoquinoline-4-carboxylic acid ((S)-1-phenyl-propyl)-amide 2da 3-((2S,5R)-2,5-Dimethyl-piperazin-1-ylmethyl)-1-oxo-2-phenyl-1,2-dihydro-isoquinoline-4-carboxylic acid ((S)-1-phenyl-propyl)-amide 2db 3-((S)-3-Methyl-piperazin-1-ylmethyl)-1-oxo-2-phenyl-1,2-dihydro-isoquinoline-4-carboxylic acid ((S)-1-phenyl-propyl)-amide 2dc 3-((R)-3-Methyl-piperazin-1-ylmethyl)-1-oxo-2-phenyl-1,2-dihydro-isoquinoline-4-carboxylic acid ((S)-1-phenyl-propyl)-amide 2dd 3-[3-(3-Chloro-phenyl)-piperazin-1-ylmethyl]-1-oxo-2-phenyl-1,2-dihydro-isoquinoline-4-carboxylic acid ((S)-1-phenyl-propyl)-amide 2de 3-[4-(1H-Indol-4-yl)-piperazin-1-ylmethyl]-1-oxo-2-phenyl-1,2-dihydro-isoquinoline-4-carboxylic acid ((S)-1-phenyl-propyl)-amide 2df 1-Oxo-3-(3-oxo-piperazin-1-ylmethyl)-2-phenyl-1,2-dihydro-isoquinoline-4-carboxylic acid ((S)-1-phenyl-propyl)-amide 2dg 3-[4-(1H-Indol-5-yl)-piperazin-1-ylmethyl]-1-oxo-2-phenyl-1,2-dihydro-isoquinoline-4-carboxylic acid ((S)-1-phenyl-propyl)-amide 2dh 3-(6,9-Diaza-spiro[4.5]dec-9-ylmethyl)-1-oxo-2-phenyl-1,2-dihydro-isoquinoline-4-carboxylic acid ((S)-1-phenyl-propyl)-amide 2di 3-(1,4-Diaza-spiro[5.5]undec-4-ylmethyl)-1-oxo-2-phenyl-1,2-dihydro-isoquinoline-4-carboxylic acid ((S)-1-phenyl-propyl)-amide 2dj 3-(3-Isopropyl-piperazin-1-ylmethyl)-1-oxo-2-phenyl-1,2-dihydro-isoquinoline-4-carboxylic acid ((S)-1-phenyl-propyl)-amide 2dk 3-(3,3-Dimethyl-piperazin-1-ylmethyl)-1-oxo-2-phenyl-1,2-dihydro-isoquinoline-4-carboxylic acid ((S)-1-phenyl-propyl)-amide 2dl 3-[3-(4-Fluoro-phenyl)-piperazin-1-ylmethyl]-1-oxo-2-phenyl-1,2-dihydro-isoquinoline-4-carboxylic acid ((S)-1-phenyl-propyl)-amide 2dm 1-Oxo-2-phenyl-3-(3-p-tolyl-piperazin-1-ylmethyl)-1,2-dihydro-isoquinoline-4-carboxylic acid ((S)-1-phenyl-propyl)-amide 2dn 4-[1-Oxo-2-phenyl-4-(1-phenyl-propylcarbamoyl)-1,2-dihydro-isoquinolin-3-ylmethyl]-piperazine-1-carboxylic acid tert-butyl ester 2do 3-(4-Methylcarbamoylmethyl-piperazin-1-ylmethyl)-1-oxo-2-phenyl-1,2-dihydro-isoquinoline-4-carboxylic acid ((S)-1-phenyl-propyl)-amide 2dp 8-Chloro-3-dimethylaminomethyl-1-oxo-2-phenyl-1,2-dihydro-isoquinoline-4-carboxylic acid ((S)-1-phenyl-propyl)-amide 2dr 3-Cyclopentylaminomethyl-1-oxo-2-phenyl-1,2-dihydro-isoquinoline-4-carboxylic acid ((S)-1-phenyl-propyl)-amide 2ds 3-Cyclohexylaminomethyl-1-oxo-2-phenyl-1,2-dihydro-isoquinoline-4-carboxylic acid ((S)-1-phenyl-propyl)-amide 2dt 3-{[(2-Hydroxy-ethyl)-methyl-amino]-methyl}-1-oxo-2-phenyl-1,2-dihydro-isoquinoline-4-carboxylic acid ((S)-1-phenyl-propyl)-amide 2du 3-Imidazol-1-ylmethyl-1-oxo-2-phenyl-1,2-dihydro-isoquinoline-4-carboxylic acid ((S)-1-phenyl-propyl)-amide 2dv 3-(2-Methyl-imidazol-1-ylmethyl)-1-oxo-2-phenyl-1,2-dihydro-isoquinoline-4-carboxylic acid ((S)-1-phenyl-propyl)-amide 2dw 3-(4-Methyl-imidazol-1-ylmethyl)-1-oxo-2-phenyl-1,2-dihydro-isoquinoline-4-carboxylic acid ((S)-1-phenyl-propyl)-amide 2dx 3-(2,5-Dihydro-pyrrol-1-ylmethyl)-1-oxo-2-phenyl-1,2-dihydro-isoquinoline-4-carboxylic acid ((S)-1-phenyl-propyl)-amide 2dy 3-(2,5-Dimethyl-2,5-dihydro-pyrrol-1-ylmethyl)-1-oxo-2-phenyl-1,2-dihydro-isoquinoline-4-carboxylic acid ((S)-1-phenyl-propyl)-amide 2dz 1-Oxo-2-phenyl-3-pyrrolidin-1-ylmethyl-1,2-dihydro-isoquinoline-4-carboxylic acid ((S)-1-phenyl-propyl)-amide 2ea 1-Oxo-2-phenyl-3-(thiazol-2-ylaminomethyl)-1,2-dihydro-isoquinoline-4-carboxylic acid ((S)-1-phenyl-propyl)-amide 2eb 1-Oxo-2-phenyl-3-(pyrimidin-4-ylaminomethyl)-1,2-dihydro-isoquinoline-4-carboxylic acid ((S)-1-phenyl-propyl)-amide 2ec 3-(tert-Butylamino-methyl)-1-oxo-2-phenyl-1,2-dihydro-isoquinoline-4-carboxylic acid ((S)-1-phenyl-propyl)-amide 2ed 3-[(2-Hydroxy-1,1-dimethyl-ethylamino)-methyl]-1-oxo-2-phenyl-1,2-dihydro-isoquinoline-4-carboxylic acid ((S)-1-phenyl-propyl)-amide 2ee 3-(Isopropylamino-methyl)-1-oxo-2-phenyl-1,2-dihydro-isoquinoline-4-carboxylic acid ((S)-1-phenyl-propyl)-amide 2ef 3-[(2-Hydroxy-1-methyl-ethylamino)-methyl]-1-oxo-2-phenyl-1,2-dihydro-isoquinoline-4-carboxylic acid ((S)-1-phenyl-propyl)-amide 2eg 3-[(1-Hydroxymethyl-propylamino)-methyl]-1-oxo-2-phenyl-1,2-dihydro-isoquinoline-4-carboxylic acid ((S)-1-phenyl-propyl)-amide 2eh 3-[(2,2-Dimethyl-propylamino)-methyl]-1-oxo-2-phenyl-1,2-dihydro-isoquinoline-4-carboxylic acid ((S)-1-phenyl-propyl)-amide 2ei 1-Oxo-2-phenyl-3-prop-2-ynylaminomethyl-1,2-dihydro-isoquinoline-4-carboxylic acid ((S)-1-phenyl-propyl)-amide 2ej 3-Allylaminomethyl-1-oxo-2-phenyl-1,2-dihydro-isoquinoline-4-carboxylic acid ((S)-1-phenyl-propyl)-amide 2ek 3-[(Methyl-prop-2-ynyl-amino)-methyl]-1-oxo-2-phenyl-1,2-dihydro-isoquinoline-4-carboxylic acid ((S)-1-phenyl-propyl)-amide 2el 3-Diallylaminomethyl-1-oxo-2-phenyl-1,2-dihydro-isoquinoline-4-carboxylic acid ((S)-1-phenyl-propyl)-amide 2em 3-Diethylaminomethyl-1-oxo-2-phenyl-1,2-dihydro-isoquinoline-4-carboxylic acid ((S)-1-phenyl-propyl)-amide 2en 3-[(Isopropyl-methyl-amino)-methyl]-1-oxo-2-phenyl-1,2-dihydro-isoquinoline-4-carboxylic acid ((S)-1-phenyl-propyl)-amide 2eo 3-[((S)-2-Hydroxy-1-methyl-ethylamino)-methyl]-1-oxo-2-phenyl-1,2-dihydro-isoquinoline-4-carboxylic acid ((S)-1-phenyl-propyl)-amide 2ep 3-[((R)-Hydroxy-1-methyl-ethylamino)-methyl]-1-oxo-2-phenyl-1,2-dihydro-isoquinoline-4-carboxylic acid ((S)-1-phenyl-propyl)-amide 2eq 3-{[(2-Methoxy-ethyl)-methyl-amino]-methyl}-1-oxo-2-phenyl-1,2-dihydro-isoquinoline-4-carboxylic acid ((S)-1-phenyl-propyl)-amide 2er 3-((R)-3-Hydroxy-pyrrolidin-1-ylmethyl)-1-oxo-2-phenyl-1,2-dihydro-isoquinoline-4-carboxylic acid ((S)-1-phenyl-propyl)-amide 2es 3-((S)-3-Hydroxy-pyrrolidin-1-ylmethyl)-1-oxo-2-phenyl-1,2-dihydro-isoquinoline-4-carboxylic acid ((S)-1-phenyl-propyl)-amide 2et 3-[(Cyclopentyl-methyl-amino)-methyl]-1-oxo-2-phenyl-1,2-dihydro-isoquinoline-4-carboxylic acid ((S)-1-phenyl-propyl)-amide 2eu 3-{[(2-Hydroxy-1-methyl-ethyl)-methyl-amino]-methyl}-1-oxo-2-phenyl-1,2-dihydro-isoquinoline-4-carboxylic acid ((S)-1-phenyl-propyl)-amide 2ev 3-{[Ethyl-(2-hydroxy-ethyl)-amino]-methyl}-1-oxo-2-phenyl-1,2-dihydro-isoquinoline-4-carboxylic acid ((S)-1-phenyl-propyl)-amide 2ew 3-[(Ethyl-methyl-amino)-methyl]-1-oxo-2-phenyl-1,2-dihydro-isoquinoline-4-carboxylic acid ((S)-1-phenyl-propyl)-amide 2ex 3-Cyclobutylaminomethyl-1-oxo-2-phenyl-1,2-dihydro-isoquinoline-4-carboxylic acid ((S)-1-phenyl-propyl)-amide 2ey 3-Azetidin-1-ylmethyl-1-oxo-2-phenyl-1,2-dihydro-isoquinoline-4-carboxylic acid ((S)-1-phenyl-propyl)-amide 2ez 3-(4-tert-Butyl-piperazin-1-ylmethyl)-1-oxo-2-phenyl-1,2-dihydro-isoquinoline-4-carboxylic acid ((S)-1-phenyl-propyl)-amide 2fa 3-[4-(2-Hydroxy-ethyl)-piperazin-1-ylmethyl]-1-oxo-2-phenyl-1,2-dihydro-isoquinoline-4-carboxylic acid ((S)-1-phenyl-propyl)-amide 2fb 3-{4-[2-(2-Hydroxy-ethoxy)-ethyl]-piperazin-1-ylmethyl}-1-oxo-2-phenyl-1,2-dihydro-isoquinoline-4-carboxylic acid ((S)-1-phenyl-propyl)-amide 2fc 3-[4-(3-Chloro-5-trifluoromethyl-pyridin-2-yl)-piperazin-1-ylmethyl]-1-oxo-2-phenyl-1,2-dihydro-isoquinoline-4-carboxylic acid ((S)-1-phenyl-propyl)-amide 2fd 3-[4-(3,5-Dichloro-pyridin-4-yl)-piperazin-1-ylmethyl]-1-oxo-2-phenyl-1,2-dihydro-isoquinoline-4-carboxylic acid ((S)-1-phenyl-propyl)-amide 2fe 4-[1-Oxo-2-phenyl-4-((S)-1-phenyl-propylcarbamoyl)-1,2-dihydro-isoquinolin-3-ylmethyl]-piperazine-1-carboxylic acid benzyl ester 2ff 3-[4-(3-Morpholin-4-yl-propyl)-piperazin-1-ylmethyl]-1-oxo-2-phenyl-1,2-dihydro-isoquinoline-4-carboxylic acid ((S)-1-phenyl-propyl)-amide 2fg 1-Oxo-2-phenyl-3-[4-(3-piperidin-1-yl-propyl)-piperazin-1-ylmethyl]-1,2-dihydro-isoquinoline-4-carboxylic acid ((S)-1-phenyl-propyl)-amide 2fh 3-[4-(4,6-Dimethoxy-pyrimidin-2-ylmethyl)-piperazin-1-ylmethyl]-1-oxo-2-phenyl-1,2-dihydro-isoquinoline-4-carboxylic acid ((S)-1-phenyl-propyl)-amide 2fi 3-[4-(3-Hydroxy-propyl)-piperazin-1-ylmethyl]-1-oxo-2-phenyl-1,2-dihydro-isoquinoline-4-carboxylic acid ((S)-1-phenyl-propyl)-amide 2fj 3-[4-(2,3-Dihydroxy-propyl)-piperazin-1-ylmethyl]-1-oxo-2-phenyl-1,2-dihydro-isoquinoline-4-carboxylic acid ((S)-1-phenyl-propyl)-amide 2fk (2-Oxo-2-{4-[1-oxo-2-phenyl-4-(1-phenyl-propylcarbamoyl)-1,2-dihydro-isoquinolin-3-ylmethyl]-piperazin-1-yl}-ethyl)-carbamic acid tert-butyl ester 2fl 3-[4-(1H-Indazol-5-yl)-piperazin-1-ylmethyl]-1-oxo-2-phenyl-1,2-dihydro-isoquinoline-4-carboxylic acid ((S)-1-phenyl-propyl)-amide 2fm 1-Oxo-2-phenyl-3-(4-quinolin-6-yl-piperazin-1-ylmethyl)-1,2-dihydro-isoquinoline-4-carboxylic acid ((S)-1-phenyl-propyl)-amide 2fn 3-[4-(6,7-Dimethoxy-quinazolin-4-yl)-piperazin-1-ylmethyl]-1-oxo-2-phenyl-1,2-dihydro-isoquinoline-4-carboxylic acid ((S)-1-phenyl-propyl)-amide 2fo 4-{4-[1-Oxo-2-phenyl-4-(1-phenyl-propylcarbamoyl)-1,2-dihydro-isoquinolin-3-ylmethyl]-piperazin-1-yl}-piperidine-1-carboxylic acid tert-butyl ester 2fp 3-{4-[2-(4-Chloro-phenoxy)-ethyl]-piperazin-1-ylmethyl}-1-oxo-2-phenyl-1,2-dihydro-isoquinoline-4-carboxylic acid ((S)-1-phenyl-propyl)-amide 2fq {4-[1-Oxo-2-phenyl-4-(1-phenyl-propylcarbamoyl)-1,2-dihydro-isoquinolin-3-ylmethyl]-piperazin-1-yl}-acetic acid tert-butyl ester 2fr 1-Oxo-2-phenyl-3-[4-(3,3,3-trifluoro-2-hydroxy-propyl)-piperazin-1-ylmethyl]-1,2-dihydro-isoquinoline-4-carboxylic acid ((S)-1-phenyl-propyl)-amide 2fs 3-[4-(2-Hydroxy-propyl)-piperazin-1-ylmethyl]-1-oxo-2-phenyl-1,2-dihydro-isoquinoline-4-carboxylic acid ((S)-1-phenyl-propyl)-amide 2fu 3-[4-(4-Amino-6,7-dimethoxy-quinazolin-2-yl)-piperazin-1-ylmethyl]-1-oxo-2-phenyl-1,2-dihydro-isoquinoline-4-carboxylic acid ((S)-1-phenyl-propyl)-amide 2fv (2-{4-[1-Oxo-2-phenyl-4-(1-phenyl-propylcarbamoyl)-1,2-dihydro-isoquinolin-3-ylmethyl]-piperazin-1-yl}-ethyl)-carbamic acid tert-butyl ester 2fw 1-Oxo-3-{4-[2-(2-oxo-imidazolidin-1-yl)-ethyl]-piperazin-1-ylmethyl}-2-phenyl-1,2-dihydro-isoquinoline-4-carboxylic acid ((S)-1-phenyl-propyl)-amide 2fx 3-{4-[(4,6-Dimethoxy-pyrimidin-2-yl)-phenyl-methyl]-piperazin-1-ylmethyl}-1-oxo-2-phenyl-1,2-dihydro-isoquinoline-4-carboxylic acid ((S)-1-phenyl-propyl)-amide 2fy 3-(4-Benzo[1,2,5]thiadiazol-4-yl-piperazin-1-ylmethyl)-1-oxo-2-phenyl-1,2-dihydro-isoquinoline-4-carboxylic acid ((S)-1-phenyl-propyl)-amide 2fz 3-[4-(2,3-Dihydro-benzo[1,4]dioxin-5-yl)-piperazin-1-ylmethyl]-1-oxo-2-phenyl-1,2-dihydro-isoquinoline-4-carboxylic acid ((S)-1-phenyl-propyl)-amide 2ga 3-[4-(4-Methyl-quinolin-2-yl)-piperazin-1-ylmethyl]-1-oxo-2-phenyl-1,2-dihydro-isoquinoline-4-carboxylic acid ((S)-1-phenyl-propyl)-amide 2gb 1-Oxo-2-phenyl-3-[4-(pyridin-2-ylcarbamoylmethyl)-piperazin-1-ylmethyl]-1,2-dihydro-isoquinoline-4-carboxylic acid ((S)-1-phenyl-propyl)-amide 2gc 3-[4-(6-Chloro-3-oxo-3,4-dihydro-2H-benzo[1,4]oxazin-8-yl)-piperazin-1-ylmethyl]-1-oxo-2-phenyl-1,2-dihydro-isoquinoline-4-carboxylic acid ((S)-1-phenyl-propyl)-amide 2gd 3-(4-Carbamoylmethyl-piperazin-1-ylmethyl)-1-oxo-2-phenyl-1,2-dihydro-isoquinoline-4-carboxylic acid ((S)-1-phenyl-propyl)-amide 2ge 3-(4-Hydroxy-4-phenyl-piperidin-1-ylmethyl)-1-oxo-2-phenyl-1,2-dihydro-isoquinoline-4-carboxylic acid ((S)-1-phenyl-propyl)-amide 2gf 3-[4-(4-Chloro-phenyl)-4-hydroxy-piperidin-1-ylmethyl]-1-oxo-2-phenyl-1,2-dihydro-isoquinoline-4-carboxylic acid ((S)-1-phenyl-propyl)-amide 2gg 1-[1-Oxo-2-phenyl-4-(1-phenyl-propylcarbamoyl)-1,2-dihydro-isoquinolin-3-ylmethyl]-piperidine-4-carboxylic acid 2gh 3-(4-Cyano-4-phenyl-piperidin-1-ylmethyl)-1-oxo-2-phenyl-1,2-dihydro-isoquinoline-4-carboxylic acid ((S)-1-phenyl-propyl)-amide 2gi 3-(4-Benzyl-4-hydroxy-piperidin-1-ylmethyl)-1-oxo-2-phenyl-1,2-dihydro-isoquinoline-4-carboxylic acid ((S)-1-phenyl-propyl)-amide 2gj 1-[1-Oxo-2-phenyl-4-(1-phenyl-propylcarbamoyl)-1,2-dihydro-isoquinolin-3-ylmethyl]-4-phenyl-piperidine-4-carboxylic acid ethyl ester 2gk 1-Oxo-2-phenyl-3-[4-(phenyl-propionyl-amino)-piperidin-1-ylmethyl]-1,2-dihydro-isoquinoline-4-carboxylic acid ((S)-1-phenyl-propyl)-amide 2gl Methyl-{1-[1-oxo-2-phenyl-4-(1-phenyl-propylcarbamoyl)-1,2-dihydro-isoquinolin-3-ylmethyl]-piperidin-4-yl}-carbamic acid tert-butyl ester 2gm 1-Oxo-2-phenyl-3-[4-(2-pyrrolidin-1-yl-ethyl)-piperidin-1-ylmethyl]-1,2-dihydro-isoquinoline-4-carboxylic acid ((S)-1-phenyl-propyl)-amide 2gn 3-{4-[5-(4-Fluoro-phenyl)-[1,3,4]oxadiazol-2-yl]-piperidin-1-ylmethyl}-1-oxo-2-phenyl-1,2-dihydro-isoquinoline-4-carboxylic acid ((S)-1-phenyl-propyl)-amide 2go 1-Oxo-2-phenyl-3-[4-(3-pyridin-4-yl-[1,2,4]oxadiazol-5-yl)-piperidin-1-ylmethyl]-1,2-dihydro-isoquinoline-4-carboxylic acid ((S)-1-phenyl-propyl)-amide 2gp 1-Oxo-2-phenyl-3-[4-(3-pyrazin-2-yl-[1,2,4]oxadiazol-5-yl)-piperidin-1-ylmethyl]-1,2-dihydro-isoquinoline-4-carboxylic acid ((S)-1-phenyl-propyl)-amide 2gq 1-Oxo-2-phenyl-3-[4-(3-pyridin-4-yl-[1,2,4]oxadiazol-5-yl)-piperidin-1-ylmethyl]-1,2-dihydro-isoquinoline-4-carboxylic acid ((S)-1-phenyl-propyl)-amide 2gr 3-(4'-Hydroxy-3',4',5',6'-tetrahydro-2'H-[2,4']bipyridinyl-1'-ylmethyl)-1-oxo-2-phenyl-1,2-dihydro-isoquinoline-4-carboxylic acid ((S)-1-phenyl-propyl)-amide 2gs 3-(spiro[isochroman-1,4'-piperidin]-1'-ylmethyl)-1-oxo-2-phenyl-1,2-dihydro-isoquinoline-4-carboxylic acid ((S)-1-phenyl-propyl)-amide 2gt 3-[4-Hydroxy-4-(3-methoxy-phenyl)-piperidin-1-ylmethyl]-1-oxo-2-phenyl-1,2-dihydro-isoquinoline-4-carboxylic acid ((S)-1-phenyl-propyl)-amide 2gu 3-[4-(3-Chloro-phenyl)-4-hydroxy-piperidin-1-ylmethyl]-1-oxo-2-phenyl-1,2-dihydro-isoquinoline-4-carboxylic acid ((S)-1-phenyl-propyl)-amide 2gv 3-(6-chloro-3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide 2gw 3-(4-{[4-Chloro-3-(4-fluoro-phenyl)-indan-1-yl]-methyl-amino}-piperidin-1-ylmethyl)-1-oxo-2-phenyl-1,2-dihydro-isoquinoline-4-carboxylic acid ((S)-1-phenyl-propyl)-amide 2gx 3-(1-acetyl-spiro[indoline-3,4'-piperidin]-1'-ylmethyl)-1-oxo-2-phenyl-1,2-dihydro-isoquinoline-4-carboxylic acid ((S)-1-phenyl-propyl)-amide 2gy 3-(1-acetyl-5-fluoro-spiro[indoline-3,4'-piperidin]-1'-ylmethyl)-1-oxo-2-phenyl-1,2-dihydro-isoquinoline-4-carboxylic acid ((S)-1-phenyl-propyl)-amide 2gz 1-Oxo-3-(4-oxo-1-phenyl-1,3,8-triaza-spiro[4.5]dec-8-ylmethyl)-2-phenyl-1,2-dihydro-isoquinoline-4-carboxylic acid ((S)-1-phenyl-propyl)-amide 2ha 3-(4-Acetylamino-piperidin-1-ylmethyl)-1-oxo-2-phenyl-1,2-dihydro-isoquinoline-4-carboxylic acid ((S)-1-phenyl-propyl)-amide 2hb 1-Oxo-3-(1-oxo-2,8-diaza-spiro[4.5]dec-8-ylmethyl)-2-phenyl-1,2-dihydro-isoquinoline-4-carboxylic acid ((S)-1-phenyl-propyl)-amide 2hc 3-[4-Hydroxy-4-(3-trifluoromethyl-phenyl)-piperidin-1-ylmethyl]-1-oxo-2-phenyl-1,2-dihydro-isoquinoline-4-carboxylic acid ((S)-1-phenyl-propyl)-amide 2hd 1-Oxo-2-phenyl-3-(4-trifluoromethyl-piperidin-1-ylmethyl)-1,2-dihydro-isoquinoline-4-carboxylic acid ((S)-1-phenyl-propyl)-amide 2he 3-[4-(4-Methyl-piperazine-1-carbonyl)-piperidin-1-ylmethyl]-1-oxo-2-phenyl-1,2-dihydro-isoquinoline-4-carboxylic acid ((S)-1-phenyl-propyl)-amide 2hf 3-(5-isopropyl-3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide 2hg 3-[4-(Acetyl-methyl-amino)-4-phenyl-piperidin-1-ylmethyl]-1-oxo-2-phenyl-1,2-dihydro-isoquinoline-4-carboxylic acid ((S)-1-phenyl-propyl)-amide 2hh 4-{1-[1-Oxo-2-phenyl-4-(1-phenyl-propylcarbamoyl)-1,2-dihydro-isoquinolin-3-ylmethyl]-piperidin-4-yl}-piperazine-1-carboxylic acid tert-butyl ester 2hi (2-{1-[1-Oxo-2-phenyl-4-(1-phenyl-propylcarbamoyl)-1,2-dihydro-isoquinolin-3-ylmethyl]-piperidin-4-yl}-ethyl)-carbamic acid tert-butyl ester 2hj 3-(4-Methylamino-4-phenyl-piperidin-1-ylmethyl)-1-oxo-2-phenyl-1,2-dihydro-isoquinoline-4-carboxylic acid ((S)-1-phenyl-propyl)-amide 2hk 3-(4-Acetylamino-4-phenyl-piperidin-1-ylmethyl)-1-oxo-2-phenyl-1,2-dihydro-isoquinoline-4-carboxylic acid ((S)-1-phenyl-propyl)-amide 2hl 3-[4-Acetylamino-4-(3-fluoro-phenyl)-piperidin-1-ylmethyl]-1-oxo-2-phenyl-1,2-dihydro-isoquinoline-4-carboxylic acid ((S)-1-phenyl-propyl)-amide 2hm 1-Oxo-3-[4-(4-oxo-piperidine-1-carbonyl)-piperidin-1-ylmethyl]-2-phenyl-1,2-dihydro-isoquinoline-4-carboxylic acid ((S)-1-phenyl-propyl)-amide 2hn 3-[4,4']Bipiperidinyl-1-ylmethyl-1-oxo-2-phenyl-1,2-dihydro-isoquinoline-4-carboxylic acid ((S)-1-phenyl-propyl)-amide 2ho {1-[1-Oxo-2-phenyl-4-(1-phenyl-propylcarbamoyl)-1,2-dihydro-isoquinolin-3-ylmethyl]-piperidin-4-yl}-carbamic acid tert-butyl ester 2hp 3-[1,4']Bipiperidinyl-1'-ylmethyl-1-oxo-2-phenyl-1,2-dihydro-isoquinoline-4-carboxylic acid [cyclopropyl-(3-fluoro-phenyl)-methyl]-amide 2hq 1-Oxo-3-(4-phenethyl-piperazin-1-ylmethyl)-2-phenyl-1,2-dihydro-isoquinoline-4-carboxylic acid [cyclopropyl-(3-fluoro-phenyl)-methyl]-amide 2hr 3-(4-Isopropyl-piperazin-1-ylmethyl)-1-oxo-2-phenyl-1,2-dihydro-isoquinoline-4-carboxylic acid [cyclopropyl-(3-fluoro-phenyl)-methyl]-amide 2hs 3-[4-(2-Morpholin-4-yl-ethyl)-piperazin-1-ylmethyl]-1-oxo-2-phenyl-1,2-dihydro-isoquinoline-4-carboxylic acid [cyclopropyl-(3-fluoro-phenyl)-methyl]-amide 2ht 3-[4-(1-Methyl-piperidin-4-yl)-piperazin-1-ylmethyl]-1-oxo-2-phenyl-1,2-dihydro-isoquinoline-4-carboxylic acid [cyclopropyl-(3-fluoro-phenyl)-methyl]-amide 2hu 1-Oxo-2-phenyl-3-[4-(2-piperidin-1-yl-ethyl)-piperazin-1-ylmethyl]-1,2-dihydro-isoquinoline-4-carboxylic acid [cyclopropyl-(3-fluoro-phenyl)-methyl]-amide 2hv 1-Oxo-2-phenyl-3-[4-(2-pyrrolidin-1-yl-ethyl)-piperazin-1-ylmethyl]-1,2-dihydro-isoquinoline-4-carboxylic acid [cyclopropyl-(3-fluoro-phenyl)-methyl]-amide 2hw 1-Oxo-2-phenyl-3-(4-pyridin-4-ylmethyl-piperazin-1-ylmethyl)-1,2-dihydro-isoquinoline-4-carboxylic acid [cyclopropyl-(3-fluoro-phenyl)-methyl]-amide 2hx 3-(4-Hydroxy-3,4,5,6-tetrahydro-2H-[4,4']bipyridinyl-1-ylmethyl)-1-oxo-2-phenyl-1,2-dihydro-isoquinoline-4-carboxylic acid [cyclopropyl-(3-fluoro-phenyl)-methyl]-amide 2hy 3-[4-(2-Morpholin-4-yl-ethyl)-piperidin-1-ylmethyl]-1-oxo-2-phenyl-1,2-dihydro-isoquinoline-4-carboxylic acid [cyclopropyl-(3-fluoro-phenyl)-methyl]-amide 2hz 3-[4-Hydroxy-4-(3-methoxy-phenyl)-piperidin-1-ylmethyl]-1-oxo-2-phenyl-1,2-dihydro-isoquinoline-4-carboxylic acid [cyclopropyl-(3-fluoro-phenyl)-methyl]-amide 2ia 3-[4-(Acetyl-methyl-amino)-4-phenyl-piperidin-1-ylmethyl]-1-oxo-2-phenyl-1,2-dihydro-isoquinoline-4-carboxylic acid [cyclopropyl-(3-fluoro-phenyl)-methyl]-amide 2ib 2-(2-Fluoro-phenyl)-1-oxo-3-(4-phenethyl-piperazin-1-ylmethyl)-1,2-dihydro-isoquinoline-4-carboxylic acid ((S)-1-phenyl-propyl)-amide 2ic 2-(2-Fluoro-phenyl)-3-(4-isopropyl-piperazin-1-ylmethyl)-1-oxo-1,2-dihydro-isoquinoline-4-carboxylic acid ((S)-1-phenyl-propyl)-amide 2id 3-[1,4']Bipiperidinyl-1'-ylmethyl-2-(2-fluoro-phenyl)-1-oxo-1,2-dihydro-isoquinoline-4-carboxylic acid ((S)-1-phenyl-propyl)-amide 2ie 2-(2-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide 2if 2-(2-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide 2ig 2-(2-Fluoro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide 2ih 2-(2-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide 2ii 2-(2-Fluoro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide 2ij 2-(2-Fluoro-phenyl)-3-(4-hydroxy-3,4,5,6-tetrahydro-2H-[4,4']bipyridinyl-1-ylmethyl)-1-oxo-1,2-dihydro-isoquinoline-4-carboxylic acid ((S)-1-phenyl-propyl)-amide 2ik 2-(2-Fluoro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide 2il 2-(2-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide 2im 3-[4-(2-Morpholin-4-yl-ethyl)-piperazin-1-ylmethyl]-1-oxo-2-o-tolyl-1,2-dihydro-isoquinoline-4-carboxylic acid ((S)-1-phenyl-propyl)-amide 2in 1-Oxo-3-[4-(2-piperidin-1-yl-ethyl)-piperazin-1-ylmethyl]-2-o-tolyl-1,2-dihydro-isoquinoline-4-carboxylic acid ((S)-1-phenyl-propyl)-amide 2io 1-Oxo-3-(4-pyridin-4-ylmethyl-piperazin-1-ylmethyl)-2-o-tolyl-1,2-dihydro-isoquinoline-4-carboxylic acid ((S)-1-phenyl-propyl)-amide 2ip 2-(3-Fluoro-phenyl)-1-oxo-3-(4-phenethyl-piperazin-1-ylmethyl)-1,2-dihydro-isoquinoline-4-carboxylic acid ((S)-1-phenyl-propyl)-amide 2iq 2-(3-Fluoro-phenyl)-3-(4-isopropyl-piperazin-1-ylmethyl)-1-oxo-1,2-dihydro-isoquinoline-4-carboxylic acid ((S)-1-phenyl-propyl)-amide 2ir 3-[1,4']Bipiperidinyl-1'-ylmethyl-2-(3-fluoro-phenyl)-1-oxo-1,2-dihydro-isoquinoline-4-carboxylic acid ((S)-1-phenyl-propyl)-amide 2is 2-(3-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide 2it 2-(3-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide 2iu 2-(3-Fluoro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide 2iv 2-(3-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide 2iw 2-(3-Fluoro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide 2ix 2-(3-Fluoro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide 2iy 2-(3-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide 2iz 3-[4-(Acetyl-methyl-amino)-4-phenyl-piperidin-1-ylmethyl]-2-(3-fluoro-phenyl)-1-oxo-1,2-dihydro-isoquinoline-4-carboxylic acid ((S)-1-phenyl-propyl)-amide 2ja 2-(3-Chloro-phenyl)-1-oxo-3-(4-phenethyl-piperazin-1-ylmethyl)-1,2-dihydro-isoquinoline-4-carboxylic acid ((S)-1-phenyl-propyl)-amide 2jb 2-(3-Chloro-phenyl)-3-(4-isopropyl-piperazin-1-ylmethyl)-1-oxo-1,2-dihydro-isoquinoline-4-carboxylic acid ((S)-1-phenyl-propyl)-amide 2jc 3-[1,4']Bipiperidinyl-1'-ylmethyl-2-(3-chloro-phenyl)-1-oxo-1,2-dihydro-isoquinoline-4-carboxylic acid ((S)-1-phenyl-propyl)-amide 2jd 2-(3-Chloro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide 2je 2-(3-Chloro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide 2jf 2-(3-Chloro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide 2jg 2-(3-Chloro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide 2jh 2-(3-Chloro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide 2ji 2-(3-Chloro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide 2jj 2-(3-Chloro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide 2jk 3-[4-(Acetyl-methyl-amino)-4-phenyl-piperidin-1-ylmethyl]-2-(3-chloro-phenyl)-1-oxo-1,2-dihydro-isoquinoline-4-carboxylic acid ((S)-1-phenyl-propyl)-amide 2jl 1-Oxo-3-(4-phenethyl-piperazin-1-ylmethyl)-2-m-tolyl-1,2-dihydro-isoquinoline-4-carboxylic acid ((S)-1-phenyl-propyl)-amide 2jm 3-[1,4']Bipiperidinyl-1'-ylmethyl-1-oxo-2-m-tolyl-1,2-dihydro-isoquinoline-4-carboxylic acid ((S)-1-phenyl-propyl)-amide 2jn 3-[4-(2-Morpholin-4-yl-ethyl)-piperazin-1-ylmethyl]-1-oxo-2-m-tolyl-1,2-dihydro-isoquinoline-4-carboxylic acid ((S)-1-phenyl-propyl)-amide 2jo 3-[4-(1-Methyl-piperidin-4-yl)-piperazin-1-ylmethyl]-1-oxo-2-m-tolyl-1,2-dihydro-isoquinoline-4-carboxylic acid ((S)-1-phenyl-propyl)-amide 2jp 1-Oxo-3-[4-(2-piperidin-1-yl-ethyl)-piperazin-1-ylmethyl]-2-m-tolyl-1,2-dihydro-isoquinoline-4-carboxylic acid ((S)-1-phenyl-propyl)-amide 2jq 1-Oxo-3-[4-(2-pyrrolidin-1-yl-ethyl)-piperazin-1-ylmethyl]-2-m-tolyl-1,2-dihydro-isoquinoline-4-carboxylic acid ((S)-1-phenyl-propyl)-amide 2jr 1-Oxo-3-(4-pyridin-4-ylmethyl-piperazin-1-ylmethyl)-2-m-tolyl-1,2-dihydro-isoquinoline-4-carboxylic acid ((S)-1-phenyl-propyl)-amide 2js 3-[4-(2-Morpholin-4-yl-ethyl)-piperidin-1-ylmethyl]-1-oxo-2-m-tolyl-1,2-dihydro-isoquinoline-4-carboxylic acid ((S)-1-phenyl-propyl)-amide 2jt 3-[4-Hydroxy-4-(3-methoxy-phenyl)-piperidin-1-ylmethyl]-1-oxo-2-m-tolyl-1,2-dihydro-isoquinoline-4-carboxylic acid ((S)-1-phenyl-propyl)-amide 2ju 3-[4-(Acetyl-methyl-amino)-4-phenyl-piperidin-1-ylmethyl]-1-oxo-2-m-tolyl-1,2-dihydro-isoquinoline-4-carboxylic acid ((S)-1-phenyl-propyl)-amide 3a 1-Oxo-3-(2-oxo-pyrrolidin-1-ylmethyl)-2-phenyl-1,2-dihydro-isoquinoline-4-carboxylic acid ((S)-1-phenyl-propyl)-amide 3b 8-Chloro-1-oxo-3-(2-oxo-pyrrolidin-1-ylmethyl)-2-phenyl-1,2-dihydro-isoquinoline-4-carboxylic acid ((S)-1-phenyl-propyl)-amide 4a 3-Cyanomethyl-1-oxo-2-phenyl-1,2-dihydro-isoquinoline-4-carboxylic acid ((S)-1-phenyl-propyl)-amide 5a 3-Methyl-1-oxo-2-phenyl-1,2-dihydro-isoquinoline-4-carboxylic acid N,N-diphenyl-hydrazide 5b N'-(3-Methyl-1-oxo-2-phenyl-1,2-dihydro-isoquinoline-4-carbonyl)-N-phenyl-hydrazinecarboxylic acid methyl ester 1aa 2-(3-Methoxy-phenyl)-3-methyl-1-oxo-1,2-dihydro-isoquinoline-4-carboxylic acid ((S)-1-phenyl-propyl)-amide 1ab 2-(4-Methoxy-phenyl)-3-methyl-1-oxo-1,2-dihydro-isoquinoline-4-carboxylic acid ((S)-1-phenyl-propyl)-amide 1ac 2-(4-Fluoro-phenyl)-3-methyl-1-oxo-1,2-dihydro-isoquinoline-4-carboxylic acid ((S)-1-phenyl-propyl)-amide 1ad 2-(4-Chloro-phenyl)-3-methyl-1-oxo-1,2-dihydro-isoquinoline-4-carboxylic acid ((S)-1-phenyl-propyl)-amide 1ae 3-Methyl-1-oxo-2-p-tolyl-1,2-dihydro-isoquinoline-4-carboxylic acid ((S)-1-phenyl-propyl)-amide 1af 2-(3-Methoxy-phenyl)-3-methyl-1-oxo-1,2-dihydro-isoquinoline-4-carboxylic acid [(S)-cyclopropyl-(3-fluoro-phenyl)-methyl]-amide 1ag 2-(4-Methoxy-phenyl)-3-methyl-1-oxo-1,2-dihydro-isoquinoline-4-carboxylic acid [(S)-cyclopropyl-(3-fluoro-phenyl)-methyl]-amide 1ah 2-(4-Fluoro-phenyl)-3-methyl-1-oxo-1,2-dihydro-isoquinoline-4-carboxylic acid [(S)-cyclopropyl-(3-fluoro-phenyl)-methyl]-amide 1ai 2-(4-Chloro-phenyl)-3-methyl-1-oxo-1,2-dihydro-isoquinoline-4-carboxylic acid [(S)-cyclopropyl-(3-fluoro-phenyl)-methyl]-amide 1aj 3-Methyl-1-oxo-2-p-tolyl-1,2-dihydro-isoquinoline-4-carboxylic acid [(S)-cyclopropyl-(3-fluoro-phenyl)-methyl]-amide 1ak 2-(2-Methoxy-phenyl)-3-methyl-1-oxo-1,2-dihydro-isoquinoline-4-carboxylic acid ((S)-1-phenyl-propyl)-amide 1al 2-(2-Methoxy-phenyl)-3-methyl-1-oxo-1,2-dihydro-isoquinoline-4-carboxylic acid [(S)-cyclopropyl-(3-fluoro-phenyl)-methyl]-amide 1am 3-Methyl-8-nitro-1-oxo-2-phenyl-1,2-dihydro-isoquinoline-4-carboxylic acid ((S)-1-phenyl-propyl)-amide 1an 3-Methyl-8-nitro-1-oxo-2-phenyl-1,2-dihydro-isoquinoline-4-carboxylic acid [(S)-cyclopropyl-(3-fluoro-phenyl)-methyl]-amide 1ao 8-Methoxy-3-methyl-1-oxo-2-phenyl-1,2-dihydro-isoquinoline-4-carboxylic acid ((S)-1-phenyl-propyl)-amide 1ap 8-Methoxy-3-methyl-1-oxo-2-phenyl-1,2-dihydro-isoquinoline-4-carboxylic acid [(S)-cyclopropyl-(3-fluoro-phenyl)-methyl]-amide 1aq 8-Amino-3-methyl-1-oxo-2-phenyl-1,2-dihydro-isoquinoline-4-carboxylic acid ((S)-1-phenyl-propyl)-amide 1ar 8-Cyano-3-methyl-1-oxo-2-phenyl-1,2-dihydro-isoquinoline-4-carboxylic acid ((S)-1-phenyl-propyl)-amide 1as 8-Chloro-3-methyl-1-oxo-2-phenyl-1,2-dihydro-isoquinoline-4-carboxylic acid [(S)-1-(4-chloro-phenyl)-propyl]-amide 1at 8-Chloro-3-methyl-1-oxo-2-phenyl-1,2-dihydro-isoquinoline-4-carboxylic acid [(S)-1-(4-fluoro-phenyl)-propyl]-amide 1au 8-Chloro-3-methyl-1-oxo-2-phenyl-1,2-dihydro-isoquinoline-4-carboxylic acid [(S)-1-(2-fluoro-phenyl)-propyl]-amide 1av 8-Chloro-3-methyl-1-oxo-2-phenyl-1,2-dihydro-isoquinoline-4-carboxylic acid [(S)-1-(3-chloro-phenyl)-propyl]-amide 1aw 8-Chloro-3-methyl-1-oxo-2-phenyl-1,2-dihydro-isoquinoline-4-carboxylic acid [(S)-(3-chloro-phenyl)-cyclopropyl-methyl]-amide 1ax 8-Chloro-3-methyl-1-oxo-2-phenyl-1,2-dihydro-isoquinoline-4-carboxylic acid [(S)-(4-chloro-phenyl)-cyclopropyl-methyl]-amide 1ay 8-Chloro-3-methyl-1-oxo-2-phenyl-1,2-dihydro-isoquinoline-4-carboxylic acid [(S)-1-(3-fluoro-phenyl)-propyl]-amide 1az 8-Chloro-3-methyl-1-oxo-2-phenyl-1,2-dihydro-isoquinoline-4-carboxylic acid ((S)-2-methyl-1-phenyl-propyl)-amide 1ba 8-Chloro-3-methyl-1-oxo-2-phenyl-1,2-dihydro-isoquinoline-4-carboxylic acid [(S)-cyclopropyl-(4-fluoro-phenyl)-methyl]-amide 1bb 8-Chloro-3-methyl-1-oxo-2-phenyl-1,2-dihydro-isoquinoline-4-carboxylic acid [(S)-1-(2-chloro-phenyl)-propyl]-amide 1bc 8-Chloro-3-methyl-1-oxo-2-phenyl-1,2-dihydro-isoquinoline-4-carboxylic acid ((S)-cyclopentyl-phenyl-methyl)-amide 1bd 8-Chloro-3-methyl-1-oxo-2-phenyl-1,2-dihydro-isoquinoline-4-carboxylic acid [(S)-(2-chloro-phenyl)-cyclopropyl-methyl]-amide 1be 8-Chloro-3-methyl-1-oxo-2-phenyl-1,2-dihydro-isoquinoline-4-carboxylic acid [(S)-cyclopropyl-(2-fluoro-phenyl)-methyl]-amide 1bf 8-Chloro-3-methyl-1-oxo-2-phenyl-1,2-dihydro-isoquinoline-4-carboxylic acid ((S)-cyclohexyl-phenyl-methyl)-amide 1bg 8-Chloro-3-methyl-1-oxo-2-phenyl-1,2-dihydro-isoquinoline-4-carboxylic acid ((S)-cyclopropyl-phenyl-methyl)-amide 1bh 8-Chloro-3-methyl-1-oxo-2-phenyl-1,2-dihydro-isoquinoline-4-carboxylic acid [(S)-cyclobutyl-(3-fluoro-phenyl)-methyl]-amide 1bi 8-Chloro-3-methyl-1-oxo-2-phenyl-1,2-dihydro-isoquinoline-4-carboxylic acid [(S)-cyclobutyl-(4-fluoro-phenyl)-methyl]-amide 1bl 8-Chloro-3-methyl-1-oxo-2-phenyl-1,2-dihydro-isoquinoline-4-carboxylic acid [(R)-cyclopropyl-(3-fluoro-phenyl)-methyl]-amide 1bn 8-Chloro-3-methyl-1-oxo-2-phenyl-1,2-dihydro-isoquinoline-4-carboxylic acid ((S)cyclobutyl-phenyl-methyl)-amide 1bo 8-Chloro-3-methyl-1-oxo-2-phenyl-1,2-dihydro-isoquinoline-4-carboxylic acid [cyclobutyl-(2-fluoro-phenyl)-methyl]-amide 2ka 3-(4-tert-Butyl-piperazin-1-ylmethyl)-8-chloro-1-oxo-2-phenyl-1,2-dihydro-isoquinoline-4-carboxylic acid [(S)-cyclopropyl-(3-fluoro-phenyl)-methyl]-amide 2kb 8-Chloro-3-(4-isopropyl-piperazin-1-ylmethyl)-1-oxo-2-phenyl-1,2-dihydro-isoquinoline-4-carboxylic acid ((S)-1-phenyl-propyl)-amide 2kc 8-Chloro-3-(4-isobutyl-piperazin-1-ylmethyl)-1-oxo-2-phenyl-1,2-dihydro-isoquinoline-4-carboxylic acid ((S)-1-phenyl-propyl)-amide 2kd 8-Chloro-3-(octahydro-pyrido[1,2-a]pyrazin-2-ylmethyl)-1-oxo-2-phenyl-1,2-dihydro-isoquinoline-4-carboxylic acid ((S)-1-phenyl-propyl)-amide 2ke 8-Chloro-3-(4-hydroxy-3,4,5,6-tetrahydro-2H-[4,4']bipyridinyl-1-ylmethyl)-1-oxo-2-phenyl-1,2-dihydro-isoquinoline-4-carboxylic acid ((S)-1-phenyl-propyl)-amide 2kf 8-Chloro-3-(4-cyclopropylmethyl-piperazin-1-ylmethyl)-1-oxo-2-phenyl-1,2-dihydro-isoquinoline-4-carboxylic acid ((S)-1-phenyl-propyl)-amide 2kg 8-Chloro-3-[4-(2-morpholin-4-yl-ethyl)-piperidin-1-ylmethyl]-1-oxo-2-phenyl-1,2-dihydro-isoquinoline-4-carboxylic acid ((S)-1-phenyl-propyl)-amide 2kh 8-Chloro-3-[1,4]diazepan-1-ylmethyl-1-oxo-2-phenyl-1,2-dihydro-isoquinoline-4-carboxylic acid ((S)-1-phenyl-propyl)-amide 2ki 8-Chloro-3-((S)-3-methyl-piperazin-1-ylmethyl)-1-oxo-2-phenyl-1,2-dihydro-isoquinoline-4-carboxylic acid ((S)-1-phenyl-propyl)-amide 2kj 8-Chloro-3-imidazol-1-ylmethyl-1-oxo-2-phenyl-1,2-dihydro-isoquinoline-4-carboxylic acid ((S)-1-phenyl-propyl)-amide 2kk 8-Chloro-3-(4-methyl-imidazol-1-ylmethyl)-1-oxo-2-phenyl-1,2-dihydro-isoquinoline-4-carboxylic acid ((S)-1-phenyl-propyl)-amide 2kl 3-(tert-Butylamino-methyl)-8-chloro-1-oxo-2-phenyl-1,2-dihydro-isoquinoline-4-carboxylic acid ((S)-1-phenyl-propyl)-amide 2km 8-Chloro-3-(isopropylamino-methyl)-1-oxo-2-phenyl-1,2-dihydro-isoquinoline-4-carboxylic acid ((S)-1-phenyl-propyl)-amide 2kn 8-Chloro-3-[4-hydroxy-4-(3-methoxy-phenyl)-piperidin-1-ylmethyl]-1-oxo-2-phenyl-1,2-dihydro-isoquinoline-4-carboxylic acid ((S)-1-phenyl-propyl)-amide 2ko 3-(4-tert-Butyl-piperazin-1-ylmethyl)-8-chloro-1-oxo-2-phenyl-1,2-dihydro-isoquinoline-4-carboxylic acid ((S)-1-phenyl-propyl)-amide 2kp 3-Benzoimidazol-1-ylmethyl-1-oxo-2-phenyl-1,2-dihydro-isoquinoline-4-carboxylic acid ((S)-1-phenyl-propyl)-amide 2kq 1-Oxo-2-phenyl-3-pyrazol-1-ylmethyl-1,2-dihydro-isoquinoline-4-carboxylic acid ((S)-1-phenyl-propyl)-amide 2kr 3-(4-Methyl-pyrazol-1-ylmethyl)-1-oxo-2-phenyl-1,2-dihydro-isoquinoline-4-carboxylic acid ((S)-1-phenyl-propyl)-amide 2ks 1-Oxo-2-phenyl-3-[1,2,3]triazol-1-ylmethyl-1,2-dihydro-isoquinoline-4-carboxylic acid ((S)-1-phenyl-propyl)-amide 2kt 2-(3-Methoxy-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide 2ku 2-(4-Methoxy-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide 2kv 2-(4-Fluoro-phenyl)-1-oxo-3-(4-phenethyl-piperazin-1-ylmethyl)-1,2-dihydro-isoquinoline-4-carboxylic acid ((S)-1-phenyl-propyl)-amide 2kw 2-(4-Fluoro-phenyl)-3-(4-isopropyl-piperazin-1-ylmethyl)-1-oxo-1,2-dihydro-isoquinoline-4-carboxylic acid ((S)-1-phenyl-propyl)-amide 2kx 3-[1,4']Bipiperidinyl-1'-ylmethyl-2-(4-fluoro-phenyl)-1-oxo-1,2-dihydro-isoquinoline-4-carboxylic acid ((S)-1-phenyl-propyl)-amide 2ky 2-(4-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide 2kz 2-(4-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide 2la 2-(4-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide 2lb 2-(4-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide 2lc 2-(4-Chloro-phenyl)-1-oxo-3-(4-phenethyl-piperazin-1-ylmethyl)-1,2-dihydro-isoquinoline-4-carboxylic acid ((S)-1-phenyl-propyl)-amide 2ld 2-(4-Chloro-phenyl)-3-(4-isopropyl-piperazin-1-ylmethyl)-1-oxo-1,2-dihydro-isoquinoline-4-carboxylic acid ((S)-1-phenyl-propyl)-amide 2le 3-[1,4']Bipiperidinyl-1'-ylmethyl-2-(4-chloro-phenyl)-1-oxo-1,2-dihydro-isoquinoline-4-carboxylic acid ((S)-1-phenyl-propyl)-amide 2lf 2-(4-Chloro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide 2lg 2-(4-Chloro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide 2lh 2-(4-Chloro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide 2li 2-(4-Chloro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide 2lj 3-(4-tert-Butyl-piperazin-1-ylmethyl)-8-fluoro-1-oxo-2-phenyl-1,2-dihydro-isoquinoline-4-carboxylic acid ((S)-1-phenyl-propyl)-amide 2lk 8-Chloro-3-cyclopropylaminomethyl-1-oxo-2-phenyl-1,2-dihydro-isoquinoline-4-carboxylic acid ((S)-1-phenyl-propyl)-amide 2ll 3-(4-tert-Butyl-piperazin-1-ylmethyl)-8-fluoro-1-oxo-2-phenyl-1,2-dihydro-isoquinoline-4-carboxylic acid [(S)-cyclopropyl-(3-fluoro-phenyl)-methyl]-amide 2lm 8-Fluoro-1-oxo-2-phenyl-3-piperazin-1-ylmethyl-1,2-dihydro-isoquinoline-4-carboxylic acid [(S)-cyclopropyl-(3-fluoro-phenyl)-methyl]-amide 2ln 8-Fluoro-1-oxo-3-(3-oxo-pyrazolidin-1-ylmethyl)-2-phenyl-1,2-dihydro-isoquinoline-4-carboxylic acid [(S)-cyclopropyl-(3-fluoro-phenyl)-methyl]-amide 2lo 8-Fluoro-1-oxo-3-(3-oxo-piperazin-1-ylmethyl)-2-phenyl-1,2-dihydro-isoquinoline-4-carboxylic acid [(S)-cyclopropyl-(3-fluoro-phenyl)-methyl]-amide 3c 1-Oxo-2-phenyl-3-(1H-[1,2,4]triazol-3-ylsulfanylmethyl)-1,2-dihydro-isoquinoline-4-carboxylic acid ((S)-1-phenyl-propyl)-amide 3d 8-Chloro-1-oxo-3-(2-oxo-pyrrolidin-1-ylmethyl)-2-phenyl-1,2-dihydro-isoquinoline-4-carboxylic acid [(S)-cyclopropyl-(3-fluoro-phenyl)-methyl]-amide 3e 8-Fluoro-1-oxo-3-(2-oxo-pyrrolidin-1-ylmethyl)-2-phenyl-1,2-dihydro-isoquinoline-4-carboxylic acid ((S)-1-phenyl-propyl)-amide 3f 8-Fluoro-1-oxo-3-(2-oxo-pyrrolidin-1-ylmethyl)-2-phenyl-1,2-dihydro-isoquinoline-4-carboxylic acid [(S)-cyclopropyl-(3-fluoro-phenyl)-methyl]-amide 3g 8-Fluoro-1-oxo-3-(5-oxo-pyrazolidin-1-ylmethyl)-2-phenyl-1,2-dihydro-isoquinoline-4-carboxylic acid [(S)-cyclopropyl-(3-fluoro-phenyl)-methyl]-amide 3h 8-Fluoro-1-oxo-3-(2-oxo-piperazin-1-ylmethyl)-2-phenyl-1,2-dihydro-isoquinoline-4-carboxylic acid [(S)-cyclopropyl-(3-fluoro-phenyl)-methyl]-amide 3i 8-Fluoro-1-oxo-3-(2-oxo-piperidin-1-ylmethyl)-2-phenyl-1,2-dihydro-isoquinoline-4-carboxylic acid [(S)-cyclopropyl-(3-fluoro-phenyl)-methyl]-amide 4b 8-Chloro-3-cyanomethyl-1-oxo-2-phenyl-1,2-dihydro-isoquinoline-4-carboxylic acid [(S)-cyclopropyl-(3-fluoro-phenyl)-methyl]-amide 6a 2-(3,4-Dichloro-phenyl)-3-methyl-1-oxo-1,2-dihydro-isoquinoline-4-carboxylic acid ((S)-1-phenyl-propyl)-amide 6b 8-Fluoro-1-oxo-3-(2-oxo-pyrrolidin-1-ylmethyl)-2-phenyl-1,2-dihydro-isoquinoline-4-carboxylic acid ((S)-cyclopropyl-phenyl-methyl)-amide 6c 8-Fluoro-3-methyl-1-oxo-2-phenyl-1,2-dihydro-isoquinoline-4-carboxylic acid ((S)-cyclopropyl-phenyl-methyl)-amide 7a 3-Ethyl-1-oxo-2-phenyl-1,2-dihydro-isoquinoline-4-carboxylic acid ((S)-1-phenyl-propyl)-amide 7b 8-Fluoro-3-methyl-1-oxo-2-phenyl-1,2-dihydro-isoquinoline-4-carboxylic acid ((S)-1-phenyl-propyl)-amide 7c 8-Fluoro-2-(3-fluoro-phenyl)-3-methyl-1-oxo-1,2-dihydro-isoquinoline-4-carboxylic acid ((S)-1-phenyl-propyl)-amide 7d 8-Fluoro-2-(4-fluoro-phenyl)-3-methyl-1-oxo-1,2-dihydro-isoquinoline-4-carboxylic acid ((S)-1-phenyl-propyl)-amide 7e 8-Fluoro-3-methyl-1-oxo-2-phenyl-1,2-dihydro-isoquinoline-4-carboxylic acid [(S)-cyclopropyl-(3-fluoro-phenyl)-methyl]-amide 7f 8-Fluoro-2-(3-fluoro-phenyl)-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide 7g 8-Fluoro-2-(4-fluoro-phenyl)-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide 7h 8-Fluoro-3-methyl-1-oxo-2-phenyl-1,2-dihydro-isoquinoline-4-carboxylic acid [(S)-cyclobutyl-(3-fluoro-phenyl)-methyl]-amide 7i 8-Fluoro-2-(2-fluoro-phenyl)-3-methyl-1-oxo-1,2-dihydro-isoquinoline-4-carboxylic acid [(S)-cyclopropyl-(3-fluoro-phenyl)-methyl]-amide 7j 8-Fluoro-2-(3-fluoro-phenyl)-3-methyl-1-oxo-1,2-dihydro-isoquinoline-4-carboxylic acid [(S)-cyclopropyl-(3-fluoro-phenyl)-methyl]-amide 7k 8-Fluoro-2-(4-fluoro-phenyl)-3-methyl-1-oxo-1,2-dihydro-isoquinoline-4-carboxylic acid [(S)-cyclopropyl-(3-fluoro-phenyl)-methyl]-amide 7l 6,8-Difluoro-3-methyl-1-oxo-2-phenyl-1,2-dihydro-isoquinoline-4-carboxylic acid [(S)-cyclopropyl-(3-fluoro-phenyl)-methyl]-amide 7m 5,8-Difluoro-3-methyl-1-oxo-2-phenyl-1,2-dihydro-isoquinoline-4-carboxylic acid [(S)-cyclopropyl-(3-fluoro-phenyl)-methyl]-amide 7n 3-Methyl-1-oxo-2-phenyl-8-trifluoromethyl-1,2-dihydro-isoquinoline-4-carboxylic acid ((S)-1-phenyl-propyl)-amide 8a 3-(1-tert-Butyl-piperidin-4-ylmethyl)-8-chloro-1-oxo-2-phenyl-1,2-dihydro-isoquinoline-4-carboxylic acid [(S)-cyclopropyl-(3-fluoro-phenyl)-methyl]-amide and pharmaceutically acceptable salts thereof.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centres and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention. In particular, when A represents CH or $CR^1$, A may be an optical centre giving rise to two optical isomers, an R form and an S form. In one embodiment, the compounds of the present invention have the S form.

In a particular embodiment, the compounds of the present invention have the following absolute configuration around A, A being CH

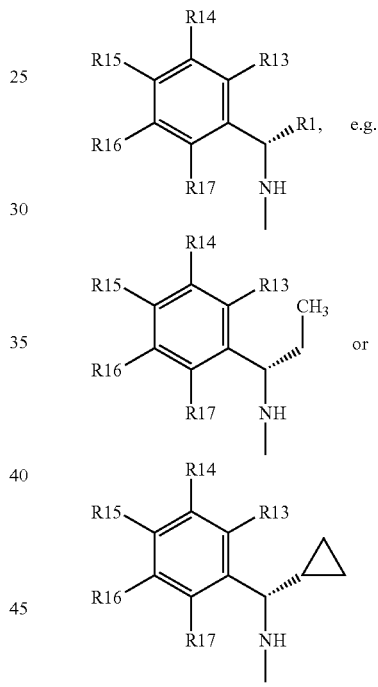

In this context is understood that when specifying the enantiomeric form, then the compound is in enantiomeric excess, e.g. essentially in a pure form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S.

Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

NK3 receptor antagonists have been implicated in various diseases in addition to psychosis and schizophrenia discussed above. Langlois et al in *J. Pharm. Exp. Ther.*, 299, 712-717, 2001, concludes that NK3 antagonists may be applicable in CNS diseases in general, and in anxiety and depression in particular. Yip et al in *Br. J. Phar.*, 122, 715-722, 1997 further implicates NK3 antagonists in diverse brain functions, such as cortical processing, learning and memory, neuroendocrine and behavioral regulation. Additional studies have shown that NKB and NK3 receptors are involved in pain, and that NK3 antagonists have an antinociceptive and analgesic effect [Fioramonti, *Neurogastroenterol. Motil.*, 15, 363-369, 2003]. Mazelin et al in *Life Sci.*, 63, 293-304, 1998 show that NK3 antagonists have an effect in gut inflammation and concludes that such antagonists may be used in the treatment of irritable bowel syndrome (IBS). In addition, NK3 antagonists have in in vivo models been demonstrated to be useful in the treatment of airway related diseases, such as asthma, airway hyperresponsiveness, cough, and bronchorestriction [Daoui, *Am. J. Respir. Crit. Care Med.*, 158, 42-48, 1998]. Maubach et al in *Neurosci.*, 83, 1047-1062, 1998 show that NKB and the NK3 agonist senktide increase the frequency and duration of epileptiform discharges, and thus by inference that NK3 antagonists have a anticonvulsive potential. Finally, Kernel et al in *J. Neurosci.*, 22, 1929-1936, 2002, suggests the use of NK3 antagonists in the treatment of Parkinson's Disease.

Accordingly, clinical, pre-clinical, in vivo and in vitro studies support that NK3 receptor antagonists are of relevance for the treatment or prevention of various disorders including psychosis, schizophrenia, depression, anxiety, cognitive impairment, obesity, Alzheimer's disease, Parkinson's disease, pain, convulsions, cough, asthma, airway hyperresponsiveness, microvascular hypersensitivity, bronchoconstriction, gut inflammation, and inflammatory bowel syndrome.

Schizophrenia is classified into subgroups. The paranoid type is characterised by delusions and hallucinations and absence of thought disorder, disorganized behavior, and affective flattening. The disorganized type, which is also named 'hebephrenic schizophrenia' in the ICD, in which thought disorder and flat affect are present together. The cataconic type, in which prominent psychomotor disturbances are evident, and symptoms may include catatonic stupor and waxy flexibility. The undifferentiated type in which psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making. The current antipsychotics are fairly successful in treating the positive symptoms but fare less well for the negative and cognitive symptoms. Contrary to that, NK3 antagonists have been shown clinically to improve on both positive and negative symptoms in schizophrenics [*Am. J. Psychiatry,* 161, 975-984, 204], and according to the above discussion they are also expected to deliver an effect on the cognitive symptoms.

Cognitive impairment include a decline in cognitive functions or cognitive domains, e.g. working memory, attention and vigilance, verbal learning and memory, visual learning and memory, reasoning and problem solving e.g. executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts.

In one embodiment, the present invention relates to the compounds of the present invention for use in therapy.

In one embodiment, the present invention relates to a method of treating a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizoptypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome the method comprising the administration of a therapeutically effective amount of a compound of the present invention to a patient in need thereof.

In one embodiment, the present invention relates to a method for the treatment of schizophrenia, the method comprising the administration of a therapeutically effective amount of a compound of the present invention to a patient in need thereof. In particular, said treatment includes the treatment of the positive, negative and/or cognitive symptoms of schizophrenia.

In one embodiment, the present invention relates to a method of treating cognitive impairment, the method comprising the administration of a therapeutically effective amount of a compound of the present invention to a patient in need thereof. In particular, said cognitive impairment is manifested as a decline in working memory, attention and vigilance, verbal learning and memory, visual learning and memory, reasoning and problem solving e.g. executive function, speed of processing and/or social cognition.

The antipsychotic effect of typical and atypical anti-psychotics, in particular D2 antagonists is exerted via an inhibition of the post-synaptic D2 receptors. Pre-synaptic D2 auto-receptors, however, are also affected by the administration of these compounds giving rise to an increase in the dopamine neuron firing rate, which, in fact, counteracts the antipsychotic effects. The increased firing rate continues until the effect of the pre-synaptic auto-receptors is blocked (the depolarization block), typically after approximately 3 weeks of chronic treatment with typical or atypical anti-psychotics. This model explains the up to 3 weeks delay of clinical effect normally seen when D2 antagonist treatment is initiated. NK3 antagonists seem to inhibit the increase in the dopamine neuron firing mediated by the pre-synaptic D2 auto-receptors brought about by D2 antagonists, wherefore the combined administration of NK3 antagonists and D2 antagonists is expected to give rise to a faster onset of the clinical effect. Moreover, D2 antagonists are known to increase prolactin levels, which may give rise to serious side effects, such as osteoporosis. It is known that NK3 agonists give rise to an increase in prolactin from which it may be deduced that a NK3 antagonist will lower an increased, i.e. normalise the prolactin level. A combined use of NK3 antagonists and D2 antagonists may thus address some of the safety aspects associated with D2 antagonists administration. Similarly, NK3 antagonists may be administered together with antagonists/inverse agonists/negative modulators/partial agonists of one or more of the targets dopamine D2 receptor, dopamine D3 receptor, dopamine D4 receptor, phosphodiesterase PDE10, serotonin 5-$HT_{1A}$ receptor, serotonin 5-$HT_{2A}$ receptor, serotonin 5-$HT_6$ receptor, adrenergic alpha 2 receptor, cannabinoid type 1 receptor, histamine H3 receptor, cyclooxygenases, sodium channels or glycine transporter GlyT1; or with agonists/positive modulators/partial agonists of one or more of the targets serotonin 5-$HT_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor.

Such combined administration of compounds of the present invention and other anti-psychotic compounds, such as D2 antagonists, D2 partial agonists, PDE10 antagonists, 5-$HT_{2A}$ antagonists, 5-$HT_6$ antagonists or KCNQ4 antagonists may be sequential or concomitant. Examples of D2 antagonists or partial agonists include haloperidol, chlorpromazine, sulpirid, risperidone, ziprasidon, olanzapine, quetiapin, and clozapine.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound of the present invention, such as 1-500 mg/day.

In one embodiment, the present invention relates to the use of the compounds of the present invention in the manufacture of a medicament for the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizoptypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome.

In one embodiment, the present invention relates to the use of a compound of the present invention in the manufacture of a medicament for the treatment of schizophrenia. In particular, said treatment includes the treatment of the positive, negative and/or cognitive symptoms of schizophrenia.

In one embodiment, the present invention relates to the use of a compound of the present invention in the manufacture of a medicament for the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

In one embodiment, the present invention relates to a compound of the present invention for use in the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizoptypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome.

In one embodiment, the present invention relates to a compound of the present invention for use in the treatment of schizophrenia. In particular, said treatment includes the treatment of the positive, negative and/or cognitive symptoms of schizophrenia.

In one embodiment, the present invention relates to a compound of the present invention for use in the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

For parenteral routes such as intravenous, intrathecal, intramuscular and similar administration, typically doses are in the order of about half the dose employed for oral administration.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

In one embodiment, the invention relates to a pharmaceutical composition comprising a compound of the present invention together with a second anti-psychotic agent. In one embodiment, said second anti-psychotic agent is selected from antagonists/inverse agonists/negative modulators/partial agonists of the targets dopamine D2 receptor, dopamine D3 receptor, dopamine D4 receptor, phosphodiesterase PDE10, serotonin 5-$HT_{1A}$ receptor, serotonin 5-$HT_{2A}$ receptor, serotonin 5-$HT_6$ receptor, adrenergic alpha 2 receptor, cannabinoid type 1 receptor, histamine H3 receptor, cyclooxygenases, sodium channels or glycine transporter GlyT1; or from agonists/positive modulators/partial agonists of the targets serotonin 5-$HT_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor. In one embodiment, said second anti-psychotic agent is selected from typical anti-psychotics, atypical anti-psychotics, D2 antagonists, partial D2 agonists, PDE10 antagonists, 5-$HT_{2A}$ antagonists, 5-$HT_6$ antagonists and KCNQ4 antagonists, and in particular atypical anti-psychotics, D2 antagonists, partial D2 agonists. Particular examples of such anti-psychotics include haloperidol, chlorpromazine, sulpirid, risperidone, ziprasidon, olanzapine, quetiapine, and clozapine.

In one embodiment, the invention relates to a pharmaceutical kit comprising a container comprising a compound of the present invention and a separate container comprising an anti-psychotic drug. Typical anti-psychotics, atypical anti-psychotics, D2 antagonists, partial D2 agonists, PDE10 antagonists, 5-$HT_{2A}$ antagonists, 5-$HT_6$ antagonists and KCNQ4 antagonists, and in particular atypical anti-psychotics, D2 antagonists, partial D2 agonists. Particular examples of such anti-psychotics include haloperidol, chlorpromazine, sulpirid, risperidone, ziprasidon, olanzapine, quetiapine, and clozapine.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Synthetic Routes

The compounds of the present invention of the general formula I, wherein $R^1$-$R^{17}$, A, and X are as defined above can be prepared by the methods outlined in the following reaction schemes and examples. In the described methods it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

In the intermediate compounds of the general formulae I-XX, R1-R17, A, and X are as defined under formula I.

For compounds, which can exist as a mixture or equilibrium between two or more tautomers, only one tautomer is represented in the schemes, although it may not be the most stable tautomer. For compounds, which can exist in enantiomeric, stereoisomeric or geometric isomeric forms their geometric configuration is specified; otherwise the structure represents a mixture of stereoisomers. Such compounds include, but not limited to 1,3-ketoesters or enamines of the general formula IV and VII, which can exist in equilibrium between keto or enol forms and the latter may also exist in isomeric Z- and E-forms as well-known to chemists skilled in the art. Such compounds also include compounds of the present invention of the general formula I, which may exist as a mixture of atropisomers due to restricted rotation around carbon-carbon single bonds similar to atropisomerism in ortho, ortho-disubstituted biaryl compounds also well-known to the person skilled in the art.

Starting materials of the general formulae III, VI, and XI are either obtained from commercial sources as summarized in the Table 2 or they can be readily prepared by standard methods or their modifications described in the literature.

2-Bromobenzoic acids of the general formula II are coupled with keto-esters of the general formula III in the presence of a strong base such as sodium hydride and copper or copper salts such as copper (I) bromide in a suitable solvent such as 1,4-dioxane, acetonitrile or an excess of the above keto-esters at suitable temperature such as reflux or at 70° C. with the formation of compounds of the general formula IV. Such arylation reaction is well-known in general as copper-catalyzed Ullmann-type coupling reaction (review: S. V. Ley, A. W. Thomas *Angew. Chem. Int. Ed.* 2003, 42, 5400). Also, in this particular case when the coupling reaction involves activated methylene compounds such as compounds of the general formula IV in the presence of copper or copper salts the reaction is known as the Hurtley reaction (W. R. H. Hurtley *J. Chem. Soc.* 1929, 1870).

The obtained compounds of the general formula IV are then reacted with anilines of the general formula VI with or without appropriate solvent under the heating conditions with the formation of isoquinolones of the general formula VIII via intermediate formation of enamines of the general formula VII which are usually not separated from the reaction mixture. Alternatively, the enamines of the general formula VII can be obtained from anilines of the general VI in the presence of the appropriate dehydrating agent such as tetraethoxysilane under heating conditions or at ambient temperature in the presence of a catalytic amount of acid such as acetic acid. Then, the cyclisation reaction with the formation of isoquinolones of the general formula VIII can be carried out under the heating conditions as mentioned above or at ambient temperature in the presence of an appropriate coupling reagent such as EDC/HOBT.

Furthermore, isoquinolinones of the general formula VIII can be obtained directly from the starting 2-bromobenzoic acids of the general formula II and deprotonated enamines of the general formula V in a modified one-pot procedure involving Hurtley reaction performed at 70° C. with the formation of the compounds of the general formula VII and subsequent cyclisation performed at higher temperature. Enamines of the general formula V are readily available from ketoesters III and anilines VI under conditions described above for preparation of enamines of the general formula VII.

Compounds of the general formula VIII are readily hydrolyzed to acids of the general formula IX under conditions for ester hydrolysis well-known to chemists skilled in the art. Finally, the subsequent coupling with amines (A=C) or hydrazines (A=N) of the general formula XI leads to the formation of the compounds of the invention of the general formula I. Such coupling reactions usually performed via activation of the acid with an appropriate coupling or activation reagent such as but not limited to thionyl chloride with the formation of corresponding acid chloride. Hydrazines of the general formula I where R1=H can be converted to disubstituted hydrazides of the same general formula where R1 is not hydrogen by acylation, alkylation or arylation reactions with appropriate acylation or alkylation reagents such as but not limited to acid chlorides, carbamoyl chlorides, chloroformates or alkylhalogenides.

Compounds of the general formula I where X is hydrogen can be converted to the compounds of the general formula XII by regioselective bromination reaction in the presence of bromination reagent such as bromine. Then the bromine atom can be substituted by various nucleophiles of the general formula X—H or X⁻ with the formation of the compounds of the invention of the general formula I. Those skilled in the art will readily appreciate that many nitrogen, carbon and sulphur nucleophiles such as but not limited to amines, aromatic amines, amides, heterocycles, alcohols, phenols, cyanides or thiols are commercially or readily available in the neutral or in the deprotonated anionic form required for such transformation.

If necessary, further derivatisation or transformation can be performed in the substituents R4-R12 and X using standard methods of organic synthesis known to the person of ordinary skill in the art.

Scheme 1
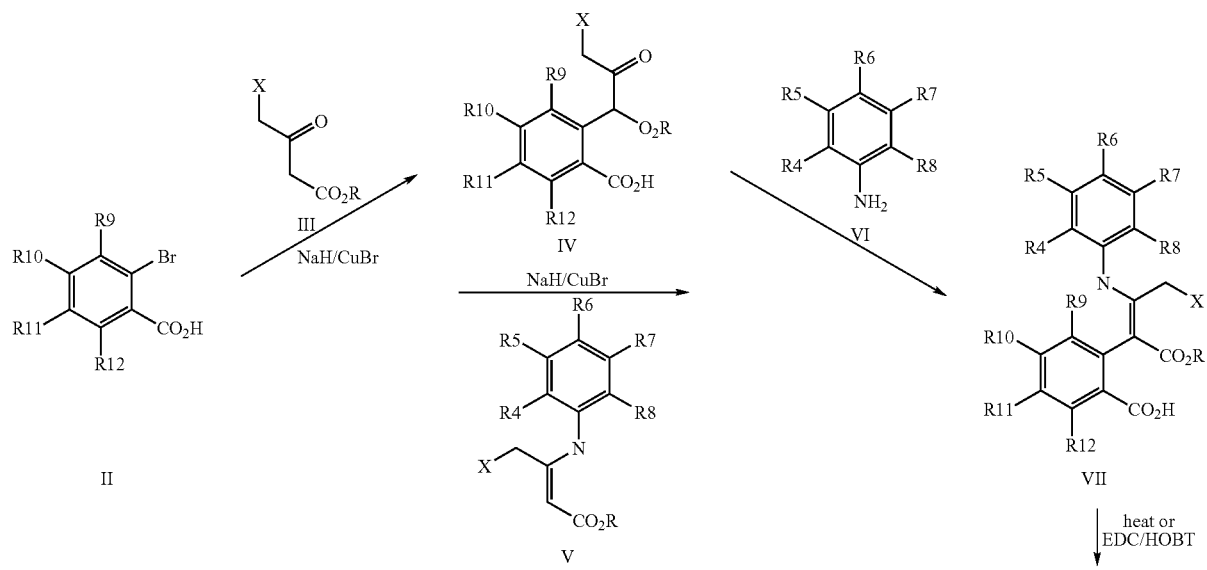
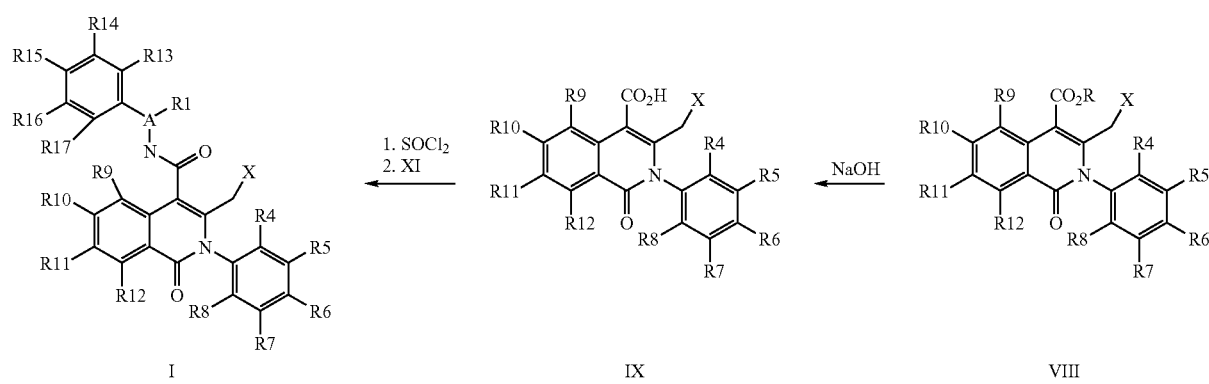
XI = 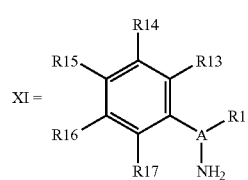

Scheme 2
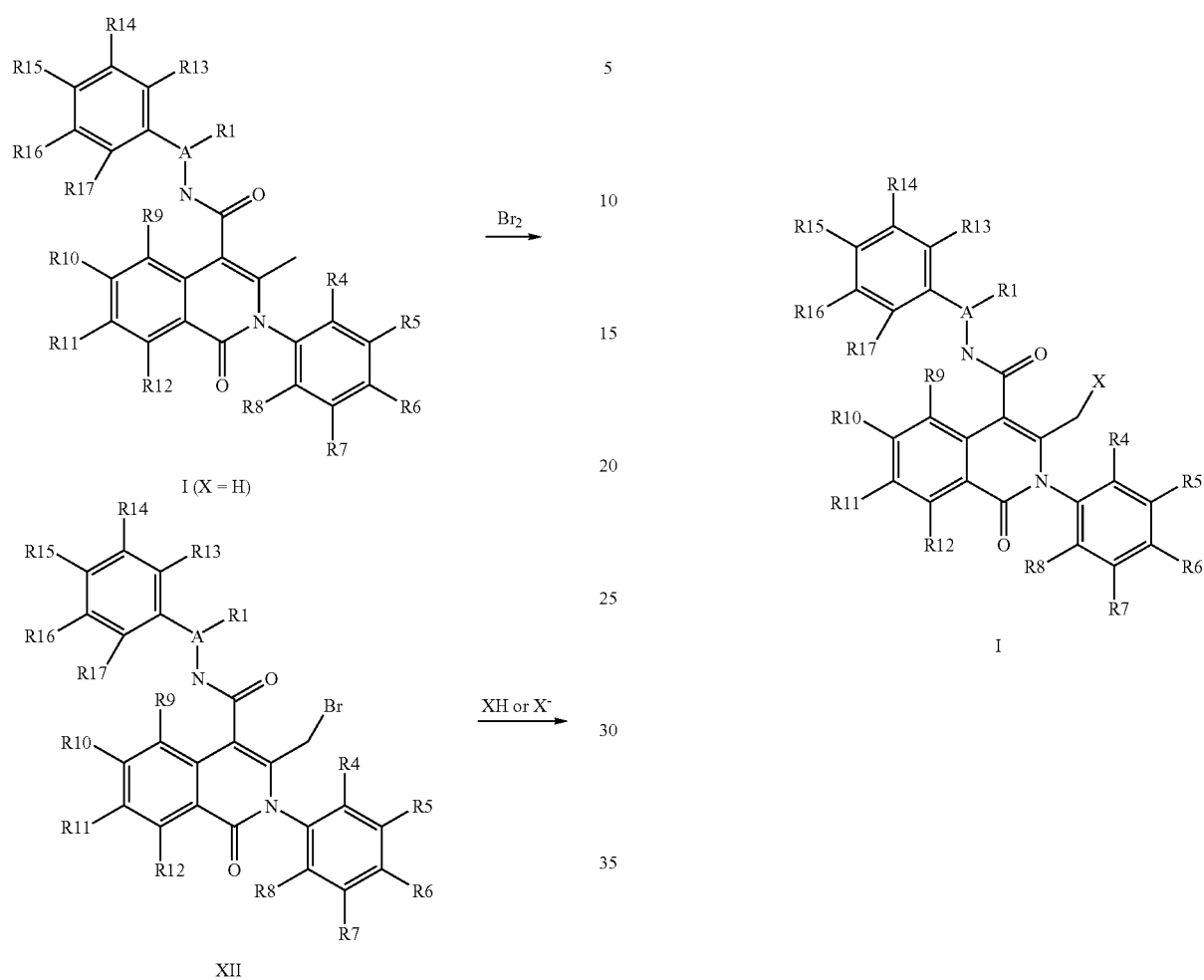
Scheme 3. Synthesis of homophthalic anhydrides
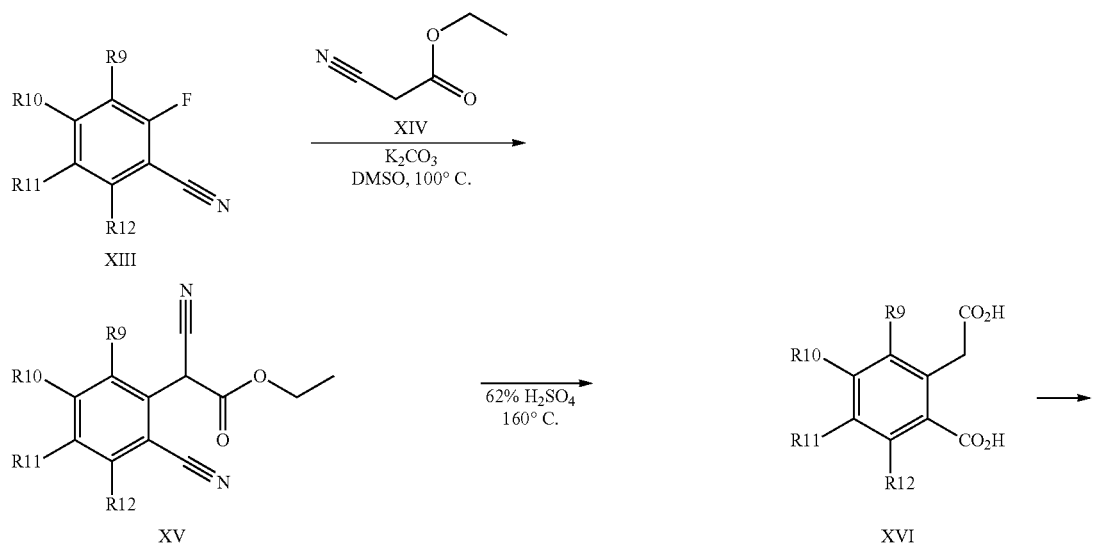

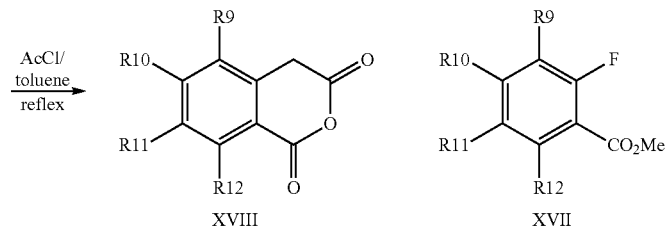
Scheme 4
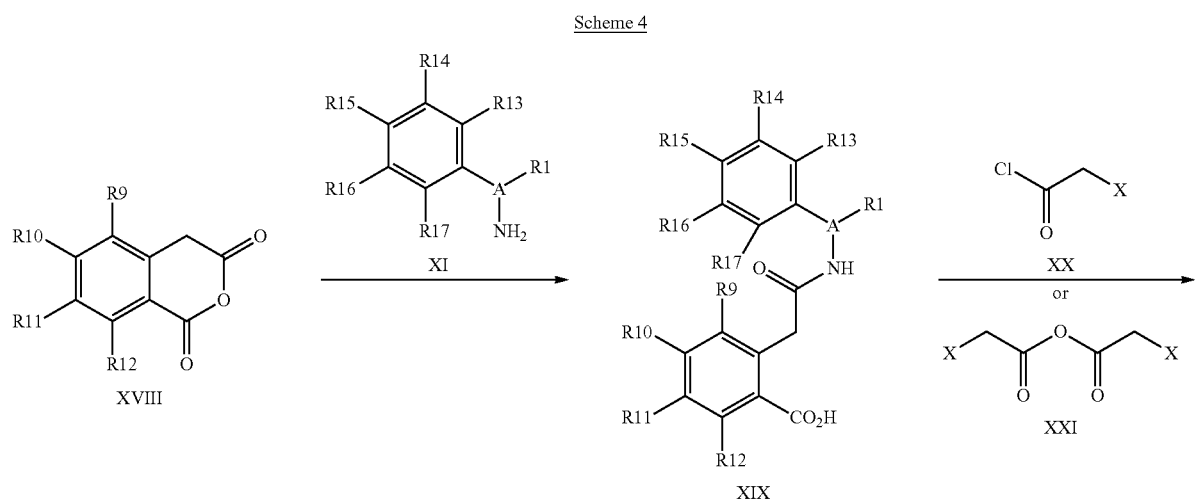
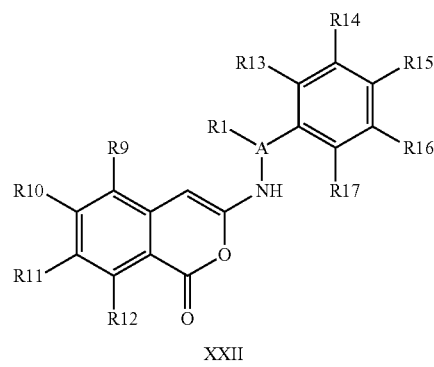

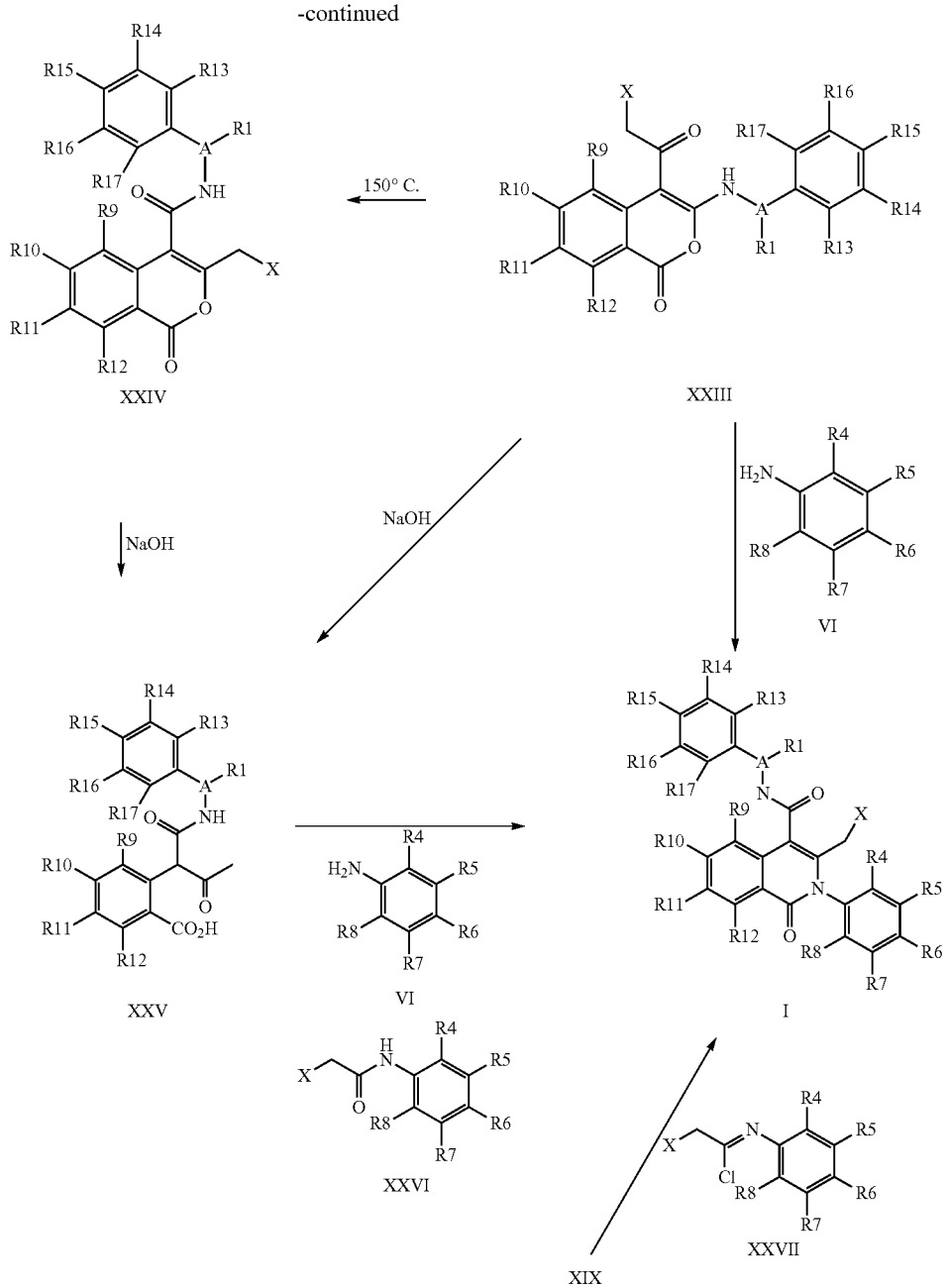

Alternatively, compounds of the general formula I can be prepared starting from substituted homophthalic anhydrides of the general formula XVIII as shown in Scheme 4. Homophthalic anhydrides are either commercially available or can be prepared as shown in scheme 3 starting from corresponding fluorobenzonitriles or fluorobenzoates of the general formula XIII and XVII, respectively. They undergo aromatic nucleophilic substitution reaction with ethyl cyanoacetate XIV in the presence of base such as potassium carbonate or cesium carbonate under heating conditions in appropriate solvent such as dimethylsulfoxide. The coupling products are hydrolyzed in the presence of the strong acids such as sulphuric or hydrochloric acids in water under heating conditions with the formation of diacids of the general formula XVI. Finally, the diacids are converted into the homophthalic anhydrides of the general formula XVIII in the presence of dehydrating agent such as but not limited to acetyl chloride without a solvent or in the appropriate solvent such as toluene under heating conditions such as reflux.

Homophthalic anhydrides of the general formula XVIII can be regioselectively converted into the acid-amides of the general formula XIX at room temperature or under heating conditions in the appropriate solvent such as acetonitrile. Then they are treated with appropriate acid anhydrides or acid chlorides of the general formula XX and XXI, respectively, in the absence or presence of base such as triethyl amine and DMAP in the appropriated solvent, usually in acetonitrile, at room temperature or under mild heating conditions (T<+100° C.). This transformation first provides intermediate keteneaminals of the general formula XXII, which undergo further acylation reaction with the formation of compounds of the general formula XXIII. Further heating at higher temperature such as at +150° C. leads to the rearrangement with the formation of amides of the general formula XIV. Both compounds of the general formula XXIII and XXIV can be readily hydrolyzed at ambient temperature with an appropriate base such as sodium hydroxide in aqueous methanol or aqueous tetrahydrofurane as a solvent. The obtained keto-acids of the general formula XXV or ketene-aminals of the general formula XXIII are converted to the final compounds of the invention of the general formula I by condensation with anilines of the general formula VI under the same conditions as described above for condensation with keto-acids of the general formula IV.

Alternatively, acid-amides of the general formula XIX can be converted directly to the compounds of the invention of the general formula I by condensation with appropriate imidoyl chlorides of the general formula XXVII which are readily available from corresponding amide of the general formula XXVI, which are easily prepared by well-known coupling between aniline of the general formula VI and corresponding carboxylic acids or their anhydrides or acid chlorides of the general formula XX and XXI, respectively.

EXAMPLES

Analytical LC-MS, method A (used in most cases unless noted otherwise): data were obtained on a Sciex API 150EX analytical LC/MS system equipped with Applied Biosystems API150EX single qaudrupole mass spectrometer and atmospheric pressure photo ionisation (APPI) ion source, Shimadzu LC10ADvp LC pumps (3×), Shimadzu SPD-M20A photodiode array detector, SEDERE Sedex 85—low temperature Evaporative Light Scattering Detector (ELSD), Shimadzu CBM-20A system controller, Gilson 215 autosampler and Gilson 864 degasser controlled by Analyst Software. Column: 30×4.6 mm Waters Symmetry C18 column with 3.5 μm particle size; Injection Volume: 15 μL; Column temperature: 60° C.; Solventsystem: A=water/trifluoroacetic acid (100:0.05) and B=water/acetonitrile/trifluoroacetic acid (5:95:0.035); Method: Linear gradient elution with 10% B to 100% B in 2.4 minutes then with 10% B in 0.4 minutes and with a flow rate of 3.3 mL/minute. The retention times ($t_R$) are expressed in minutes based on UV-trace at 254 nm.

Analytical LC-MS, method B: data were obtained on a Sciex API300 analytical LC/MS system equipped with Applied Biosystems API300 triple qaudrupole mass spectrometer with atmospheric pressure photo ionisation (APPI) ion source, Shimadzu LC10ADvp LC pumps (3×), Shimadzu SPD-M20A photodiode array detector, Polymer Labs PL-ELS 2100—low temperature Evaporative Light Scattering Detector (ELSD), Shimadzu SCL10A VP system controller, Gilson 215 autosampler and Gilson 864 degasser controlled by Analyst Software. Column: Symmetry C18 3.5 μm, 4.6× 30 mm 30×4.6 mm; Injection Volume: 5 μL; Column temperature: 60° C.; Solventsystem: A=water/trifluoroacetic acid (100:0.05) and B water/acetonitrile/trifluoroacetic acid (5:95: 0.035); Method: Linear gradient elution with 10% B to 100% B in 1.45 minutes then with 10% B in 0.55 minutes and with a flow rate of 5.5 mL/minute:

| Time, min. | % B |
|---|---|
| 0.00 | 10.0 |
| 1.45 | 100.0 |
| 1.55 | 10.0 |
| 2.0 | 10.0 |

The retention times ($t_R$) are expressed in minutes based on UV-trace at 254 nm.

Preparative LC-MS purification was performed on the same Sciex API 150EX system equipped with Gilson 333 and 334 pumps, Shimadzu LC10ADvp pump, Gilson UV/VIS 155 UV detector, Gilson 233XL autosampler, Gilson FC204 fraction, Gilson 506C system interface, Gilson 864 degasser, DIY flowsplitter (approx. 1:1000), and LC Packings Accurate flowsplitter (1:10.000 @ 140 ml/min). The MS and fraction collector was controlled by Masschrom software (Macintosh PC), the LC system was controlled by Unipoint software. For a small scale (<20 mg) purification fractions were collected in 4 ml vials using Symmetry C18 5 μm, 10×50 mm column, injection volume of 0-300 μL, flow rate of 5.7 ml/min and duration of 8 min. Gradient:

| Time, min. | % B |
|---|---|
| 0.00 | 10.0-50.0 (variable, depending on the sample) |
| 7.00 | 100.0 |
| 7.10 | 10.0-50.0 |
| 8.00 | 10.0-50.0 |

$^1$H NMR spectra were recorded at 500.13 MHz on a Bruker Avance DRX-500 instrument at T=303.3 K. Variable temperature $^1$H NMR spectra were recorded at 250 MHz on a Bruker Avance DPX-250 instrument. Deuterated dimethyl sulfoxide (DMSO-$d_6$, 99.8% D) was used as solvent unless noted otherwise. Tetramethylsilane was used as internal reference standard. Chemical shift values are expressed in ppm-values relative to tetramethylsilane. The following abbreviations or their combinations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and br=broad or broad singlet.

Microwave experiments were performed in sealed process vials or reactors using an Emrys Synthesizer or Emrys Optimizer EXP from Personal Chemistry or a Milestone Microsynth instrument from Milestone. Before sealing the process vial it was flashed with argon. When a reaction was heated in a microwave instrument, it was cooled to 25° C. before the next process step.

Preparation of Intermediates

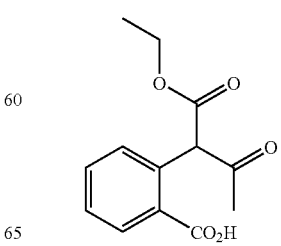

2-(1-Ethoxycarbonyl-2-oxo-propyl)-benzoic acid

To a cold (ice/water bath) stirred mixture of 2-bromobenzoic acid (20.1 g, 0.1 mol) and ethyl acetoacetate (13.01 g, 0.1 mol) in 1,4-dioxane (200 ml) sodium hydride (8 g, 0.2 mol, 60% dispersion in mineral oil) was added in small portions. After addition the cold bath was removed and the reaction mixture was allowed to stir at ambient temperature for 10 min. Copper (I) bromide (15.2 g, 0.106 mol) was added in portions and the obtained mixture was heated at reflux for 1 h. It was allowed to cool and stirred overnight at ambient temperature. The obtained green suspension was quenched with ethyl acetate (200 ml) and ice (300 g) and acidified with concentrated HCl (50 ml). The organic phase was washed with aq. 2 M HCl (2×100 ml) and brine, dried ($Na_2SO_4$) and evaporated in vacuo. The remaining mineral oil was removed by decantation after shaking with heptane (3×100 ml) and evaporation. Yield ca. 20 g, pale-yellow oil. The crude product was used in the next step without further purification. LC-MS (m/z) 205 ([M–$CO_2$]$^+$); $t_R$=0.91. $^1$H NMR (500 MHz, DMSO-$d_6$): mixture of at least 3 tautomers.

The following compounds were prepared analogously from corresponding 2-bromobenzoic acids and used in the next step without further purification and characterisation unless noted otherwise:

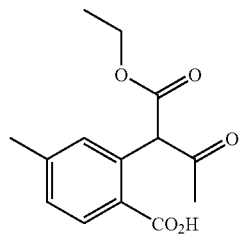

2-(1-Ethoxycarbonyl-2-oxo-propyl)-4-methyl-benzoic acid

LC-MS (m/z) 247.2 ([MH–$H_2O$]$^+$); $t_R$=1.05.

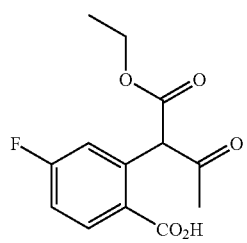

2-(1-Ethoxycarbonyl-2-oxo-propyl)-4-fluoro-benzoic acid

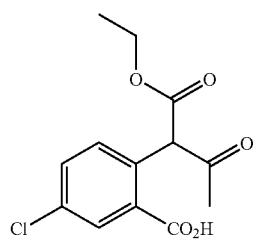

5-Chloro-2-(1-ethoxycarbonyl-2-oxo-propyl)-benzoic acid

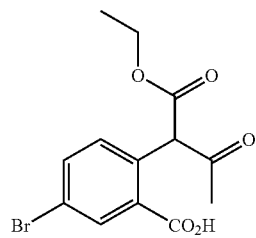

5-Bromo-2-(1-ethoxycarbonyl-2-oxo-propyl)-benzoic acid

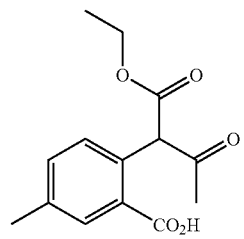

2-(1-Ethoxycarbonyl-2-oxo-propyl)-5-methyl-benzoic acid

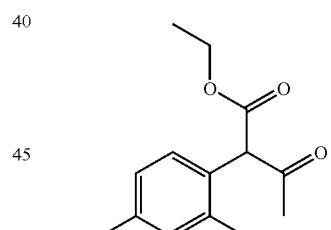

2-(1-Ethoxycarbonyl-2-oxo-propyl)-5-fluoro-benzoic acid

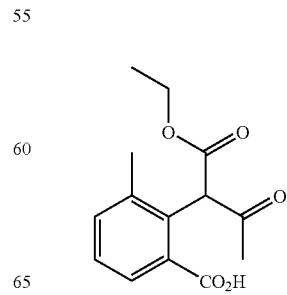

2-(1-Ethoxycarbonyl-2-oxo-propyl)-3-methyl-benzoic acid

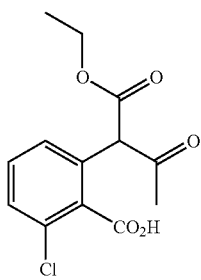

2-Chloro-6-(1-ethoxycarbonyl-2-oxo-propyl)-benzoic acid

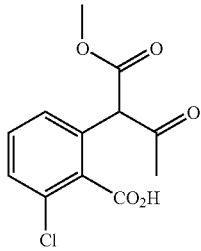

2-Chloro-6-(1-methoxycarbonyl-2-oxo-propyl)-benzoic acid

To a stirred mixture of 2-bromo-6-chlorobenzoic acid (20 g, 85 mmol), methylacetoacetate (310 ml, excess), and copper (I) bromide 12.2 g, 85 mmol) sodium hydride (8.5 g, 212 mmol, 60% in oil) was added by portions and then heated at 70° C. for 16 hours. The resulting mixture was diluted with water (600 ml) and extracted with diethyl ether (3×500 ml). Aqueous phase was acidified with 2M HCl and extracted with ethyl acetate (2×800 ml). The combined organic solution was washed with brine (100 ml), dried ($Na_2SO_4$) and evaporated. The obtained oil was treated with a hot mixture of ethyl acetate (20 ml) and heptane (200 ml) and decanted for 2 times, dried in vacuo to give 8 g of yellow-brown solid, yield 34%. $^1$H NMR (500 MHz, DMSO-$d_6$): 1.73 (s, 3H), 3.6 (s, 3H), 7.24 (d, 1H), 7.44 (t, 2H), 7.5 (d, 1H), 12.85 (s, 1H, OH of enol form), 13.4 (br, 1H, $CO_2H$).

2-(1-Methoxycarbonyl-2-oxo-propyl)-6-nitro-benzoic acid

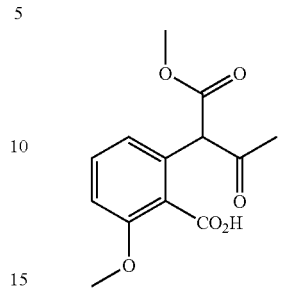

2-Methoxy-6-(1-methoxycarbonyl-2-oxo-propyl)-benzoic acid

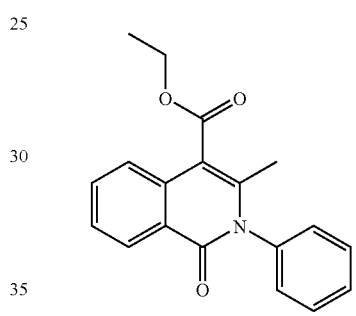

3-Methyl-1-oxo-2-phenyl-1,2-dihydro-isoquinoline-4-carboxylic acid ethyl ester A mixture of 2-(1-ethoxycarbonyl-2-oxo-propyl)-benzoic acid (7.6 g, 30.4 mmol) and aniline (10 ml, 108 mmol) was flushed with argon, sealed in the Emrys process vial and heated at 150° C. for 15 min under microwave irradiation. The volatiles were removed in vacuo and the obtained residue was partitioned between ethyl acetate (100 ml) and 2M HCl (100 ml). The organic layer was washed with brine (2×20 ml), dried ($Na_2SO_4$) and evaporated to give 8.7 g of brown oil that solidified. The obtained crude product was of ca. 90% purity according to $^1$H NMR and can be used in the next step without further purification. Alternatively, the crude product was dissolved in hot ethyl acetate (20 ml), precipitated with heptane (60 ml), allowed to cool, filtered and washed with diethyl ether to give 4.2 g of a pale-brown crystalline solid, yield 45%. LC-MS (m/z) 308.2 (MH$^+$); $t_R$=1.43. $^1$H NMR (500 MHz, DMSO-$d_6$): 1.34 (t, 3H), 1.97 (s, 3H), 4.41 (q, 2H), 7.38 (d, 2H), 7.51 (t, 1H), 7.56 (t overlapping m, 3H), 7.62 (d, 1H), 7.8 (t, 1H), 8.22 (d, 1H).

The following compounds were prepared analogously from corresponding crude 2-(1-ethoxycarbonyl-2-oxo-propyl)-4-methylbenzoic acids and corresponding anilines.

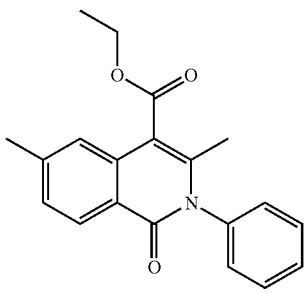

3,6-Dimethyl-1-oxo-2-phenyl-1,2-dihydro-isoquinoline-4-carboxylic acid ethyl ester The crude product was used in the next step without crystallization. LC-MS (m/z) 322.1 (MH$^+$); $t_R$=1.53. $^1$H NMR (500 MHz, DMSO-d$_6$): 1.34 (t, 3H), 1.96 (s, 3H), 2.47 (s, 3H), 4.41 (q, 2H), 7.28 (t, 1H), 7.37 (m, 3H), 7.50 (d, 1H), 7.56 (m, 2H), 8.11 (d, 1H).

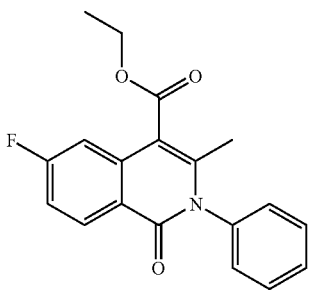

6-Fluoro-3-methyl-1-oxo-2-phenyl-1,2-dihydro-isoquinoline-4-carboxylic acid ethyl ester The crude product was used in the next step without crystallization. LC-MS (m/z) 326.3 (MH$^+$); $t_R$=1.54. $^1$H NMR (500 MHz, DMSO-d$_6$): 1.33 (t, 3H), 2.0 (s, 3H), 4.41 (q, 2H), 7.28 (t, 1H), 7.39 (d, 2H), 7.42 (m, 1H), 7.51 (t, 1H), 7.57 (t, 2H), 8.29 (dd, 1H).

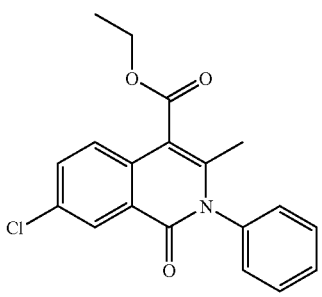

7-Chloro-3-methyl-1-oxo-2-phenyl-1,2-dihydro-isoquinoline-4-carboxylic acid ethyl ester The crude product was used in the next step without crystallization. LC-MS (m/z) 342.0 (MH$^+$); $t_R$=1.67. $^1$H NMR (500 MHz, DMSO-d$_6$): 1.33 (t, 3H), 1.98 (s, 3H), 4.41 (q, 2H), 7.4 (d, 2H), 7.51 (t, 1H), 7.57 (t, 2H), 7.7 (d, 1H), 7.85 (dd, 1H), 8.15 (d, 1H).

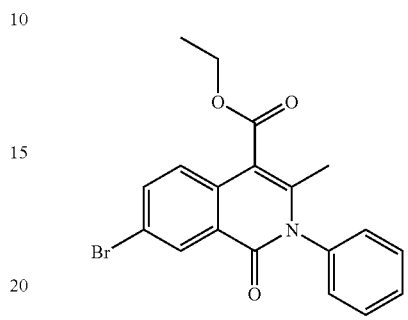

7-Bromo-3-methyl-1-oxo-2-phenyl-1,2-dihydro-isoquinoline-4-carboxylic acid ethyl ester The crude product was used in the next step without crystallization. LC-MS (m/z) 386.1 (MH$^+$, $^{79}$Br); $t_R$=1.71. $^1$H NMR (500 MHz, DMSO-d$_6$): 1.33 (t, 3H), 1.98 (s, 3H), 4.4 (q, 2H), 7.39 (d, 2H), 7.51 (t, 1H), 7.57 (t, 2H), 7.62 (d, 1H), 7.96 (dd, 1H), 8.29 (d, 1H).

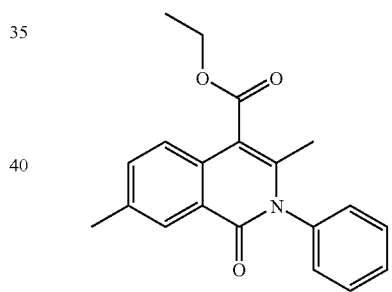

3,7-Dimethyl-1-oxo-2-phenyl-1,2-dihydro-isoquinoline-4-carboxylic acid ethyl ester The crude product as a brown oil was used in the next step without purification. LC-MS (m/z) 322.2 (MH$^+$); $t_R$=1.59.

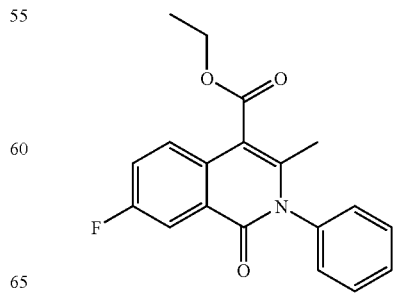

7-Fluoro-3-methyl-1-oxo-2-phenyl-1,2-dihydro-iso-
quinoline-4-carboxylic acid ethyl ester The crude product as a brown oil was used in the next step without purification. LC-MS (m/z) 326.1 (MH$^+$); $t_R$=0.79 (method B).

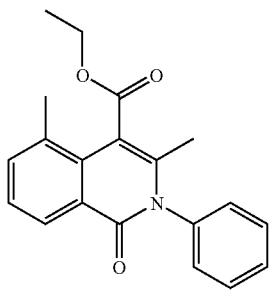

3,5-Dimethyl-1-oxo-2-phenyl-1,2-dihydro-isoquino-
line-4-carboxylic acid ethyl ester The crude product was used in the next step without purification. LC-MS (m/z) 322.1 (MH$^+$); $t_R$=1.63.

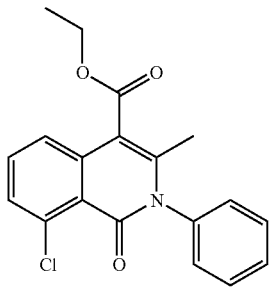

8-Chloro-3-methyl-1-oxo-2-phenyl-1,2-dihydro-
isoquinoline-4-carboxylic acid ethyl ester The crude product was used in the next step without purification. LC-MS (m/z) 342.0 (MH$^+$); $t_R$=1.55.

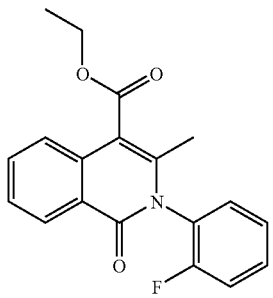

2-(2-Fluoro-phenyl)-3-methyl-1-oxo-1,2-dihydro-
isoquinoline-4-carboxylic acid ethyl ester LC-MS (m/z) 326.5 (MH$^+$); $t_R$=1.46.

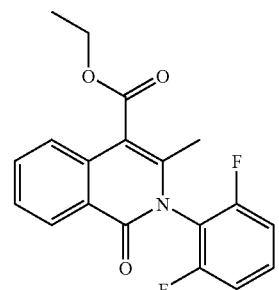

2-(2,6-Difluoro-phenyl)-3-methyl-1-oxo-1,2-dihy-
dro-isoquinoline-4-carboxylic acid ethyl ester The crude product was used in the next step without purification and characterization.

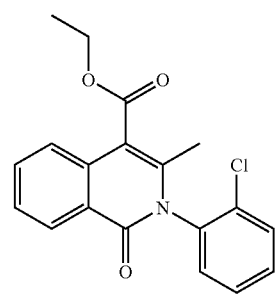

2-(2-Chloro-phenyl)-3-methyl-1-oxo-1,2-dihydro-
isoquinoline-4-carboxylic acid ethyl ester The crude product was used in the next step without purification and characterization.

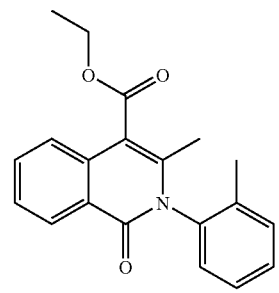

3-Methyl-1-oxo-2-o-tolyl-1,2-dihydro-isoquinoline-4-carboxylic acid ethyl ester The crude product was used in the next step without purification and characterization.

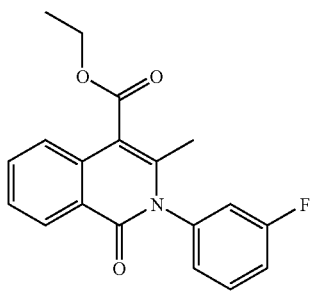

2-(3-Fluoro-phenyl)-3-methyl-1-oxo-1,2-dihydro-isoquinoline-4-carboxylic acid ethyl ester LC-MS (m/z) 326.3 (MH$^+$); t$_R$=1.47.

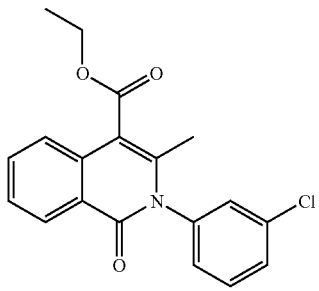

2-(3-Chloro-phenyl)-3-methyl-1-oxo-1,2-dihydro-isoquinoline-4-carboxylic acid ethyl ester LC-MS (m/z) 342.1 (MH$^+$); t$_R$=1.61.

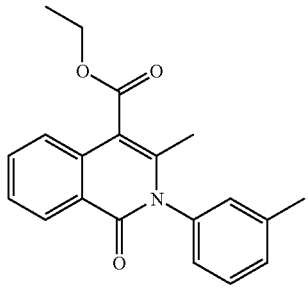

3-Methyl-1-oxo-2-m-tolyl-1,2-dihydro-isoquinoline-4-carboxylic acid ethyl ester LC-MS (m/z) 322.1 (MH$^+$); t$_R$=1.57.

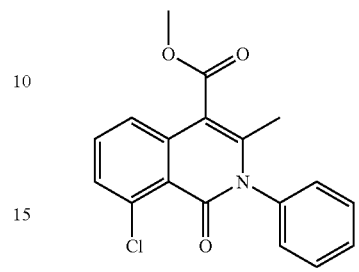

8-Chloro-3-methyl-1-oxo-2-phenyl-1,2-dihydro-isoquinoline-4-carboxylic acid methyl ester A mixture of 2-chloro-6-(1-methoxycarbonyl-2-oxo-propyl)-benzoic acid (4 g, 15 mmol), aniline (1.369 ml, 15 mmol) and tetraethoxysilane (6.65 ml, 30 mmol) in methanol (20 ml) was sealed and heated under microwave irradiation at +150° C. for 20 min. The obtained solution was diluted with water (150 ml) and extracted with ethyl acetate (2×300 ml). The combined organic solution was dried (MgSO$_4$) and evaporated. The obtained crude enamine (2-chloro-6-(1-methoxycarbonyl-2-phenylamino-propenyl)-benzoic acid) was dissolved in dimethylformamide (80 ml) followed by addition of 1-ethyl-3-(3-dimethylaminopropyl)carbodiimide hydrochloride (EDC, 4.3 g, 22.5 mmol) and 1-hydroxybenzotriazole (HOBT, 3.04 g, 22.5 mmol). It was stirred for 16 hours and partitioned between water (250 ml), diethyl ether (250 ml) and ethyl acetate (150 ml). The organic phase was washed with 0.5 M NaOH (2×100 ml), brine (2×200 ml), dried (MgSO$_4$) and evaporated to give 4.25 g of brown oil, which was used in the next step without further purification. Yield 87%. LC-MS (m/z) 328.0 (MH$^+$); t$_R$=1.36. $^1$H NMR (500 MHz, CDCl$_3$): 2.02 (s, 3H), 3.98 (s, 3H), 7.23 (d, 2H), 7.44-7.55 (m, 6H).

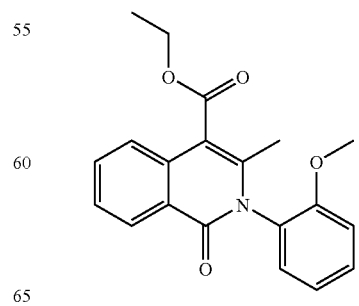

2-(2-Methoxy-phenyl)-3-methyl-1-oxo-1,2-dihydro-isoquinoline-4-carboxylic acid ethyl ester The title compound was used in the next step without purification. LC-MS (m/z) 338.3 (MH$^+$); $t_R$=1.38.

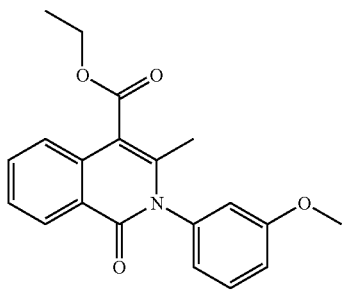

2-(3-Methoxy-phenyl)-3-methyl-1-oxo-1,2-dihydro-isoquinoline-4-carboxylic acid ethyl ester The title compound was used in the next step without purification. LC-MS (m/z) 338.5 (MH$^+$); $t_R$=1.41.

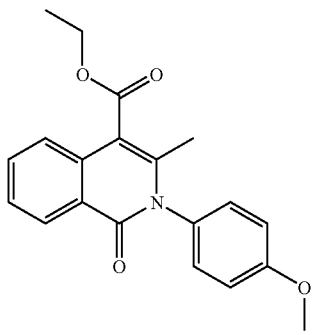

2-(4-Methoxy-phenyl)-3-methyl-1-oxo-1,2-dihydro-isoquinoline-4-carboxylic acid ethyl ester The title compound was used in the next step without purification. LC-MS (m/z) 338.5 (MH$^+$); $t_R$=1.4.

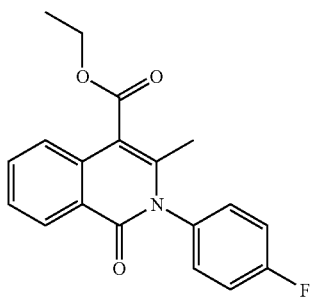

2-(4-Fluoro-phenyl)-3-methyl-1-oxo-1,2-dihydro-isoquinoline-4-carboxylic acid ethyl ester The title compound was used in the next step without purification. LC-MS (m/z) 326.2 (MH$^+$); $t_R$=1.41.

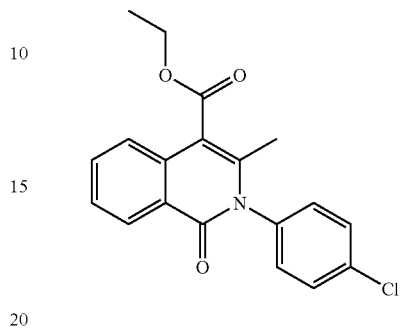

2-(4-Chloro-phenyl)-3-methyl-1-oxo-1,2-dihydro-isoquinoline-4-carboxylic acid ethyl ester The title compound was used in the next step without purification. LC-MS (m/z) 342.2 (MH$^+$); $t_R$=1.53.

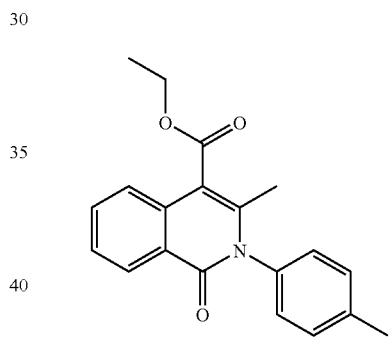

3-Methyl-1-oxo-2-p-tolyl-1,2-dihydro-isoquinoline-4-carboxylic acid ethyl ester The title compound was used in the next step without purification. LC-MS (m/z) 321.7 (MH$^+$); $t_R$=1.51.

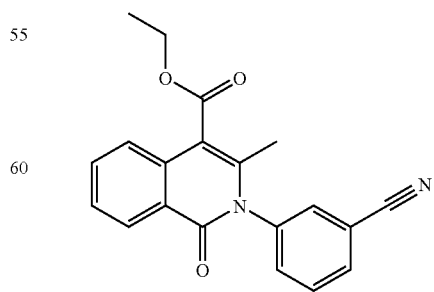

2-(3-Cyano-phenyl)-3-methyl-1-oxo-1,2-dihydro-isoquinoline-4-carboxylic acid ethyl ester The title compound was used in the next step without purification. LC-MS (m/z) 333.0 (MH$^+$); t$_R$=1.3.

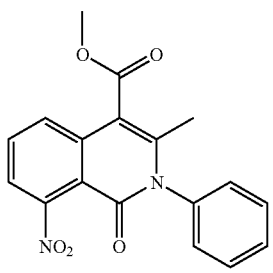

3-Methyl-8-nitro-1-oxo-2-phenyl-1,2-dihydro-isoquinoline-4-carboxylic acid methyl ester The title compound was used in the next step without purification. LC-MS (m/z) 339.3 (MH$^+$); t$_R$=1.26.

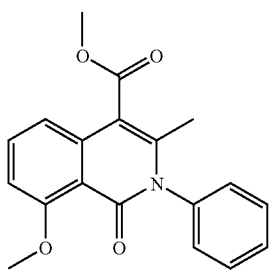

8-Methoxy-3-methyl-1-oxo-2-phenyl-1,2-dihydro-isoquinoline-4-carboxylic acid methyl ester The title compound was used in the next step without purification. LC-MS (m/z) 324.3 (MH$^+$); t$_R$=1.12.

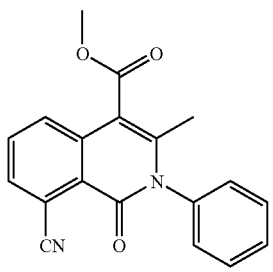

8-Cyano-3-methyl-1-oxo-2-phenyl-1,2-dihydro-isoquinoline-4-carboxylic acid methyl ester A suspension of 3-methyl-8-nitro-1-oxo-2-phenyl-1,2-dihydro-isoquinoline-4-carboxylic acid methyl ester (320 mg, 0.95 mmol) and Zn (898 mg, 13.8 mmol) in THF (4.5 ml) and 2M aq. HCl (4.5 ml) was stirred for 10 min, filtered and partitioned between ethyl acetate (3×150 ml) and sat. aq. NaHCO$_3$ (100 ml). The combined organic solution was dried (MgSO$_4$) and evaporated to give 8-amino-3-methyl-1-oxo-2-phenyl-1,2-dihydro-isoquinoline-4-carboxylic acid methyl ester as a dark oil (200 mg, 0.645 mmol, 69% yield. LC-MS (m/z) 309.4 (MH$^+$); t$_R$=1.2. It was dissolved in conc. aq. HCl (0.4 ml) and H$_2$O (3.25 ml). To the obtained solution NaNO$_2$ (46.3 mg, 0.645 mmol, in 0.12 ml H$_2$O) was added dropwise at 0° C. After 15 min it was neutralized (pH=6-7) with sat. aq. NaHCO$_3$ to give diazonium salt solution. To a solution of KCN (202 mg, 3 mmol) in water (0.4 ml) solution of CuSO$_4$× 5H$_2$O (197 mg, 0.774 mmol) in water (0.8 ml) was added dropwise at 0° C. After addition completion benzene (2 ml) was added and the mixture was warmed to +60° C. To this mixture diazonium salt solution was added dropwise during 15 min then kept at 70° C. for 85 min. It was allowed to cool to r.t., diluted with ethyl acetate (10 ml) and filtered via plug of cellite. The organic layer was washed with brine (10 ml), dried (MgSO$_4$) and evaporated to give 97.9 mg of the title compound (48% yield). LC-MS (m/z) 319.2 (MH$^+$); t$_R$=1.15.

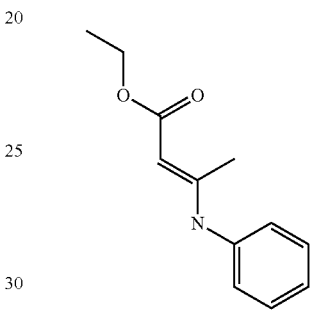

3-Phenylamino-but-2-enoic acid ethyl ester

The compound was prepared according to the described procedure (Q. Dai, W. Yang, and X. Zhang *Org. Letters* 2005, 5343).

$^1$H NMR (500 MHz, DMSO-d$_6$): 1.19 (t, 3H), 2.01 (s, 3H), 4.06 (q, 2H), 4.7 (s, 1H), 7.17 (overlapping t, 1H), 7.18 (overlapping d, 2H), 7.36 (t, 2H), 10.36 (s, 1H).

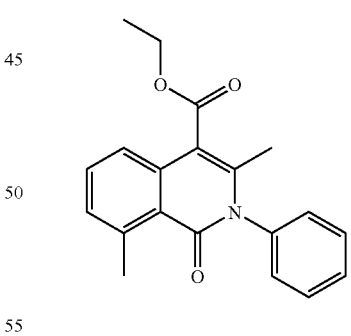

3,8-Dimethyl-1-oxo-2-phenyl-1,2-dihydro-isoquinoline-4-carboxylic acid ethyl ester To a cold (ice/water bath) solution of 2-bromo-6-methyl-benzoic acid (650 mg, 3.023 mmol) and 3-phenylamino-but-2-enoic acid ethyl ester (750 mg, 3.65 mmol) in acetonitrile (10 ml), sodium hydride (267 mg, 6.67 mmol, 60% dispersion in mineral oil) was added in portions. The cold bath was removed and the mixture was sonicated at ambient temperature until gas evolution ceased (10 min). Copper (I) bromide was added (957 mg, 6.67 mmol) and the obtained suspension was flushed with argon, sealed and heated under microwave irradiation at +80° C. for 30 min. LC-MS indicated a full conversion to 2-(1-ethoxycarbonyl-2-phenylamino-propenyl)-6-methyl-benzoic acid (LC-MS (m/z) 340.4 (MH$^+$); $t_R$=1.59. The obtained suspension was heated at +160° C. under microwave irradiation for 30 min. It was diluted with ethyl acetate (50 ml) and filtered. The obtained organic solution was washed with 1M HCl (3×50 ml), water (2×10 ml) and sat. aq. NaHCO$_3$ solution (30 ml), absorbed on SiO$_2$ (3 g) and flash chromatographed on SiO$_2$ (50 g, gradient heptane-30% ethyl acetate in heptane) to give 217 mg of yellow oil. Yield 22%. LC-MS (m/z) 322.2 (MH$^+$); $t_R$=1.62. $^1$H NMR (500 MHz, DMSO-d$_6$): 1.32 (t, 3H), 1.91 (s, 3H), 2.74 (s, 3H), 4.39 (q, 2H), 7.3 (d, 1H), 7.36 (overlapping m, 3H), 7.49 (m, 1H), 7.55 (t, 2H), 7.61 (t, 1H).

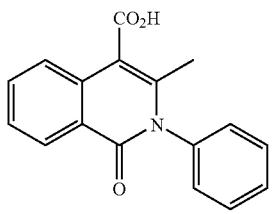

3-Methyl-1-oxo-2-phenyl-1,2-dihydro-isoquinoline-4-carboxylic acid

3-Methyl-1-oxo-2-phenyl-1,2-dihydro-isoquinoline-4-carboxylic acid ethyl ester (4.2 g, 13.7 mmol) was dissolved in 100 ml of hot methanol and a solution of NaOH (6 g) in water (20 ml) was added. The reaction mixture was heated at reflux for 2 hrs, diluted with water (200 ml) and stirred overnight at ambient temperature. Organic volatiles were removed under reduced pressure and the obtained aqueous solution was extracted with ethyl acetate (2×50 ml). The aqueous solution was poured into ice/2M HCl (150 ml). The obtained suspension was sonicated, and the product was separated by filtration, washed with water and dried in vacuo to give 2.9 g of a colourless solid, yield 76%. LC-MS (m/z) 280.2 (MH$^+$); $t_R$=0.9. $^1$H NMR (500 MHz, DMSO-d$_6$): 2.01 (s, 3H), 7.36 (d, 2H), 7.50 (t, 1H), 7.56 (q (overlapping m), 3H), 7.72 (d, 1H), 7.81 (t, 1H), 8.22 (d, 1H), 13.5 (br, 1H).

The following acids were prepared analogously from corresponding ethyl esters:

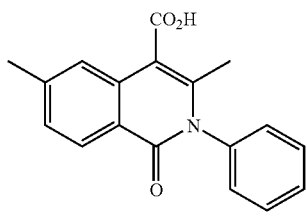

3,6-Dimethyl-1-oxo-2-phenyl-1,2-dihydro-isoquinoline-4-carboxylic acid

LC-MS (m/z) 293.9 (MH$^+$); $t_R$=0.99. $^1$H NMR (500 MHz, DMSO-d$_6$): 2.0 (s, 3H), 2.47 (s, 3H), 7.34 (d, 2H), 7.38 (d, 1H), 7.47 (s, 1H), 7.50 (d, 1H), 7.56 (t, 2H), 8.11 (d, 1H), 13.4 (br, 1H).

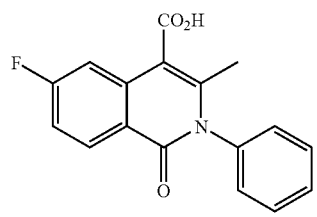

6-Fluoro-3-methyl-1-oxo-2-phenyl-1,2-dihydro-isoquinoline-4-carboxylic acid

LC-MS (m/z) 298.4 (MH$^+$); $t_R$=0.99. $^1$H NMR (500 MHz, DMSO-d$_6$): 2.05 (s, 3H), 7.37 (d, 2H), 7.41 (dt, 1H), 7.48 (dd, 1H), 7.51 (t, 1H), 7.57 (t, 2H), 8.28 (dd, 1H), 13.6 (b, 1H).

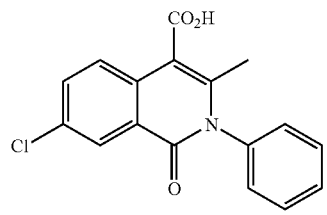

7-Chloro-3-methyl-1-oxo-2-phenyl-1,2-dihydro-isoquinoline-4-carboxylic acid

The crude product was used in the next step without crystallization. LC-MS (m/z) 314.2 (MH$^+$); $t_R$=1.13. $^1$H NMR (500 MHz, DMSO-d$_6$): $^1$H NMR (500 MHz, DMSO-d$_6$): 2.03 (s, 3H), 7.38 (d, 2H), 7.51 (t, 1H), 7.57 (t, 2H), 7.79 (d, 1H), 7.86 (dd, 1H), 8.15 (d, 1H), 13.55 (b, 1H).

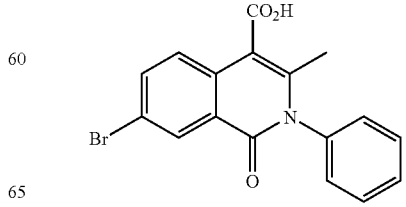

7-Bromo-3-methyl-1-oxo-2-phenyl-1,2-dihydro-isoquinoline-4-carboxylic acid

LC-MS (m/z) 358.1 (MH$^+$, $^{79}$Br); $t_R$=1.2. $^1$H NMR (500 MHz, DMSO-d$_6$): 2.02 (s, 3H), 7.38 (d, 2H), 7.51 (t, 1H), 7.57 (t, 2H), 7.72 (d, 1H), 7.97 (dd, 1H), 8.29 (d, 1H), 13.55 (b, 1H).

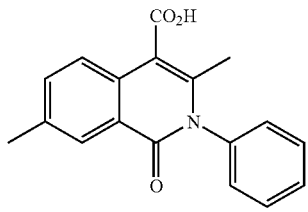

3,7-Dimethyl-1-oxo-2-phenyl-1,2-dihydro-isoquinoline-4-carboxylic acid

LC-MS (m/z) 293.9 (MH$^+$); $t_R$=1.02. $^1$H NMR (500 MHz, DMSO-d$_6$): 2.0 (s, 3H), 2.45 (s, 3H), 7.34 (d, 2H), 7.5 (t, 1H), 7.56 (t, 2H), 7.63 (m, 2H), 8.02 (s, 1H), 13.38 (br, 1H).

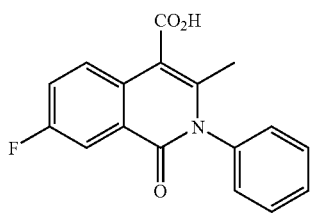

7-Fluoro-3-methyl-1-oxo-2-phenyl-1,2-dihydro-isoquinoline-4-carboxylic acid

LC-MS (m/z) 298.2 (MH$^+$); $t_R$=1.01. $^1$H NMR (500 MHz, DMSO-d$_6$): 2.02 (s, 3H), 7.37 (d, 2H), 7.51 (t, 1H), 7.57 (t, 2H), 7.71 (dt, 1H), 7.83 (dd, 1H), 7.88 (dd, 1H), 13.54 (br, 1H).

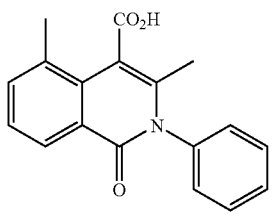

3,5-Dimethyl-1-oxo-2-phenyl-1,2-dihydro-isoquinoline-4-carboxylic acid

LC-MS (m/z) 294.1 (MH$^+$); $t_R$=1.09. $^1$H NMR (500 MHz, DMSO-d$_6$): 1.95 (s, 3H), 2.74 (s, 3H), 7.27-7.64 (m, 8H), 13.35 (b, 1H).

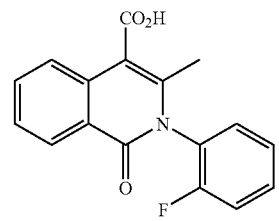

2-(2-Fluoro-phenyl)-3-methyl-1-oxo-1,2-dihydro-isoquinoline-4-carboxylic acid LC-MS (m/z) 298.4 (MH$^+$); $t_R$=0.83.

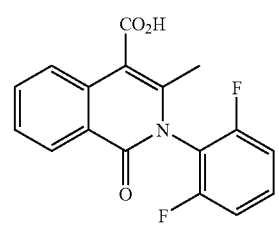

2-(2,6-Difluoro-phenyl)-3-methyl-1-oxo-1,2-dihydro-isoquinoline-4-carboxylic acid LC-MS (m/z) 316.2 (MH$^+$); $t_R$=1.03.

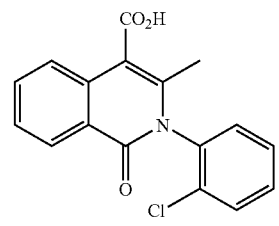

2-(2-Chloro-phenyl)-3-methyl-1-oxo-1,2-dihydro-isoquinoline-4-carboxylic acid LC-MS (m/z) 314.2 (MH$^+$); $t_R$=1.0.

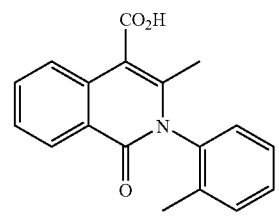

3-Methyl-1-oxo-2-o-tolyl-1,2-dihydro-isoquinoline-4-carboxylic acid

LC-MS (m/z) 294.1 (MH$^+$); $t_R$=0.99.

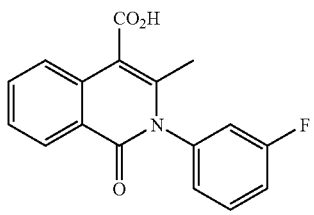

2-(3-Fluoro-phenyl)-3-methyl-1-oxo-1,2-dihydro-isoquinoline-4-carboxylic acid LC-MS (m/z) 298.4 (MH$^+$); $t_R$=0.96. $^1$H NMR (250 MHz, DMSO-d$_6$): 2.02 (s, 3H), 7.24 (d, 1H), 7.32-7.42 (m, 2H), 7.5-7.65 (m, 2H), 7.71 (d, 1H), 7.81 (m, 1H), 8.21 (d, 1H), 13.49 (br, 1H).

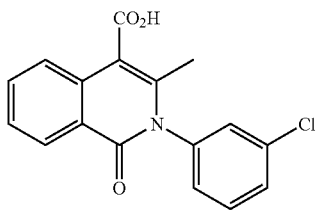

2-(3-Chloro-phenyl)-3-methyl-1-oxo-1,2-dihydro-isoquinoline-4-carboxylic acid LC-MS (m/z) 314.2 (MH$^+$); $t_R$=1.09. $^1$H NMR (500 MHz, DMSO-d$_6$): 2.04 (s, 3H), 7.39 (t, 1H), 7.56 (t, 1H), 7.58-7.62 (m, 3H), 7.72 (d, 1H), 7.81 (t, 1H), 8.21 (d, 1H), 13.5 (br, 1H).

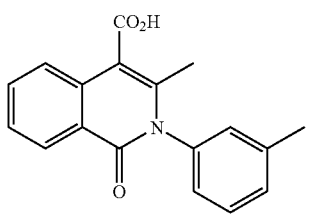

3-Methyl-1-oxo-2-m-tolyl-1,2-dihydro-isoquinoline-4-carboxylic acid

LC-MS (m/z) 293.9 (MH$^+$); $t_R$=1.03. $^1$H NMR (250 MHz, DMSO-d$_6$): 2.02 (s, 3H), 2.38 (s, 3H), 7.14 (overlapping d, 1H), 7.16 (overlapping s, 1H), 7.31 (d, 1H), 7.44 (t, 1H), 7.54 (t, 1H), 7.71 (d, 1H), 7.8 (t, 1H), 8.21 (d, 1H), 13.46 (br, 1H).

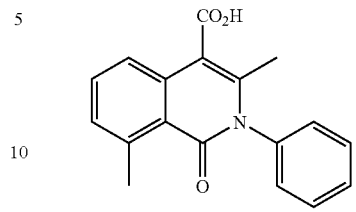

3,8-Dimethyl-1-oxo-2-phenyl-1,2-dihydro-isoquinoline-4-carboxylic acid

A solution of 3,8-dimethyl-1-oxo-2-phenyl-1,2-dihydro-isoquinoline-4-carboxylic acid ethyl ester (200 mg, 0.62 mmol) in DMSO (3 ml) and aqueous 1N NaOH (2 ml, 2 mmol) was heated under microwave irradiation at +120° C. for 20 min and diluted with water (30 ml). Uncharged impurities were extracted with diethyl ether (30 ml) and the aqueous solution was poured into ice (50 g) with aqueous 2M HCl (10 ml). The obtained precipitate was filtered, washed with water and dried in vacuo to give 75 mg of yellow solid. Yield 41%. LC-MS (m/z) 293.9 (MH$^+$); $t_R$=1.09. $^1$H NMR (500 MHz, DMSO-d$_6$): 1.95 (s, 3H), 2.74 (s, 3H), 7.3 (d, 1H), 7.32 (d, 2H), 7.48 (two overlapping m, 2H), 7.55 (t, 2H), 7.62 (t, 1H), 13.42 (b, 1H).

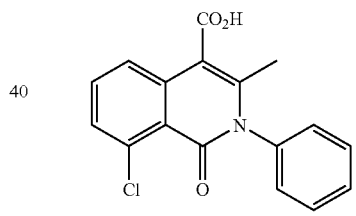

8-Chloro-3-methyl-1-oxo-2-phenyl-1,2-dihydro-isoquinoline-4-carboxylic acid

The title compound was prepared analogously by hydrolysis of the corresponding methyl or ethyl ester at 100° C. LC-MS (m/z) 314.1 (MH$^+$); $t_R$=1.03.

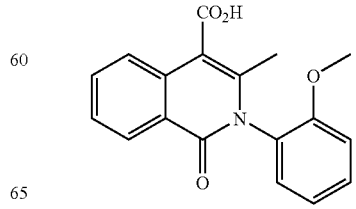

2-(2-Methoxy-phenyl)-3-methyl-1-oxo-1,2-dihydro-isoquinoline-4-carboxylic acid The title compound was used in the next step without purification. LC-MS (m/z) 310.3 (MH$^+$); $t_R$=0.87.

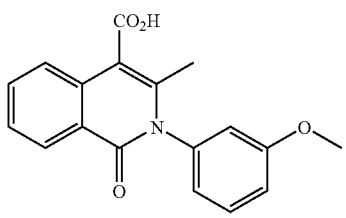

2-(3-Methoxy-phenyl)-3-methyl-1-oxo-1,2-dihydro-isoquinoline-4-carboxylic acid The title compound was used in the next step without purification. LC-MS (m/z) 310.4 (MH$^+$); $t_R$=0.9

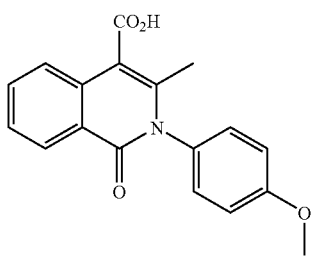

2-(4-Methoxy-phenyl)-3-methyl-1-oxo-1,2-dihydro-isoquinoline-4-carboxylic acid The title compound was used in the next step without purification. LC-MS (m/z) 310.4 (MH$^+$); $t_R$=0.89.

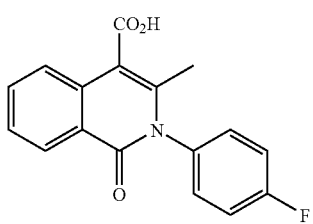

2-(4-Fluoro-phenyl)-3-methyl-1-oxo-1,2-dihydro-isoquinoline-4-carboxylic acid The title compound was used in the next step without purification. LC-MS (m/z) 298.2 (MH$^+$); $t_R$=0.9

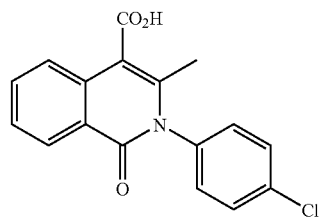

2-(4-Chloro-phenyl)-3-methyl-1-oxo-1,2-dihydro-isoquinoline-4-carboxylic acid The title compound was used in the next step without purification. LC-MS (m/z) 314.2 (MH$^+$); $t_R$=1.53.

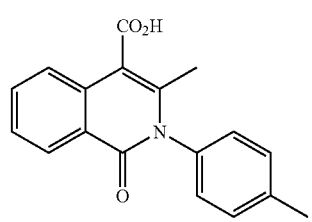

3-Methyl-1-oxo-2-p-tolyl-1,2-dihydro-isoquinoline-4-carboxylic acid

The title compound was used in the next step without purification. LC-MS (m/z) 293.9 (MH$^+$); $t_R$=0.99.

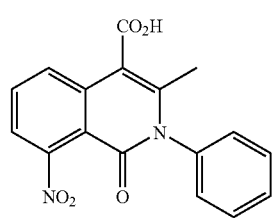

3-Methyl-8-nitro-1-oxo-2-phenyl-1,2-dihydro-iso-quinoline-4-carboxylic acid

The title compound was used in the next step without purification. LC-MS (m/z) 325.5 (MH$^+$); $t_R$=0.94.

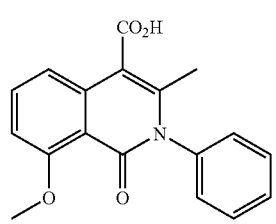

8-Methoxy-3-methyl-1-oxo-2-phenyl-1,2-dihydro-isoquinoline-4-carboxylic acid

The title compound was used in the next step without purification. LC-MS (m/z) 310.6 (MH$^+$); $t_R$=0.73.

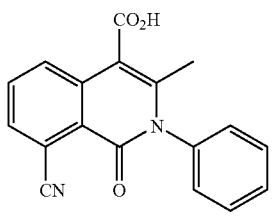

8-Cyano-3-methyl-1-oxo-2-phenyl-1,2-dihydro-iso-quinoline-4-carboxylic acid

LC-MS (m/z) 305.0 (MH$^+$); $t_R$=0.82.

Synthesis of homophthalic anhydrides of the general formula XVIII:

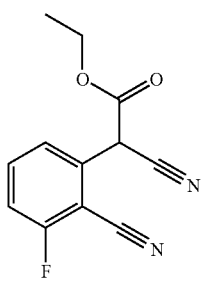

Cyano-(2-cyano-3-fluoro-phenyl)-acetic acid ethyl ester

A mixture of cyanoacetic acid ethyl ester (26.7 mL, 251 mmol), 2,6-difluorobenzonitrile (33.2 g, 239 mmol) and potassium carbonate (82.5 g, 597 mmol) in dimethyl sulfoxide (120 mL) was stirred at +55° C. for 16 hours and poured into ice-water mixture (ca. 400 mL). It was acidified with conc. aq. HCl with caution (CO$_2$ evolution) and extracted with ethyl acetate (600 ml). The organic phase was washed with brine (100 mL) and evaporated to give 55.1 g of a pale yellow solid that was used in the next step without further purification. $^1$H NMR (500 MHz, CDCl$_3$): 1.35 (t, J=7.0 Hz, 3H), 4.34 (m, 2H), 5.13 (s, 1H), 7.33 (t, J=8.4 Hz, 1H), 7.57 (d, J=7.9 Hz, 1H), 7.33 (dd, J=7.9 Hz, J=13.9 Hz, 1H).

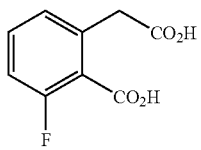

2-Carboxymethyl-6-fluoro-benzoic acid

A mixture of 62% sulfuric acid (2:1 conc. H$_2$SO$_4$ in water, 400 ml) and cyano-(2-cyano-3-fluoro-phenyl)-acetic acid ethyl ester (52.0 g, 224 mmol) was stirred at +150° C. overnight (16 hours). The reaction mixture was poured into ice (ca. 500 g) and neutralised with 10.8 N aq. NaOH (500 mL) with cooling. The mixture was extracted with ethyl acetate (3×500 mL) and the combined organic solution was washed with brine, dried over MgSO$_4$ and evaporated to give 40.28 g of crude product that was used in the next step without further purification. The analytical sample was prepared by recrystallisation from toluene-ethyl acetate. $^1$H NMR (500 MHz, DMSO-d$_6$): 3.4 (br, CO$_2$H+H$_2$O), 3.77 (s, 2H), 7.17 (d, J=7.9 Hz, 1H), 7.2 (overlapping t (unres. dd), 1H), 7.45 (dd, J=7.9 Hz, J=13.9 Hz, 1H), 12.95 (br, CO$_2$H).

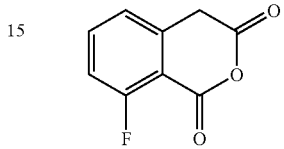

8-Fluoro-isochroman-1,3-dione

2-Carboxymethyl-6-fluoro-benzoic acid (130 mg, 0.65 mmol) in acetyl chloride (2 ml) was heated under microwave irradiation at 150° C. for 10 min then concentrated in vacuo to give the title product (120 mg, 100% yield). The compound is hydroscopic and slowly decomposes back to the starting diacid in wet solvents or under moisturised atmosphere. $^1$H NMR (500 MHz, DMSO-d$_6$): 4.29 (s, 2H), 7.27 (d, J=7.8 Hz, 1H), 7.34 (dd, J=8.5 Hz, J=1 Hz, 1H), 7.76 (dt, J=5.3 Hz, J=8 Hz, 1H).

The following homophthalic anhydrides were obtained analogously by the described above 3-step procedure from corresponding fluorobenzonitriles and ethyl cyanoacetate:

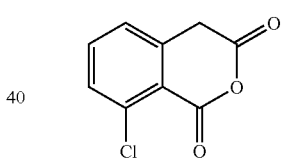

8-Chloro-isochroman-1,3-dione

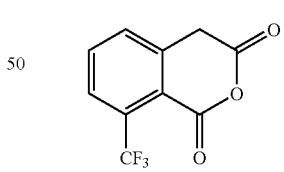

8-Trifluoromethyl-isochroman-1,3-dione

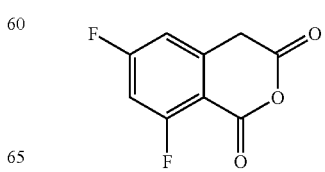

6,8-Difluoro-isochroman-1,3-dione

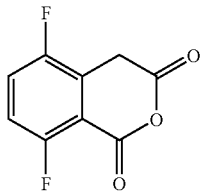

5,8-Difluoro-isochroman-1,3-dione

Synthesis of chiral and racemic amines of the general formula XI:

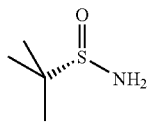

(S)-(−)-2-Methyl-2-propanesulfinamide

The title chiral auxiliary was prepared according to a described procedure for the (R)-(+)-enantiomer by D. J. Weix and J. A. Ellman *Organic Syntheses* 2005, 82, 157.

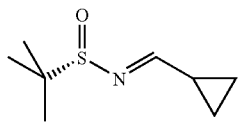

(S)-2-Methyl-2-propanesulfinic acid
1-cyclopropyl-methylideneamide

The title compound was prepared according to a general procedure described by G. Liu, D. A. Cogan, T. D. Owens, T. P. Tang, and J. A. Ellman *J. Org. Chem.* 1999, 64, 1278: A mixture of cyclopropanecarboxaldehyde (35.0 g, 0.5 mol), 2-methyl-2-propanesulfinic acid 1-cyclopropyl-methylideneamide (30 g, 0.25 mol) and anhydrous CuSO$_4$ (120 g, 0.75 mol) in CH$_2$Cl$_2$ (1500 mL) was stirred at room temperature overnight. The reaction mixture was filtered and evaporated to give the title compound (39 g, yield 95%), which was used in the next step without further purification.

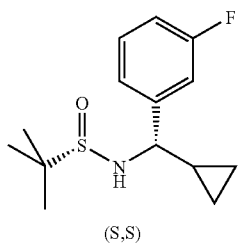 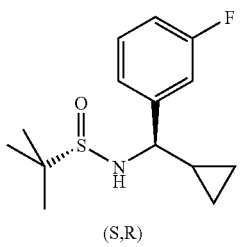

(S,S)         (S,R)

(S)-2-Methyl-2-propanesulfinic acid [(S)-cyclopropyl-(3-fluoro-phenyl)-methyl]-amide and (S)-2-Methyl-2-propanesulfinic acid [(R)-cyclopropyl-(3-fluoro-phenyl)-methyl]-amide The title compounds were obtained according to a general described procedure for 1,2-stereoselective addition of organometallic reagents to sulfinyl imines by D. A. Cogan, G. Liu, J. A. Ellman, *Tetrahedron* 1999, 55, 8883.

Procedure A: To an anhydrous lithium chloride (1.7 g, 40 mmol) THF (20 ml) was added under nitrogen followed by slow addition of i-PrMgCl (22 mL, 2 M in THF) and the obtained mixture was stirred at r.t. overnight. The obtained i-PrMgCl.LiCl solution was added dropwise to a stirred solution of 1-bromo-3-fluorobenzene (5.6 g, 33 mmol) in THF (25 ml) at 0° C. and stirring continued for 2 hours. The obtained Grignard reagent was added to a solution of (S)-2-methyl-2-propanesulfinic acid 1-cyclopropyl-methylideneamide (2.5 g, 14 mmol) in CH$_2$Cl$_2$ (60 mL) at −48° C. The mixture was stirred at −48° C. for 5 hours and then at room temperature overnight. The reaction mixture was quenched by addition of aq. sat. NH$_4$Cl (50 mL) and extracted with CH$_2$Cl$_2$ (3×100 mL). The combined organic solution was dried (Na$_2$SO$_4$) and evaporated to give a crude mixture, which was purified by column chromatography on silica gel (EtOAc/petroleum ether=1/10). The obtained mixture of diastereoisomers was resolved by SFC to give the title (S,S)-isomer as the major product (1.5 g, yield 37.5%) and the title (S,R)-isomer (0.16 g, yield: 4.0%).

Procedure B: Alternatively, to a suspension of Mg (13.4 g, 0.55 mol) in 50 mL of anhydrous THF at 50° C. a solution of 1-bromo-3-fluorobenzene (89.0 g, 0.50 mol) was added dropwise. The mixture was stirred for 2 hours at +50° C. and then it was added dropwise to a solution of (S)-2-methyl-2-propanesulfinic acid 1-cyclopropyl-methylideneamide (78.0 g, 0.46 mol) in 100 mL of THF at 50-60° C. and stirred for 2 hours. It was quenched with aq. sat. NH$_4$Cl (100 ml), water (300 mL), filtered, and the both solid and filtrate were extracted with hot ethyl acetate (600 mL) and evaporated in vacuo. The residue was crystallized from a mixture of ethyl acetate and petroleum ether (1:1, 200 mL) at −20° C. to give 80 g of the title (S,S)-isomer as a white powder, 66% yield, de 100% according to chiral HPLC. $^1$H NMR (CDCl$_3$, 400 MHz, TMS=0 ppm): 7.34-7.28 (m, 1H), 7.16-7.12 (m, 2H), 7.00-6.96 (m, 1H), 3.68 (dd, J=8.8 Hz, 3.2 Hz, 1H), 3.52 (s, 1H), 1.42 (s, 9H), 1.15-1.08 (m, 1H), 0.84-0.75 (m, 1H), 0.69-0.61 (m, 1H), 0.55-0.46 (m, 1H), 0.28-0.21 (m, 1H).

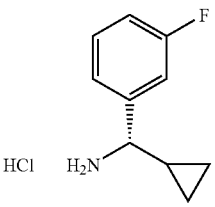

(S)-(+)-C—[C-Cyclopropyl-C-(3-fluoro-phenyl)]-methylamine hydrochloride

To a saturated solution of HCl in anhydrous dioxane (400 ml) (S)-2-methyl-2-propanesulfinic acid [(S)-cyclopropyl-(3-fluoro-phenyl)-methyl]-amide (80 g, 0.3 mol) was added at 0° C. After stirring at r.t. for 1 hour, the reaction mixture was evaporated in vacuo. The residue was washed with anhydrous ether (2×100 ml) and dried in vacuo to give 56 g of the title compound as a white solid, yield 93%, ee 100% according to chiral HPLC. $[\alpha]_D^{20}$=+52.69 (c=10 mg/mL, $CH_3OH$).
$^1H$ NMR ($CD_3OD$, 400 MHz, TMS=0): 7.44-7.39 (m, 1H), 7.25-7.19 (m, 2H), 7.12-7.07 (m, 1H), 3.56 (d, J=10.0 Hz, 1H), 1.37-1.28 (m, 1H), 0.78-0.75 (m, 1H), 0.61-0.55 (m, 2H), 0.39-0.36 (m, 1H).

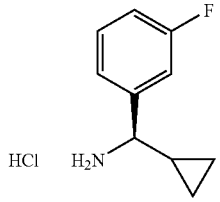

(R)-(−)—C—[C-Cyclopropyl-C-(3-fluoro-phenyl)]-methylamine hydrochloride

The title compound was prepared according to the above identical procedure from (S)-2-methyl-2-propanesulfinic acid [(R)-cyclopropyl-(3-fluoro-phenyl)-methyl]-amide (0.16 g, 0.6 mmol) to give 0.116 g of the title compound as a white solid. $[\alpha]_D^{20}$=−49.18 (c=10 mg/mL, $CH_3OH$), ee 100%. $^1H$ NMR ($CD_3OD$, 400 MHz, TMS=0): identical with (S)-enantiomer.

The following enantiomerically pure amine hydrochlorides were obtained analogously in three-step procedure starting from condensation of the corresponding aldehyde with chiral auxiliary, stereoselective Grignard addition where the mixture of diastereoisomers was resolved either by recrystallisation or by chromatography (SFC or column) and the major (S,S)-diastereoisomer was finally converted to a chiral amine with HCl.

| Structure (HCl salt) | Chemical name | $[\alpha]_D^{20}$, (10 mg/ml) MeOH | ee (chiral HPLC) | $^1H$ NMR ($CD_3OD$, 400 MHz) |
|---|---|---|---|---|
| | C-[(S)-C-cyclopropyl-C-(2-fluoro-phenyl)]-methylamine | +19.61 | 100 | 7.31-7.28 (m, 1H), 7.14-7.01 (m, 3H), 3.74 (d, J = 9.6 Hz, 1H), 1.12-1.05 (m, 1H), 0.47-0.42 (m, 1H), 0.29-0.28 (m, 2H), 0.10-0.07 (m, 1H) |
| | C-[(S)-C-Cyclopropyl-C-(4-fluoro-phenyl)]-methylamine | +47.25 | 98.9 | 7.50-7.46 (m, 2H), 7.19-7.14 (m, 2H), 3.56 (d, J = 10.0 Hz, 1H), 1.40-1.31 (m, 1H), 0.83-0.76 (m, 1H), 0.67-0.54 (m, 2H), 0.40-0.31 (m, 1H) |
| | C-[(S)-C-(2-Chloro-phenyl)-C-cyclopropyl]-methylamine | +20.56 | 100 | 7.68 (dd, J = 7.6 Hz, 1.6 Hz, 1H), 7.52-7.38 (m, 3H), 4.12 (d, J = 9.6 Hz, 1H), 1.51-1.42 (m, 1H), 0.86-0.80 (m, 1H), 0.68-0.58 (m, 2H), 0.49-0.41 (m, 1H) |
| | C-[(S)-C-(3-Chloro-phenyl)-C-cyclopropyl]-methylamine | +54.25 | 96.9 | 7.55 (s, 1H), 7.50-7.42 (m, 3H), 3.61 (d, J = 10.0 Hz, 1H), 1.42-1.34 (m, 1H), 0.89-0.83 (m, 1H), 0.74-0.62 (m, 2H). |
| | C-[(S)-C-(4-Chloro-phenyl)-C-cyclopropyl]-methylamine | +59.1 | 96.2 | 7.47 (s, 4H), 3.60 (d, J = 10.4 Hz, 1H), 1.41-1.34 (m, 1H), 0.86-0.81 (m, 1H), 0.71-0.66 (m, 2H), 0.43-0.39 (m, 1H). |
| | (S)-1-(2-Fluoro-phenyl)-propylamine | −9.71 | 100 | 7.54-7.46 (m, 2H), 7.34-7.22 (m, 2H), 4.49 (dd, J = 9.2 Hz, 6.0 Hz, 1H), 2.13-1.96 (m, 2H), 0.95 (t, J = 6.8 Hz, 3H). |

-continued

| Structure (HCl salt) | Chemical name | $[\alpha]_D^{20}$, (10 mg/ml) MeOH | ee (chiral HPLC) | $^1$H NMR (CD$_3$OD, 400 MHz) |
|---|---|---|---|---|
| 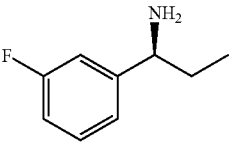 | (S)-1-(3-Fluoro-phenyl)-propylamine | +13.9 | 100 | 7.51-7.46 (m, 1H), 7.27-7.14 (m, 3H), 4.20 (dd, J = 9.2 Hz, 6.0 Hz, 1H), 2.07-1.89 (m, 2H), 0.89 (t, J = 7.2 Hz, 3H). |
| 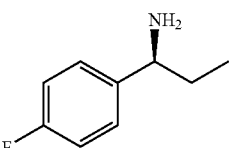 | (S)-1-(4-Fluoro-phenyl)-propylamine | +14.83 | 98.7 | 7.53-7.50 (m, 2H), 7.24-7.19 (m, 2H), 4.21 (dd, J = 9.2 Hz, 5.6 Hz, 1H), 2.13-1.91 (m, 2H), 0.89 (t, J = 7.2 Hz, 3H). |
| 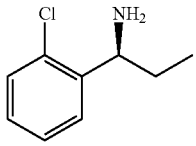 | (S)-1-(2-Chloro-phenyl)-propylamine | −1.64 | 100 | 7.56-7.38 (m, 4H), 4.73 (dd, J = 8.8 Hz, 6.4 Hz, 1H), 2.08-1.96 (m, 2H), 0.92 (t, J = 7.6 Hz, 3H). |
| 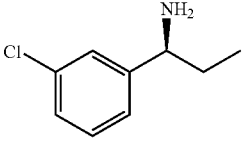 | (S)-1-(3-Chloro-phenyl)-propylamine | +14.46 | 100 | 7.48-7.35 (m, 4H), 4.17 (dd, J = 9.2 Hz, 6.0 Hz, 1H), 2.06-1.88 (m, 2H), 0.88 (t, J = 7.2 Hz, 3H). |
| 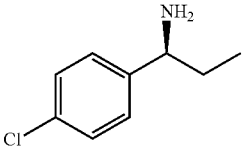 | (S)-1-(4-Chloro-phenyl)-propylamine | +14.73 | 100 | 7.50-7.47 (m, 2H), 7.44-7.41 (m, 2H), 4.18 (dd, J = 9.6 Hz, 6.0 Hz, 1H), 2.07-1.90 (m, 2H), 0.89 (t, J = 7.6 Hz, 3H). |
| 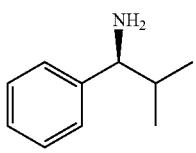 | (S)-2-Methyl-1-phenyl-propylamine | +7.12 | 100 | 7.47-7.37 (m, 5H), 3.91 (d, J = 9.2 Hz, 1H), 2.21-2.16 (m, 1H), 1.13 (d, J = 6.8 Hz, 3H), 0.78 (d, J = 6.8 Hz, 3H). |
| 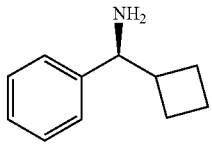 | C-((S)-C-Cyclobutyl-C-phenyl)-methylamine | +17.57 | 95.4 | 7.37-7.31 (m, 5H), 4.12 (d, J = 10.4 Hz, 1H), 2.84-2.75 (m, 1H), 2.21-2.13 (m, 1H), 1.99-1.64 (m, 5H). |
| 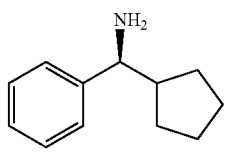 | C-((S)-C-Cyclopentyl-C-phenyl)-methylamine | +6.97 | 99.2 | 7.43 (br, 5H), 3.99 (d, J = 10.4 Hz, 1H), 2.46-2.40 (m, 1H), 2.02 (br, 1H), 1.76-1.08 (m, 8H). |
| 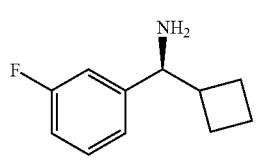 | C-[(S)-C-Cyclobutyl-C-(3-fluoro-phenyl)]-methylamine | +19.45 | 100 | 7.48-7.44 (m, 1H), 7.24-7.15 (m, 3H), 4.26 (d, J = 10.4 Hz, 1H), 2.87-2.84 (m, 1H), 2.25-2.24 (m, 1H), 2.05-1.76 (m, 5H). |

-continued

| Structure (HCl salt) | Chemical name | $[\alpha]_D^{20}$, (10 mg/ml) MeOH | ee (chiral HPLC) | $^1$H NMR (CD$_3$OD, 400 MHz) |
|---|---|---|---|---|
| ![structure with NH2, cyclobutyl, 4-fluorophenyl] | C-[(S)-C-Cyclobutyl-C-(4-fluoro-phenyl)]-methylamine | +26.98 | 100 | 7.45-7.41 (m, 2H), 7.18-7.14 (m, 2H), 4.22 (d, J = 10.6 Hz, 1H), 2.89-2.81 (m, 1H), 2.28-2.21 (m, 1H), 2.05-1.71 (m, 5H). |
| ![structure with NH2, cyclohexyl, phenyl] | C-((S)-C-Cyclohexyl-C-phenyl)-methylamine | +4.8 | 100 | 7.46-7.34 (m, 5H), 3.92 (d, J = 9.2 Hz, 1H), 1.97-1.94 (m, 1H), 1.86-1.83 (m, 2H), 1.68-1.66 (m, 2H), 1.33-1.30 (m, 2H), 1.20-1.11 (m, 3H), 0.91-0.88 (m, 1H). |

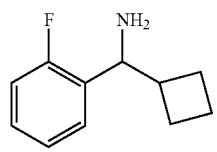

C-Cyclobutyl-C-(2-fluoro-phenyl)-methylamine

One third of a solution of cyclobutyl bromide (5.0 g, 41.3 mmol) in anhydrous tetrahydrofuran (24 mL) was stirred with magnesium (1.11 g, 46.3 mmol) under reflux. The remaining solution was added dropwise over a period of 15 minutes, and the stirring at reflux continued for 30 min. To the obtained solution 2-fluorobenzonitrile (1.2 g) in THF (15 ml) was added dropwise at 0° C. The mixture was stirred for 5.5 h at 0° C. followed by addition of methanol (30 ml) and sodium borohydride (1.13 g). The reaction mixture was stirred for 16 hours at ambient temperature and concentrated. The residue was partitioned between chloroform (3×100 ml) and water, and the pH was adjusted to 1. The mixture was extracted with chloroform. The aqueous phase was adjusted to pH=10, and extracted with chloroform (3×100 ml). The combined organic layers were dried, evaporated and purified by column chromatography on silica gel (ethyl acetate/petroleum ether=1/1) to afford the title amine (0.45 g, yield: 7.9%) $^1$H NMR (CD$_3$OD, 400 MHz) 7.49-7.38 (m, 2H), 7.30-7.15 (m, 2H), 4.50 (d, J=10.4 Hz, 1H), 3.00-2.90 (m, 1H), 2.29-2.21 (m, 1H), 2.09-1.71 (m, 5H).

Synthesis of acid-amides of the general formula XIX:

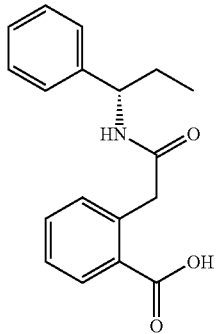

2-[((S)-1-Phenyl-propylcarbamoyl)-methyl]-benzoic acid

A mixture of homophthalic anhydride (810 mg, 5 mmol) and (S)-(−)-1-phenylpropylamine (676 mg, 5 mmol) in acetonitrile (15 ml) was heated under microwave irradiation at +150° C. for 15 min. White precipitate was collected by filtration, washed with heptane and dried in vacuo to give pure title compound in 72% yield (1.065 g). Alternatively, to a stirred solution of homophthalic anhydride (16.214 g, 0.1 mol) in acetonitrile (100 ml) (S)-(−)-1-phenylpropylamine (13.83 g, 0.102 mol) was added dropwise (exothermic reaction) and the obtained reaction mixture was refluxed for 5 min. It was allowed to cool and the product was isolated by filtration as above to give 23.4 g of colourless solid, 79% yield. LC-MS (m/z) 298.5 (MH$^+$); $t_R$=1.11. $^1$H NMR (500 MHz, DMSO-d$_6$): 0.84 (t, J=7.3 Hz, 3H), 1.67 (quintet, J=7.3 Hz, 2H), 3.85 (d of AB system, J=15.1 Hz, 1H), 3.95 (d of AB system, J=15.1 Hz, 1H), 4.66 (q, J=7.6 Hz, 1H), 7.2 (unres. m, 1H), 7.25-7.34 (m, 5H), 7.45 (t, J=7.3 Hz, 1H), 7.8 (d, J=7.8 Hz, 1H), 8.39 (br. d, J=7.7 Hz, 1H, NH).

The following compounds were obtained analogously from corresponding homophthalic anhydrides of general formula and amines of the general formula XVIII and XI, respectively. The reactions were usually run at room temperature and the products were isolated by extraction or filtration and used in the next steps without further purification.

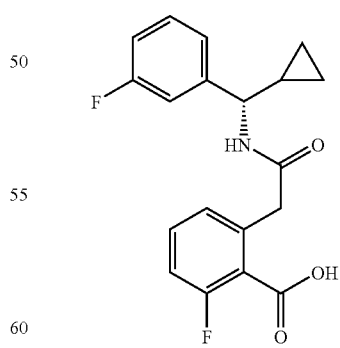

2-({[(S)-Cyclopropyl-(3-fluoro-phenyl)-methyl]-carbamoyl}-methyl)-6-fluoro-benzoic acid LC-MS (m/z) 346.2 (MH$^+$); $t_R$=1.14. $^1$H NMR (500 MHz, DMSO-d$_6$): 0.35 (m, 1H), 0.39 (m, 1H), 0.5 (m, 2H), 1.12 (m, 1H), 3.68 & 3.74 (two d of AB system, J=15.2 Hz, 2H, CH₂), 4.25 (t, J=8.5 Hz, 1H), 7.05 (dt, J=2.2, 8.05 Hz, 1H), 7.13 (d, J=8.1 Hz, 1H), 7.16-7.21 (m, 2H), 7.35 (m, 1H), 7.42 (m, 1H), 8.66 (d, J=8.2 Hz, 1H, NH), 13.44 (br., CO₂H).

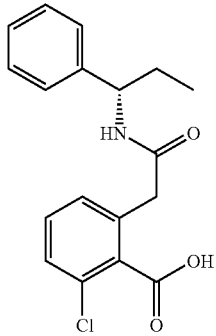

2-Chloro-6-[((S)-1-phenyl-propylcarbamoyl)-methyl]-benzoic acid

LC-MS (m/z) 332.2 (MH⁺); $t_R$=1.19. ¹H NMR (500 MHz, DMSO-d₆): 0.84 (t, J=7.3 Hz, 3H), 1.68 (quintet, J=7.3 Hz, 2H), 3.54 & 3.61 (two d of AB system, J=15.3 Hz, 2H, CH₂), 4.67 (q, J=7.5 Hz, 1H), 7.19-7.4 (m, 8H), 8.48 (d, J=8.3 Hz, 1H, NH), 13.64 (br., CO₂H).

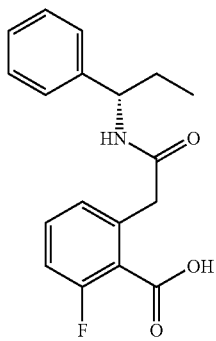

2-Fluoro-6-[((S)-1-phenyl-propylcarbamoyl)-methyl]-benzoic acid

LC-MS (m/z) 316.3 (MH⁺); $t_R$=1.13. ¹H NMR (500 MHz, CDCl₃): 0.79 (t, J=7.4 Hz, 3H), 1.76 (d of quintet, 2H, diastereotopic CH₂ of Et), 3.64 (s, 2H, CH₂), 4.75 (q, J=7.7 Hz, 1H), 7.04 (t, J=8.5 Hz, 1H), 7.08 (d, J=7.7 Hz, 1H), 7.17-7.23 (overlapping m, 3H), 7.24-7.28 (overlapping m, 2H), 7.32 (m, 1H), 7.45 (br d, J=8.1 Hz, 1H, NH). 8.48 (d, J=8.3 Hz, 1H, NH), 11.14 (br., CO₂H).

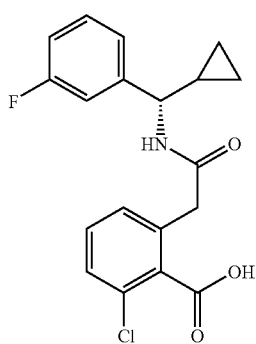

2-Chloro-6-({[(S)-cyclopropyl-(3-fluoro-phenyl)-methyl]-carbamoyl}-methyl)-benzoic acid

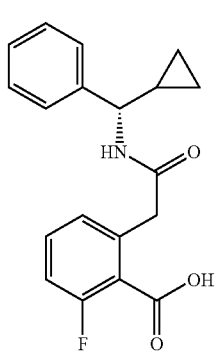

2-{[((S)-Cyclopropyl-phenyl-methyl)-carbamoyl]-methyl}-6-fluoro-benzoic acid

LC-MS (m/z) 328.4 (MH⁺); $t_R$=1.12.

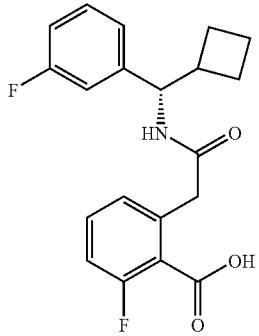

2-({[(S)-Cyclobutyl-(3-fluoro-phenyl)-methyl]-carbamoyl}-methyl)-6-fluoro-benzoic acid LC-MS (m/z) 360.2 (MH⁺); $t_R$=1.31.

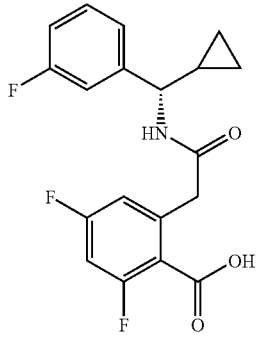

2-({[(S)-Cyclopropyl-(3-fluoro-phenyl)-methyl]-carbamoyl}-methyl)-4,6-difluoro-benzoic acid

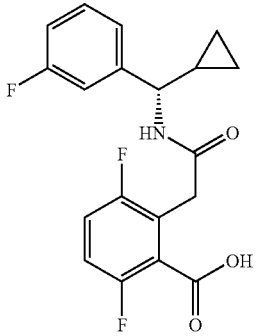

2-({[(S)-Cyclopropyl-(3-fluoro-phenyl)-methyl]-carbamoyl}-methyl)-3,6-difluoro-benzoic acid

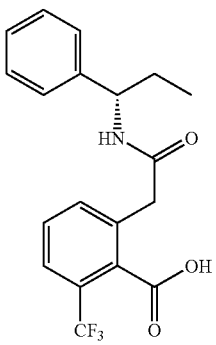

2-[((S)-1-Phenyl-propylcarbamoyl)-methyl]-6-trifluoromethyl-benzoic acid

LC-MS (m/z) 366.4 (MH$^+$); $t_R$=1.24.
Synthesis of compounds of the general formula XXIII:

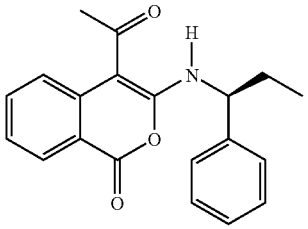

4-Acetyl-3-((S)-1-phenyl-propylamino)-isochromen-1-one

A mixture of 2-[((S)-1-phenyl-propylcarbamoyl)-methyl]-benzoic acid (10 g), acetic anhydride (50 ml), and N,N-dimethylaminopyridine (100 mg) was heated at gentle reflux ($T_{max}$=+124° C.) for 7 min and evaporated in vacuo at +50° C. to give the title compound as a yellow-brown solid (11.1 g, purity 98% by NMR). LC-MS (m/z) 322.3 (MH$^+$); $t_R$=1.72.

$^1$H NMR (500 MHz, DMSO-d$_6$): 0.89 (t, J=7.2 Hz, 3H), 1.86-1.97 (m, 2H), 2.56 (s, 3H), 4.95 (q, J=7.1 Hz, 1H, CH—NH), 7.26 (t, J=7.5 Hz, 1H), 7.29 (unres. m, 1H), 7.36-7.41 (unres m., 3H), 7.71 (t, J=7.5 Hz, 1H), 7.75 (d, J=8.3 Hz, 1H), 7.98 (d, J=7.8 Hz, 1H), 11.53 (d, J=7.6 Hz, 1H, NH). $^{13}$C APT NMR (125 MHz, DMSO-d$_6$, δ(DMSO-d$_6$)=39.87 ppm): 10.68 (CH$_3$), 30.0 (CH$_2$), 31.57 (CH$_3$), 57.01 (CH), 92.44 (C), 114.88 (C), 124.2 (CH), (CH), 124.26 (CH), 126.65 (CH), 127.8 (CH), 129.05 (CH), 129.93 (CH), 135.71 (CH), 138.68 (C), 141.86 (C), 158.51 (C), 160.55 (C), 194.82 (C, MeCO).

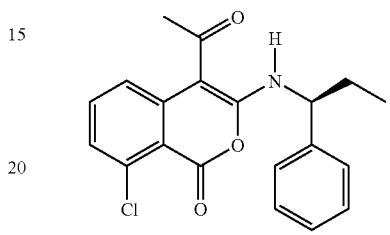

4-Acetyl-8-chloro-3-((S)-1-phenyl-propylamino)-isochromen-1-one

2-Chloro-6-[((S)-1-phenyl-propylcarbamoyl)-methyl]-benzoic acid (11.4 g) and acetic anhydride (50 ml) were heated at 103° C. for 60 min and evaporated to give 12.45 g of brown oil (purity ca 95% according to $^1$H NMR). LC-MS (m/z) 355.2 (MH$^+$); $t_R$=1.82. Analytically pure sample was prepared by recrystallisation (9 g from 30 ml of hot MeCN) to give the title compound (4.41 g) as a pale yellow solid after cooling (dry ice—EtOH bath) and filtration. LC-MS (m/z) 355.2 (MH$^+$); $t_R$=1.82. $^1$H NMR (500 MHz, DMSO-d$_6$): 0.88 (t, J=7.4 Hz, 3H), 1.92 (m, 2H), 2.5 (s, 3H), 4.92 (q, J=7.3 Hz, 1H, CH—NH), 7.27-7.33 (m, 2H), 7.39 (d unres. m), J=4.3 Hz, 4H), 7.59-7.66 (m, 2H), 11.11 (d, J=7.8 Hz, 1H, NH).

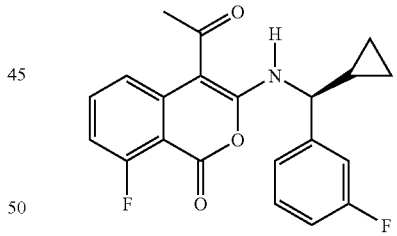

4-Acetyl-3-{[(S)-cyclopropyl-(3-fluoro-phenyl)-methyl]-amino}-8-fluoro-isochromen-1-one A mixture of 2-({[(S)-cyclopropyl-(3-fluoro-phenyl)-methyl]-carbamoyl}-methyl)-6-fluoro-benzoic acid (12.92 g, 37.41 mmol) and acetic anhydride (100 mL, 1 mol) was stirred at +65° C. for 20 hours and evaporated in vacuo (65° C., 10 mbar, 2 hours) to give the title compound as a thick brown oil, which was used in the next step without purification (14.30 g, yield 103.5%, purity 95% according to $^1$H NMR). LC-MS (m/z) 370.1 (MH$^+$); $t_R$=1.65. $^1$H NMR (500 MHz, DMSO-d$_6$): 0.45-0.59 (m, 3H), 0.64 (m, 1H), 1.41 (m, 1H), 2.53 (s, 3H), 4.36 (t (unres. dd), 1H), 7.03 (dd, J=8.3, 10.7 Hz, 1H), 7.12 (dt, J=1.9, 8.5 Hz, 1H), 7.27 (d, J=10.2 Hz, 1H), 7.3 (d, J=7.8 Hz, 1H), 7.42 (q, J=7.8 Hz, 1H), 7.53 (d, 8.5 Hz, 1H), 7.7 (m, 1H), 11.3 (d, J=7.3 Hz, 1H, NH).

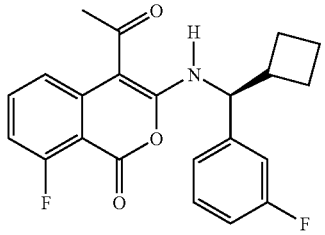

4-Acetyl-3-{[(S)-cyclobutyl-(3-fluoro-phenyl)-methyl]-amino}-8-fluoro-isochromen-1-one LC-MS (m/z) 384.4 (MH$^+$); $t_R$=1.82.

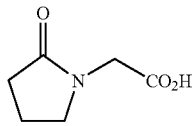

(2-Oxo-pyrrolidin-1-yl)-acetic acid

A mixture of 2-pyrrolidone (2.66 ml, 34 mmol) and NaH (60% in oil, 1.25 g, 31.3 mmol) in THF (75 ml) was stirred until gas evolution ceased (30 min). tert-Butyl 2-bromoacetate (4.45 ml, 30 mmol) was added and stirred at r.t. overnight then partitioned between water (200 ml) and ethyl acetate (200 ml) to give intermediate 2-(oxo-pyrrolidin-1-yl)-acetic acid tert-butyl ester (5.8 g). It was dissolved in acetic acid (40 ml) and conc. aq. HCl (6 ml) with gas evolution observed. After stirring at r.t. for 2 hours it was evaporated and recrystallized from toluene/ethanol to give 2.58 g of the title compound (60% yield). $^1$H NMR (500 MHz, DMSO-d$_6$): 1.95 (quintet, J=7.7 Hz, 2H), 2.24 (t, J=8.1 Hz, 2H), 3.38 (m, overalapping with H$_2$O (3.35 ppm), 2H), 3.91 (s, 2H), 12.77 (br., 1H).

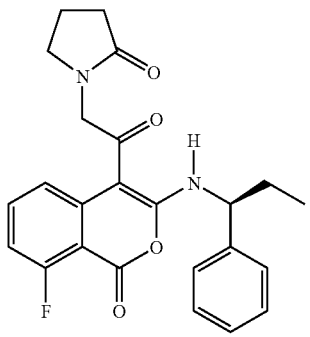

1-{2-[8-Fluoro-1-oxo-3-((S)-1-phenyl-propylamino)-1H-isochromen-4-yl]-2-oxo-ethyl}-pyrrolidin-2-one To a solution of 2-oxo-pyrrolidin-1-yl-acetic acid (1.56 g, 10.9 mmol) in 1,2-dichloroethane (40 ml) oxalyl chloride (0.95 ml, 10.9 mmol) and DMF (1 drop) were added with gas evolution observed. After stirring at r.t. for 1 hour, 2-fluoro-6-[((S)-1-phenyl-propylcarbamoyl)-methyl]-benzoic acid (1.56 g, 4.95 mmol), triethylamine (2.1 ml, 14.9 mmol) and DMAP (85 mg, 0.1 eq.) were added and stirred at r.t. overnight. It was partitioned between mixture of 0.2 M aq. HCl (100 ml)-brine (100 ml) and ethyl acetate (250 ml), washed with water and evaporated to give 1.89 g of crude title compound used in the next step without further purification.

$^1$H NMR (500 MHz, DMSO-d$_6$, selected resonances): 4.51 & 4.58 (two d of AB system, J=16.3 Hz, N—CH$_2$—CO), 4.99 (q, J=7.5 Hz, 1H, CH—NH), 11.31 (d, J=7.9 Hz, 1H, NH).

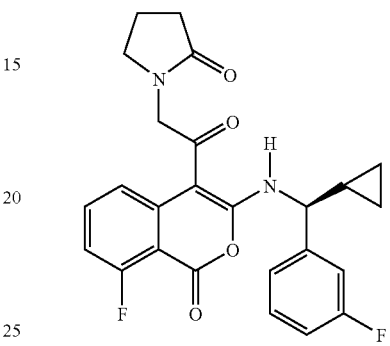

1-[2-(3-{[(S)-Cyclopropyl-(3-fluoro-phenyl)-methyl]-amino}-8-fluoro-1-oxo-1H-isochromen-4-yl)-2-oxo-ethyl]-pyrrolidin-2-one The title compound was prepared analogously and purified by flash chromatography on SiO$_2$. LC-MS (m/z) 453.3 (MH$^+$); $t_R$=1.48.

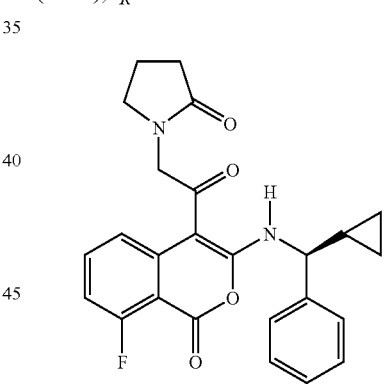

1-(2-{3-[((S)-Cyclopropyl-phenyl-methyl)-amino]-8-fluoro-1-oxo-1H-isochromen-4-yl}-2-oxo-ethyl)-pyrrolidin-2-one The title compound was prepared analogously. LC-MS (m/z) 435.3 (MH$^+$); $t_R$=1.43.

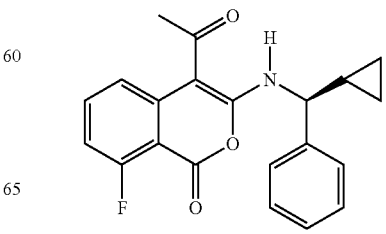

4-Acetyl-3-[((S)-cyclopropyl-phenyl-methyl)-amino]-8-fluoro-isochromen-1-one LC-MS (m/z) 352.6 (MH$^+$); $t_R$=1.62. $^1$H NMR (500 MHz, DMSO-d$_6$): 0.48 (m, 2H), 0.54 (m, 1H), 0.64 (m, 1H), 1.39 (m, 1H), 2.53 (s, 3H), 4.39 (t (unres. dd), 1H), 7.04 (dd, J=8.2, 10.8 Hz, 1H), 7.3 (t, J=7.3 Hz, 1H), 7.39 (t, J=7.6 Hz, 2H), 7.43 (d, J=7.3 Hz, 2H), 7.53 (d, 8.5 Hz, 1H), 7.7 (m, 1H), 11.39 (d, J=7.5 Hz, 1H, NH).

Hydrolysis of compounds of the general formula XXIII into compounds of the general formula XXV:

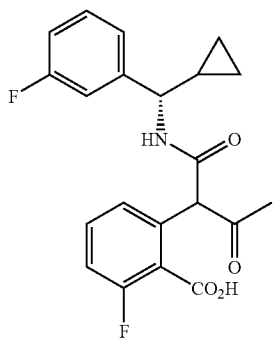

2-(1-{[(S)-Cyclopropyl-(3-fluoro-phenyl)-methyl]-carbamoyl}-2-oxo-propyl)-6-fluoro-benzoic acid 4-Acetyl-3-{[(S)-cyclopropyl-(3-fluoro-phenyl)-methyl]-amino}-8-fluoro-2-benzopyran-1-one (14.30 g, 38.72 mmol) was dissolved in a mixture of tetrahydrofuran (50 mL) and methanol (50 mL) and placed on an ice/water bath with stirring. NaOH (1 M in H$_2$O, 100 ml) was added and stirring continued for 1 hour. The cold bath removed and the mixture was allowed to warm to r.t. (20° C.) during 1 hour. The reaction mixture was poured into ice-water mixture (200 g+200 ml), followed by slow addition of 2 M aq. HCl (200 mL) and extracted with ethyl acetate (200 mL), washed with sat. aq. NaCl, dried (Na$_2$SO$_4$), filtered and evaporated to give the title compound (14.65 g, yield 97.7%) as a pale brown foam. The crude product was used in the next step without further purification. LC-MS (m/z) 388.3 (MH$^+$); $t_R$=1.2. $^1$H NMR (500 MHz, DMSO-d$_6$): a mixture of tautomers and diastereoisomers. The following compounds were prepared analogously:

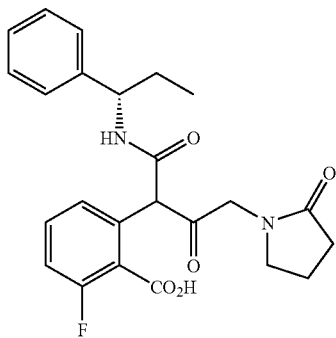

2-Fluoro-6-[2-oxo-3-(2-oxo-pyrrolidin-1-yl)-1-((S)-1-phenyl-propylcarbamoyl)-propyl]-benzoic acid

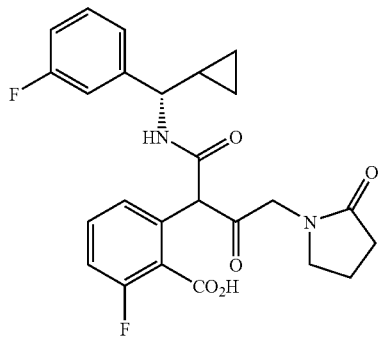

2-[1-{[(S)-Cyclopropyl-(3-fluoro-phenyl)-methyl]-carbamoyl}-2-oxo-3-(2-oxo-pyrrolidin-1-yl)-propyl]-6-fluoro-benzoic acid LC-MS (m/z) 471.4 (MH$^+$); $t_R$=1.17.

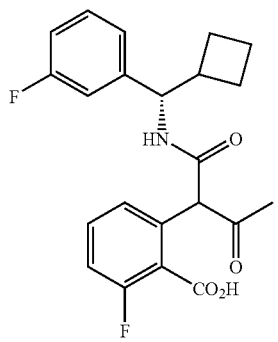

2-(1-{[(S)-Cyclobutyl-(3-fluoro-phenyl)-methyl]-carbamoyl}-2-oxo-propyl)-6-fluoro-benzoic acid LC-MS (m/z) 402.2 (MH$^+$); $t_R$=1.36.

Synthesis of compounds of the general formula XXIV and XXV: Compounds of general formula XXIV obtained analogously as described above for compounds of general formula XXIII but at higher temperature (150° C., 15 min) and they are usually hydrolyzed to compounds of the general formula XXV without isolation and characterization, so only two examples of compounds XXIV are given below.

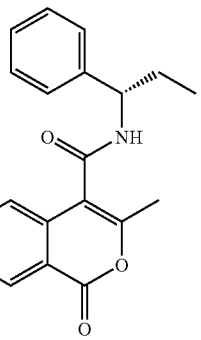

3-Methyl-1-oxo-1H-isochromene-4-carboxylic acid ((S)-1-phenyl-propyl)-amide

The title compound was purified by flash chromatography on SiO$_2$. LC-MS (m/z) 322.1 (MH$^+$); t$_R$=1.27. $^1$H NMR (500 MHz, CDCl$_3$): 1.03 (t, J=7.3 Hz, 3H), 1.91-2.06 (complex m, 2H, CH$_2$), 2.19 (s, 3H), 5.11 (q, J=7.8 Hz, 1H), 7.06 (br. d, J=8.3 Hz, 1H, NH), 7.22-7.33 (m, 3H), 7.36-7.43 (m, 4H), 7.54 (t, J=7.6 Hz, 1H), 7.95 (d, J=7.8 Hz, 1H). $^1$H NMR (500 MHz, DMSO-d$_6$): 0.92 (t, J=7.3 Hz, 3H), 1.76 (m, 2H), 2.18 (s, 3H), 4.93 (q, J=8.3 Hz, 1H), 7.21-7.41 (m, 6H), 7.59 (t, J=7.7 Hz, 1H), 7.82 (t, J=7.2 Hz, 1H), 8.17 (d, J=7.8 Hz, 1H), 9.1 (br. d, J=8.4 Hz, 1H, NH).

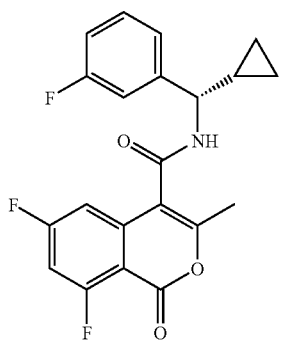

6,8-Difluoro-3-methyl-1-oxo-1H-isochromene-4-carboxylic acid [(S)-cyclopropyl-(3-fluoro-phenyl)-methyl]-amide The title compound was purified by flash chromatography on SiO$_2$. LC-MS (m/z) 388.4 (MH$^+$); t$_R$=1.39.

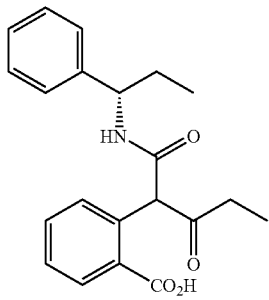

2-[2-Oxo-1-((S)-1-phenyl-propylcarbamoyl)-butyl]-benzoic acid

A sealed mixture of 2-[((S)-1-phenyl-propylcarbamoyl)-methyl]-benzoic acid (409 mg, 1.38 mmol), propionic anhydride (10 ml) and 4-N,N-dimethylaminopyridine (15 mg) was heated under microwave irradiation at 150° C. for 20 min and partitioned between 1M HCl (50 ml) and ethyl acetate (100 ml). The organic layer was washed with sat. aq. NaHCO$_3$ (2×50 ml) and brine and concentrated in vacuo. To the obtained residue methanol (25 ml) tetrahydrofurane (25 ml) and 2M aq. NaOH (50 ml) was added and stirred at r.t. for 1 hour. The organic volatiles were removed in vacuo and the pH was adjusted to 1 with 3M aq. HCl. The crude title product (495 mg) was separated by extraction with ethyl acetate (150 ml) and used in the next step without further purification. $^1$H NMR (500 MHz, DMSO-d$_6$): a mixture of tautomers and diastereoisomers.

The following compounds were obtained analogously:

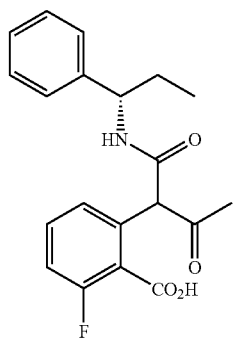

2-Fluoro-6-[2-oxo-1-((S)-1-phenyl-propylcarbamoyl)-propyl]-benzoic acid

LC-MS (m/z) 358.4 (MH$^+$); t$_R$=1.17.

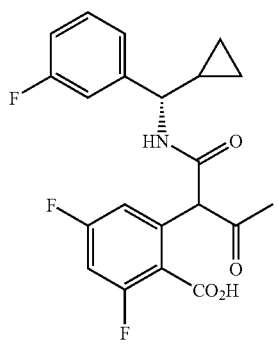

2-(1-{[(S)-Cyclopropyl-(3-fluoro-phenyl)-methyl]-carbamoyl}-2-oxo-propyl)-4,6-difluoro-benzoic acid LC-MS (m/z) 406.7 (MH$^+$); t$_R$=1.3.

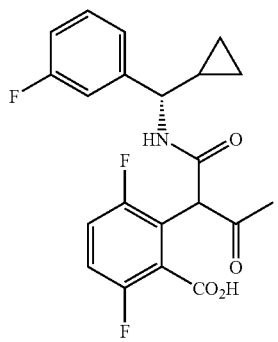

2-(1-{[(S)-Cyclopropyl-(3-fluoro-phenyl)-methyl]-carbamoyl}-2-oxo-propyl)-3,6-difluoro-benzoic acid LC-MS (m/z) 406.0 (MH+); $t_R$=0.72 (method B).

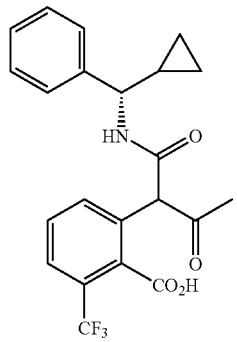

2-[2-Oxo-1-((S)-1-phenyl-propylcarbamoyl)-propyl]-6-trifluoromethyl-benzoic acid The title compound was used in the next step directly.

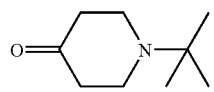

1-tert-Butyl-piperidin-4-one

The title compound was prepared according to the described procedure: J. S. Amato, J. Y. L. Chung, R. J. Cvetovich, X. Gong, M. McLaughlin, R. A. Reamer *J. Org. Chem.* 2005, 70, 1930.

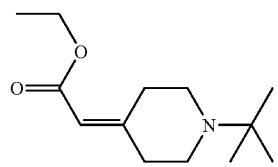

(1-tert-Butyl-piperidin-4-ylidene)-acetic acid ethyl ester

A mixture of 1-tert-Butyl-piperidin-4-one (4.59 g, 23.6 mmol) and ethyl (triphenylphosphorylidene)acetate (10.3 g, 23.6 mmol) in toluene (100 mL) was stirred at reflux for 24 hours under nitrogen and evaporated in vacuo. The residue was purified by column chromatography on silica gel (petroleum ether/triethylamine=100/1) to afford 5.1 g of the title compound as a pale yellow oil, 76.5% yield.

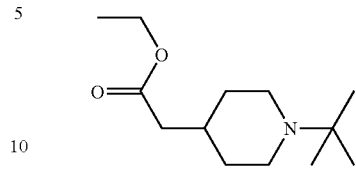

(1-tert-Butyl-piperidin-4-yl)-acetic acid ethyl ester

To a solution of (1-tert-butyl-piperidin-4-ylidene)-acetic acid ethyl ester (5.1 g, 22.7 mmol) in ethanol (50 mL) 10% Pd/C (0.6 g) was added and the mixture was stirred under the hydrogen atmosphere (42 psi) at ambient temperature for 14 hours. The catalyst was removed by filtration, and the filtrate was concentrated to give the title (4.03 g, yield 78%), which was used in the next step directly.

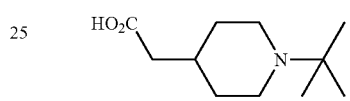

(1-tert-Butyl-piperidin-4-yl)-acetic acid

To a solution of NaOH in water/ethanol (v/v=40/10, 50 mL) (1-tert-butyl-piperidin-4-yl)-acetic acid ethyl ester (4.03 g, 17.8 mmol) was added and the mixture was stirred at r.t. overnight. 1 N aq. HCl was added to adjust the pH to 5. Volotiles were evaporated in vacuo, the residue was diluted with methanol (30 mL), and the insoluble inorganic salts were removed by filtration. The filtrate was concentrated and purified by column chromatography on silica gel ($CH_2Cl_2$/MeOH=20/1 to 5/1) to give 0.7 g of title compound as a light grey powder. $^1$H NMR (400 MHz, DMSO-$d_6$): 3.15-3.08 (br m, 2H), 2.30 (br t, J=11.2 Hz, 2H), 2.05 (d, J=6.4 Hz, 2H), 1.71-1.68 (m, 3H), 1.30-1.27 (m, 2H), 1.10 (s, 9H).

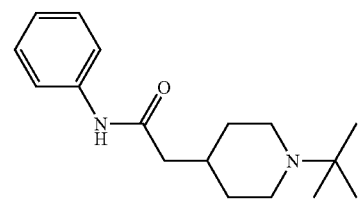

2-(1-tert-Butyl-piperidin-4-yl)-N-phenyl-acetamide

To a mixture of (1-tert-butyl-piperidin-4-yl)-acetic acid (672 mg, 3.37 mmol), aniline (0.32 ml, 3.5 mmol), and HOBt (568 mg, 4.2 mmol) in DMF (20 ml), EDC (805 mg, 4.2 mmol) was added. It was stirred at r.t. for 2 hours and partitioned between water (200 ml) and ethyl acetate (200 ml). The organic phase was washed with 0.5 N aq. NaOH (2×50 ml) and brine (3×50 ml), dried ($MgSO_4$) and concentrated in vacuo. The residue was purified by flash chromatography on ($SiO_2$, gradient heptane-ethyl acetate) to give 250 mg of the title compound. $^1$H NMR (500 MHz, DMSO-$d_6$): 1.07 (s, 9H), 1.32 (br. m, 2H), 1.81 (br. d, 2H), 1.89 (m, 1H), 2.11 (br. t, 2H), 2.25 (d, 2H), 3.03 (br. d, 2H), 7.1 (t, 1H), 7.24 (br., 1H), 7.31 (t, 2H), 7.52 (d, 2H).

Compounds of the Invention
Example 1

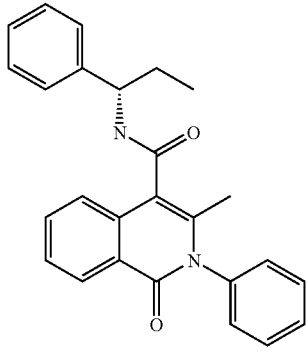

1a 3-Methyl-1-oxo-2-phenyl-1,2-dihydro-isoquinoline-4-carboxylic acid ((S)-1-phenyl-propyl)-amide A solution of 3-methyl-1-oxo-2-phenyl-1,2-dihydro-isoquinoline-4-carboxylic acid (212 mg, 0.76 mmol) in SOCl$_2$ (1.5 ml) and dimethylformamide (ca. 5 µL) was heated at reflux for 5 min. Volatiles were removed in vacuo to give 228 mg of the corresponding acid chloride as a pale brown solid. A portion of the acid chloride (110 mg, 0.37 mmol) was dissolved in 1,2-dichloroethane (2 ml) and (S)-(−)-1-phenyl-propylamine (150 µL, 1.1 mmol) was added. The obtained suspension was shaked for 5 min, diluted with 1,2-dichloroethane (10 ml), washed with 1M aqueous HCl (3×5 ml) and water (5 ml). The organic phase was poured into SiO$_2$ (5 g), eluted with 1,2-dichloroethane (50 ml) and the product was eluted with 1:1 ethyl acetate-heptane to give 140 mg of colourless crystalline solid. Yield 95%. Alternatively, in another run the reaction mixture was partitioned between 2M HCl and heptane (10 ml) and the product was separated by filtration from the obtained biphasic system. LC-MS (m/z) 397.1 (MH$^+$); $t_R$=1.44. $^1$H NMR (500 MHz, CDCl$_3$): 1.0 (t, 3H), 1.93 (m, 5H), 5.16 (q, 1H), 6.7 (d, 1H), 7.07 (d, 2H), 7.31 (m, 1H), 7.36 (d, 4H), 7.4-7.5 (m, 5H), 7.63 (unres. t, 1H), 8.31 (d, 1H).

The following compounds were obtained analogously from the corresponding acid and amine and purified by preparative LC-MS:

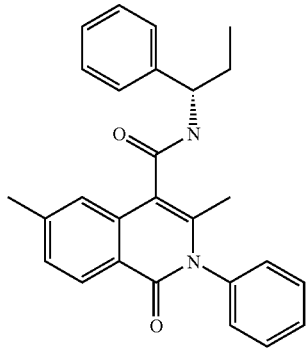

1b 3,6-Dimethyl-1-oxo-2-phenyl-1,2-dihydro-isoquinoline-4-carboxylic acid ((S)-1-phenyl-propyl)-amide LC-MS (m/z) 411.3 (MH$^+$); $t_R$=0.8 (method B).

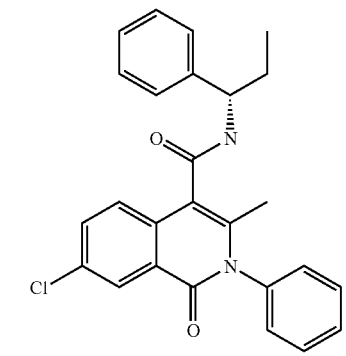

1c 7-Chloro-3-methyl-1-oxo-2-phenyl-1,2-dihydro-isoquinoline-4-carboxylic acid ((S)-1-phenyl-propyl)-amide LC-MS (m/z) 431.3 (MH$^+$); $t_R$=0.86 (method B).

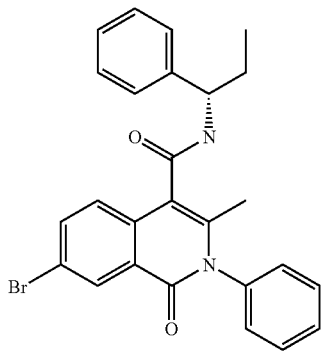

1d 7-Bromo-3-methyl-1-oxo-2-phenyl-1,2-dihydro-isoquinoline-4-carboxylic acid ((S)-1-phenyl-propyl)-amide LC-MS (m/z) 475.1 (MH$^+$, $^{79}$Br); $t_R$=0.87 (method B).

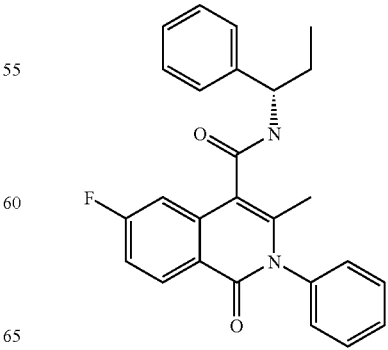

1e 6-Fluoro-3-methyl-1-oxo-2-phenyl-1,2-dihydro-isoquinoline-4-carboxylic acid ((S)-1-phenyl-propyl)-amide LC-MS (m/z) 415.5 (MH$^+$); t$_R$=0.80 (method B).

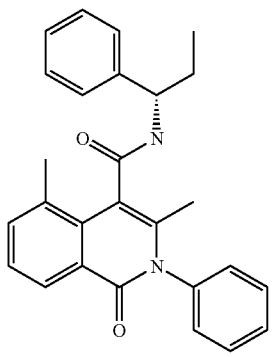

1f 3,5-Dimethyl-1-oxo-2-phenyl-1,2-dihydro-isoquinoline-4-carboxylic acid ((S)-1-phenyl-propyl)-amide LC-MS (m/z) 411.3 (MH$^+$); t$_R$=0.84 (method B).

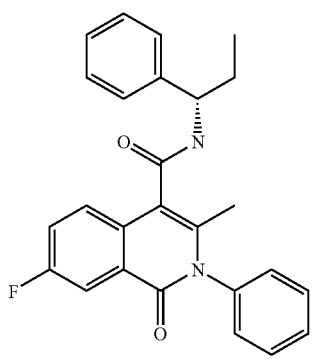

1g 7-Fluoro-3-methyl-1-oxo-2-phenyl-1,2-dihydro-isoquinoline-4-carboxylic acid ((S)-1-phenyl-propyl)-amide LC-MS (m/z) 415.4 (MH$^+$); t$_R$=1.49.

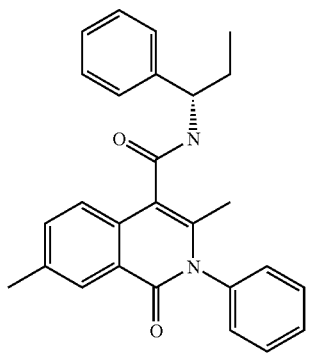

1h 3,7-Dimethyl-1-oxo-2-phenyl-1,2-dihydro-isoquinoline-4-carboxylic acid ((S)-1-phenyl-propyl)-amide LC-MS (m/z) 411.4 (MH$^+$); t$_R$=1.5.

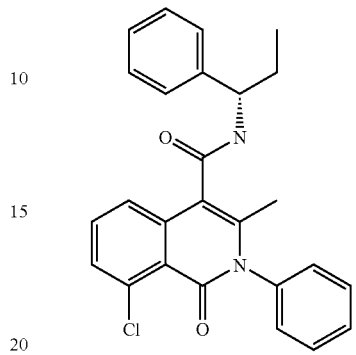

1i 8-Chloro-3-methyl-1-oxo-2-phenyl-1,2-dihydro-isoquinoline-4-carboxylic acid ((S)-1-phenyl-propyl)-amide LC-MS (m/z) 431.4 (MH$^+$); t$_R$=1.54.

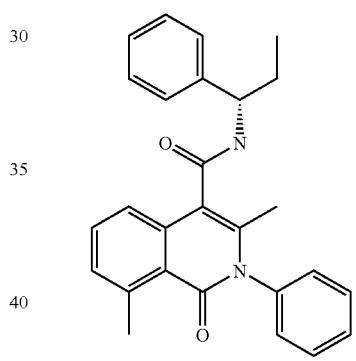

1j 3,8-Dimethyl-1-oxo-2-phenyl-1,2-dihydro-isoquinoline-4-carboxylic acid ((S)-1-phenyl-propyl)-amide LC-MS (m/z) 411.4 (MH$^+$); t$_R$=1.5. $^1$H NMR (250 MHz, DMSO-d$_6$, T=343K): 0.91 (t, 3H), 1.78 (overlapping s, 3H), 1.79 (overlapping m, 1H), 2.75 (s, 3H), 4.94 (q, 1H), 7.15-7.27 (m, 5H), 7.27-7.39 (m, 4H), 7.41-7.58 (m, 4H), 8.67 (d, 1H).

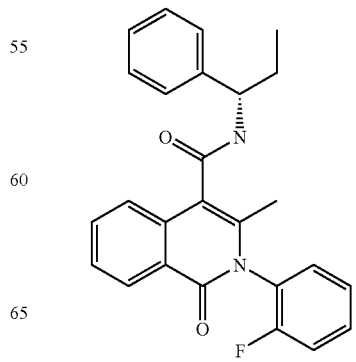

1k 2-(2-Fluoro-phenyl)-3-methyl-1-oxo-1,2-dihydro-isoquinoline-4-carboxylic acid ((S)-1-phenyl-propyl)-amide LC-MS (m/z) 415.5 (MH$^+$); t$_R$=1.49.

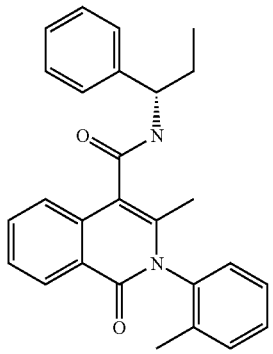

1l 3-Methyl-1-oxo-2-o-tolyl-1,2-dihydro-isoquinoline-4-carboxylic acid ((S)-1-phenyl-propyl)-amide LC-MS (m/z) 411.5 (MH$^+$); t$_R$=1.5.

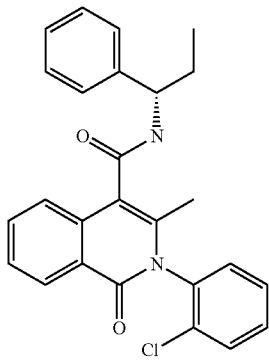

1m 2-(2-Chloro-phenyl)-3-methyl-1-oxo-1,2-dihydro-isoquinoline-4-carboxylic acid ((S)-1-phenyl-propyl)-amide LC-MS (m/z) 431.2 (MH$^+$); t$_R$=1.51.

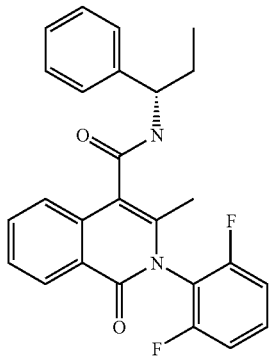

1n 2-(2,6-Difluoro-phenyl)-3-methyl-1-oxo-1,2-dihydro-isoquinoline-4-carboxylic acid ((S)-1-phenyl-propyl)-amide LC-MS (m/z) 433.4 (MH$^+$); t$_R$=1.54.

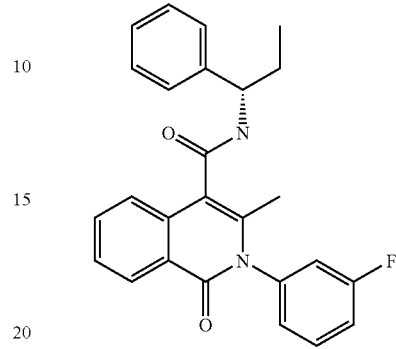

1o 2-(3-Fluoro-phenyl)-3-methyl-1-oxo-1,2-dihydro-isoquinoline-4-carboxylic acid ((S)-1-phenyl-propyl)-amide LC-MS (m/z) 415.1 (MH$^+$); t$_R$=1.48.

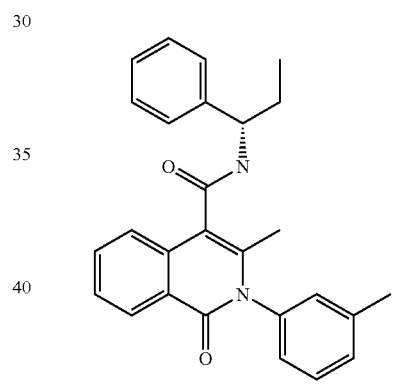

1p 3-Methyl-1-oxo-2-m-tolyl-1,2-dihydro-isoquinoline-4-carboxylic acid ((S)-1-phenyl-propyl)-amide LC-MS (m/z) 411.5 (MH$^+$); t$_R$=1.53.

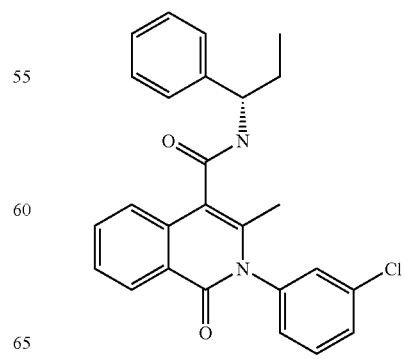

1q 2-(3-Chloro-phenyl)-3-methyl-1-oxo-1,2-dihydro-isoquinoline-4-carboxylic acid ((S)-1-phenyl-propyl)-amide LC-MS (m/z) 431.2 (MH$^+$); $t_R$=1.57.

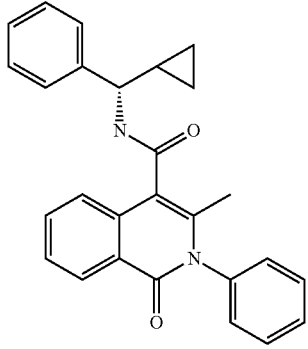

1r 3-Methyl-1-oxo-2-phenyl-1,2-dihydro-isoquinoline-4-carboxylic acid ((S)-cyclopropyl-phenyl-methyl)-amide LC-MS (m/z) 409.4 (MH$^+$); $t_R$=1.43. $^1$H NMR (250 MHz, DMSO-d$_6$, T=343K): 0.45 (m, 2H), 0.56 (m, 2H), 1.25 (m, 1H), 1.88 (s, 3H), 4.51 (t, 1H), 7.21-7.37 (m, 5H), 7.42-7.59 (m, 7H), 7.7 (dt, 1H), 8.21 (dd, 1H), 8.89 (d, 1H).

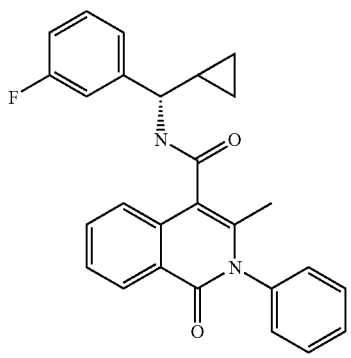

1s 3-Methyl-1-oxo-2-phenyl-1,2-dihydro-isoquinoline-4-carboxylic acid [(S)-cyclopropyl-(3-fluoro-phenyl)-methyl]-amide LC-MS (m/z) 427.1 (MH$^+$); $t_R$=1.48. $^1$H NMR (250 MHz, DMSO-d$_6$, T=343K): 0.48 (m, 2H), 0.57 (m, 2H), 1.24 (m, 1H), 1.89 (s, 3H), 4.51 (t, 1H), 7.05 (m, 1H), 7.21-7.31 (m, 4H), 7.33-7.6 (m, 6H), 7.7 (dt, 1H), 8.21 (dd, 1H), 8.94 (d, 1H).

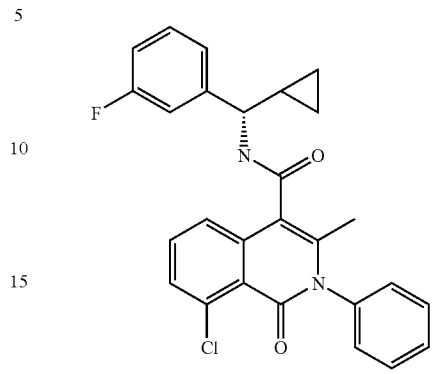

1t 8-Chloro-3-methyl-1-oxo-2-phenyl-1,2-dihydro-isoquinoline-4-carboxylic acid [(S)-cyclopropyl-(3-fluoro-phenyl)-methyl]-amide LC-MS (m/z) 461.6 (MH$^+$); $t_R$=1.51. $^1$H NMR (250 MHz, DMSO-d$_6$, T=343K): 0.48 (m, 2H), 0.58 (m, 2H), 1.27 (m, 1H), 1.87 (s, 3H), 4.5 (t, 1H), 7.06 (m, 1H), 7.21-7.32 (m, 4H), 7.32-7.45 (m, 2H), 7.45-7.66 (m, 5H), 8.95 (d, 1H).

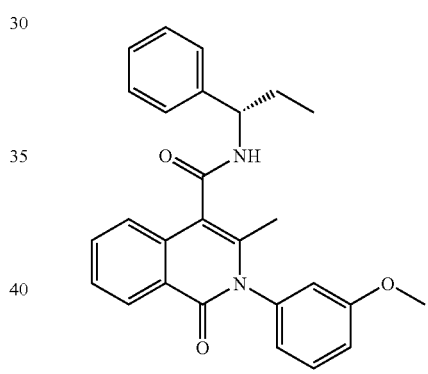

1aa 2-(3-Methoxy-phenyl)-3-methyl-1-oxo-1,2-dihydro-isoquinoline-4-carboxylic acid ((S)-1-phenyl-propyl)-amide LC-MS (m/z) 426.7 (MH$^+$); $t_R$=1.43.

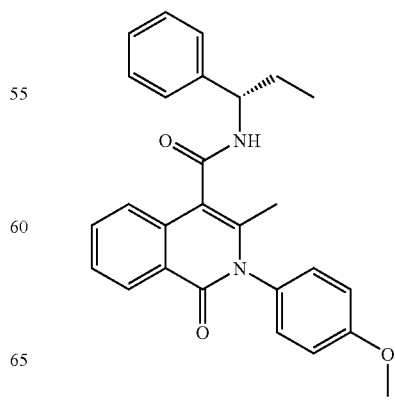

1ab 2-(4-Methoxy-phenyl)-3-methyl-1-oxo-1,2-dihydro-isoquinoline-4-carboxylic acid ((S)-1-phenyl-propyl)-amide LC-MS (m/z) 427.0 (MH⁺); $t_R$=1.43.

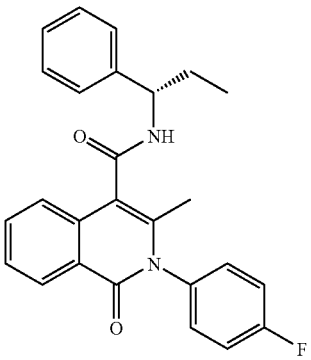

1ac 2-(4-Fluoro-phenyl)-3-methyl-1-oxo-1,2-dihydro-isoquinoline-4-carboxylic acid ((S)-1-phenyl-propyl)-amide LC-MS (m/z) 415.0 (MH⁺); $t_R$=1.43.

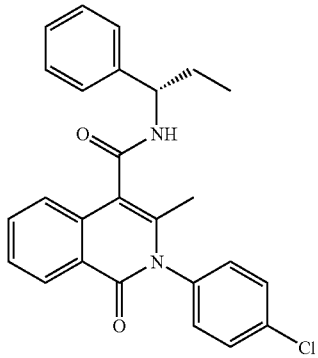

1ad 2-(4-Chloro-phenyl)-3-methyl-1-oxo-1,2-dihydro-isoquinoline-4-carboxylic acid ((S)-1-phenyl-propyl)-amide LC-MS (m/z) 431.1 (MH⁺); $t_R$=1.54.

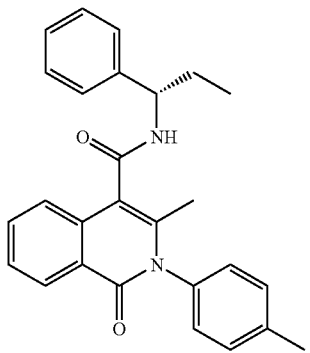

1ae 3-Methyl-1-oxo-2-p-tolyl-1,2-dihydro-isoquinoline-4-carboxylic acid ((S)-1-phenyl-propyl)-amide LC-MS (m/z) 411.2 (MH⁺); $t_R$=1.51.

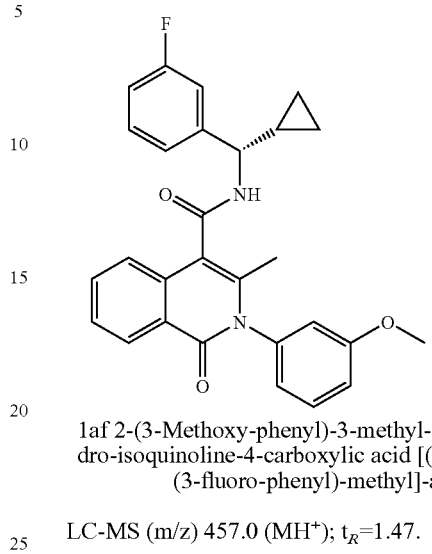

1af 2-(3-Methoxy-phenyl)-3-methyl-1-oxo-1,2-dihydro-isoquinoline-4-carboxylic acid [(S)-cyclopropyl-(3-fluoro-phenyl)-methyl]-amide LC-MS (m/z) 457.0 (MH⁺); $t_R$=1.47.

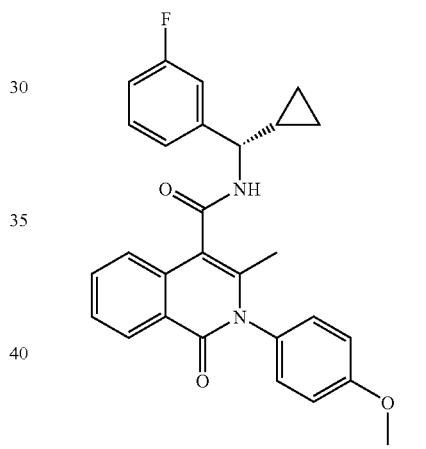

1ag 2-(4-Methoxy-phenyl)-3-methyl-1-oxo-1,2-dihydro-isoquinoline-4-carboxylic acid [(S)-cyclopropyl-(3-fluoro-phenyl)-methyl]-amide LC-MS (m/z) 457.1 (MH⁺); $t_R$=1.46.

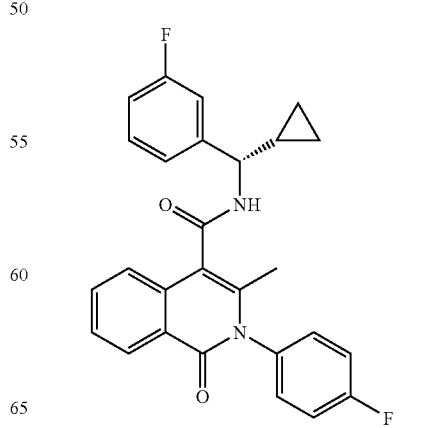

1ah 2-(4-Fluoro-phenyl)-3-methyl-1-oxo-1,2-dihydro-isoquinoline-4-carboxylic acid [(S)-cyclopropyl-(3-fluoro-phenyl)-methyl]-amide LC-MS (m/z) 445.6 (MH$^+$); t$_R$=1.48.

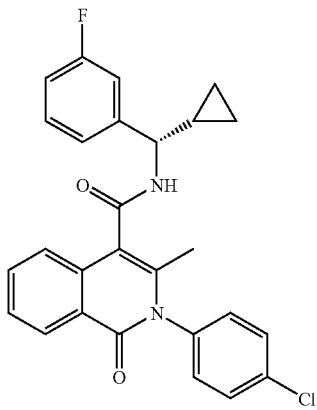

1ai 2-(4-Chloro-phenyl)-3-methyl-1-oxo-1,2-dihydro-isoquinoline-4-carboxylic acid [(S)-cyclopropyl-(3-fluoro-phenyl)-methyl]-amide LC-MS (m/z) 461.3 (MH$^+$); t$_R$=1.57.

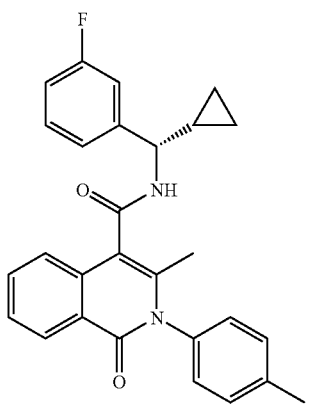

1aj 3-Methyl-1-oxo-2-p-tolyl-1,2-dihydro-isoquinoline-4-carboxylic acid [(S)-cyclopropyl-(3-fluoro-phenyl)-methyl]-amide LC-MS (m/z) 440.9 (MH$^+$); t$_R$=1.54.

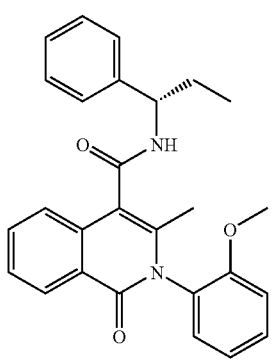

1ak 2-(2-Methoxy-phenyl)-3-methyl-1-oxo-1,2-dihydro-isoquinoline-4-carboxylic acid ((S)-1-phenyl-propyl)-amide LC-MS (m/z) 427.0 (MH$^+$); t$_R$=1.39.

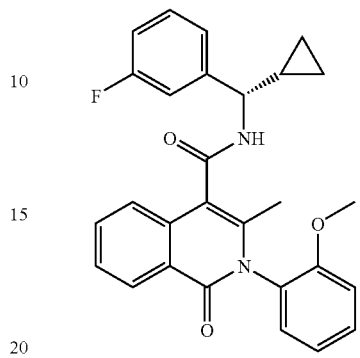

1al 2-(2-Methoxy-phenyl)-3-methyl-1-oxo-1,2-dihydro-isoquinoline-4-carboxylic acid [(S)-cyclopropyl-(3-fluoro-phenyl)-methyl]-amide LC-MS (m/z) 457.4 (MH$^+$); t$_R$=1.43.

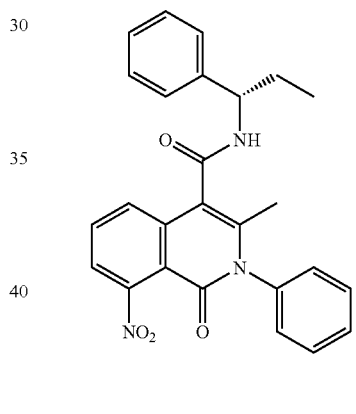

1am 3-Methyl-8-nitro-1-oxo-2-phenyl-1,2-dihydro-isoquinoline-4-carboxylic acid ((S)-1-phenyl-propyl)-amide LC-MS (m/z) 442.4 (MH$^+$); t$_R$=1.46.

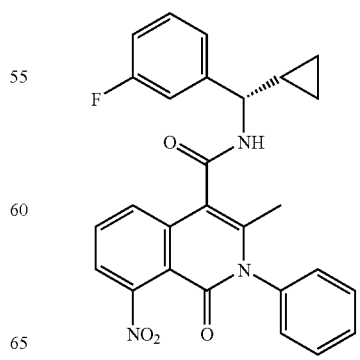

1an 3-Methyl-8-nitro-1-oxo-2-phenyl-1,2-dihydro-isoquinoline-4-carboxylic acid [(S)-cyclopropyl-(3-fluoro-phenyl)-methyl]-amide LC-MS (m/z) 442.4 (MH$^+$); $t_R$=1.46.

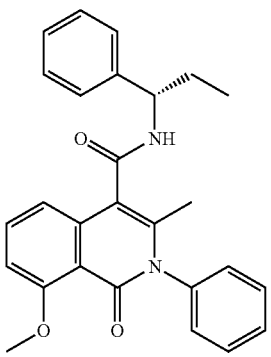

1ao 8-Methoxy-3-methyl-1-oxo-2-phenyl-1,2-dihydro-isoquinoline-4-carboxylic acid ((S)-1-phenyl-propyl)-amide LC-MS (m/z) 427.1 (MH$^+$); $t_R$=1.32.

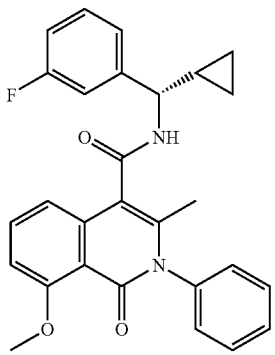

1ap 8-Methoxy-3-methyl-1-oxo-2-phenyl-1,2-dihydro-isoquinoline-4-carboxylic acid [(S)-cyclopropyl-(3-fluoro-phenyl)-methyl]-amide LC-MS (m/z) 457.4 (MH$^+$); $t_R$=1.36.

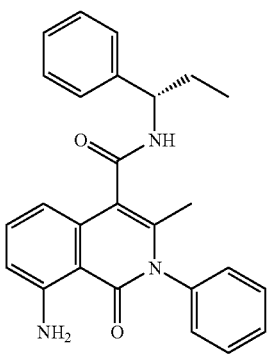

1aq 8-Amino-3-methyl-1-oxo-2-phenyl-1,2-dihydro-isoquinoline-4-carboxylic acid ((S)-1-phenyl-propyl)-amide To a stirred solution of 3-methyl-8-nitro-1-oxo-2-phenyl-1,2-dihydro-isoquinoline-4-carboxylic acid ((S)-1-phenyl-propyl)-amide (1am, 10 mg, 0.023 mmol) in tetrahydrofurane (0.15 ml) 2M aq. HCl (0.12 ml, 0.25 mmol) and Zn powder (45 mg, 0.69 mmol) was added. After 30 min the mixture was filtered and partitioned between ethyl acetate (4 ml) and sat. aq. NaHCO$_3$ (2 ml), then brine (3 ml). The organic solution was dried (MgSO$_4$) and evaporated to afford 5.9 mg of the title compound (70% yield). LC-MS (m/z) 412.4 (MH$^+$); $t_R$=1.37.

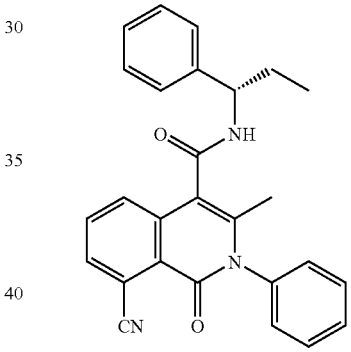

1ar 8-Cyano-3-methyl-1-oxo-2-phenyl-1,2-dihydro-isoquinoline-4-carboxylic acid ((S)-1-phenyl-propyl)-amide LC-MS (m/z) 422.1 (MH$^+$); $t_R$=1.37.

The following compounds were obtained according to the general procedure: the corresponding acid of the general formula IX (0.04 mmol) and amine of the general formula XI (0.06 mmol) in DMF (0.5 ml) was stirred in the presence of Et$_3$N (3 eq.), EDC (1.5 eq.), and HOBT (1.5 eq.) at r.t. overnight followed by partitioning between ethyl acetate (2 ml) and 0.5 M NaOH (1 ml) and flash chromatography on SiO$_2$.

| | Chemical name | structure | $t_R$ (min) | MW | m/z (MH+) |
|---|---|---|---|---|---|
| 1as | 8-Chloro-3-methyl-1-oxo-2-phenyl-1,2-dihydro-isoquinoline-4-carboxylic acid [(S)-1-(4-chloro-phenyl)-propyl]-amide | 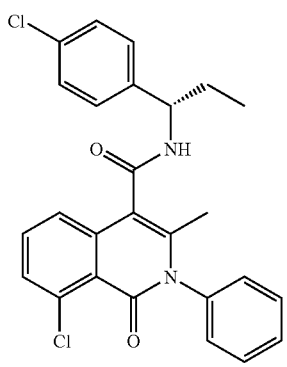 | 1.63 | 465.4 | 465.4 |
| 1at | 8-Chloro-3-methyl-1-oxo-2-phenyl-1,2-dihydro-isoquinoline-4-carboxylic acid [(S)-1-(4-fluoro-phenyl)-propyl]-amide | 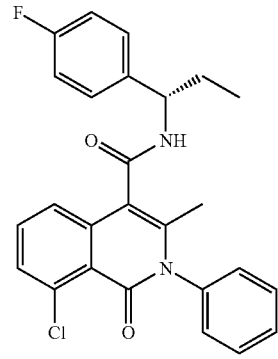 | 1.52 | 448.9 | 449.3 |
| 1au | 8-Chloro-3-methyl-1-oxo-2-phenyl-1,2-dihydro-isoquinoline-4-carboxylic acid [(S)-1-(2-fluoro-phenyl)-propyl]-amide | 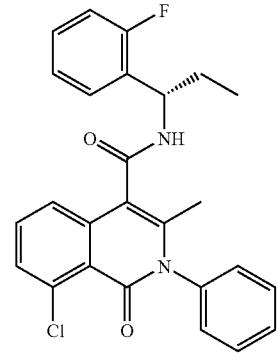 | 1.52 | 448.9 | 449.4 |
| 1av | 8-Chloro-3-methyl-1-oxo-2-phenyl-1,2-dihydro-isoquinoline-4-carboxylic acid [(S)-1-(3-chloro-phenyl)-propyl]-amide | 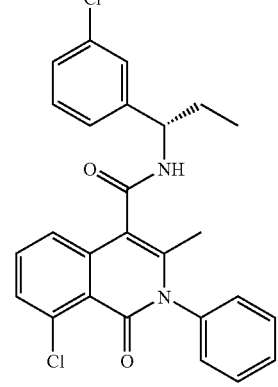 | 1.62 | 465.4 | 465.3 |

-continued

| | Chemical name | structure | t_R (min) | MW | m/z (MH+) |
|---|---|---|---|---|---|
| 1aw | 8-Chloro-3-methyl-1-oxo-2-phenyl-1,2-dihydro-isoquinoline-4-carboxylic acid [(S)-(3-chloro-phenyl)-cyclopropyl-methyl]-amide | 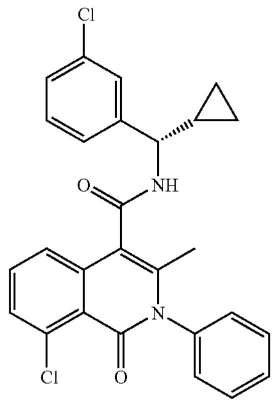 | 1.64 | 477.4 | 477.3 |
| 1ax | 8-Chloro-3-methyl-1-oxo-2-phenyl-1,2-dihydro-isoquinoline-4-carboxylic acid [(S)-(4-chloro-phenyl)-cyclopropyl-methyl]-amide | 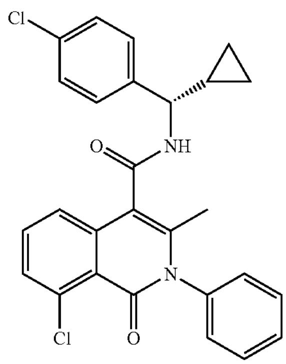 | 1.64 | 477.4 | 477.4 |
| 1ay | 8-Chloro-3-methyl-1-oxo-2-phenyl-1,2-dihydro-isoquinoline-4-carboxylic acid [(S)-1-(3-fluoro-phenyl)-propyl]-amide | 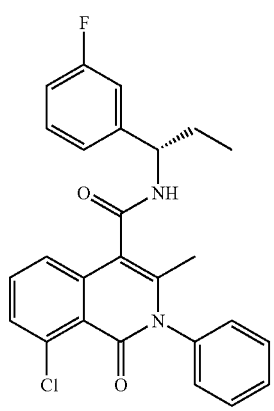 | 1.53 | 448.9 | 449.3 |
| 1az | 8-Chloro-3-methyl-1-oxo-2-phenyl-1,2-dihydro-isoquinoline-4-carboxylic acid ((S)-2-methyl-1-phenyl-propyl)-amide | 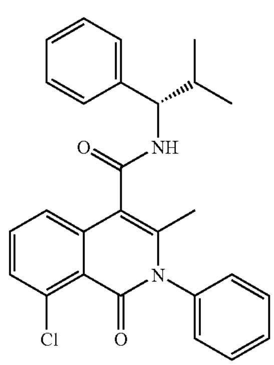 | 1.59 | 444.96 | 445.7 |

-continued

| | Chemical name | structure | t$_R$ (min) | MW | m/z (MH$^+$) |
|---|---|---|---|---|---|
| 1ba | 8-Chloro-3-methyl-1-oxo-2-phenyl-1,2-dihydro-isoquinoline-4-carboxylic acid [(S)-cyclopropyl-(4-fluoro-phenyl)-methyl]-amide | 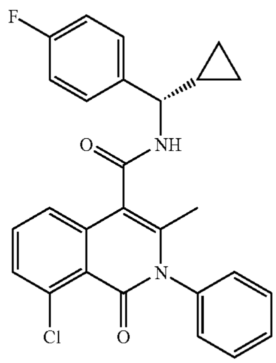 | 1.53 | 460.9 | 461.5 |
| 1bb | 8-Chloro-3-methyl-1-oxo-2-phenyl-1,2-dihydro-isoquinoline-4-carboxylic acid [(S)-1-(2-chloro-phenyl)-propyl]-amide | 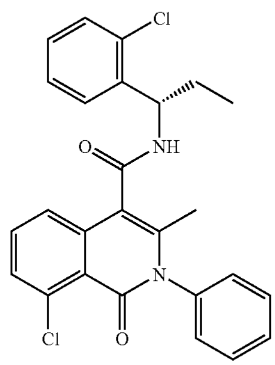 | 1.61 | 465.4 | 465.3 |
| 1bc | 8-Chloro-3-methyl-1-oxo-2-phenyl-1,2-dihydro-isoquinoline-4-carboxylic acid ((S)-cyclopentyl-phenyl-methyl)-amide | 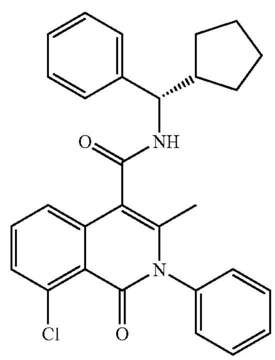 | 1.72 | 470.99 | 471.8 |
| 1bd | 8-Chloro-3-methyl-1-oxo-2-phenyl-1,2-dihydro-isoquinoline-4-carboxylic acid [(S)-(2-chloro-phenyl)-cyclopropyl-methyl]-amide | 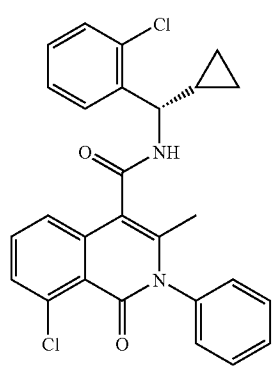 | 1.6 | 477.4 | 477.2 |

-continued

| | Chemical name | structure | $t_R$ (min) | MW | m/z (MH$^+$) |
|---|---|---|---|---|---|
| 1be | 8-Chloro-3-methyl-1-oxo-2-phenyl-1,2-dihydro-isoquinoline-4-carboxylic acid [(S)-cyclopropyl-(2-fluoro-phenyl)-methyl]-amide | 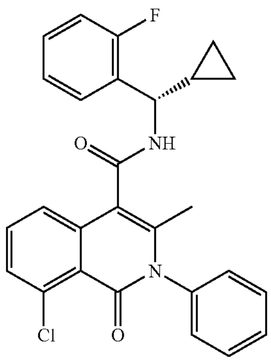 | 1.6 | 460.9 | 461.6 |
| 1bf | 8-Chloro-3-methyl-1-oxo-2-phenyl-1,2-dihydro-isoquinoline-4-carboxylic acid ((S)-cyclohexyl-phenyl-methyl)-amide | 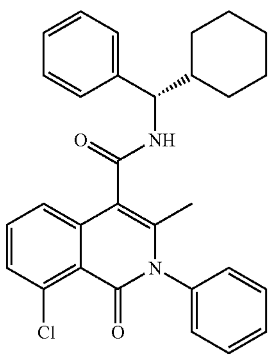 | 1.8 | 485.0 | 485.4 |
| 1bg | 8-Chloro-3-methyl-1-oxo-2-phenyl-1,2-dihydro-isoquinoline-4-carboxylic acid ((S)-cyclopropyl-phenyl-methyl)-amide | 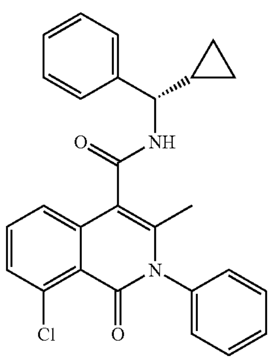 | 1.5 | 442.9 | 443.5 |
| 1bh | 8-Chloro-3-methyl-1-oxo-2-phenyl-1,2-dihydro-isoquinoline-4-carboxylic acid [(S)-cyclobutyl-(3-fluoro-phenyl)-methyl]-amide | 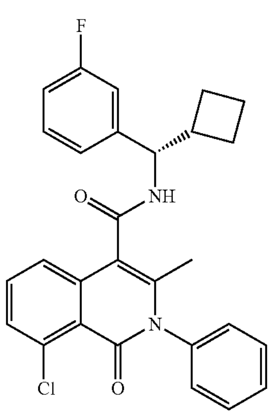 | 1.65 | 474.96 | 475.5 |

| Chemical name | structure | $t_R$ (min) | MW | m/z (MH+) |
|---|---|---|---|---|
| 1bi 8-Chloro-3-methyl-1-oxo-2-phenyl-1,2-dihydro-isoquinoline-4-carboxylic acid [(S)-cyclobutyl-(4-fluoro-phenyl)-methyl]-amide | | 1.64 | 474.96 | 475.5 |
| 1bl 8-Chloro-3-methyl-1-oxo-2-phenyl-1,2-dihydro-isoquinoline-4-carboxylic acid [(R)-cyclopropyl-(3-fluoro-phenyl)-methyl]-amide | | 1.52 | 460.9 | 461.5 |
| 1bn 8-Chloro-3-methyl-1-oxo-2-phenyl-1,2-dihydro-isoquinoline-4-carboxylic acid ((S)cyclobutyl-phenyl-methyl)-amide | | 1.61 | 456.97 | 457.3 |
| 1bo 8-Chloro-3-methyl-1-oxo-2-phenyl-1,2-dihydro-isoquinoline-4-carboxylic acid [cyclobutyl-(2-fluoro-phenyl)-methyl]-amide | | 1.64 | 474.96 | 475.4 |

Example 2

Preparation of Intermediates

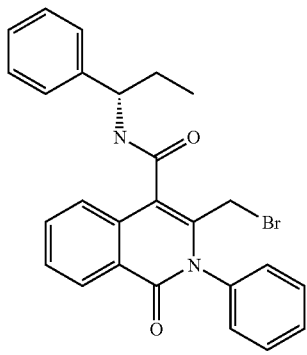

3-Bromomethyl-1-oxo-2-phenyl-1,2-dihydro-isoquinoline-4-carboxylic acid ((S)-1-phenyl-propyl)-amide To a suspension of $CaCO_3$ (500 mg, 5 mmol) and 3-methyl-1-oxo-2-phenyl-1,2-dihydro-isoquinoline-4-carboxylic acid ((S)-1-phenyl-propyl)-amide (115 mg, 0.29 mmol) in 1,2-dichloroethane (5 ml) bromine (600 mg, 3.75 mmol) was added. The obtained mixture was sonicated at +33° C. for 2 hours, diluted with 1,2-dichloroethane (20 ml) and poured into silica gel column (5 g). The excess of bromine was eluted with 1,2-dichloroethane and the product was eluted with 1:1 ethyl acetate-heptane to give 135 mg of brown solid. It was dissolved in ethyl acetate (0.5 ml) and precipitated with heptane (20 ml) to give 100 mg of yellow-brown solid. Yield 72%. LC-MS (m/z) 475.2 (MH$^+$, $^{79}$Br); $t_R$=1.59. $^1$H NMR (500 MHz, DMSO-d$_6$, a mixture of two interconverting rotamers): 0.95 (br, 3H, CH$_3$), 1.74 and 1.82 (two unres. m, 2×1H, CH$_2$), 4.0 (unres. m, 1H, CH$_2$Br), 4.21 and 4.35 (two unres. m, 2×0.5H, CH$_2$Br), 4.97 (q, 1H, CH), 7.1 (br, 0.5H), 7.24 (br, 0.5H), 7.28-7.21 (br m, 11.5H), 7.89 (br, 0.5H), 8.25 (br, 1H), 9.28 (d, 1H, NH).

The following compounds were obtained analogously:

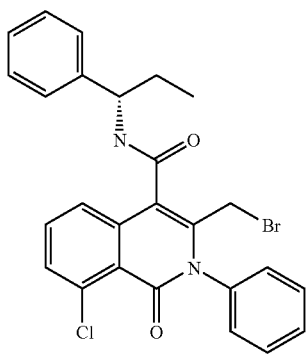

3-Bromomethyl-8-chloro-1-oxo-2-phenyl-1,2-dihydro-isoquinoline-4-carboxylic acid ((S)-1-phenyl-propyl)-amide The crude product was used in the next step without further purification. LC-MS (m/z) 511.3 (MH$^+$, $^{79}$Br); $t_R$=1.68.

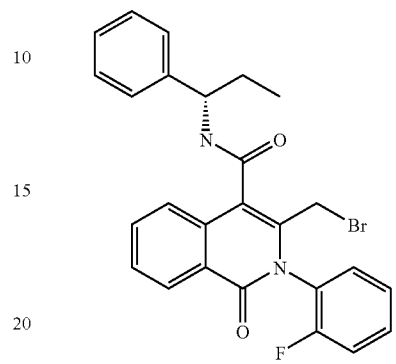

3-Bromomethyl-2-(2-fluoro-phenyl)-1-oxo-1,2-dihydro-isoquinoline-4-carboxylic acid ((S)-1-phenyl-propyl)-amide The crude product was used in the next step without further purification. LC-MS (m/z) 493.3 (MH$^+$, $^{79}$Br); $t_R$=1.62.

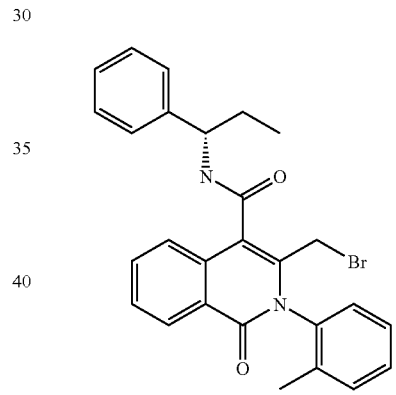

3-Bromomethyl-1-oxo-2-o-tolyl-1,2-dihydro-isoquinoline-4-carboxylic acid ((S)-1-phenyl-propyl)-amide The crude product was used in the next step without further purification. LC-MS (m/z) 489.3 (MH$^+$, $^{79}$Br); $t_R$=1.65.

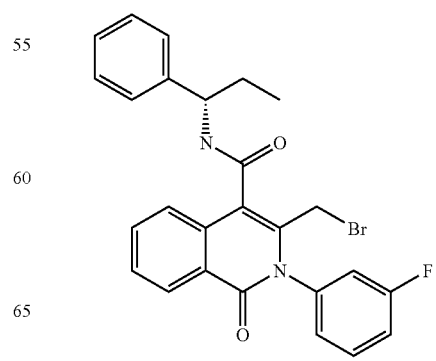

133

3-Bromomethyl-2-(3-fluoro-phenyl)-1-oxo-1,2-dihydro-isoquinoline-4-carboxylic acid ((S)-1-phenyl-propyl)-amide LC-MS (m/z) 493.5 (MH$^+$, $^{79}$Br); t$_R$=0.80 (method B).

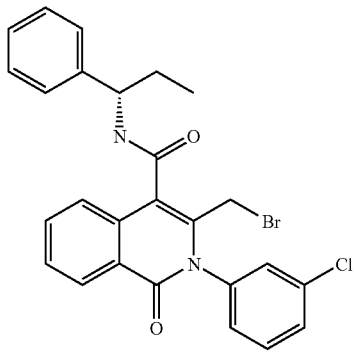

3-Bromomethyl-2-(3-chloro-phenyl)-1-oxo-1,2-dihydro-isoquinoline-4-carboxylic acid ((S)-1-phenyl-propyl)-amide LC-MS (m/z) 511.5 (MH$^+$, $^{81}$Br); t$_R$=0.84 (method B).

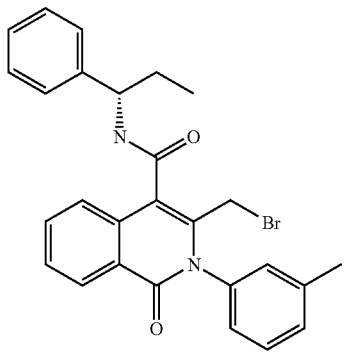

3-Bromomethyl-1-oxo-2-m-tolyl-1,2-dihydro-isoquinoline-4-carboxylic acid ((S)-1-phenyl-propyl)-amide LC-MS (m/z) 489.2 (MH$^+$, $^{79}$Br); t$_R$=0.86 (method B).

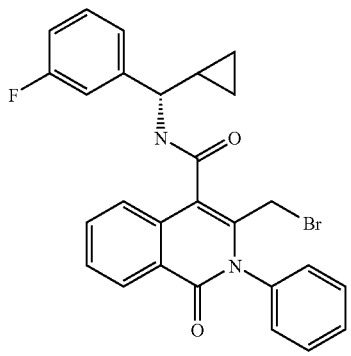

134

3-Bromomethyl-1-oxo-2-phenyl-1,2-dihydro-isoquinoline-4-carboxylic acid [(S)-cyclopropyl-(3-fluoro-phenyl)-methyl]-amide LC-MS (m/z) 505.1 (MH$^+$); t$_R$=1.62.

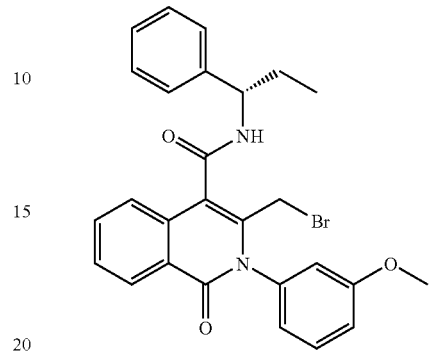

3-Bromomethyl-2-(3-methoxy-phenyl)-1-oxo-1,2-dihydro-isoquinoline-4-carboxylic acid ((S)-1-phenyl-propyl)-amide The product was purified by flash chromatography on SiO$_2$ (gradient heptane-ethyl acetate) and used in the next step directly.

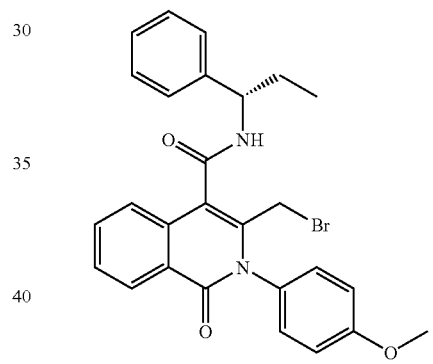

3-Bromomethyl-2-(4-methoxy-phenyl)-1-oxo-1,2-dihydro-isoquinoline-4-carboxylic acid ((S)-1-phenyl-propyl)-amide The product was purified by flash chromatography on SiO$_2$ (gradient heptane-ethyl acetate). LC-MS (m/z) 505.1 & 507.2 (MH$^+$); t$_R$=1.52.

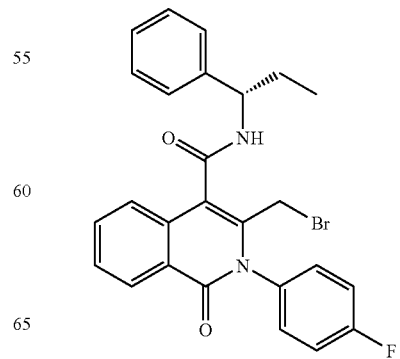

3-Bromomethyl-2-(4-fluoro-phenyl)-1-oxo-1,2-dihydro-isoquinoline-4-carboxylic acid ((S)-1-phenyl-propyl)-amide The product was purified by flash chromatography on SiO$_2$ (gradient heptane-ethyl acetate). LC-MS (m/z) 493.3 & 495.3 (MH$^+$); $t_R$=1.54.

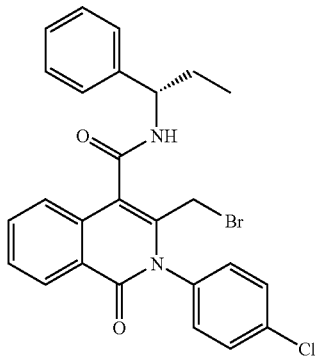

3-Bromomethyl-2-(4-chloro-phenyl)-1-oxo-1,2-dihydro-isoquinoline-4-carboxylic acid ((S)-1-phenyl-propyl)-amide LC-MS (m/z) 509.2 & 511.1 (MH$^+$); $t_R$=1.63.

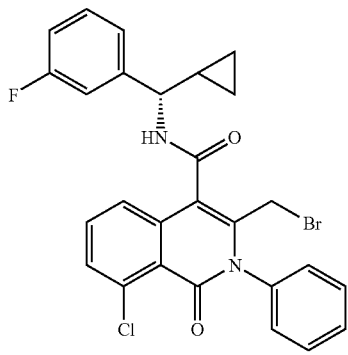

3-Bromomethyl-8-chloro-1-oxo-2-phenyl-1,2-dihydro-isoquinoline-4-carboxylic acid [(S)-cyclopropyl-(3-fluoro-phenyl)-methyl]-amide LC-MS (m/z) 539.1 & 541.4 (MH$^+$); $t_R$=1.69.

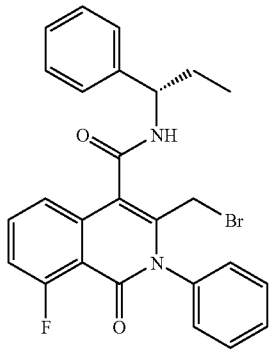

3-Bromomethyl-8-fluoro-1-oxo-2-phenyl-1,2-dihydro-isoquinoline-4-carboxylic acid ((S)-1-phenyl-propyl)-amide LC-MS (m/z) 493.3 & 495.2 (MH$^+$); $t_R$=1.52.

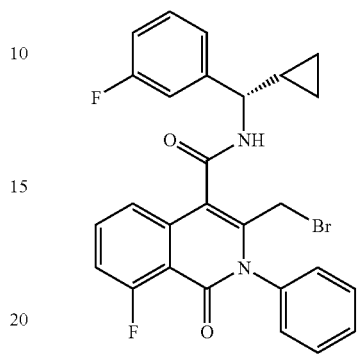

3-Bromomethyl-8-fluoro-1-oxo-2-phenyl-1,2-dihydro-isoquinoline-4-carboxylic acid [(S)-cyclopropyl-(3-fluoro-phenyl)-methyl]-amide LC-MS (m/z) 523.5 & 525.6 (MH$^+$); $t_R$=1.56.

Compounds of the Invention

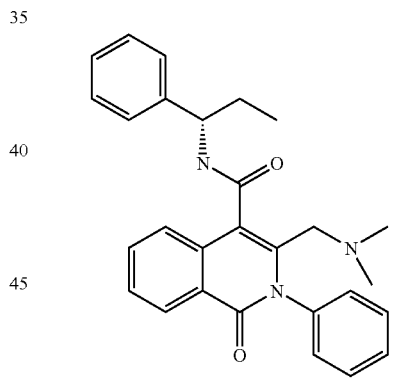

2a 3-Dimethylaminomethyl-1-oxo-2-phenyl-1,2-dihydro-isoquinoline-4-carboxylic acid ((S)-1-phenyl-propyl)-amide A mixture of 3-bromomethyl-1-oxo-2-phenyl-1,2-dihydro-isoquinoline-4-carboxylic acid ((S)-1-phenyl-propyl)-amide (70 mg, 0.147 mmol) and dimethylamine (1 ml of 33% solution in abs. ethanol, excess) was kept at 50° C. for 10 min and then evaporated in vacuo. The residue was dissolved in methanol and passed through SCX cation exchange column (1 g, RSO$_3$H form). Uncharged impurities were eluted with methanol and the product was eluted with 4M NH$_3$ in methanol to give 53 mg of colourless glass-like solid. It was further purified by flash chromatography on SiO$_2$ (5 g, gradient 1,2- dichloroethane—10% ethyl acetate in 1,2-dichloroethane) to give 45 mg of colourless solid. Yield 70%. LC-MS (m/z) 440.1 (MH$^+$); $t_R$=0.88. $^1$H NMR (250 MHz, DMSO-d$_6$, T=333 K): 0.92 (t, 2H), 1.83 (two overlapping m, 2H), 1.66 (s, 6H), 2.96 and 3.08 (two d of CH$_A$H$_B$N, 2H), 4.96 (q, 1H), 7.19-7.56 (m, 12H), 7.68 (t, 1H), 8.21 (d, 1H), 8.75 (d, 1H).

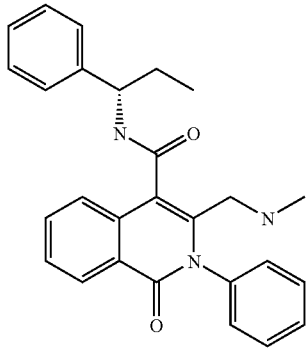

2b 3-Methylaminomethyl-1-oxo-2-phenyl-1,2-dihydro-isoquinoline-4-carboxylic acid ((S)-1-phenyl-propyl)-amide A mixture of 3-bromomethyl-1-oxo-2-phenyl-1,2-dihydro-isoquinoline-4-carboxylic acid ((S)-1-phenyl-propyl)-amide (4.7 mg, 0.01 mmol) and methylamine (1 ml of 2M solution in tetrahydrofurane, excess) was kept at ambient temperature for 20 min and then evaporated in vacuo. The product was used for biological testing without further purification. LC-MS (m/z) 426.3 (MH$^+$); $t_R$=0.85.

The following 3-aminomethyl derivatives were prepared analogously from corresponding 3-bromomethyl derivatives and 1.2-5 molar equivalents of appropriate aliphatic or aromatic primary or secondary amine in tetrahydrofurane as a solvent at ambient temperature. The reactions were monitored by LC-MS. In several cases longer reaction times were used or the reaction mixture was heated to 50° C. and/or diisopropylethylamine (2 eq.) was added as a base. After evaporation of the reaction mixture the compounds were of sufficient purity as detected by analytical LC-MS; otherwise further purification by SCX column or by preparative LC-MS was performed.

List of Compounds from Example 2

|  | Chemical name | $t_R$ (min) | MW | m/z (MH+) |
| --- | --- | --- | --- | --- |
| 2c | 3-Ethylaminomethyl-1-oxo-2-phenyl-1,2-dihydro-isoquinoline-4-carboxylic acid ((S)-1-phenyl-propyl)-amide | 0.45 (method B) | 439.6 | 440.6 |
| 2d | 3-Cyclopropylaminomethyl-1-oxo-2-phenyl-1,2-dihydro-isoquinoline-4-carboxylic acid ((S)-1-phenyl-propyl)-amide | 0.49 (method B) | 451.6 | 452.1 |
| 2e | 3-[(Cyclopropylmethyl-amino)-methyl]-1-oxo-2-phenyl-1,2-dihydro-isoquinoline-4-carboxylic acid ((S)-1-phenyl-propyl)-amide | 0.51 (method B) | 465.6 | 466.4 |
| 2f | 3-(3,6-Dihydro-2H-pyridin-1-ylmethyl)-1-oxo-2-phenyl-1,2-dihydro-isoquinoline-4-carboxylic acid ((S)-1-phenyl-propyl)-amide | 0.99 | 477.6 | 478.1 |
| 2g | 3-[4-(2-Methoxy-phenyl)-piperazin-1-ylmethyl]-1-oxo-2-phenyl-1,2-dihydro-isoquinoline-4-carboxylic acid ((S)-1-phenyl-propyl)-amide | 1.14 | 586.7 | 587.5 |
| 2h | 3-[4-(4-Fluoro-phenyl)-piperazin-1-ylmethyl]-1-oxo-2-phenyl-1,2-dihydro-isoquinoline-4-carboxylic acid ((S)-1-phenyl-propyl)-amide | 1.35 | 574.7 | 575.6 |
| 2i | 3-(4-Formyl-piperazin-1-ylmethyl)-1-oxo-2-phenyl-1,2-dihydro-isoquinoline-4-carboxylic acid ((S)-1-phenyl-propyl)-amide | 1.12 | 508.6 | 509.3 |
| 2j | 4-[1-Oxo-2-phenyl-4-(1-phenyl-propylcarbamoyl)-1,2-dihydro-isoquinolin-3-ylmethyl]-piperazine-1-carboxylic acid ethyl ester | 1.33 | 552.7 | 553.7 |
| 2k | 3-(4-Methyl-piperazin-1-ylmethyl)-1-oxo-2-phenyl-1,2-dihydro-isoquinoline-4-carboxylic acid ((S)-1-phenyl-propyl)-amide | 0.87 | 494.6 | 495.7 |
| 2l | 1-Oxo-2-phenyl-3-(1,3,4,9-tetrahydro-beta-carbolin-2-ylmethyl)-1,2-dihydro-isoquinoline-4-carboxylic acid ((S)-1-phenyl-propyl)-amide | 1.27 | 566.7 | 567.7 |
| 2m | 1-Oxo-2-phenyl-3-piperazin-1-ylmethyl-1,2-dihydro-isoquinoline-4-carboxylic acid ((S)-1-phenyl-propyl)-amide | 0.86 | 480.6 | 481.2 |
| 2n | 3-(3-Methyl-piperazin-1-ylmethyl)-1-oxo-2-phenyl-1,2-dihydro-isoquinoline-4-carboxylic acid ((S)-1-phenyl-propyl)-amide | 0.88 | 494.6 | 495.7 |
| 2o | 3-(3,5-Dimethyl-piperazin-1-ylmethyl)-1-oxo-2-phenyl-1,2-dihydro-isoquinoline-4-carboxylic acid ((S)-1-phenyl-propyl)-amide | 0.9 | 508.7 | 509.3 |
| 2p | 3-(4-Benzyl-piperazin-1-ylmethyl)-1-oxo-2-phenyl-1,2-dihydro-isoquinoline-4-carboxylic acid ((S)-1-phenyl-propyl)-amide | 1.02 | 570.7 | 571.5 |
| 2q | 1-Oxo-3-[4-(2-oxo-2-pyrrolidin-1-yl-ethyl)-piperazin-1-ylmethyl]-2-phenyl-1,2-dihydro-isoquinoline-4-carboxylic acid ((S)-1-phenyl-propyl)-amide | 0.92 | 591.8 | 592.4 |

-continued

| | Chemical name | $t_R$ (min) | MW | m/z (MH+) |
|---|---|---|---|---|
| 2r | 3-Morpholin-4-ylmethyl-1-oxo-2-phenyl-1,2-dihydro-isoquinoline-4-carboxylic acid ((S)-1-phenyl-propyl)-amide | 1.08 | 481.6 | 482.2 |
| 2s | 3-(2,6-Dimethyl-morpholin-4-ylmethyl)-1-oxo-2-phenyl-1,2-dihydro-isoquinoline-4-carboxylic acid ((S)-1-phenyl-propyl)-amide | 1.21 | 509.6 | 510.2 |
| 2t | 1-Oxo-2-phenyl-3-thiomorpholin-4-ylmethyl-1,2-dihydro-isoquinoline-4-carboxylic acid ((S)-1-phenyl-propyl)-amide | 1.22 | 497.7 | 498.8 |
| 2u | 3-(1,4-Dioxa-8-aza-spiro[4.5]dec-8-ylmethyl)-1-oxo-2-phenyl-1,2-dihydro-isoquinoline-4-carboxylic acid ((S)-1-phenyl-propyl)-amide | 1.01 | 537.7 | 538.4 |
| 2v | 1-Oxo-2-phenyl-3-piperidin-1-ylmethyl-1,2-dihydro-isoquinoline-4-carboxylic acid ((S)-1-phenyl-propyl)-amide | 1 | 479.6 | 480.3 |
| 2w | 3-(2-Methyl-piperidin-1-ylmethyl)-1-oxo-2-phenyl-1,2-dihydro-isoquinoline-4-carboxylic acid ((S)-1-phenyl-propyl)-amide | 1.07 | 493.6 | 494.4 |
| 2x | 3-(2,6-Dimethyl-piperidin-1-ylmethyl)-1-oxo-2-phenyl-1,2-dihydro-isoquinoline-4-carboxylic acid ((S)-1-phenyl-propyl)-amide | 1.09 | 507.7 | 508.4 |
| 2y | 3-(2-Hydroxymethyl-piperidin-1-ylmethyl)-1-oxo-2-phenyl-1,2-dihydro-isoquinoline-4-carboxylic acid ((S)-1-phenyl-propyl)-amide | 0.93 | 509.6 | 510.3 |
| 2z | 1-[1-Oxo-2-phenyl-4-(1-phenyl-propylcarbamoyl)-1,2-dihydro-isoquinolin-3-ylmethyl]-piperidine-3-carboxylic acid ethyl ester | 1.14 | 551.7 | 552.4 |
| 2aa | 3-(3-Methyl-piperidin-1-ylmethyl)-1-oxo-2-phenyl-1,2-dihydro-isoquinoline-4-carboxylic acid ((S)-1-phenyl-propyl)-amide | 1.09 | 493.6 | 494.5 |
| 2ab | 3-(4-Hydroxy-piperidin-1-ylmethyl)-1-oxo-2-phenyl-1,2-dihydro-isoquinoline-4-carboxylic acid ((S)-1-phenyl-propyl)-amide | 0.83 | 495.6 | 496.5 |
| 2ac | 1-Oxo-2-phenyl-3-(4-phenyl-piperidin-1-ylmethyl)-1,2-dihydro-isoquinoline-4-carboxylic acid ((S)-1-phenyl-propyl)-amide | 1.27 | 555.7 | 556.5 |
| 2ad | 1-[1-Oxo-2-phenyl-4-(1-phenyl-propylcarbamoyl)-1,2-dihydro-isoquinolin-3-ylmethyl]-piperidine-4-carboxylic acid ethyl ester | 1.11 | 551.7 | 552.5 |
| 2ae | 3-(4-Methyl-piperidin-1-ylmethyl)-1-oxo-2-phenyl-1,2-dihydro-isoquinoline-4-carboxylic acid ((S)-1-phenyl-propyl)-amide | 1.1 | 493.6 | 494.6 |
| 2af | 1-Oxo-2-phenyl-3-(4-pyridin-2-yl-piperazin-1-ylmethyl)-1,2-dihydro-isoquinoline-4-carboxylic acid ((S)-1-phenyl-propyl)-amide | 0.97 | 557.7 | 558.4 |
| 2ag | 3-(Octahydro-quinolin-1-ylmethyl)-1-oxo-2-phenyl-1,2-dihydro-isoquinoline-4-carboxylic acid ((S)-1-phenyl-propyl)-amide | 1.18 | 533.7 | 534.4 |
| 2ah | 3-Azepan-1-ylmethyl-1-oxo-2-phenyl-1,2-dihydro-isoquinoline-4-carboxylic acid ((S)-1-phenyl-propyl)-amide | 1.08 | 493.6 | 494.6 |
| 2ai | 3-(3-Hydroxy-piperidin-1-ylmethyl)-1-oxo-2-phenyl-1,2-dihydro-isoquinoline-4-carboxylic acid ((S)-1-phenyl-propyl)-amide | 0.88 | 495.6 | 496.5 |
| 2aj | 3-[4-(2,4-Dimethyl-phenyl)-piperazin-1-ylmethyl]-1-oxo-2-phenyl-1,2-dihydro-isoquinoline-4-carboxylic acid ((S)-1-phenyl-propyl)-amide | 1.45 | 584.8 | 585.5 |
| 2ak | 3-[4-(3,4-Dimethyl-phenyl)-piperazin-1-ylmethyl]-1-oxo-2-phenyl-1,2-dihydro-isoquinoline-4-carboxylic acid ((S)-1-phenyl-propyl)-amide | 1.29 | 584.8 | 585.6 |
| 2al | 3-(4-Dimethylamino-piperidin-1-ylmethyl)-1-oxo-2-phenyl-1,2-dihydro-isoquinoline-4-carboxylic acid ((S)-1-phenyl-propyl)-amide | 0.81 | 522.7 | 523.5 |
| 2am | 3-[4-(2,5-Dimethyl-phenyl)-piperazin-1-ylmethyl]-1-oxo-2-phenyl-1,2-dihydro-isoquinoline-4-carboxylic acid ((S)-1-phenyl-propyl)-amide | 1.47 | 584.8 | 585.6 |
| 2an | 3-[4-(2-Fluoro-phenyl)-piperazin-1-ylmethyl]-1-oxo-2-phenyl-1,2-dihydro-isoquinoline-4-carboxylic acid ((S)-1-phenyl-propyl)-amide | 1.42 | 574.7 | 575.4 |
| 2ao | 3-[4-(3-Methoxy-phenyl)-piperazin-1-ylmethyl]-1-oxo-2-phenyl-1,2-dihydro-isoquinoline-4-carboxylic acid ((S)-1-phenyl-propyl)-amide | 1.32 | 586.7 | 587.3 |
| 2ap | 1-Oxo-2-phenyl-3-(4-m-tolyl-piperazin-1-ylmethyl)-1,2-dihydro-isoquinoline-4-carboxylic acid ((S)-1-phenyl-propyl)-amide | 1.33 | 570.7 | 571.7 |
| 2aq | 3-[4-(4-Methoxy-phenyl)-piperazin-1-ylmethyl]-1-oxo-2-phenyl-1,2-dihydro-isoquinoline-4-carboxylic acid ((S)-1-phenyl-propyl)-amide | 1.11 | 586.7 | 587.6 |

-continued

| | Chemical name | $t_R$ (min) | MW | m/z (MH+) |
|---|---|---|---|---|
| 2ar | 1-Oxo-3-(4-phenethyl-piperazin-1-ylmethyl)-2-phenyl-1,2-dihydro-isoquinoline-4-carboxylic acid ((S)-1-phenyl-propyl)-amide | 1.09 | 584.8 | 585.5 |
| 2as | 1-Oxo-2-phenyl-3-(4-pyrimidin-2-yl-piperazin-1-ylmethyl)-1,2-dihydro-isoquinoline-4-carboxylic acid ((S)-1-phenyl-propyl)-amide | 1.18 | 558.7 | 559.3 |
| 2at | 3-[4-(2-Cyano-phenyl)-piperazin-1-ylmethyl]-1-oxo-2-phenyl-1,2-dihydro-isoquinoline-4-carboxylic acid ((S)-1-phenyl-propyl)-amide | 1.43 | 581.7 | 582.7 |
| 2au | 3-[4-(4-Chloro-phenyl)-piperazin-1-ylmethyl]-1-oxo-2-phenyl-1,2-dihydro-isoquinoline-4-carboxylic acid ((S)-1-phenyl-propyl)-amide | 1.54 | 591.2 | 591.3 |
| 2av | 3-((1S,3R,5R)-3-Hydroxy-8-aza-bicyclo[3.2.1]oct-8-ylmethyl)-1-oxo-2-phenyl-1,2-dihydro-isoquinoline-4-carboxylic acid ((S)-1-phenyl-propyl)-amide | 0.88 | 521.7 | 522.7 |
| 2aw | 3-(4-Acetyl-piperazin-1-ylmethyl)-1-oxo-2-phenyl-1,2-dihydro-isoquinoline-4-carboxylic acid ((S)-1-phenyl-propyl)-amide | 1.07 | 522.6 | 523.5 |
| 2ax | 3-(4-Methyl-[1,4]diazepan-1-ylmethyl)-1-oxo-2-phenyl-1,2-dihydro-isoquinoline-4-carboxylic acid ((S)-1-phenyl-propyl)-amide | 0.89 | 508.7 | 509.2 |
| 2ay | 3-(4-Ethyl-piperazin-1-ylmethyl)-1-oxo-2-phenyl-1,2-dihydro-isoquinoline-4-carboxylic acid ((S)-1-phenyl-propyl)-amide | 0.89 | 508.7 | 509.2 |
| 2az | 3-((2S,6R)-2,6-Dimethyl-morpholin-4-ylmethyl)-1-oxo-2-phenyl-1,2-dihydro-isoquinoline-4-carboxylic acid ((S)-1-phenyl-propyl)-amide | 1.21 | 509.6 | 510.2 |
| 2ba | 3-[4-(2,4-Difluoro-phenyl)-piperazin-1-ylmethyl]-1-oxo-2-phenyl-1,2-dihydro-isoquinoline-4-carboxylic acid ((S)-1-phenyl-propyl)-amide | 1.48 | 592.7 | 593.6 |
| 2bb | 3-[4-(3-Dimethylamino-propyl)-piperazin-1-ylmethyl]-1-oxo-2-phenyl-1,2-dihydro-isoquinoline-4-carboxylic acid ((S)-1-phenyl-propyl)-amide | 0.76 | 565.8 | 566.7 |
| 2bc | 3-(4-Isopropyl-piperazin-1-ylmethyl)-1-oxo-2-phenyl-1,2-dihydro-isoquinoline-4-carboxylic acid ((S)-1-phenyl-propyl)-amide | 0.91 | 522.7 | 523.5 |
| 2bd | 3-(3-Aza-bicyclo[3.2.2]non-3-ylmethyl)-1-oxo-2-phenyl-1,2-dihydro-isoquinoline-4-carboxylic acid ((S)-1-phenyl-propyl)-amide | 1.21 | 519.7 | 520.4 |
| 2be | 3-(4-Cyclopentyl-piperazin-1-ylmethyl)-1-oxo-2-phenyl-1,2-dihydro-isoquinoline-4-carboxylic acid ((S)-1-phenyl-propyl)-amide | 0.98 | 548.7 | 549.6 |
| 2bf | 3-[1,4']Bipiperidinyl-1'-ylmethyl-1-oxo-2-phenyl-1,2-dihydro-isoquinoline-4-carboxylic acid ((S)-1-phenyl-propyl)-amide | 0.86 | 562.8 | 563.2 |
| 2bg | 3-(3,4-Dihydro-1H-isoquinolin-2-ylmethyl)-1-oxo-2-phenyl-1,2-dihydro-isoquinoline-4-carboxylic acid ((S)-1-phenyl-propyl)-amide | 1.22 | 527.7 | 528.7 |
| 2bh | 3-[4-(2-Dimethylamino-ethyl)-piperazin-1-ylmethyl]-1-oxo-2-phenyl-1,2-dihydro-isoquinoline-4-carboxylic acid ((S)-1-phenyl-propyl)-amide | 0.74 | 551.7 | 552.5 |
| 2bi | 3-(4-Hydroxymethyl-piperidin-1-ylmethyl)-1-oxo-2-phenyl-1,2-dihydro-isoquinoline-4-carboxylic acid ((S)-1-phenyl-propyl)-amide | 0.86 | 509.6 | 510.3 |
| 2bj | 1-Oxo-2-phenyl-3-[4-(tetrahydro-furan-2-carbonyl)-piperazin-1-ylmethyl]-1,2-dihydro-isoquinoline-4-carboxylic acid ((S)-1-phenyl-propyl)-amide | 1.16 | 578.7 | 579.9 |
| 2bk | 3-(4-Isobutyl-piperazin-1-ylmethyl)-1-oxo-2-phenyl-1,2-dihydro-isoquinoline-4-carboxylic acid ((S)-1-phenyl-propyl)-amide | 0.98 | 536.7 | 537.4 |
| 2bl | 3-[4-(2-Methoxy-ethyl)-piperazin-1-ylmethyl]-1-oxo-2-phenyl-1,2-dihydro-isoquinoline-4-carboxylic acid ((S)-1-phenyl-propyl)-amide | 0.91 | 538.7 | 539.6 |
| 2bm | 3-[4-(2-Morpholin-4-yl-ethyl)-piperazin-1-ylmethyl]-1-oxo-2-phenyl-1,2-dihydro-isoquinoline-4-carboxylic acid ((S)-1-phenyl-propyl)-amide | 0.75 | 593.8 | 594.7 |
| 2bn | 3-(1,3-Dihydro-isoindol-2-ylmethyl)-1-oxo-2-phenyl-1,2-dihydro-isoquinoline-4-carboxylic acid ((S)-1-phenyl-propyl)-amide | 1.16 | 513.6 | 514.8 |
| 2bo | 3-[4-(1-Methyl-piperidin-4-yl)-piperazin-1-ylmethyl]-1-oxo-2-phenyl-1,2-dihydro-isoquinoline-4-carboxylic acid ((S)-1-phenyl-propyl)-amide | 0.72 | 577.8 | 578.5 |
| 2bp | 1-Oxo-2-phenyl-3-[4-(2-piperidin-1-yl-ethyl)-piperazin-1-ylmethyl]-1,2-dihydro-isoquinoline-4-carboxylic acid ((S)-1-phenyl-propyl)-amide | 0.75 | 591.8 | 592.5 |

-continued

| | Chemical name | $t_R$ (min) | MW | m/z (MH+) |
|---|---|---|---|---|
| 2bq | 1-Oxo-2-phenyl-3-[4-(2-pyrrolidin-1-yl-ethyl)-piperazin-1-ylmethyl]-1,2-dihydro-isoquinoline-4-carboxylic acid ((S)-1-phenyl-propyl)-amide | 0.74 | 577.8 | 578.4 |
| 2br | 3-(4-Dimethylcarbamoylmethyl-piperazin-1-ylmethyl)-1-oxo-2-phenyl-1,2-dihydro-isoquinoline-4-carboxylic acid ((S)-1-phenyl-propyl)-amide | 0.89 | 565.7 | 566.6 |
| 2bs | 3-(Octahydro-pyrido[1,2-a]pyrazin-2-ylmethyl)-1-oxo-2-phenyl-1,2-dihydro-isoquinoline-4-carboxylic acid ((S)-1-phenyl-propyl)-amide | 0.93 | 534.7 | 535.4 |
| 2bt | 3-(4-Formyl-[1,4]diazepan-1-ylmethyl)-1-oxo-2-phenyl-1,2-dihydro-isoquinoline-4-carboxylic acid ((S)-1-phenyl-propyl)-amide | 0.94 | 522.6 | 523.6 |
| 2bu | 3-[4-(4-Cyano-phenyl)-piperazin-1-ylmethyl]-1-oxo-2-phenyl-1,2-dihydro-isoquinoline-4-carboxylic acid ((S)-1-phenyl-propyl)-amide | 1.46 | 581.7 | 582.6 |
| 2bv | 1-Oxo-2-phenyl-3-(4-pyridin-4-ylmethyl-piperazin-1-ylmethyl)-1,2-dihydro-isoquinoline-4-carboxylic acid ((S)-1-phenyl-propyl)-amide | 0.77 | 571.7 | 572.4 |
| 2bw | 1-Oxo-2-phenyl-3-[4-(3-pyrrolidin-1-yl-propyl)-piperazin-1-ylmethyl]-1,2-dihydro-isoquinoline-4-carboxylic acid ((S)-1-phenyl-propyl)-amide | 0.75 | 591.8 | 592.6 |
| 2bx | 1-Oxo-2-phenyl-3-(4-pyridin-2-ylmethyl-piperazin-1-ylmethyl)-1,2-dihydro-isoquinoline-4-carboxylic acid ((S)-1-phenyl-propyl)-amide | 0.93 | 571.7 | 572.5 |
| 2by | 3-(4-Ethanesulfonyl-piperazin-1-ylmethyl)-1-oxo-2-phenyl-1,2-dihydro-isoquinoline-4-carboxylic acid ((S)-1-phenyl-propyl)-amide | 1.38 | 572.7 | 573.7 |
| 2bz | 3-(4-sec-Butyl-piperazin-1-ylmethyl)-1-oxo-2-phenyl-1,2-dihydro-isoquinoline-4-carboxylic acid ((S)-1-phenyl-propyl)-amide | 0.96 | 536.7 | 537.4 |
| 2ca | 3-[4-(1-Ethyl-propyl)-piperazin-1-ylmethyl]-1-oxo-2-phenyl-1,2-dihydro-isoquinoline-4-carboxylic acid ((S)-1-phenyl-propyl)-amide | 1.01 | 550.7 | 551.8 |
| 2cb | 3-[4-(2-Cyano-ethyl)-piperazin-1-ylmethyl]-1-oxo-2-phenyl-1,2-dihydro-isoquinoline-4-carboxylic acid ((S)-1-phenyl-propyl)-amide | 0.9 | 533.7 | 534.4 |
| 2cc | 3-(4-Methanesulfonyl-piperazin-1-ylmethyl)-1-oxo-2-phenyl-1,2-dihydro-isoquinoline-4-carboxylic acid ((S)-1-phenyl-propyl)-amide | 1.31 | 558.7 | 559.2 |
| 2cd | {1-[1-Oxo-2-phenyl-4-(1-phenyl-propylcarbamoyl)-1,2-dihydro-isoquinolin-3-ylmethyl]-piperidin-4-yl}-acetic acid ethyl ester | 1.12 | 565.7 | 566.7 |
| 2ce | 3-[4-(3-Fluoro-phenyl)-piperazin-1-ylmethyl]-1-oxo-2-phenyl-1,2-dihydro-isoquinoline-4-carboxylic acid ((S)-1-phenyl-propyl)-amide | 1.48 | 574.7 | 575.5 |
| 2cf | 1-Oxo-2-phenyl-3-((S)-3-phenyl-piperidin-1-ylmethyl)-1,2-dihydro-isoquinoline-4-carboxylic acid ((S)-1-phenyl-propyl)-amide | 1.27 | 555.7 | 556.5 |
| 2cg | 1-Oxo-2-phenyl-3-[4-(pyrrolidine-1-carbonyl)-piperazin-1-ylmethyl]-1,2-dihydro-isoquinoline-4-carboxylic acid ((S)-1-phenyl-propyl)-amide | 1.11 | 577.7 | 578.6 |
| 2ch | 3-[4-(Morpholine-4-carbonyl)-piperazin-1-ylmethyl]-1-oxo-2-phenyl-1,2-dihydro-isoquinoline-4-carboxylic acid ((S)-1-phenyl-propyl)-amide | 1.04 | 593.7 | 594.7 |
| 2ci | 3-(4-Methoxy-piperidin-1-ylmethyl)-1-oxo-2-phenyl-1,2-dihydro-isoquinoline-4-carboxylic acid ((S)-1-phenyl-propyl)-amide | 0.98 | 509.6 | 510.2 |
| 2cj | 3-(4'-Hydroxy-3',4',5',6'-tetrahydro-2'H-[3,4']bipyridinyl-1'-ylmethyl)-1-oxo-2-phenyl-1,2-dihydro-isoquinoline-4-carboxylic acid ((S)-1-phenyl-propyl)-amide | 0.71 | 572.7 | 573.8 |
| 2ck | 3-(4-Hydroxy-3,4,5,6-tetrahydro-2H-[4,4']bipyridinyl-1-ylmethyl)-1-oxo-2-phenyl-1,2-dihydro-isoquinoline-4-carboxylic acid ((S)-1-phenyl-propyl)-amide | 0.71 | 572.7 | 573.8 |
| 2cl | 3-(3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide | 1.25 | 583.7 | 584.5 |
| 2cm | 3-(4-Hydroxy-4-methyl-piperidin-1-ylmethyl)-1-oxo-2-phenyl-1,2-dihydro-isoquinoline-4-carboxylic acid ((S)-1-phenyl-propyl)-amide | 0.91 | 509.6 | 510.1 |
| 2cn | 3-(hexahydro-spiro[benzo[1,3]dioxole-2,4'-piperidin]-1'-ylmethyl)-1-oxo-2-phenyl-1,2-dihydro-isoquinoline-4-carboxylic acid ((S)-1-phenyl-propyl)-amide | 1.27 | 591.7 | 592.5 |
| 2co | 1-Oxo-2-phenyl-3-(3,4,5,6-tetrahydro-2H-[4,4']bipyridinyl-1-ylmethyl)-1,2-dihydro-isoquinoline-4-carboxylic acid ((S)-1-phenyl-propyl)-amide | 0.71 | 556.7 | 557.4 |

-continued

| | Chemical name | $t_R$ (min) | MW | m/z (MH+) |
|---|---|---|---|---|
| 2cp | 3-[4-(2-Dimethylamino-ethyl)-piperidin-1-ylmethyl]-1-oxo-2-phenyl-1,2-dihydro-isoquinoline-4-carboxylic acid ((S)-1-phenyl-propyl)-amide | 0.68 | 550.7 | 551.4 |
| 2cq | 3-(4-Dimethylsulfamoyl-piperazin-1-ylmethyl)-1-oxo-2-phenyl-1,2-dihydro-isoquinoline-4-carboxylic acid ((S)-1-phenyl-propyl)-amide | 1.43 | 587.7 | 588.3 |
| 2cr | 3-(1,1-Dioxo-thiomorpholin-4-ylmethyl)-1-oxo-2-phenyl-1,2-dihydro-isoquinoline-4-carboxylic acid ((S)-1-phenyl-propyl)-amide | 1.29 | 529.7 | 530.3 |
| 2cs | 1-Oxo-2-phenyl-3-(2-pyridin-2-ylmethyl-piperidin-1-ylmethyl)-1,2-dihydro-isoquinoline-4-carboxylic acid ((S)-1-phenyl-propyl)-amide | 1.05 | 570.7 | 571.6 |
| 2ct | 3-(2-Morpholin-4-ylmethyl-piperidin-1-ylmethyl)-1-oxo-2-phenyl-1,2-dihydro-isoquinoline-4-carboxylic acid ((S)-1-phenyl-propyl)-amide | 1.08 | 578.8 | 579.8 |
| 2cu | 3-(4-Furo[3,2-c]pyridin-4-yl-piperazin-1-ylmethyl)-1-oxo-2-phenyl-1,2-dihydro-isoquinoline-4-carboxylic acid ((S)-1-phenyl-propyl)-amide | 1.01 | 597.7 | 598.5 |
| 2cv | 3-(4-Cyclopropylmethyl-piperazin-1-ylmethyl)-1-oxo-2-phenyl-1,2-dihydro-isoquinoline-4-carboxylic acid ((S)-1-phenyl-propyl)-amide | 0.95 | 534.7 | 535.3 |
| 2cw | 3-[4-(2-Morpholin-4-yl-ethyl)-piperidin-1-ylmethyl]-1-oxo-2-phenyl-1,2-dihydro-isoquinoline-4-carboxylic acid ((S)-1-phenyl-propyl)-amide | 0.69 | 592.8 | 593.5 |
| 2cx | 1-Oxo-2-phenyl-3-(4-pyrimidin-2-yl-[1,4]diazepan-1-ylmethyl)-1,2-dihydro-isoquinoline-4-carboxylic acid ((S)-1-phenyl-propyl)-amide | 1.05 | 572.7 | 573.5 |
| 2cy | 3-(4-Methyl-6,7-dihydro-4H-thieno[3,2-c]pyridin-5-ylmethyl)-1-oxo-2-phenyl-1,2-dihydro-isoquinoline-4-carboxylic acid ((S)-1-phenyl-propyl)-amide | 1.23 | 547.7 | 548.5 |
| 2cz | 3-[1,4]Diazepan-1-ylmethyl-1-oxo-2-phenyl-1,2-dihydro-isoquinoline-4-carboxylic acid ((S)-1-phenyl-propyl)-amide | 0.89 | 494.6 | 495.7 |
| 2da | 3-((2S,5R)-2,5-Dimethyl-piperazin-1-ylmethyl)-1-oxo-2-phenyl-1,2-dihydro-isoquinoline-4-carboxylic acid ((S)-1-phenyl-propyl)-amide | 0.92 | 508.7 | 509.2 |
| 2db | 3-((S)-3-Methyl-piperazin-1-ylmethyl)-1-oxo-2-phenyl-1,2-dihydro-isoquinoline-4-carboxylic acid ((S)-1-phenyl-propyl)-amide | 0.88 | 494.6 | 495.7 |
| 2dc | 3-((R)-3-Methyl-piperazin-1-ylmethyl)-1-oxo-2-phenyl-1,2-dihydro-isoquinoline-4-carboxylic acid ((S)-1-phenyl-propyl)-amide | 0.88 | 494.6 | 495.7 |
| 2dd | 3-[3-(3-Chloro-phenyl)-piperazin-1-ylmethyl]-1-oxo-2-phenyl-1,2-dihydro-isoquinoline-4-carboxylic acid ((S)-1-phenyl-propyl)-amide | 1.11 | 591.2 | 591.4 |
| 2de | 3-[4-(1H-Indol-4-yl)-piperazin-1-ylmethyl]-1-oxo-2-phenyl-1,2-dihydro-isoquinoline-4-carboxylic acid ((S)-1-phenyl-propyl)-amide | 1.1 | 595.7 | 596.6 |
| 2df | 1-Oxo-3-(3-oxo-piperazin-1-ylmethyl)-2-phenyl-1,2-dihydro-isoquinoline-4-carboxylic acid ((S)-1-phenyl-propyl)-amide | 1.09 | 494.6 | 495.7 |
| 2dg | 3-[4-(1H-Indol-5-yl)-piperazin-1-ylmethyl]-1-oxo-2-phenyl-1,2-dihydro-isoquinoline-4-carboxylic acid ((S)-1-phenyl-propyl)-amide | 1.04 | 595.7 | 596.7 |
| 2dh | 3-(6,9-Diaza-spiro[4.5]dec-9-ylmethyl)-1-oxo-2-phenyl-1,2-dihydro-isoquinoline-4-carboxylic acid ((S)-1-phenyl-propyl)-amide | 0.97 | 534.7 | 535.3 |
| 2di | 3-(1,4-Diaza-spiro[5.5]undec-4-ylmethyl)-1-oxo-2-phenyl-1,2-dihydro-isoquinoline-4-carboxylic acid ((S)-1-phenyl-propyl)-amide | 1.01 | 548.7 | 549.7 |
| 2dj | 3-(3-Isopropyl-piperazin-1-ylmethyl)-1-oxo-2-phenyl-1,2-dihydro-isoquinoline-4-carboxylic acid ((S)-1-phenyl-propyl)-amide | 0.96 | 522.7 | 523.5 |
| 2dk | 3-(3,3-Dimethyl-piperazin-1-ylmethyl)-1-oxo-2-phenyl-1,2-dihydro-isoquinoline-4-carboxylic acid ((S)-1-phenyl-propyl)-amide | 0.9 | 508.7 | 509.2 |
| 2dl | 3-[3-(4-Fluoro-phenyl)-piperazin-1-ylmethyl]-1-oxo-2-phenyl-1,2-dihydro-isoquinoline-4-carboxylic acid ((S)-1-phenyl-propyl)-amide | 1.05 | 574.7 | 575.4 |
| 2dm | 1-Oxo-2-phenyl-3-(3-p-tolyl-piperazin-1-ylmethyl)-1,2-dihydro-isoquinoline-4-carboxylic acid ((S)-1-phenyl-propyl)-amide | 1.08 | 570.7 | 571.7 |
| 2dn | 4-[1-Oxo-2-phenyl-4-(1-phenyl-propylcarbamoyl)-1,2-dihydro-isoquinolin-3-ylmethyl]-piperazine-1-carboxylic acid tert-butyl ester | 1.49 | 580.7 | 581.9 |
| 2do | 3-(4-Methylcarbamoylmethyl-piperazin-1-ylmethyl)-1-oxo-2-phenyl-1,2-dihydro-isoquinoline-4-carboxylic acid ((S)-1-phenyl-propyl)-amide | 0.86 | 551.7 | 552.9 |

-continued

| | Chemical name | $t_R$ (min) | MW | m/z (MH+) |
|---|---|---|---|---|
| 2dp | 8-Chloro-3-dimethylaminomethyl-1-oxo-2-phenyl-1,2-dihydro-isoquinoline-4-carboxylic acid ((S)-1-phenyl-propyl)-amide | 0.95 | 474.0 | 474.6 |
| 2dr | 3-Cyclopentylaminomethyl-1-oxo-2-phenyl-1,2-dihydro-isoquinoline-4-carboxylic acid ((S)-1-phenyl-propyl)-amide | 1.03 | 479.6 | 480.4 |
| 2ds | 3-Cyclohexylaminomethyl-1-oxo-2-phenyl-1,2-dihydro-isoquinoline-4-carboxylic acid ((S)-1-phenyl-propyl)-amide | 1.1 | 493.6 | 494.4 |
| 2dt | 3-{[(2-Hydroxy-ethyl)-methyl-amino]-methyl}-1-oxo-2-phenyl-1,2-dihydro-isoquinoline-4-carboxylic acid ((S)-1-phenyl-propyl)-amide | 0.84 | 469.6 | 470.6 |
| 2du | 3-Imidazol-1-ylmethyl-1-oxo-2-phenyl-1,2-dihydro-isoquinoline-4-carboxylic acid ((S)-1-phenyl-propyl)-amide | 0.86 | 462.6 | 463.4 |
| 2dv | 3-(2-Methyl-imidazol-1-ylmethyl)-1-oxo-2-phenyl-1,2-dihydro-isoquinoline-4-carboxylic acid ((S)-1-phenyl-propyl)-amide | 0.88 | 476.6 | 477.3 |
| 2dw | 3-(4-Methyl-imidazol-1-ylmethyl)-1-oxo-2-phenyl-1,2-dihydro-isoquinoline-4-carboxylic acid ((S)-1-phenyl-propyl)-amide | 0.89 | 476.6 | 477.3 |
| 2dx | 3-(2,5-Dihydro-pyrrol-1-ylmethyl)-1-oxo-2-phenyl-1,2-dihydro-isoquinoline-4-carboxylic acid ((S)-1-phenyl-propyl)-amide | 0.92 | 463.6 | 464.5 |
| 2dy | 3-(2,5-Dimethyl-2,5-dihydro-pyrrol-1-ylmethyl)-1-oxo-2-phenyl-1,2-dihydro-isoquinoline-4-carboxylic acid ((S)-1-phenyl-propyl)-amide | 1.06 | 491.6 | 492.4 |
| 2dz | 1-Oxo-2-phenyl-3-pyrrolidin-1-ylmethyl-1,2-dihydro-isoquinoline-4-carboxylic acid ((S)-1-phenyl-propyl)-amide | 0.92 | 465.6 | 466.3 |
| 2ea | 1-Oxo-2-phenyl-3-(thiazol-2-ylaminomethyl)-1,2-dihydro-isoquinoline-4-carboxylic acid ((S)-1-phenyl-propyl)-amide | 0.88 | 494.6 | 495.6 |
| 2eb | 1-Oxo-2-phenyl-3-(pyrimidin-4-ylaminomethyl)-1,2-dihydro-isoquinoline-4-carboxylic acid ((S)-1-phenyl-propyl)-amide | 0.85 | 489.6 | 490.4 |
| 2ec | 3-(tert-Butylamino-methyl)-1-oxo-2-phenyl-1,2-dihydro-isoquinoline-4-carboxylic acid ((S)-1-phenyl-propyl)-amide | 1 | 467.6 | 468.7 |
| 2ed | 3-[(2-Hydroxy-1,1-dimethyl-ethylamino)-methyl]-1-oxo-2-phenyl-1,2-dihydro-isoquinoline-4-carboxylic acid ((S)-1-phenyl-propyl)-amide | 0.91 | 483.6 | 484.3 |
| 2ee | 3-(Isopropylamino-methyl)-1-oxo-2-phenyl-1,2-dihydro-isoquinoline-4-carboxylic acid ((S)-1-phenyl-propyl)-amide | 0.93 | 453.6 | 454.3 |
| 2ef | 3-[(2-Hydroxy-1-methyl-ethylamino)-methyl]-1-oxo-2-phenyl-1,2-dihydro-isoquinoline-4-carboxylic acid ((S)-1-phenyl-propyl)-amide | 0.86 | 469.6 | 470.5 |
| 2eg | 3-[(1-Hydroxymethyl-propylamino)-methyl]-1-oxo-2-phenyl-1,2-dihydro-isoquinoline-4-carboxylic acid ((S)-1-phenyl-propyl)-amide | 0.92 | 483.6 | 484.4 |
| 2eh | 3-[(2,2-Dimethyl-propylamino)-methyl]-1-oxo-2-phenyl-1,2-dihydro-isoquinoline-4-carboxylic acid ((S)-1-phenyl-propyl)-amide | 1.13 | 481.6 | 482.2 |
| 2ei | 1-Oxo-2-phenyl-3-prop-2-ynylaminomethyl-1,2-dihydro-isoquinoline-4-carboxylic acid ((S)-1-phenyl-propyl)-amide | 0.95 | 449.6 | 450.2 |
| 2ej | 3-Allylaminomethyl-1-oxo-2-phenyl-1,2-dihydro-isoquinoline-4-carboxylic acid ((S)-1-phenyl-propyl)-amide | 0.94 | 451.6 | 452.4 |
| 2ek | 3-[(Methyl-prop-2-ynyl-amino)-methyl]-1-oxo-2-phenyl-1,2-dihydro-isoquinoline-4-carboxylic acid ((S)-1-phenyl-propyl)-amide | 1.22 | 463.6 | 464.5 |
| 2el | 3-Diallylaminomethyl-1-oxo-2-phenyl-1,2-dihydro-isoquinoline-4-carboxylic acid ((S)-1-phenyl-propyl)-amide | 1.19 | 491.6 | 492.4 |
| 2em | 3-Diethylaminomethyl-1-oxo-2-phenyl-1,2-dihydro-isoquinoline-4-carboxylic acid ((S)-1-phenyl-propyl)-amide | 0.98 | 467.6 | 468.5 |
| 2en | 3-[(Isopropyl-methyl-amino)-methyl]-1-oxo-2-phenyl-1,2-dihydro-isoquinoline-4-carboxylic acid ((S)-1-phenyl-propyl)-amide | 0.96 | 467.6 | 468.7 |
| 2eo | 3-[((S)-2-Hydroxy-1-methyl-ethylamino)-methyl]-1-oxo-2-phenyl-1,2-dihydro-isoquinoline-4-carboxylic acid ((S)-1-phenyl-propyl)-amide | 0.86 | 469.6 | 470.5 |
| 2ep | 3-[((R)-2-Hydroxy-1-methyl-ethylamino)-methyl]-1-oxo-2-phenyl-1,2-dihydro-isoquinoline-4-carboxylic acid ((S)-1-phenyl-propyl)-amide | 0.87 | 469.6 | 470.5 |
| 2eq | 3-{[(2-Methoxy-ethyl)-methyl-amino]-methyl}-1-oxo-2-phenyl-1,2-dihydro-isoquinoline-4-carboxylic acid ((S)-1-phenyl-propyl)-amide | 0.96 | 483.6 | 484.4 |
| 2er | 3-((R)-3-Hydroxy-pyrrolidin-1-ylmethyl)-1-oxo-2-phenyl-1,2-dihydro-isoquinoline-4-carboxylic acid ((S)-1-phenyl-propyl)-amide | 0.85 | 481.6 | 482.3 |
| 2es | 3-((S)-3-Hydroxy-pyrrolidin-1-ylmethyl)-1-oxo-2-phenyl-1,2-dihydro-isoquinoline-4-carboxylic acid ((S)-1-phenyl-propyl)-amide | 0.84 | 481.6 | 482.3 |

-continued

| | Chemical name | t_R (min) | MW | m/z (MH+) |
|---|---|---|---|---|
| 2et | 3-[(Cyclopentyl-methyl-amino)-methyl]-1-oxo-2-phenyl-1,2-dihydro-isoquinoline-4-carboxylic acid ((S)-1-phenyl-propyl)-amide | 1.09 | 493.6 | 494.5 |
| 2eu | 3-{[(2-Hydroxy-1-methyl-ethyl)-methyl-amino]-methyl}-1-oxo-2-phenyl-1,2-dihydro-isoquinoline-4-carboxylic acid ((S)-1-phenyl-propyl)-amide | 0.89 | 483.6 | 484.4 |
| 2ev | 3-{[Ethyl-(2-hydroxy-ethyl)-amino]-methyl}-1-oxo-2-phenyl-1,2-dihydro-isoquinoline-4-carboxylic acid ((S)-1-phenyl-propyl)-amide | 0.89 | 483.6 | 484.4 |
| 2ew | 3-[(Ethyl-methyl-amino)-methyl]-1-oxo-2-phenyl-1,2-dihydro-isoquinoline-4-carboxylic acid ((S)-1-phenyl-propyl)-amide | 0.92 | 453.6 | 454.4 |
| 2ex | 3-Cyclobutylaminomethyl-1-oxo-2-phenyl-1,2-dihydro-isoquinoline-4-carboxylic acid ((S)-1-phenyl-propyl)-amide | 0.98 | 465.6 | 466.4 |
| 2ey | 3-Azetidin-1-ylmethyl-1-oxo-2-phenyl-1,2-dihydro-isoquinoline-4-carboxylic acid ((S)-1-phenyl-propyl)-amide | 0.86 | 451.6 | 452.3 |
| 2ez | 3-(4-tert-Butyl-piperazin-1-ylmethyl)-1-oxo-2-phenyl-1,2-dihydro-isoquinoline-4-carboxylic acid ((S)-1-phenyl-propyl)-amide | 0.91 | 536.7 | 537.3 |
| 2fa | 3-[4-(2-Hydroxy-ethyl)-piperazin-1-ylmethyl]-1-oxo-2-phenyl-1,2-dihydro-isoquinoline-4-carboxylic acid ((S)-1-phenyl-propyl)-amide | 0.86 | 524.7 | 525.6 |
| 2fb | 3-{4-[2-(2-Hydroxy-ethoxy)-ethyl]-piperazin-1-ylmethyl}-1-oxo-2-phenyl-1,2-dihydro-isoquinoline-4-carboxylic acid ((S)-1-phenyl-propyl)-amide | 0.86 | 568.7 | 569.6 |
| 2fc | 3-[4-(3-Chloro-5-trifluoromethyl-pyridin-2-yl)-piperazin-1-ylmethyl]-1-oxo-2-phenyl-1,2-dihydro-isoquinoline-4-carboxylic acid (S)-1-phenyl-propyl)-amide | 1.77 | 660.1 | 660.8 |
| 2fd | 3-[4-(3,5-Dichloro-pyridin-4-yl)-piperazin-1-ylmethyl]-1-oxo-2-phenyl-1,2-dihydro-isoquinoline-4-carboxylic acid ((S)-1-phenyl-propyl)-amide | 1.45 | 626.6 | 626.5 |
| 2fe | 4-[1-Oxo-2-phenyl-4-((S)-1-phenyl-propylcarbamoyl)-1,2-dihydro-isoquinolin-3-ylmethyl]-piperazine-1-carboxylic acid benzyl ester | 1.57 | 614.7 | 615.4 |
| 2ff | 3-[4-(3-Morpholin-4-yl-propyl)-piperazin-1-ylmethyl]-1-oxo-2-phenyl-1,2-dihydro-isoquinoline-4-carboxylic acid ((S)-1-phenyl-propyl)-amide | 0.74 | 607.8 | 609.0 |
| 2fg | 1-Oxo-2-phenyl-3-[4-(3-piperidin-1-yl-propyl)-piperazin-1-ylmethyl]-1,2-dihydro-isoquinoline-4-carboxylic acid ((S)-1-phenyl-propyl)-amide | 0.76 | 605.8 | 607.1 |
| 2fh | 3-[4-(4,6-Dimethoxy-pyrimidin-2-ylmethyl)-piperazin-1-ylmethyl]-1-oxo-2-phenyl-1,2-dihydro-isoquinoline-4-carboxylic acid ((S)-1-phenyl-propyl)-amide | 1.05 | 632.8 | 633.9 |
| 2fi | 3-[4-(3-Hydroxy-propyl)-piperazin-1-ylmethyl]-1-oxo-2-phenyl-1,2-dihydro-isoquinoline-4-carboxylic acid ((S)-1-phenyl-propyl)-amide | 0.86 | 538.7 | 539.4 |
| 2fj | 3-[4-(2,3-Dihydroxy-propyl)-piperazin-1-ylmethyl]-1-oxo-2-phenyl-1,2-dihydro-isoquinoline-4-carboxylic acid ((S)-1-phenyl-propyl)-amide | 0.84 | 554.7 | 555.7 |
| 2fk | (2-Oxo-2-{4-[1-oxo-2-phenyl-4-(1-phenyl-propylcarbamoyl)-1,2-dihydro-isoquinolin-3-ylmethyl]-piperazin-1-yl}-ethyl)-carbamic acid tert-butyl ester | 1.39 | 637.8 | 638.5 |
| 2fl | 3-[4-(1H-Indazol-5-yl)-piperazin-1-ylmethyl]-1-oxo-2-phenyl-1,2-dihydro-isoquinoline-4-carboxylic acid ((S)-1-phenyl-propyl)-amide | 0.99 | 596.7 | 597.7 |
| 2fm | 1-Oxo-2-phenyl-3-(4-quinolin-6-yl-piperazin-1-ylmethyl)-1,2-dihydro-isoquinoline-4-carboxylic acid ((S)-1-phenyl-propyl)-amide | 0.95 | 607.8 | 608.7 |
| 2fn | 3-[4-(6,7-Dimethoxy-quinazolin-4-yl)-piperazin-1-ylmethyl]-1-oxo-2-phenyl-1,2-dihydro-isoquinoline-4-carboxylic acid ((S)-1-phenyl-propyl)-amide | 1.06 | 668.8 | 669.3 |
| 2fo | 4-{1-Oxo-2-phenyl-4-(1-phenyl-propylcarbamoyl)-1,2-dihydro-isoquinolin-3-ylmethyl]-piperazin-1-yl}-piperidine-1-carboxylic acid tert-butyl ester | 1.09 | 663.9 | 664.8 |
| 2fp | 3-{4-[2-(4-Chloro-phenoxy)-ethyl]-piperazin-1-ylmethyl}-1-oxo-2-phenyl-1,2-dihydro-isoquinoline-4-carboxylic acid ((S)-1-phenyl-propyl)-amide | 1.19 | 635.2 | 635.9 |
| 2fq | {4-[1-Oxo-2-phenyl-4-(1-phenyl-propylcarbamoyl)-1,2-dihydro-isoquinolin-3-ylmethyl]-piperazin-1-yl}-acetic acid tert-butyl ester | 1.08 | 594.8 | 595.9 |
| 2fr | 1-Oxo-2-phenyl-3-[4-(3,3,3-trifluoro-2-hydroxy-propyl)-piperazin-1-ylmethyl]-1,2-dihydro-isoquinoline-4-carboxylic acid ((S)-1-phenyl-propyl)-amide | 0.96 | 592.7 | 593.6 |
| 2fs | 3-[4-(2-Hydroxy-propyl)-piperazin-1-ylmethyl]-1-oxo-2-phenyl-1,2-dihydro-isoquinoline-4-carboxylic acid ((S)-1-phenyl-propyl)-amide | 0.86 | 538.7 | 539.5 |

| | Chemical name | $t_R$ (min) | MW | m/z (MH+) |
|---|---|---|---|---|
| 2fu | 3-[4-(4-Amino-6,7-dimethoxy-quinazolin-2-yl)-piperazin-1-ylmethyl]-1-oxo-2-phenyl-1,2-dihydro-isoquinoline-4-carboxylic acid ((S)-1-phenyl-propyl)-amide | 1.03 | 683.8 | 684.7 |
| 2fv | (2-{4-[1-Oxo-2-phenyl-4-(1-phenyl-propylcarbamoyl)-1,2-dihydro-isoquinolin-3-ylmethyl]-piperazin-1-yl}-ethyl)-carbamic acid tert-butyl ester | 1.06 | 623.8 | 624.5 |
| 2fw | 1-Oxo-3-{4-[2-(2-oxo-imidazolidin-1-yl)-ethyl]-piperazin-1-ylmethyl}-2-phenyl-1,2-dihydro-isoquinoline-4-carboxylic acid ((S)-1-phenyl-propyl)-amide | 0.85 | 592.7 | 593.7 |
| 2fx | 3-{4-[(4,6-Dimethoxy-pyrimidin-2-yl)-phenyl-methyl]-piperazin-1-ylmethyl}-1-oxo-2-phenyl-1,2-dihydro-isoquinoline-4-carboxylic acid ((S)-1-phenyl-propyl)-amide | 1.21 | 708.9 | 709.4 |
| 2fy | 3-(4-Benzo[1,2,5]thiadiazol-4-yl-piperazin-1-ylmethyl)-1-oxo-2-phenyl-1,2-dihydro-isoquinoline-4-carboxylic acid ((S)-1-phenyl-propyl)-amide | 1.48 | 614.8 | 615.4 |
| 2fz | 3-[4-(2,3-Dihydro-benzo[1,4]dioxin-5-yl)-piperazin-1-ylmethyl]-1-oxo-2-phenyl-1,2-dihydro-isoquinoline-4-carboxylic acid ((S)-1-phenyl-propyl)-amide | 1.2 | 614.7 | 615.3 |
| 2ga | 3-[4-(4-Methyl-quinolin-2-yl)-piperazin-1-ylmethyl]-1-oxo-2-phenyl-1,2-dihydro-isoquinoline-4-carboxylic acid ((S)-1-phenyl-propyl)-amide | 1.15 | 621.8 | 622.7 |
| 2gb | 1-Oxo-2-phenyl-3-[4-(pyridin-2-ylcarbamoylmethyl)-piperazin-1-ylmethyl]-1,2-dihydro-isoquinoline-4-carboxylic acid ((S)-1-phenyl-propyl)-amide | 0.93 | 614.7 | 615.4 |
| 2gc | 3-[4-(6-Chloro-3-oxo-3,4-dihydro-2H-benzo[1,4]oxazin-8-yl)-piperazin-1-ylmethyl]-1-oxo-2-phenyl-1,2-dihydro-isoquinoline-4-carboxylic acid ((S)-1-phenyl-propyl)-amide | 1.21 | 662.2 | 662.8 |
| 2gd | 3-(4-Carbamoylmethyl-piperazin-1-ylmethyl)-1-oxo-2-phenyl-1,2-dihydro-isoquinoline-4-carboxylic acid ((S)-1-phenyl-propyl)-amide | 0.85 | 537.7 | 538.5 |
| 2ge | 3-(4-Hydroxy-4-phenyl-piperidin-1-ylmethyl)-1-oxo-2-phenyl-1,2-dihydro-isoquinoline-4-carboxylic acid ((S)-1-phenyl-propyl)-amide | 1.12 | 571.7 | 572.6 |
| 2gf | 3-[4-(4-Chloro-phenyl)-4-hydroxy-piperidin-1-ylmethyl]-1-oxo-2-phenyl-1,2-dihydro-isoquinoline-4-carboxylic acid ((S)-1-phenyl-propyl)-amide | 1.23 | 606.2 | 606.8 |
| 2gg | 1-[1-Oxo-2-phenyl-4-(1-phenyl-propylcarbamoyl)-1,2-dihydro-isoquinolin-3-ylmethyl]-piperidine-4-carboxylic acid | 0.9 | 523.6 | 524.5 |
| 2gh | 3-(4-Cyano-4-phenyl-piperidin-1-ylmethyl)-1-oxo-2-phenyl-1,2-dihydro-isoquinoline-4-carboxylic acid ((S)-1-phenyl-propyl)-amide | 1.59 | 580.7 | 581.9 |
| 2gi | 3-(4-Benzyl-4-hydroxy-piperidin-1-ylmethyl)-1-oxo-2-phenyl-1,2-dihydro-isoquinoline-4-carboxylic acid ((S)-1-phenyl-propyl)-amide | 1.16 | 585.7 | 586.0 |
| 2gj | 1-[1-Oxo-2-phenyl-4-(1-phenyl-propylcarbamoyl)-1,2-dihydro-isoquinolin-3-ylmethyl]-4-phenyl-piperidine-4-carboxylic acid ethyl ester | 1.35 | 627.8 | 628.5 |
| 2gk | 1-Oxo-2-phenyl-3-[4-(phenyl-propionyl-amino)-piperidin-1-ylmethyl]-1,2-dihydro-isoquinoline-4-carboxylic acid ((S)-1-phenyl-propyl)-amide | 1.17 | 626.8 | 627.6 |
| 2gl | Methyl-{1-[1-oxo-2-phenyl-4-(1-phenyl-propylcarbamoyl)-1,2-dihydro-isoquinolin-3-ylmethyl]-piperidin-4-yl}-carbamic acid tert-butyl ester | 1.25 | 608.8 | 609.8 |
| 2gm | 1-Oxo-2-phenyl-3-[4-(2-pyrrolidin-1-yl-ethyl)-piperidin-1-ylmethyl]-1,2-dihydro-isoquinoline-4-carboxylic acid ((S)-1-phenyl-propyl)-amide | 0.72 | 576.8 | 577.5 |
| 2gn | 3-{4-[5-(4-Fluoro-phenyl)-[1,3,4]oxadiazol-2-yl]-piperidin-1-ylmethyl}-1-oxo-2-phenyl-1,2-dihydro-isoquinoline-4-carboxylic acid ((S)-1-phenyl-propyl)-amide | 1.22 | 641.7 | 642.3 |
| 2go | 1-Oxo-2-phenyl-3-[4-(3-pyridin-4-yl-[1,2,4]oxadiazol-5-yl)-piperidin-1-ylmethyl]-1,2-dihydro-isoquinoline-4-carboxylic acid ((S)-1-phenyl-propyl)-amide | 0.96 | 624.7 | 625.5 |
| 2gp | 1-Oxo-2-phenyl-3-[4-(3-pyrazin-2-yl-[1,2,4]oxadiazol-5-yl)-piperidin-1-ylmethyl]-1,2-dihydro-isoquinoline-4-carboxylic acid ((S)-1-phenyl-propyl)-amide | 1.04 | 625.7 | 626.5 |
| 2gq | 1-Oxo-2-phenyl-3-[4-(3-pyridin-4-yl-[1,2,4]oxadiazol-5-yl)-piperidin-1-ylmethyl]-1,2-dihydro-isoquinoline-4-carboxylic acid ((S)-1-phenyl-propyl)-amide | 1.04 | 624.7 | 625.5 |
| 2gr | 3-(4'-Hydroxy-3',4',5',6'-tetrahydro-2'H-[2,4']bipyridinyl-1'-ylmethyl)-1-oxo-2-phenyl-1,2-dihydro-isoquinoline-4-carboxylic acid ((S)-1-phenyl-propyl)-amide | 0.83 | 572.7 | 573.5 |
| 2gs | 3-(spiro[isochroman-1,4'-piperidin]-1'-ylmethyl)-1-oxo-2-phenyl-1,2-dihydro-isoquinoline-4-carboxylic acid ((S)-1-phenyl-propyl)-amide | 1.24 | 597.8 | 598.6 |

-continued

| | Chemical name | t_R (min) | MW | m/z (MH+) |
|---|---|---|---|---|
| 2gt | 3-[4-Hydroxy-4-(3-methoxy-phenyl)-piperidin-1-ylmethyl]-1-oxo-2-phenyl-1,2-dihydro-isoquinoline-4-carboxylic acid ((S)-1-phenyl-propyl)-amide | 1.13 | 601.7 | 602.4 |
| 2gu | 3-[4-(3-Chloro-phenyl)-4-hydroxy-piperidin-1-ylmethyl]-1-oxo-2-phenyl-1,2-dihydro-isoquinoline-4-carboxylic acid ((S)-1-phenyl-propyl)-amide | 1.23 | 606.2 | 606.8 |
| 2gv | 3-(6-chloro-3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide | 1.36 | 618.2 | 618.4 |
| 2gw | 3-(4-{[4-Chloro-3-(4-fluoro-phenyl)-indan-1-yl]-methyl-amino}-piperidin-1-ylmethyl)-1-oxo-2-phenyl-1,2-dihydro-isoquinoline-4-carboxylic acid ((S)-1-phenyl-propyl)-amide | 1.36 | 753.4 | 753.4 |
| 2gx | 3-(1-acetyl-spiro[indoline-3,4'-piperidin]-1'-ylmethyl)-1-oxo-2-phenyl-1,2-dihydro-isoquinoline-4-carboxylic acid ((S)-1-phenyl-propyl)-amide | 1.15 | 624.8 | 625.6 |
| 2gy | 3-(1-acetyl-5-fluoro-spiro[indoline-3,4'-piperidin]-1'-ylmethyl)-1-oxo-2-phenyl-1,2-dihydro-isoquinoline-4-carboxylic acid ((S)-1-phenyl-propyl)-amide | 1.2 | 642.8 | 643.4 |
| 2gz | 1-Oxo-3-(4-oxo-1-phenyl-1,3,8-triaza-spiro[4.5]dec-8-ylmethyl)-2-phenyl-1,2-dihydro-isoquinoline-4-carboxylic acid ((S)-1-phenyl-propyl)-amide | 1.15 | 625.8 | 626.6 |
| 2ha | 3-(4-Acetylamino-piperidin-1-ylmethyl)-1-oxo-2-phenyl-1,2-dihydro-isoquinoline-4-carboxylic acid ((S)-1-phenyl-propyl)-amide | 0.83 | 536.7 | 537.4 |
| 2hb | 1-Oxo-3-(1-oxo-2,8-diaza-spiro[4.5]dec-8-ylmethyl)-2-phenyl-1,2-dihydro-isoquinoline-4-carboxylic acid ((S)-1-phenyl-propyl)-amide | 0.85 | 548.7 | 549.7 |
| 2hc | 3-[4-Hydroxy-4-(3-trifluoromethyl-phenyl)-piperidin-1-ylmethyl]-1-oxo-2-phenyl-1,2-dihydro-isoquinoline-4-carboxylic acid ((S)-1-phenyl-propyl)-amide | 1.29 | 639.7 | 640.3 |
| 2hd | 1-Oxo-2-phenyl-3-(4-trifluoromethyl-piperidin-1-ylmethyl)-1,2-dihydro-isoquinoline-4-carboxylic acid ((S)-1-phenyl-propyl)-amide | 1.3 | 547.6 | 548.4 |
| 2he | 3-[4-(4-Methyl-piperazine-1-carbonyl)-piperidin-1-ylmethyl]-1-oxo-2-phenyl-1,2-dihydro-isoquinoline-4-carboxylic acid ((S)-1-phenyl-propyl)-amide | 0.7 | 605.8 | 607.0 |
| 2hf | 3-(5-isopropyl-3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide | 1.48 | 625.8 | 626.6 |
| 2hg | 3-[4-(Acetyl-methyl-amino)-4-phenyl-piperidin-1-ylmethyl]-1-oxo-2-phenyl-1,2-dihydro-isoquinoline-4-carboxylic acid ((S)-1-phenyl-propyl)-amide | 1.13 | 626.8 | 627.7 |
| 2hh | 4-{1-[1-Oxo-2-phenyl-4-(1-phenyl-propylcarbamoyl)-1,2-dihydro-isoquinolin-3-ylmethyl]-piperidin-4-yl}-piperazine-1-carboxylic acid tert-butyl ester | 1.03 | 663.9 | 664.7 |
| 2hi | (2-{1-[1-Oxo-2-phenyl-4-(1-phenyl-propylcarbamoyl)-1,2-dihydro-isoquinolin-3-ylmethyl]-piperidin-4-yl}-ethyl)-carbamic acid tert-butyl ester | 1.19 | 622.8 | 623.5 |
| 2hj | 3-(4-Methylamino-4-phenyl-piperidin-1-ylmethyl)-1-oxo-2-phenyl-1,2-dihydro-isoquinoline-4-carboxylic acid ((S)-1-phenyl-propyl)-amide | 1.01 | 584.8 | 585.5 |
| 2hk | 3-(4-Acetylamino-4-phenyl-piperidin-1-ylmethyl)-1-oxo-2-phenyl-1,2-dihydro-isoquinoline-4-carboxylic acid ((S)-1-phenyl-propyl)-amide | 1.06 | 612.8 | 613.3 |
| 2hl | 3-[4-Acetylamino-4-(3-fluoro-phenyl)-piperidin-1-ylmethyl]-1-oxo-2-phenyl-1,2-dihydro-isoquinoline-4-carboxylic acid ((S)-1-phenyl-propyl)-amide | 1.06 | 630.8 | 631.5 |
| 2hm | 1-Oxo-3-[4-(4-oxo-piperidine-1-carbonyl)-piperidin-1-ylmethyl]-2-phenyl-1,2-dihydro-isoquinoline-4-carboxylic acid ((S)-1-phenyl-propyl)-amide | 0.89 | 604.7 | 605.3 |
| 2hn | 3-[4,4']Bipiperidinyl-1-ylmethyl-1-oxo-2-phenyl-1,2-dihydro-isoquinoline-4-carboxylic acid ((S)-1-phenyl-propyl)-amide | 0.7 | 562.8 | 563.2 |
| 2ho | {1-[1-Oxo-2-phenyl-4-(1-phenyl-propylcarbamoyl)-1,2-dihydro-isoquinolin-3-ylmethyl]-piperidin-4-yl}-carbamic acid tert-butyl ester | 1.15 | 594.8 | 595.8 |
| 2hp | 3-[1,4']Bipiperidinyl-1'-ylmethyl-1-oxo-2-phenyl-1,2-dihydro-isoquinoline-4-carboxylic acid [cyclopropyl-(3-fluoro-phenyl)-methyl]-amide | 0.95 | 592.8 | 593.5 |
| 2hq | 1-Oxo-3-(4-phenethyl-piperazin-1-ylmethyl)-2-phenyl-1,2-dihydro-isoquinoline-4-carboxylic acid [cyclopropyl-(3-fluoro-phenyl)-methyl]-amide | 1.15 | 614.8 | 615.5 |
| 2hr | 3-(4-Isopropyl-piperazin-1-ylmethyl)-1-oxo-2-phenyl-1,2-dihydro-isoquinoline-4-carboxylic acid [cyclopropyl-(3-fluoro-phenyl)-methyl]-amide | 0.97 | 552.7 | 553.8 |

-continued

| | Chemical name | $t_R$ (min) | MW | m/z (MH+) |
|---|---|---|---|---|
| 2hs | 3-[4-(2-Morpholin-4-yl-ethyl)-piperazin-1-ylmethyl]-1-oxo-2-phenyl-1,2-dihydro-isoquinoline-4-carboxylic acid [cyclopropyl-(3-fluoro-phenyl)-methyl]-amide | 0.81 | 623.8 | 624.6 |
| 2ht | 3-[4-(1-Methyl-piperidin-4-yl)-piperazin-1-ylmethyl]-1-oxo-2-phenyl-1,2-dihydro-isoquinoline-4-carboxylic acid [cyclopropyl-(3-fluoro-phenyl)-methyl]-amide | 0.78 | 607.8 | 608.9 |
| 2hu | 1-Oxo-2-phenyl-3-[4-(2-piperidin-1-yl-ethyl)-piperazin-1-ylmethyl]-1,2-dihydro-isoquinoline-4-carboxylic acid [cyclopropyl-(3-fluoro-phenyl)-methyl]-amide | 0.82 | 621.8 | 622.6 |
| 2hv | 1-Oxo-2-phenyl-3-[4-(2-pyrrolidin-1-yl-ethyl)-piperazin-1-ylmethyl]-1,2-dihydro-isoquinoline-4-carboxylic acid [cyclopropyl-(3-fluoro-phenyl)-methyl]-amide | 0.8 | 607.8 | 608.8 |
| 2hw | 1-Oxo-2-phenyl-3-(4-pyridin-4-ylmethyl-piperazin-1-ylmethyl)-1,2-dihydro-isoquinoline-4-carboxylic acid [cyclopropyl-(3-fluoro-phenyl)-methyl]-amide | 0.84 | 601.7 | 602.6 |
| 2hx | 3-(4-Hydroxy-3,4,5,6-tetrahydro-2H-[4,4']bipyridinyl-1-ylmethyl)-1-oxo-2-phenyl-1,2-dihydro-isoquinoline-4-carboxylic acid [cyclopropyl-(3-fluoro-phenyl)-methyl]-amide | 0.77 | 602.7 | 603.7 |
| 2hy | 3-[4-(2-Morpholin-4-yl-ethyl)-piperidin-1-ylmethyl]-1-oxo-2-phenyl-1,2-dihydro-isoquinoline-4-carboxylic acid [cyclopropyl-(3-fluoro-phenyl)-methyl]-amide | 0.75 | 622.8 | 623.7 |
| 2hz | 3-[4-Hydroxy-4-(3-methoxy-phenyl)-piperidin-1-ylmethyl]-1-oxo-2-phenyl-1,2-dihydro-isoquinoline-4-carboxylic acid [cyclopropyl-(3-fluoro-phenyl)-methyl]-amide | 1.17 | 631.7 | 632.6 |
| 2ia | 3-[4-(Acetyl-methyl-amino)-4-phenyl-piperidin-1-ylmethyl]-1-oxo-2-phenyl-1,2-dihydro-isoquinoline-4-carboxylic acid [cyclopropyl-(3-fluoro-phenyl)-methyl]-amide | 1.18 | 656.8 | 657.8 |
| 2ib | 2-(2-Fluoro-phenyl)-1-oxo-3-(4-phenethyl-piperazin-1-ylmethyl)-1,2-dihydro-isoquinoline-4-carboxylic acid ((S)-1-phenyl-propyl)-amide | 1.12 | 602.8 | 603.8 |
| 2ic | 2-(2-Fluoro-phenyl)-3-(4-isopropyl-piperazin-1-ylmethyl)-1-oxo-1,2-dihydro-isoquinoline-4-carboxylic acid ((S)-1-phenyl-propyl)-amide | 0.96 | 540.7 | 541.7 |
| 2id | 3-[1,4']Bipiperidinyl-1'-ylmethyl-2-(2-fluoro-phenyl)-1-oxo-1,2-dihydro-isoquinoline-4-carboxylic acid ((S)-1-phenyl-propyl)-amide | 1 | 580.7 | 581.7 |
| 2ie | 2-(2-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide | 0.82 | 611.8 | 612.5 |
| 2if | 2-(2-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide | 0.76 | 595.8 | 596.8 |
| 2ig | 2-(2-Fluoro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide | 0.81 | 609.8 | 610.5 |
| 2ih | 2-(2-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide | 0.8 | 595.8 | 596.7 |
| 2ii | 2-(2-Fluoro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide | 0.84 | 589.7 | 590.4 |
| 2ij | 2-(2-Fluoro-phenyl)-3-(4-hydroxy-3,4,5,6-tetrahydro-2H-[4,4']bipyridinyl-1-ylmethyl)-1-oxo-1,2-dihydro-isoquinoline-4-carboxylic acid ((S)-1-phenyl-propyl)-amide | 0.85 | 590.7 | 591.3 |
| 2ik | 2-(2-Fluoro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide | 0.76 | 610.8 | 611.7 |
| 2il | 2-(2-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide | 1.21 | 619.7 | 620.3 |
| 2im | 3-[4-(2-Morpholin-4-yl-ethyl)-piperazin-1-ylmethyl]-1-oxo-2-o-tolyl-1,2-dihydro-isoquinoline-4-carboxylic acid ((S)-1-phenyl-propyl)-amide | 0.82 | 607.8 | 608.8 |
| 2in | 1-Oxo-3-[4-(2-piperidin-1-yl-ethyl)-piperazin-1-ylmethyl]-2-o-tolyl-1,2-dihydro-isoquinoline-4-carboxylic acid ((S)-1-phenyl-propyl)-amide | 0.81 | 605.8 | 606.9 |
| 2io | 1-Oxo-3-(4-pyridin-4-ylmethyl-piperazin-1-ylmethyl)-2-o-tolyl-1,2-dihydro-isoquinoline-4-carboxylic acid ((S)-1-phenyl-propyl)-amide | 0.84 | 585.7 | 586.4 |
| 2ip | 2-(3-Fluoro-phenyl)-1-oxo-3-(4-phenethyl-piperazin-1-ylmethyl)-1,2-dihydro-isoquinoline-4-carboxylic acid ((S)-1-phenyl-propyl)-amide | 1.13 | 602.8 | 603.8 |

| | Chemical name | t$_R$ (min) | MW | m/z (MH+) |
|---|---|---|---|---|
| 2iq | 2-(3-Fluoro-phenyl)-3-(4-isopropyl-piperazin-1-ylmethyl)-1-oxo-1,2-dihydro-isoquinoline-4-carboxylic acid ((S)-1-phenyl-propyl)-amide | 0.96 | 540.7 | 541.3 |
| 2ir | 3-[1,4']Bipiperidinyl-1'-ylmethyl-2-(3-fluoro-phenyl)-1-oxo-1,2-dihydro-isoquinoline-4-carboxylic acid ((S)-1-phenyl-propyl)-amide | 0.98 | 580.7 | 581.8 |
| 2is | 2-(3-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide | 0.81 | 611.8 | 612.6 |
| 2it | 2-(3-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide | 0.75 | 595.8 | 596.8 |
| 2iu | 2-(3-Fluoro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide | 0.8 | 609.8 | 610.7 |
| 2iv | 2-(3-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide | 0.79 | 595.8 | 596.8 |
| 2iw | 2-(3-Fluoro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide | 0.83 | 589.7 | 590.2 |
| 2ix | 2-(3-Fluoro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide | 0.73 | 610.8 | 611.6 |
| 2iy | 2-(3-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide | 1.18 | 619.7 | 620.7 |
| 2iz | 3-[4-(Acetyl-methyl-amino)-4-phenyl-piperidin-1-ylmethyl]-2-(3-fluoro-phenyl)-1-oxo-1,2-dihydro-isoquinoline-4-carboxylic acid ((S)-1-phenyl-propyl)-amide | 1.2 | 644.8 | 645.7 |
| 2ja | 2-(3-Chloro-phenyl)-1-oxo-3-(4-phenethyl-piperazin-1-ylmethyl)-1,2-dihydro-isoquinoline-4-carboxylic acid ((S)-1-phenyl-propyl)-amide | 1.17 | 619.2 | 619.4 |
| 2jb | 2-(3-Chloro-phenyl)-3-(4-isopropyl-piperazin-1-ylmethyl)-1-oxo-1,2-dihydro-isoquinoline-4-carboxylic acid ((S)-1-phenyl-propyl)-amide | 1 | 557.1 | 557.5 |
| 2jc | 3-[1,4']Bipiperidinyl-1'-ylmethyl-2-(3-chloro-phenyl)-1-oxo-1,2-dihydro-isoquinoline-4-carboxylic acid ((S)-1-phenyl-propyl)-amide | 1.04 | 597.2 | 597.8 |
| 2jd | 2-(3-Chloro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide | 0.86 | 628.2 | 628.6 |
| 2je | 2-(3-Chloro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide | 0.79 | 612.2 | 612.2 |
| 2jf | 2-(3-Chloro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide | 0.84 | 626.2 | 626.7 |
| 2jg | 2-(3-Chloro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide | 0.83 | 612.2 | 612.4 |
| 2jh | 2-(3-Chloro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide | 0.88 | 606.2 | 606.1 |
| 2ji | 2-(3-Chloro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide | 0.78 | 627.2 | 627.4 |
| 2jj | 2-(3-Chloro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide | 1.23 | 636.2 | 636.7 |
| 2jk | 3-[4-(Acetyl-methyl-amino)-4-phenyl-piperidin-1-ylmethyl]-2-(3-chloro-phenyl)-1-oxo-1,2-dihydro-isoquinoline-4-carboxylic acid ((S)-1-phenyl-propyl)-amide | 1.26 | 661.2 | 662.0 |
| 2jl | 1-Oxo-3-(4-phenethyl-piperazin-1-ylmethyl)-2-m-tolyl-1,2-dihydro-isoquinoline-4-carboxylic acid ((S)-1-phenyl-propyl)-amide | 1.15 | 598.8 | 599.6 |
| 2jm | 3-[1,4']Bipiperidinyl-1'-ylmethyl-1-oxo-2-m-tolyl-1,2-dihydro-isoquinoline-4-carboxylic acid ((S)-1-phenyl-propyl)-amide | 0.96 | 576.8 | 577.5 |
| 2jn | 3-[4-(2-Morpholin-4-yl-ethyl)-piperazin-1-ylmethyl]-1-oxo-2-m-tolyl-1,2-dihydro-isoquinoline-4-carboxylic acid ((S)-1-phenyl-propyl)-amide | 0.83 | 607.8 | 609.0 |
| 2jo | 3-[4-(1-Methyl-piperidin-4-yl)-piperazin-1-ylmethyl]-1-oxo-2-m-tolyl-1,2-dihydro-isoquinoline-4-carboxylic acid ((S)-1-phenyl-propyl)-amide | 0.78 | 591.8 | 592.6 |

| | Chemical name | $t_R$ (min) | MW | m/z (MH+) |
|---|---|---|---|---|
| 2jp | 1-Oxo-3-[4-(2-piperidin-1-yl-ethyl)-piperazin-1-ylmethyl]-2-m-tolyl-1,2-dihydro-isoquinoline-4-carboxylic acid ((S)-1-phenyl-propyl)-amide | 0.83 | 605.8 | 607.1 |
| 2jq | 1-Oxo-3-[4-(2-pyrrolidin-1-yl-ethyl)-piperazin-1-ylmethyl]-2-m-tolyl-1,2-dihydro-isoquinoline-4-carboxylic acid ((S)-1-phenyl-propyl)-amide | 0.81 | 591.8 | 592.6 |
| 2jr | 1-Oxo-3-(4-pyridin-4-ylmethyl-piperazin-1-ylmethyl)-2-m-tolyl-1,2-dihydro-isoquinoline-4-carboxylic acid ((S)-1-phenyl-propyl)-amide | 0.85 | 585.7 | 586.0 |
| 2js | 3-[4-(2-Morpholin-4-yl-ethyl)-piperidin-1-ylmethyl]-1-oxo-2-m-tolyl-1,2-dihydro-isoquinoline-4-carboxylic acid ((S)-1-phenyl-propyl)-amide | 0.73 | 606.8 | 608.1 |
| 2jt | 3-[4-Hydroxy-4-(3-methoxy-phenyl)-piperidin-1-ylmethyl]-1-oxo-2-m-tolyl-1,2-dihydro-isoquinoline-4-carboxylic acid ((S)-1-phenyl-propyl)-amide | 1.18 | 615.8 | 616.3 |
| 2ju | 3-[4-(Acetyl-methyl-amino)-4-phenyl-piperidin-1-ylmethyl]-1-oxo-2-m-tolyl-1,2-dihydro-isoquinoline-4-carboxylic acid ((S)-1-phenyl-propyl)-amide | 1.19 | 640.8 | 641.7 |
| 2ka | 3-(4-tert-Butyl-piperazin-1-ylmethyl)-8-chloro-1-oxo-2-phenyl-1,2-dihydro-isoquinoline-4-carboxylic acid [(S)-cyclopropyl-(3-fluoro-phenyl)-methyl]-amide | 1.06 | 601.2 | 601.5 |
| 2kb | 8-Chloro-3-(4-isopropyl-piperazin-1-ylmethyl)-1-oxo-2-phenyl-1,2-dihydro-isoquinoline-4-carboxylic acid ((S)-1-phenyl-propyl)-amide | 1.01 | 557.1 | 557.5 |
| 2kc | 8-Chloro-3-(4-isobutyl-piperazin-1-ylmethyl)-1-oxo-2-phenyl-1,2-dihydro-isoquinoline-4-carboxylic acid ((S)-1-phenyl-propyl)-amide | 1.07 | 571.2 | 571.7 |
| 2kd | 8-Chloro-3-(octahydro-pyrido[1,2-a]pyrazin-2-ylmethyl)-1-oxo-2-phenyl-1,2-dihydro-isoquinoline-4-carboxylic acid ((S)-1-phenyl-propyl)-amide | 1.03 | 569.1 | 569.6 |
| 2ke | 8-Chloro-3-(4-hydroxy-3,4,5,6-tetrahydro-2H-[4,4']bipyridinyl-1-ylmethyl)-1-oxo-2-phenyl-1,2-dihydro-isoquinoline-4-carboxylic acid ((S)-1-phenyl-propyl)-amide | 0.8 | 607.2 | 607.9 |
| 2kf | 8-Chloro-3-(4-cyclopropylmethyl-piperazin-1-ylmethyl)-1-oxo-2-phenyl-1,2-dihydro-isoquinoline-4-carboxylic acid ((S)-1-phenyl-propyl)-amide | 1.04 | 569.1 | 569.8 |
| 2kg | 8-Chloro-3-[4-(2-morpholin-4-yl-ethyl)-piperidin-1-ylmethyl]-1-oxo-2-phenyl-1,2-dihydro-isoquinoline-4-carboxylic acid ((S)-1-phenyl-propyl)-amide | 0.75 | 627.2 | 627.4 |
| 2kh | 8-Chloro-3-[1,4]diazepan-1-ylmethyl-1-oxo-2-phenyl-1,2-dihydro-isoquinoline-4-carboxylic acid ((S)-1-phenyl-propyl)-amide | 0.98 | 529.1 | 529.3 |
| 2ki | 8-Chloro-3-((S)-3-methyl-piperazin-1-ylmethyl)-1-oxo-2-phenyl-1,2-dihydro-isoquinoline-4-carboxylic acid ((S)-1-phenyl-propyl)-amide | 0.98 | 529.1 | 529.2 |
| 2kj | 8-Chloro-3-imidazol-1-ylmethyl-1-oxo-2-phenyl-1,2-dihydro-isoquinoline-4-carboxylic acid ((S)-1-phenyl-propyl)-amide | 0.92 | 497.0 | 497.4 |
| 2kk | 8-Chloro-3-(4-methyl-imidazol-1-ylmethyl)-1-oxo-2-phenyl-1,2-dihydro-isoquinoline-4-carboxylic acid ((S)-1-phenyl-propyl)-amide | 0.97 | 511.0 | 511.3 |
| 2kl | 3-(tert-Butylamino-methyl)-8-chloro-1-oxo-2-phenyl-1,2-dihydro-isoquinoline-4-carboxylic acid ((S)-1-phenyl-propyl)-amide | 1.06 | 502.1 | 502.5 |
| 2km | 8-Chloro-3-(isopropylamino-methyl)-1-oxo-2-phenyl-1,2-dihydro-isoquinoline-4-carboxylic acid ((S)-1-phenyl-propyl)-amide | 1 | 488.0 | 488.6 |
| 2kn | 8-Chloro-3-[4-hydroxy-4-(3-methoxy-phenyl)-piperidin-1-ylmethyl]-1-oxo-2-phenyl-1,2-dihydro-isoquinoline-4-carboxylic acid ((S)-1-phenyl-propyl)-amide | 1.2 | 636.2 | 636.8 |
| 2ko | 3-(4-tert-Butyl-piperazin-1-ylmethyl)-8-chloro-1-oxo-2-phenyl-1,2-dihydro-isoquinoline-4-carboxylic acid ((S)-1-phenyl-propyl)-amide | 1.03 | 571.2 | 571.4 |
| 2kp | 3-Benzoimidazol-1-ylmethyl-1-oxo-2-phenyl-1,2-dihydro-isoquinoline-4-carboxylic acid ((S)-1-phenyl-propyl)-amide | 1.02 | 512.6 | 513.3 |
| 2kq | 1-Oxo-2-phenyl-3-pyrazol-1-ylmethyl-1,2-dihydro-isoquinoline-4-carboxylic acid ((S)-1-phenyl-propyl)-amide | 1.54 | 462.6 | 463.4 |
| 2kr | 3-(4-Methyl-pyrazol-1-ylmethyl)-1-oxo-2-phenyl-1,2-dihydro-isoquinoline-4-carboxylic acid ((S)-1-phenyl-propyl)-amide | 1.65 | 476.6 | 477.3 |
| 2ks | 1-Oxo-2-phenyl-3-[1,2,3]triazol-1-ylmethyl-1,2-dihydro-isoquinoline-4-carboxylic acid ((S)-1-phenyl-propyl)-amide | 1.23 | 463.5 | 464.4 |
| 2kt | 2-(3-Methoxy-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide | 0.82 | 601.7 | 602.7 |

-continued

| | Chemical name | $t_R$ (min) | MW | m/z (MH+) |
|---|---|---|---|---|
| 2ku | 2-(4-Methoxy-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide | 0.8 | 623.8 | 624.5 |
| 2kv | 2-(4-Fluoro-phenyl)-1-oxo-3-(4-phenethyl-piperazin-1-ylmethyl)-1,2-dihydro-isoquinoline-4-carboxylic acid ((S)-1-phenyl-propyl)-amide | 1.13 | 602.8 | 603.8 |
| 2kw | 2-(4-Fluoro-phenyl)-3-(4-isopropyl-piperazin-1-ylmethyl)-1-oxo-1,2-dihydro-isoquinoline-4-carboxylic acid ((S)-1-phenyl-propyl)-amide | 0.95 | 540.7 | 541.7 |
| 2kx | 3-[1,4']Bipiperidinyl-1'-ylmethyl-2-(4-fluoro-phenyl)-1-oxo-1,2-dihydro-isoquinoline-4-carboxylic acid ((S)-1-phenyl-propyl)-amide | 0.98 | 580.7 | 581.9 |
| 2ky | 2-(4-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide | 0.79 | 611.8 | 612.6 |
| 2kz | 2-(4-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide | 0.74 | 595.8 | 596.8 |
| 2la | 2-(4-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide | 0.78 | 595.8 | 596.7 |
| 2lb | 2-(4-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide | 1.18 | 619.7 | 620.4 |
| 2lc | 2-(4-Chloro-phenyl)-1-oxo-3-(4-phenethyl-piperazin-1-ylmethyl)-1,2-dihydro-isoquinoline-4-carboxylic acid ((S)-1-phenyl-propyl)-amide | 1.17 | 619.2 | 619.3 |
| 2ld | 2-(4-Chloro-phenyl)-3-(4-isopropyl-piperazin-1-ylmethyl)-1-oxo-1,2-dihydro-isoquinoline-4-carboxylic acid ((S)-1-phenyl-propyl)-amide | 0.99 | 557.1 | 557.4 |
| 2le | 3-[1,4']Bipiperidinyl-1'-ylmethyl-2-(4-chloro-phenyl)-1-oxo-1,2-dihydro-isoquinoline-4-carboxylic acid ((S)-1-phenyl-propyl)-amide | 1.04 | 597.2 | 597.8 |
| 2lf | 2-(4-Chloro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide | 0.85 | 628.2 | 628.6 |
| 2lg | 2-(4-Chloro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide | 0.77 | 612.2 | 612.3 |
| 2lh | 2-(4-Chloro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide | 0.84 | 626.2 | 626.8 |
| 2li | 2-(4-Chloro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide | 0.81 | 612.2 | 612.6 |
| 2lj | 3-(4-tert-Butyl-piperazin-1-ylmethyl)-8-fluoro-1-oxo-2-phenyl-1,2-dihydro-isoquinoline-4-carboxylic acid ((S)-1-phenyl-propyl)-amide | 0.96 | 554.7 | 555.7 |
| 2lk | 8-Chloro-3-cyclopropylaminomethyl-1-oxo-2-phenyl-1,2-dihydro-isoquinoline-4-carboxylic acid ((S)-1-phenyl-propyl)-amide | 0.61 (method B) | 486.0 | 486.4 |
| 2ll | 3-(4-tert-Butyl-piperazin-1-ylmethyl)-8-fluoro-1-oxo-2-phenyl-1,2-dihydro-isoquinoline-4-carboxylic acid [(S)-cyclopropyl-(3-fluoro-phenyl)-methyl]-amide | 0.98 | 584.7 | 585.5 |
| 2lm | 8-Fluoro-1-oxo-2-phenyl-3-piperazin-1-ylmethyl-1,2-dihydro-isoquinoline-4-carboxylic acid [(S)-cyclopropyl-(3-fluoro-phenyl)-methyl]-amide (*) | 0.89 | 528.6 | 529.4 |
| 2ln | 8-Fluoro-1-oxo-3-(3-oxo-pyrazolidin-1-ylmethyl)-2-phenyl-1,2-dihydro-isoquinoline-4-carboxylic acid [(S)-cyclopropyl-(3-fluoro-phenyl)-methyl]-amide | 1.14 | 528.6 | 528.8 |
| 2lo | 8-Fluoro-1-oxo-3-(3-oxo-piperazin-1-ylmethyl)-2-phenyl-1,2-dihydro-isoquinoline-4-carboxylic acid [(S)-cyclopropyl-(3-fluoro-phenyl)-methyl]-amide | 1.13 | 542.6 | 543.5 |

(*): 1-(tert-Butoxycarbonyl)piperazine was used as amine and the BOC-group was removed in the next step by 2 M HCl in diethyl ether and methanol (1:1) at r.t.

Example 3

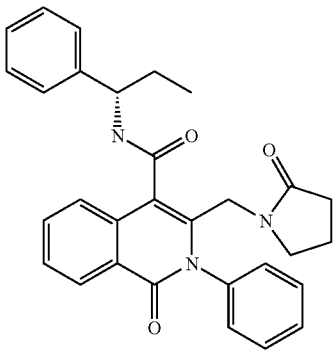

3a 1-Oxo-3-(2-oxo-pyrrolidin-1-ylmethyl)-2-phenyl-1,2-dihydro-isoquinoline-4-carboxylic acid ((S)-1-phenyl-propyl)-amide To a solution of 2-pyrrolidinone (0.1 ml) in tetrahydrofurane (2 ml) sodium hydride (20 mg, 60% dispersion in mineral oil) was added. The reaction mixture was stirred at ambient temperature until the gas evolution ceased then 3-bromomethyl-1-oxo-2-phenyl-1,2-dihydro-isoquinoline-4-carboxylic acid ((S)-1-phenyl-propyl)-amide (30 mg) was added. After 30 min acetic acid (0.05 ml) was added and volatiles were removed in vacuo. The product was purified by flash chromatography on SiO$_2$ (5 g, 1,2-dichloroethane then gradient 50% to 100% ethyl acetate in heptane) to give 17 mg of white solid. Yield 56%. LC-MS (m/z) 480.5 (MH$^+$); t$_R$=1.21.

The following compound was obtained analogously:

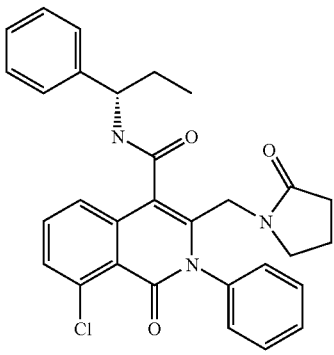

3b 8-Chloro-1-oxo-3-(2-oxo-pyrrolidin-1-ylmethyl)-2-phenyl-1,2-dihydro-isoquinoline-4-carboxylic acid ((S)-1-phenyl-propyl)-amide LC-MS (m/z) 514.7 (MH$^+$); t$_R$=1.33.
Synthesis of Intermediates:

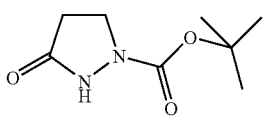

3-Oxo-pyrazolidine-1-carboxylic acid tert-butyl ester

To a mixture of 3-pyrazolidinone hydrochloride (55.3 mg, 0.45 mmol), Na$_2$CO$_3$ (133 mg, 1.24 mol), water (0.5 ml) and dioxane (0.054 ml) BOC-anhydride (101 mg, 0.46 mmol) in dioxane (0.16 ml) was added and stirred at r.t. overnight. It was filtered, evaporated and used in the next step without further purification. $^1$H NMR (500 MHz, DMSO-d$_6$): 1.4 (s, 9H), 2.32 (t, J=9 Hz, 2H), 3.6 (t, J=9 Hz, 2H).

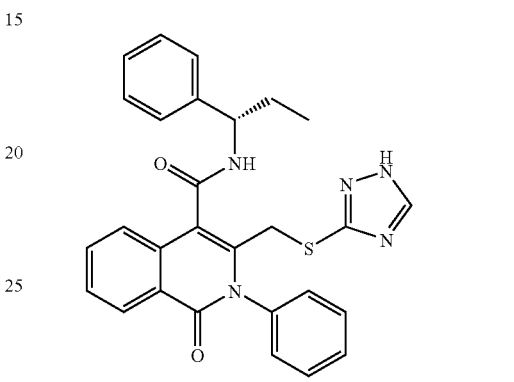

3c 1-Oxo-2-phenyl-3-(1H-[1,2,4]triazol-3-ylsulfanylmethyl)-1,2-dihydro-isoquinoline-4-carboxylic acid ((S)-1-phenyl-propyl)-amide LC-MS (m/z) 496.6 (MH$^+$); t$_R$=0.64 (method B).

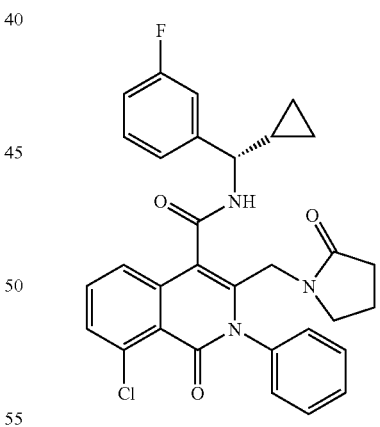

3d 8-Chloro-1-oxo-3-(2-oxo-pyrrolidin-1-ylmethyl)-2-phenyl-1,2-dihydro-isoquinoline-4-carboxylic acid [(S)-cyclopropyl-(3-fluoro-phenyl)-methyl]-amide LC-MS (m/z) 544.3 (MH$^+$); t$_R$=1.39. $^1$H NMR (250 MHz, 70° C., DMSO-d$_6$): 0.4-0.64 (m, 4H), 1.28 (m, 1H), 1.74 (m, 2H), 1.97 (m, 2H), 2.89 (br, 1H), 3.06 (H$_2$O), 4.02-4.14 (br, 2H), 4.51 (t, J=8.6 Hz, 1H), 7.08 (dt, 1H), 7.2-7.3 (m, 4H), 7.37-7.7 (m, 7H), 9.07 (d, J=8.1 Hz, 1H, NH).

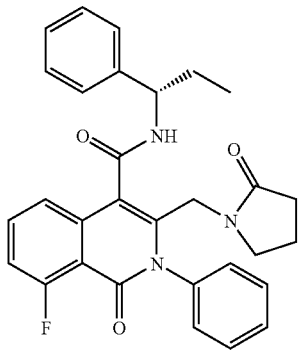

3e 8-Fluoro-1-oxo-3-(2-oxo-pyrrolidin-1-ylmethyl)-2-phenyl-1,2-dihydro-isoquinoline-4-carboxylic acid ((S)-1-phenyl-propyl)-amide LC-MS (m/z) 498.8 (MH+); $t_R$=1.23, $t_R$=0.68 (method B). 
$^1$H NMR (250 MHz, 70° C., DMSO-$d_6$): 0.93 (t, J=7.3 Hz, 3H), 1.66-2.0 (m, 6H), 2.84 (br t, 1H), 3.01 (overlapped H$_2$O signal), 3.98-4.08 (br, 2H), 4.97 (t, J=7.6 Hz, 1H), 7.2-7.54 (m, 12H), 7.69 (m, 1H), 8.77 (d, J=7.9 Hz, 1H, NH).

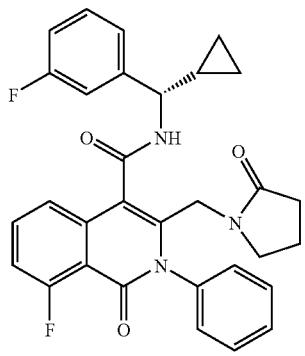

3f 8-Fluoro-1-oxo-3-(2-oxo-pyrrolidin-1-ylmethyl)-2-phenyl-1,2-dihydro-isoquinoline-4-carboxylic acid [(S)-cyclopropyl-(3-fluoro-phenyl)-methyl]-amide LC-MS (m/z) 528.7 (MH+); $t_R$=1.29, $t_R$=0.7 (method B). 
$^1$H NMR (250 MHz, 80° C., DMSO-$d_6$): 0.37-0.62 (m, 4H), 1.25 (m, 1H), 1.71 (quintet, J=7.5 Hz, 2H), 1.94 (t, J=7.9 Hz, 2H), 2.85 (br, 2H), 2.94 (H$_2$O), 4.05 (br, 2H), 4.5 (t, J=8.6 Hz, 1H), 7.04 (m, 1H), 7.17-7.32 (m, 5H), 7.32-7.52 (m, 5H), 7.7 (m, 1H), 8.97 (d, J=8.1 Hz, 1H, NH).

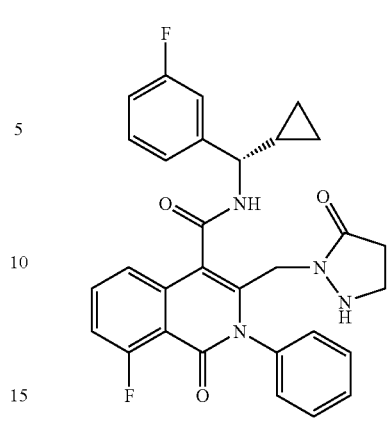

3g 8-Fluoro-1-oxo-3-(5-oxo-pyrazolidin-1-ylmethyl)-2-phenyl-1,2-dihydro-isoquinoline-4-carboxylic acid [(S)-cyclopropyl-(3-fluoro-phenyl)-methyl]-amide 3-Oxo-pyrazolidine-1-carboxylic acid tert-butyl ester was used in the coupling reaction promoted by NaH. The BOC-group in the obtained intermediate 2-(4-{[(S)-cyclopropyl-(3-fluoro-phenyl)-methyl]-carbamoyl}-8-fluoro-1-oxo-2-phenyl-1,2-dihydro-isoquinolin-3-ylmethyl)-3-oxo-yrazolidine-1-carboxylic acid tert-butyl ester was removed with 2M HCl in ethyl ether-methanol (1:1) at r.t., 30 min and the title compound was purified by preparative LC-MS. LC-MS (m/z) 529.3 (MH+); $t_R$=1.15.

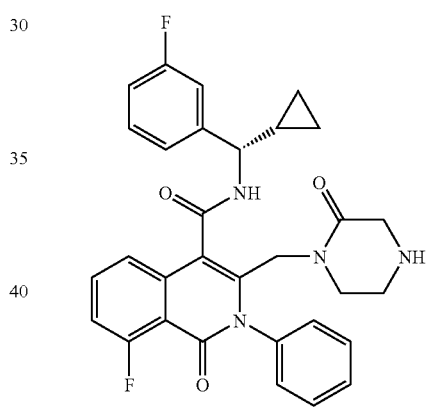

3h 8-Fluoro-1-oxo-3-(2-oxo-piperazin-1-ylmethyl)-2-phenyl-1,2-dihydro-isoquinoline-4-carboxylic acid [(S)-cyclopropyl-(3-fluoro-phenyl)-methyl]-amide The title compound was prepared analogously from 2-oxo-4-(tert-butoxycarbonyl)piperazine followed by BOC group removal. LC-MS (m/z) 543.6 (MH+); $t_R$=0.84.

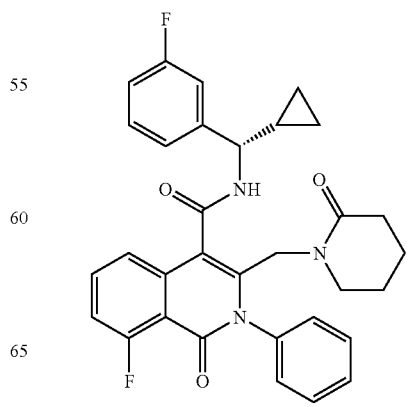

3i 8-Fluoro-1-oxo-3-(2-oxo-piperidin-1-ylmethyl)-2-phenyl-1,2-dihydro-isoquinoline-4-carboxylic acid [(S)-cyclopropyl-(3-fluoro-phenyl)-methyl]-amide The title compound was prepared analogously from 2-piperidone. LC-MS (m/z) 542.5 (MH$^+$); $t_R$=1.35.

Example 4

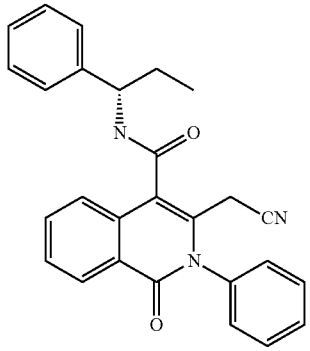

4a 3-Cyanomethyl-1-oxo-2-phenyl-1,2-dihydro-isoquinoline-4-carboxylic acid ((S)-1-phenyl-propyl)-amide To a solution of 3-bromomethyl-1-oxo-2-phenyl-1,2-dihydro-isoquinoline-4-carboxylic acid ((S)-1-phenyl-propyl)-amide (83 mg, 0.174 mmol) in THF (1.5 ml, anhydrous) and DMF (1.5 ml, anhydrous) sodium cyanide (83 mg, excess) was added. After 5 min the obtained suspension was poured into water (50 ml) followed by addition of heptane (20 ml). The crude product was separated by filtration and purified by flash chromatography on SiO$_2$ (5 g, 1:1 EA-heptane) to give 50 mg of colourless solid, yield 68%. LC-MS (m/z) 422.4 (MH$^+$); $t_R$=1.39. $^1$H NMR (250 MHz, DMSO-d$_6$, T=343 K): 0.94 (t, 3H), 1.78 and 1.85 (two overlapping qui of ABX$_4$, 2H, CH$_2$ of Et), 3.45 and 3.54 (two d of AB, 2H, CH$_2$CN), 4.98 (q, 1H), 7.22-7.44 (m, 8H), 7.53-7.64 (m, 4H), 7.72 (dt, 1H), 8.25 (dd, 1H), 9.05 (d, 1H).

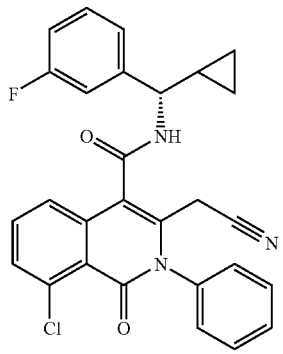

4b 8-Chloro-3-cyanomethyl-1-oxo-2-phenyl-1,2-dihydro-isoquinoline-4-carboxylic acid [(S)-cyclopropyl-(3-fluoro-phenyl)-methyl]-amide LC-MS (m/z) 486.5 (MH$^+$); $t_R$=1.81.

Example 5

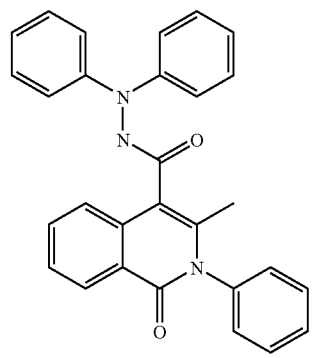

5a 3-Methyl-1-oxo-2-phenyl-1,2-dihydro-isoquinoline-4-carboxylic acid N',N'-diphenyl-hydrazide A mixture of 3-methyl-1-oxo-2-phenyl-1,2-dihydro-isoquinoline-4-carbonyl chloride (the synthesis is described above in example 1a) (25 mg, 0.08 mmol) and 1,1-diphenyl-hydrazine hydrochloride (56 mg, 0.25 mmol) in 1,2-dichloroethane (1 ml) was heated under microwave irradiation for 20 min at 140° C. Volatiles were removed in vacuo and the product was purified by preparative LC-MS to give 14 mg of colorless solid. LC-MS (m/z) 446.7 (MH$^+$); $t_R$=1.58.

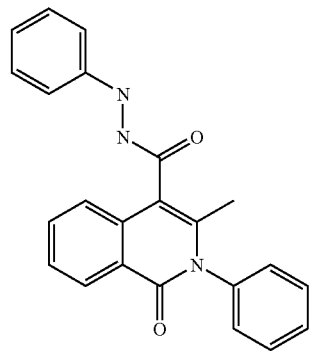

3-Methyl-1-oxo-2-phenyl-1,2-dihydro-isoquinoline-4-carboxylic acid N'-phenyl-hydrazide. [740-170]

The title compound was prepared analogously. LC-MS (m/z) 370.2 (MH$^+$); $t_R$=1.15. $^1$H NMR (500 MHz, DMSO-d$_6$): 2.01 (s, 3H), 6.76 (t, 1H), 6.83 (d, 2H), 7.2 (t, 2H), 7.33

(br, 2H), 7.5-7.62 (m, 5H), 7.83 (t, 1H), 8.11 (br, 1H), 8.24 (d, 1H), 10.33 (s, 1H).

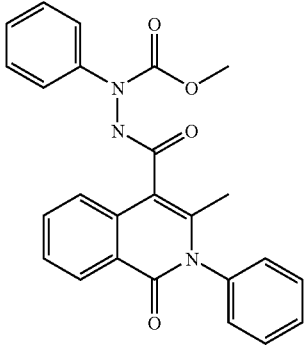

5b N'-(3-Methyl-1-oxo-2-phenyl-1,2-dihydro-iso-quinoline-4-carbonyl)-N-phenyl-hydrazinecarboxylic acid methyl ester

A mixture of 3-methyl-1-oxo-2-phenyl-1,2-dihydro-isoquinoline-4-carboxylic acid N'-phenyl-hydrazide (5a, 490 mg, 1.3 mmol) and methyl chloroformate (0.6 ml, 8 mmol) in 1,2-dichloroethane (10 ml) was heated under microwave irradiation for 10 min at 100° C. Volatiles were removed in vacuo and the product was purified by flash chromatography (SiO$_2$, gradient heptane-1:1 ethyl acetate/heptane) to give 190 mg of solid. LC-MS (m/z) 428.8 (MH$^+$); t$_R$=1.22.

Example 6

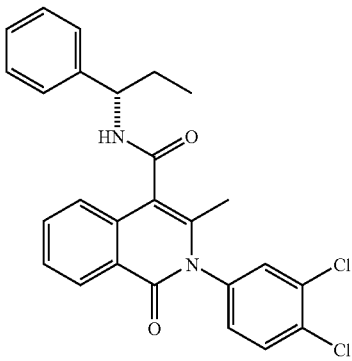

6a 2-(3,4-Dichloro-phenyl)-3-methyl-1-oxo-1,2-dihydro-isoquinoline-4-carboxylic acid ((S)-1-phenyl-propyl)-amide

A mixture of 4-acetyl-3-((S)-1-phenyl-propylamino)-isochromen-1-one (60 mg) and 3,4-dichloroaniline (250 mg) in acetonitrile (0.5 ml) were heated under microwave irradiation at 160° C. for 15 min. The reaction mixture was partitioned between 2M HCl (3 ml) and ethyl acetate (3 ml). The organic solution was absorbed on SiO$_2$ (600 mg) and flash chromatographed on SiO$_2$ (20 g) with gradient heptane-ethyl acetate to give 22 mg of the title compound as a white solid. LC-MS (m/z) 465.4 & 467.4 (MH$^+$); t$_R$=1.63.

The following compounds were obtained analogously from corresponding compounds of the general formula XXIII and appropriate anilines of the general formula VI:

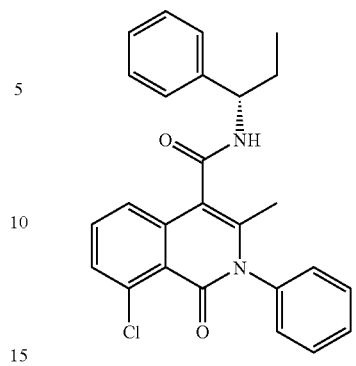

8-Chloro-3-methyl-1-oxo-2-phenyl-1,2-dihydro-isoquinoline-4-carboxylic acid ((S)-1-phenyl-propyl)-amide (1i)

The title compound and its alternative method of preparation was described in the example 1i.

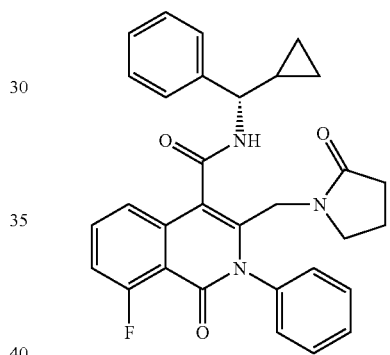

6b 8-Fluoro-1-oxo-3-(2-oxo-pyrrolidin-1-ylmethyl)-2-phenyl-1,2-dihydro-isoquinoline-4-carboxylic acid ((S)-cyclopropyl-phenyl-methyl)-amide

LC-MS (m/z) 510.3 (MH$^+$); t$_R$=1.25.

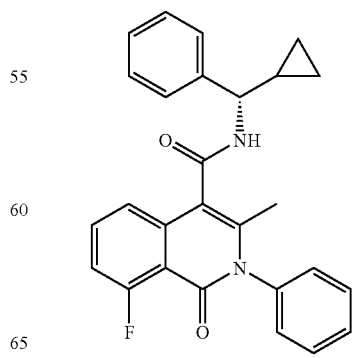

6c 8-Fluoro-3-methyl-1-oxo-2-phenyl-1,2-dihydro-isoquinoline-4-carboxylic acid ((S)-cyclopropyl-phenyl-methyl)-amide LC-MS (m/z) 427.3 (MH$^+$); t$_R$=1.39.

Example 7

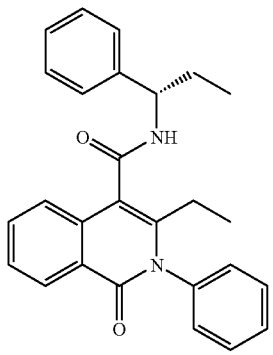

7a 3-Ethyl-1-oxo-2-phenyl-1,2-dihydro-isoquinoline-4-carboxylic acid ((S)-1-phenyl-propyl)-amide A sealed mixture of 2-[2-oxo-1-((S)-1-phenyl-propylcarbamoyl)-butyl]-benzoic acid (82 mg, 0.2 mmol) and aniline (0.3 ml, 3.3 mmol) in acetonitrile (0.3 ml) was heated under microwave irradiation at +160° C. for 10 min. The mixture was partitioned between ethyl acetate (20 ml) and 3M aq. HCl (2×8 ml), sat. aq. NaHCO$_3$ (2×10 ml and brine, dried (MgSO$_4$) and evaporated. The residue was purified by flash chromatography (SiO$_2$, gradient heptane-ethyl acetate) to give 32 mg of the title compound. LC-MS (m/z) 411.5 (MH$^+$); t$_R$=1.48. $^1$H NMR (500 MHz, DMSO-d$_6$): a mixture of two atropisomers.

The following compounds were obtained analogously by condensation of compounds of the general formula XXV with appropriate aniline of the general formula VI:

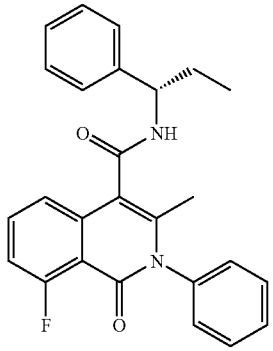

7b 8-Fluoro-3-methyl-1-oxo-2-phenyl-1,2-dihydro-isoquinoline-4-carboxylic acid ((S)-1-phenyl-propyl)-amide LC-MS (m/z) 415.5 (MH$^+$); t$_R$=1.39.

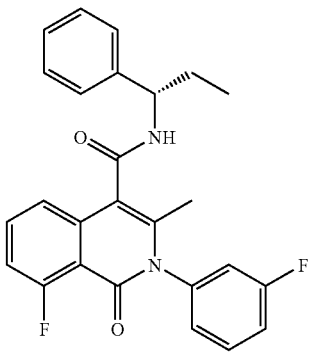

7c 8-Fluoro-2-(3-fluoro-phenyl)-3-methyl-1-oxo-1,2-dihydro-isoquinoline-4-carboxylic acid ((S)-1-phenyl-propyl)-amide LC-MS (m/z) 433.5 (MH$^+$); t$_R$=1.41.

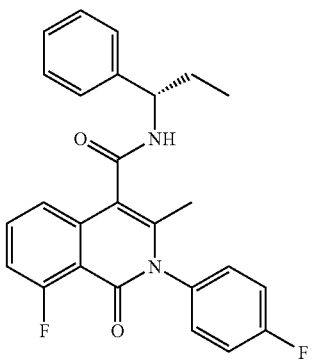

7d 8-Fluoro-2-(4-fluoro-phenyl)-3-methyl-1-oxo-1,2-dihydro-isoquinoline-4-carboxylic acid ((S)-1-phenyl-propyl)-amide LC-MS (m/z) 433.6 (MH$^+$); t$_R$=1.4.

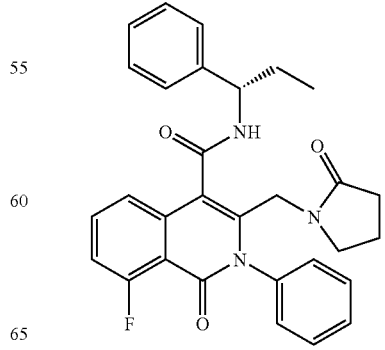

8-Fluoro-1-oxo-3-(2-oxo-pyrrolidin-1-ylmethyl)-2-phenyl-1,2-dihydro-isoquinoline-4-carboxylic acid ((S)-1-phenyl-propyl)-amide (3e)

The title compound and its alternative method of preparation was described above in the example 3.

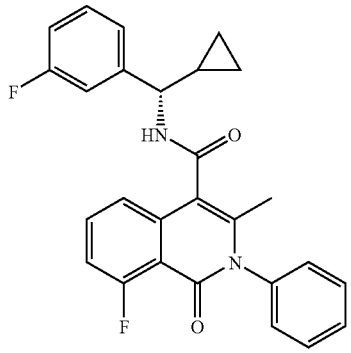

7e 8-Fluoro-3-methyl-1-oxo-2-phenyl-1,2-dihydro-isoquinoline-4-carboxylic acid [(S)-cyclopropyl-(3-fluoro-phenyl)-methyl]-amide LC-MS (m/z) 445.6 (MH$^+$); $t_R$=1.44. $^1$H NMR (250 MHz, 70° C., DMSO-d$_6$): 0.41-0.61 (m, 4H), 1.25 (m, 1H), 1.86 (s, 3H), 4.49 (t, J=8.9 Hz, 1H), 7.04 (m, 1H), 7.13-7.31 (m, 6H), 7.37 (m, 1H), 7.42-7.6 (m, 3H), 7.67 (m, 1H), 8.93 (br d, J=8.5 Hz, 1H, NH).

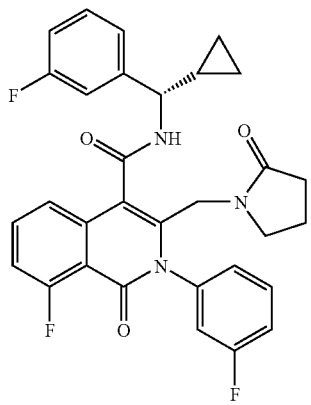

7f 8-Fluoro-2-(3-fluoro-phenyl)-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide The title product was isolated by preparative TLC on silica gel. LC-MS (m/z) 546.4 (MH$^+$); $t_R$=0.71 (method B).

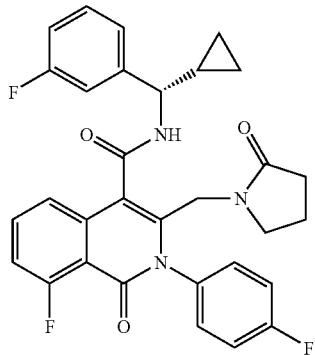

7g 8-Fluoro-2-(4-fluoro-phenyl)-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide The title product was isolated by preparative TLC on silica gel. LC-MS (m/z) 546.3 (MH$^+$); $t_R$=0.71 (method B).

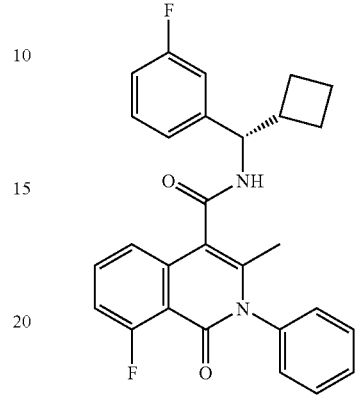

7h 8-Fluoro-3-methyl-1-oxo-2-phenyl-1,2-dihydro-isoquinoline-4-carboxylic acid [(S)-cyclobutyl-(3-fluoro-phenyl)-methyl]-amide LC-MS (m/z) 459.4 (MH$^+$); $t_R$=1.54.

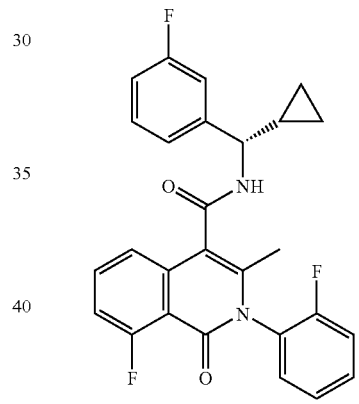

7i 8-Fluoro-2-(2-fluoro-phenyl)-3-methyl-1-oxo-1,2-dihydro-isoquinoline-4-carboxylic acid [(S)-cyclopropyl-(3-fluoro-phenyl)-methyl]-amide LC-MS (m/z) 463.3 (MH$^+$); $t_R$=1.46.

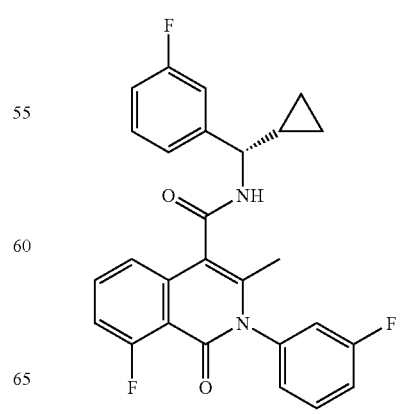

7j 8-Fluoro-2-(3-fluoro-phenyl)-3-methyl-1-oxo-1,2-dihydro-isoquinoline-4-carboxylic acid [(S)-cyclopropyl-(3-fluoro-phenyl)-methyl]-amide LC-MS (m/z) 463.3 (MH$^+$); t$_R$=1.46.

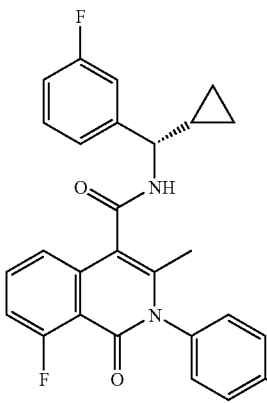

7k 8-Fluoro-2-(4-fluoro-phenyl)-3-methyl-1-oxo-1,2-dihydro-isoquinoline-4-carboxylic acid [(S)-cyclopropyl-(3-fluoro-phenyl)-methyl]-amide LC-MS (m/z) 463.4 (MH$^+$); t$_R$=1.45.

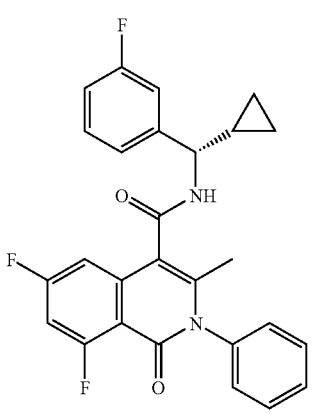

7l 6,8-Difluoro-3-methyl-1-oxo-2-phenyl-1,2-dihydro-isoquinoline-4-carboxylic acid [(S)-cyclopropyl-(3-fluoro-phenyl)-methyl]-amide LC-MS (m/z) 463.2 (MH$^+$); t$_R$=0.82 (method B).

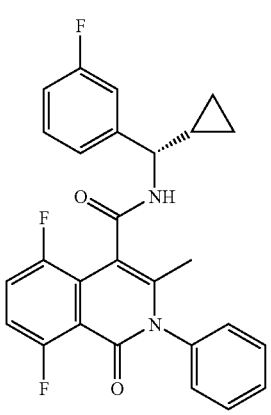

7m 5,8-Difluoro-3-methyl-1-oxo-2-phenyl-1,2-dihydro-isoquinoline-4-carboxylic acid [(S)-cyclopropyl-(3-fluoro-phenyl)-methyl]-amide LC-MS (m/z) 463.4 (MH$^+$); t$_R$=1.39.

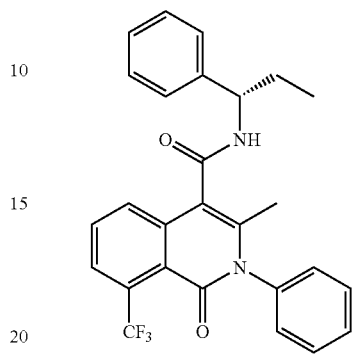

7n 3-Methyl-1-oxo-2-phenyl-8-trifluoromethyl-1,2-dihydro-isoquinoline-4-carboxylic acid ((S)-1-phenyl-propyl)-amide LC-MS (m/z) 465.3 (MH$^+$); t$_R$=1.57.

Example 8

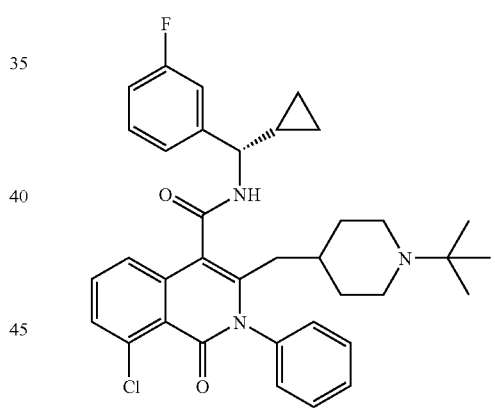

8a 3-(1-tert-Butyl-piperidin-4-ylmethyl)-8-chloro-1-oxo-2-phenyl-1,2-dihydro-isoquinoline-4-carboxylic acid [(S)-cyclopropyl-(3-fluoro-phenyl)-methyl]-amide To a cold (ice bath) mixture of 2-(1-tert-butyl-piperidin-4-yl)-N-phenyl-acetamide (250 mg, 0.91 mmol) and 2,6-dimethylpyridine (0.139 ml, 1.2 mmol) in 1,2-dichloroethane (8 ml) oxalyl chloride (0.07 ml, 0.8 mmol) was added and stirred at 0° C. for 15 min. 2-Chloro-6-({[(S)-cyclopropyl-(3-fluoro-phenyl)-methyl]-carbamoyl}-methyl)-benzoic acid (70 mg, 0.2 mmol) was added and the reaction mixture was stirred in a sealed vessel at 90° C. for 15 hours. It was partitioned between 0.5 M aq. NaOH (40 ml) and ethyl acetate (200 ml), the organic phase washed with water, dried and evaporated. The residue was purified by flash chromatography (SiO$_2$, ethyl acetate-methanol) to give 19 mg of the title compound.

LC-MS (m/z) 600.6 (MH$^+$); $t_R$=1.1. $^1$H NMR (500 MHz, r.t., DMSO-d$_6$): broad signals, a mixture of two atropisomers.

Reagents used for the preparation of the compounds.

| Name | Supplier | CAS no. | Cat. no. |
|---|---|---|---|
| Ethyl acetoacetate | Aldrich | 141-97-9 | E 964-1 |
| Methyl acetoacetate | Aldrich | 105-45-3 | 53,736-5 |
| Sodium hydride, 60% dispersion in mineral oil | Aldrich | 7646-69-7 | 45,291-2 |
| Copper (I) bromide | Aldrich | 7787-70-4 | 21,286-5 |
| 2-Bromobenzoic acid | Janssen Chimica | 88-65-3 | 41066/1 |
| 2-Bromo-4-methylbenzoic acid | Matrix Scientific | 7697-27-0 | 001816 |
| 2-Bromo-6-methylbenzoic acid | Matrix Scientific | 90259-31-7 | 001819 |
| 2,5-Dibromobenzoic acid | ABCR | 610-71-9 | AV15077 |
| 2-Bromo-4-fluorobenzoic acid | Fluorochem | 1006-41-3 | 005470 |
| 2-Bromo-5-chlorobenzoic acid | ABCR | 21739-93-5 | AV10103 |
| 2-Bromo-5-fluorobenzoic acid | Aldrich | 394-28-5 | 56,349-8 |
| 2-Bromo-3-methylbenzoic acid | Fluorochem | 53663-39-1 | 112800 |
| 2-Bromo-5-methylbenzoic acid | Fluorochem | 6967-82-4 | B2947-E |
| 2-Bromo-6-chlorobenzoic acid | Fluorochem | 93224-85-2 | 19332 |
| Aniline | Aldrich | 62-53-3 | 13,293-4 |
| 2-Fluoroaniline | Lancaster | 348-54-9 | 1236 |
| 2,6-Difluoroaniline | Aldrich | 5509-65-9 | 196614 |
| 2-Chloroaniline | Aldrich | 95-51-2 | 23300 |
| o-Toluidine | Aldrich | 95-53-4 | 18,542-6 |
| 3-Fluoroaniline | Flrochem | 372-19-0 | 1438 |
| 3-Chloroaniline | Fluka | 108-42-9 | 23330 |
| m-Toluidine | Aldrich | 108-44-1 | 511218 |
| (S)-(−)-1-Phenylpropylamine | Lancaster | 3789-59-1 | X16320G0025 |
| C-((S)-C-Cyclopropyl-C-phenyl)-methylamine | The compound was prepared according to a described procedure in WO 2005/014575 | | |
| C-[(S)-C-Cyclopropyl-C-(3-fluoro-phenyl)]-methylamine | The compound was prepared according to a described procedure in WO 2005/014575 | | |
| Tetraethoxysilane | Aldrich | 78-10-4 | 236209 |
| 1-Ethyl-3-(3-dimethylaminopropyl)carbodiimide hydrochloride (EDC) | Aldrich | 25952-53-8 | 16,146-2 |
| 1-Hydroxybenzotriazole (HOBT) | ABCR | 2592-95-2 | AV21700 |
| Dimethylamine, 33% solution in abs. Ethanol | Fluka | 124-40-3 | 38950 |
| Methylamine, 2M solution in THF | Aldrich | 74-89-5 | 42,646-6 |
| 2-Pyrrolidone | Aldrich | 616-45-5 | 240338 |
| 1,1-Diphenylhydrazine hydrochloride | Aldrich | 530-47-2 | 11,459-6 |
| Phenylhydrazine | Aldrich | 100-63-0 | P2,625-2 |
| Methyl chloroformate | Aldrich | 79-22-1 | M35304 |
| Sodium cyanide | Aldrich | 143-33-9 | 380970 |

Reagents used for the preparation of the compounds, continued.

| Name | Supplier | CAS no. | Cat. no. |
|---|---|---|---|
| Homophthalic anhydride | ABCR | 703-59-3 | AV15538 |
| Cyclopropanecarboxaldehyde | Aldrich | 1489-69-6 | 27,221-3 |
| 1-Bromo-3-fluorobenzene | Aldrich | 1073-06-9 | B67007 |
| (S)-3-Amino-3-phenylpropanenitrile | Netchem | — | 331516 |
| 3,4-Dichloroaniline | Aldrich | 95-76-1 | 56042 |
| 2-Bromo-6-nitrobenzoic acid | Ref. 1 | 38876-67-4 | — |
| 2-Bromo-6-methoxybenzoic acid | Ref. 2 | 31786-45-5 | — |
| tert-Butyl 2-bromoacetate | Aldrich | 5292-43-3 | 12,426-0 |
| Ethyl (triphenyl-phosphorylidene)acetate | Aldrich | 1099-45-2 | C510-6 |
| 1-(tert-Butoxycarbonyl)piperazine | Lancaster | 57260-71-6 | 13363 |
| 3-Pyrazolidinone hydrochloride | Acros | 1752-88-1 | 335490050 |
| 2-Oxo-4-(tert-butoxycarbonyl)piperazine | Aldrich | 76003-29-7 | 64,105-7 |
| 2-Piperidone | Aldrich | 675-20-7 | V20-9 |

Ref. 1. The compound was prepared according to a described procedure: S. C. Glossop Synthesis 2007, 7, 981.
Ref. 2. The compound was prepared according to a described procedure: T. Sugaya, Y. Mimura, N. Kato, M. Ikuta, T. Mimura et al. Synthesis 1994, 73.

Example 9

NK3 Receptor Binding Assay

Membranepreparation: BHK cells stably expressing the human NK3 receptor were seeded in harvesting plates in Dulbeccos MEM containing GlutaMax (862 mg/l), 1 mM sodium pyruvate, 10% fetal calf serum, 1% Pen/Strep, 1 mg/ml G418 and were grown at 34° C. in a humidified atmosphere containing 10% $CO_2$. To increase receptor expression, 10 μM trichotatin A was added to the media 24 hours before harvest of the cells at a confluency of app 90%. Prior to the harvesting, the cells were washed twice with PBS without $Mg^{2+}$ or $Ca^{2+}$ and subsequently scrapped of in 10 ml PBS pr harvesting plate. The cells suspension were centrifuged at 1500×G in three minutes before resuspension in 15 mM Tris-HCl pH 7.5 buffer containing 2 mM $MgCl_2$; 0.3 mM EDTA and 1 mM EGTA (buffer A). The cell suspension was homogenised and subsequently centrifuged at 4000×G in 30 minutes. The membrane-pellet was resuspended in buffer A containing 250 mM sucrose, aliquoted and stored at −80° C.

Affinity assay description: The assay was performed as a SPA-based competition-binding assay in a 50 mM Tris pH 7.4 assay buffer containing 120 mM NaCl, 3 mM $MnCl_2$, 40 µg/ml bacitracin, 2 µg/ml Chymostatin, 1 µg/ml Phosphoramidon and 4 µg/ml Leupeptin. App 0.02 nM $^{125}I$—NKB was mixed with test compounds before addition of 4 µg of the homogenised NK3 membrane preparation and 0.025 mg SPA beads in a total volume of 60 µl. The assay plate was subsequently under agitation incubated for 90 min at RT. The plate was centrifugated 10 minutes at 500×G and counted in a topcounter 5 minutes pr well.

The total binding, which comprised less than 5% of added radioligand, was defined using assay buffer whereas the non-specific binding was defined in the presence of 1 µM osanetant. The non-specific binding constituted app 5% of the total binding.

Data points were expressed in percent of the specific binding of $^{125}I$—NKB and the $IC_{50}$ values (concentration causing 50 percent inhibition of $^{125}I$—NKB specific binding) were determined by non-linear regression analysis using a sigmoidal variable slope curve fitting. The dissociation constant ($K_i$) were calculated from the Cheng Prusoff equation ($K_i=IC_{50}/(1+(L/K_D))$), where the concentration of free radioligand L is approximated to the concentration of added $^{125}I$—NKB in the assay (app 0.02 nM). The $K_D$ of $^{125}I$—NKB was determined to be 0.7 nM from three independent saturation assays each performed with duplicate determinations. Bmax was app 2 pmol/mg.

The compounds of the present invention generally have $K_i$ values of 500 nM or less. Many compounds, in fact, have $K_i$ values below 100 nM and down to single digit values. The table below shows the $K_i$ for the NK3 receptor

| Compound | $K_i$ nM |
|---|---|
| Ex 2a | 180 |
| Ex 2bm | 8.2 |
| Ex 2hs | 5.3 |
| Ex 2hz | 3 |
| Ex 3a | 72 |
| Ex 5a | 55 |

See also the table in Example 10 for more affinity data for the compounds of the present invention.

Example 10

NK3 Receptor Efficacy and Potency Assay

BHK cells stably expressing the human NK3 receptor were seeded in 100 µl media in black walled clear-base 96-wells plates (Costar) aiming at a confluency of 95-100% at the day of assay. The assay was performed according to the FLIPR Calcium 4 Assay kit (Molecular Devices). At the day of the assay, the media was removed and the cells were washed once with the HBSS buffer (Hanks BSS buffer, pH 7.4 containing 20 mM Hepes) before 100 µl of a solution of the calcium assay reagent dissolved in the HBSS buffer containing 2.5 mM probinicid was added to the cells. The plates were incubated for 60 min at 34° C., 10% $CO_2$ before use in the FLIPR for examination of fluorescence.

One representative plate was examined with a dose-response curve with NKB in a setup in which the wells initially were added HBSS buffer and 15 min later the various concentrations of NKB were added in order to determine the $EC_{50}$ and $EC_{85}$ of NKB. All compound plates used for NKB were precoated with a 1% BSA solution and subsequently washed three times with $H_2O$. NKB was diluted in HBSS buffer containing 0.1% BSA.

For efficacy and potency evaluation of compounds, these were diluted in HBSS buffer prior to test. For test of agonist activity, 25 µl of the diluted compound solution was added and the plate was analyzed for 5 minutes in the FLIPR. For test of antagonist activity, the plate was incubated for another 45 minutes before addition of 25 µl of the $EC_{85}$ concentration of NKB (app. 4 nM) as described above. The plates were subsequently analyzed for 5 minutes before the assay was terminated. The maximal increase in fluorescence over background following each ligand addition was determined. The $IC_{50}$ value was calculated using sigmoidal variable slope curve fitting, and the $cIC_{50}$ value was determined using the equation ($cIC_{50}=IC_{50}/(1+(EC_{85}/EC_{50}))$), where $EC_{85}$ and $EC_{50}$ for NKB were determined as described above.

All isoquinolinones of the present invention characterized in the NK3 receptor efficacy and potency assay have been antagonists without any observed significant agonist activity at relevant doses. The table shows affinity data (obtained as described in Example 9) and potency data obtained with the compounds of the invention. Minor differences between the tabulated values in Example 9 and 10 only reflects that more than one batch have been tested and/or that one batch has been tested more than once.

| Example No | Affinity $K_i$/nM | Potency $cIC_{50}$/nM |
|---|---|---|
| 2e | 330 | 470 |
| 1i | 41 | 130 |
| 3a | 88 | 270 |
| 2r | 320 | 420 |
| 2s | 200 | 340 |
| 2u | 90 | 96 |
| 2ah | 290 | 360 |
| 2bg | 160 | 220 |
| 2bm | 8.8 | 14 |
| 2bn | 160 | 300 |
| 2cw | 8.4 | 45 |
| 2cz | 76 | 49 |
| 2df | 340 | 450 |
| 2ec | 210 | 520 |
| 2eg | 240 | 610 |
| 2es | 140 | 240 |
| 2ey | 240 | 480 |
| 2fm | 33 | 140 |
| 2gt | 9.2 | 22 |
| 2hq | 10 | 44 |
| 2hs | 7.5 | 21 |
| 2hu | 6.2 | 29 |
| 2hv | 14 | 35 |
| 2hw | 8.2 | 63 |
| 2hx | 9.3 | 68 |
| 2hy | 8.8 | 63 |
| 2hz | 4.5 | 35 |
| 2ia | 12 | 100 |
| 2iy | 17 | 92 |
| 1t | 27 | 44 |
| 2kh | 82 | 120 |
| 2kn | 8.7 | 41 |
| 2ko | 11 | 5.6 |
| 3d | 16 | 46 |

-continued

| Example No | Affinity $K_i$/nM | Potency $cIC_{50}$/nM |
|---|---|---|
| 2lj | 18 | 16 |
| 3b | 32 | 47 |
| 1bh | 21 | 81 |
| 2ll | 7.9 | 6.3 |
| 8a | 7 | 9.9 |
| 1bn | 23 | 23 |
| 6c | 23 | 24 |
| 1bl | 470 | |

The invention claimed is:

1. A compound according to formula I

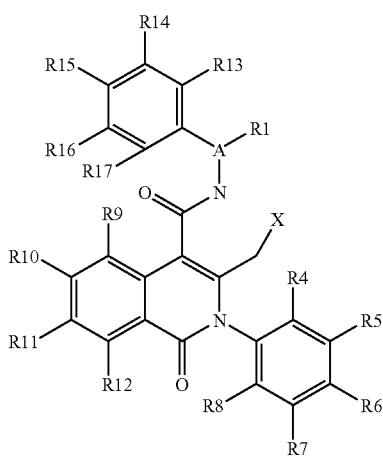

[I]

wherein A is N, CH or CR$^1$;
wherein each R$^1$ is independently hydrogen, C$_{1-6}$alkyl, C$_{2-6}$alkenyl, C$_{2-6}$alkynyl, —C(O)—C$_{1-6}$alkyl, —C(O)—C$_{2-6}$alkenyl, —C(O)—C$_{2-6}$alkynyl, —C(O)—O—C$_{1-6}$alkyl, —C(O)—O—C$_{2-6}$alkenyl, —C(O)—O—C$_{2-6}$alkynyl or phenyl, wherein said phenyl, C$_{1-6}$alkyl, C$_{2-6}$alkenyl or C$_{2-6}$alkynyl is optionally substituted with one or more substituents selected from the group consisting of halogen, hydroxyl, haloC$_{1-6}$alkyl, nitro, C$_{1-6}$alkoxy, and NR$^2$R$^3$;
wherein X is hydrogen, C$_{1-6}$alkyl, C$_{2-6}$alkenyl, C$_{2-6}$alkynyl, cyano, —OR$^2$, —O—C(O)R$^2$, —OC(O)NR$^2$R$^3$, —C(O)—NR$^2$R$^3$, —N(R$^2$)C(O)R$^3$, —N(R$^2$)—C(O)NR$^2$R$^3$ or NR$^2$R$^3$, or X is a mono-cyclic, bi-cyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from the group consisting of hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{2-6}$alkenyl, C$_{2-6}$alkynyl, C$_{1-6}$alkoxy, —C(O)—C$_{1-6}$alkyl, —C(O)—C$_{2-6}$alkenyl, —C(O)—C$_{2-6}$alkynyl, —C(O)—O—C$_{1-6}$alkyl, —C(O)—O—C$_{2-6}$alkenyl, —C(O)—O—C$_{2-6}$alkynyl, —O—C(O)—C$_{1-6}$alkyl, —O—C(O)—C$_{2-6}$alkenyl, —O—C(O)—C$_{2-6}$alkynyl, —C(O)H, COOH; or wherein W is a moiety of the formula —(CH$_2$)$_a$—Y—(CH$_2$)$_b$—Z;
wherein each of a and b is independently an integer selected from 0, 1, 2 and 3;

wherein Y is a bond, C(O), O, S, —O—C(O), —C(O)—O—, —NR$^2$—, —NR$^2$—C(O)—, —C(O)—NH—, or S(O)$_2$;
wherein Z is hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;
wherein each of R$^4$-R$^8$, R$^9$-R$^{12}$, and R$^{13}$-R$^{17}$ is independently hydrogen, C$_{1-6}$alkyl, C$_{2-6}$alkenyl, C$_{2-6}$alkynyl, halogen, NR$^2$R$^3$, hydroxy, cyano, nitro, C$_{1-6}$alkoxy, haloC$_{1-6}$alkyl or hydroxyC$_{1-6}$alkyl;
wherein each of R$^2$ and R$^3$ is independently hydrogen, C$_{1-6}$alkyl, C$_{2-6}$alkenyl, C$_{2-6}$alkynyl, hydroxyC$_{1-6}$alkyl, haloC$_{1-6}$alkyl or phenyl;
or a pharmaceutically acceptable salt thereof.

2. A compound according to claim 1, wherein each of R$^4$-R$^8$ is hydrogen.

3. A compound according to claim 1, wherein each of R$^9$-R$^{12}$ is hydrogen.

4. A compound according to claim 1, wherein each of R$^{13}$-R$^{17}$ is hydrogen.

5. A compound according to claim 1 of the formula I$_a$

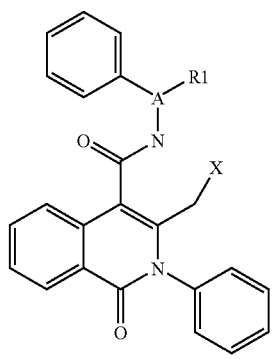

[Ia]

wherein A is N, CH or CR$^1$;
wherein each R$^1$ is independently hydrogen, C$_{1-6}$alkyl, —C(O)—C$_{1-6}$alkyl, —C(O)—O—C$_{1-6}$alkyl, or phenyl, wherein said phenyl or C$_{1-6}$alkyl, is optionally substituted with one or more substituents selected from the group consisting of halogen, hydroxyl, haloC$_{1-6}$alkyl, nitro, C$_{1-6}$alkoxy, and NR$^2$R$^3$;
wherein X is hydrogen, C$_{1-6}$alkyl, cyano, —OR$^2$, —O—C(O)R$^2$, —OC(O)NR$^2$R$^3$, —C(O)—NR$^2$R$^3$, —N(R$^2$)C(O)R$^3$, —N(R$^2$)—C(O)NR$^2$R$^3$ or NR$^2$R$^3$, or X is a mono-cyclic, bicyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from the group consisting of hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{1-6}$alkoxy, —C(O)—C$_{1-6}$alkyl, —C(O)—O—C$_{1-6}$alkyl, —O—C(O)—C$_{1-6}$alkyl, —C(O)H, COOH; or wherein W is a moiety of the formula —(CH₂)ₐ—Y—(CH₂)ᵦ—Z;

wherein each of a and b is independently an integer selected from 0, 1, 2 and 3;

wherein Y is a bond, C(O), O, S, —O—C(O), —C(O)—O—, —NR², —NR²—C(O)—, —C(O)—NH—, or S(O)₂;

wherein Z is hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;

wherein each of R⁴-R⁸, R⁹-R¹², and R¹³-R¹⁷ is independently represent hydrogen, $C_{1-6}$alkyl, $C_{2-6}$alkenyl, $C_{2-6}$alkynyl, halogen, NR²R³, hydroxy, cyano, nitro, $C_{1-6}$alkoxy, halo$C_{1-6}$alkyl or hydroxy$C_{1-6}$alkyl;

wherein each of R² and R³ is independently hydrogen, $C_{1-6}$alkyl, $C_{2-6}$alkenyl, $C_{2-6}$alkynyl, hydroxy$C_{1-6}$alkyl, halo$C_{1-6}$alkyl or phenyl;

or a pharmaceutically acceptable salt thereof.

6. A compound according to claim 5, wherein A is CH.

7. A compound according to claim 6, wherein R¹ is $C_{1-6}$alkyl.

8. A compound according to claim 5, wherein X is hydrogen, $C_{1-6}$alkyl, cyano, —OR², —O—C(O)R², —OC(O)NR²R³, —C(O)—NR²R³, —N(R²)C(O)R³, —N(R²)—C(O)NR²R³ or NR²R³, wherein each of R² and R³ is independently hydrogen, $C_{1-6}$alkyl, hydroxy$C_{1-6}$alkyl, halo$C_{1-6}$alkyl or phenyl.

9. A compound according to claim 8, wherein X represents hydrogen, methyl, or NR²R³, wherein each of R² and R³ is independently hydrogen, $C_{1-6}$alkyl, or hydroxy$C_{1-6}$alkyl.

10. A compound according to claim 9, wherein each of R² and R³ is independently hydrogen, cyclopropylmethyl, methyl, ethyl or cyclopropyl.

11. A compound according to claim 5, wherein X is a mono-cyclic, bi-cyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from the group consisting of hydrogen, hydroxy, halogen, cyano, (=O), —O—(CH₂)c—O—, wherein c is 2 or 3 (spiro), (CH₂)d, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —O—C(O)—, —C(O)H, COOH; or wherein W is a moiety of the formula —(CH₂)ₐ—Y—(CH₂)ᵦ—Z;

wherein each of a and b is independently an integer selected from 0, 1, 2 and 3;

wherein Y is a bond, C(O), O, S, —O—C(O), —C(O)—O—, —NR², —NR²—C(O)—, —C(O)—NH—, or S(O)₂;

wherein Z is hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;

wherein each of R² and R³ is independently hydrogen, $C_{1-6}$alkyl, hydroxy$C_{1-6}$alkyl, halo$C_{1-6}$alkyl or phenyl.

12. A compound according to claim 1 of the formula $I_b$

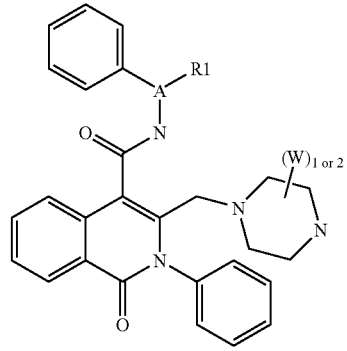

[Ib]

wherein A is N, CH or CR¹;

wherein each R¹ is independently hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from the group consisting of halogen, hydroxyl, halo$C_{1-6}$alkyl, nitro, $C_{1-6}$alkoxy, and NR²R³;

wherein W is selected from the group consisting of hydrogen, hydroxy, halogen, cyano, (=O), —o—(CH₂)c—O—, wherein c is 2 or 3 (spiro), (CH₂)d, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W is a moiety of the formula —(CH₂)ₐ—Y—(CH₂)ᵦ—Z;

wherein each of a and b is independently an integer selected from 0, 1, 2 and 3;

wherein Y a bond, C(O), O, S, —O—C(O), —C(O)—O—, —NR², —NR²—C(O)—, —C(O)—NH—, or S(O)₂;

wherein Z is hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;

wherein each of R² and R³ is independently hydrogen, $C_{1-6}$alkyl, hydroxy$C_{1-6}$alkyl, halo$C_{1-6}$alkyl or phenyl;

or a pharmaceutically acceptable salt thereof.

13. A compound according to claim 12, wherein A is CH, and R¹ represents $C_{1-6}$alkyl.

14. A compound according to claim 1 of formula Ic

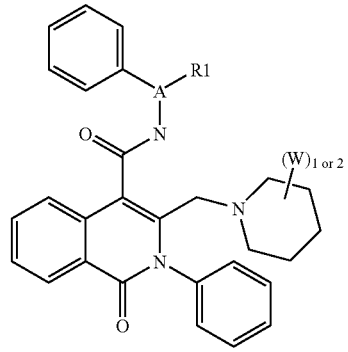

[Ic]

wherein A represents is N, CH or CR¹;
wherein R¹ is independently hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from the group consisting of halogen, hydroxyl, halo$C_{1-6}$alkyl, nitro, $C_{1-6}$alkoxy, and NR²R³;
wherein W is selected from the group consisting of hydrogen, hydroxy, halogen, cyano, (=O), —O—(CH₂)$_c$—O—, wherein c is 2 or 3 (spiro), (CH₂)$_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W represents a moiety of the formula —(CH₂)$_a$—Y—(CH₂)$_b$—Z;
wherein each of a and b is independently an integer selected from 0, 1, 2 and 3;
wherein Y is a bond, C(O), O, S, —O—C(O), —C(O)—O—, —NR²—, —NR²—C(O)—, —C(O)—NH—, or S(O)₂;
wherein Z is hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein each of R² and R³ is independently hydrogen, $C_{1-6}$alkyl, hydroxy$C_{1-6}$alkyl, halo$C_{1-6}$alkyl or phenyl;
or a pharmaceutically acceptable salt thereof.

15. A compound according to claim 14, wherein A is CH, and R¹ is $C_{1-6}$alkyl.

16. A compound according to claim 1 of the formula I$_d$

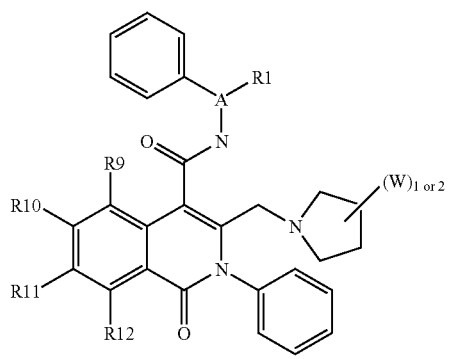

[Id]

wherein A is N, CH or CR¹;
wherein R¹ is independently represent hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from the group consisting of halogen, hydroxyl, halo$C_{1-6}$alkyl, nitro, $C_{1-6}$alkoxy, and NR²R³;
wherein W is selected from the group consisting of hydrogen, hydroxy, halogen, cyano, (=O), —O—(CH₂)$_c$—O—, wherein c is 2 or 3 (spiro), (CH₂)$_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH;

wherein each of R² and R³ is independently hydrogen, $C_{1-6}$alkyl, hydroxy$C_{1-6}$alkyl, halo$C_{1-6}$alkyl or phenyl;
wherein each of R⁹-R¹² is independently hydrogen or halogen;
or a pharmaceutically acceptable salt thereof.

17. A compound according to claim 16, wherein A is CH; R¹ is $C_{1-6}$alkyl; and each of R⁹-R¹² is independently hydrogen or halogen.

18. A compound according to claim 1 of the formula I$_e$

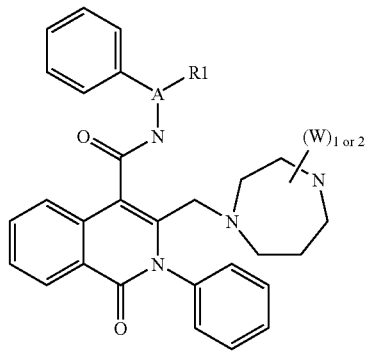

[Ie]

wherein A is N, CH or CR¹;
wherein each R¹ is independently hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from the group consisting of halogen, hydroxyl, halo$C_{1-6}$alkyl, nitro, $C_{1-6}$alkoxy, and NR²R³;
wherein W is selected from the group consisting of hydrogen, hydroxy, halogen, cyano, (=O), —O—(CH₂)$_c$—O—, wherein c is 2 or 3 (spiro), (CH₂)$_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W represents is a moiety of the formula —(CH₂)$_a$—Y—(CH₂)$_b$—Z;
wherein each of a and b is independently an integer selected from 0, 1, 2 and 3;
wherein Y is a bond, C(O), O, S, —O—C(O), —C(O)—O—, NR², —NR²—C(O)—, —C(O)—NH—, or S(O)₂;
wherein Z is hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;
wherein each of R² and R³ is independently hydrogen, $C_{1-6}$alkyl, hydroxy$C_{1-6}$alkyl, halo$C_{1-6}$alkyl or phenyl;
or a pharmaceutically acceptable salt thereof.

19. A compound according to claim 18, wherein A is CH, and $R^1$ is $C_{1-6}$alkyl.

20. A compound according to claim 1 of the formula $I_f$

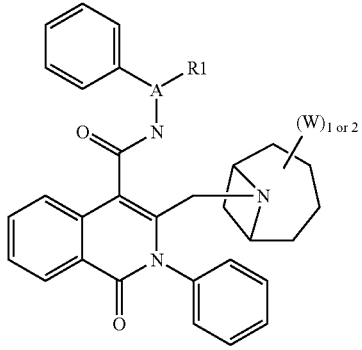

[If]

wherein A is N, CH or $CR^1$;

wherein each $R^1$ is independently hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from the group consisting of halogen, hydroxyl, halo$C_{1-6}$alkyl, nitro, $C_{1-6}$alkoxy, and $NR^2R^3$;

wherein W is selected from the group consisting of hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —C(O)H, COOH; or wherein W is a moiety of the formula —$(CH_2)_a$—Y—$(CH_2)_b$—Z;

wherein each of a and b is independently an integer selected from 0, 1, 2 and 3;

wherein Y is a bond, C(O), O, S, —O—C(O), —C(O)—O—, $NR^2$, —$NR^2$—C(O)—, —C(O)—NH—, or $S(O)_2$;

wherein Z is hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;

wherein each of $R^2$ and $R^3$ is independently hydrogen, $C_{1-6}$alkyl, hydroxy$C_{1-6}$alkyl, halo$C_{1-6}$alkyl or phenyl;

or a pharmaceutically acceptable salt thereof.

21. A compound according to claim 20, wherein A is CH, and $R^1$ is $C_{1-6}$alkyl.

22. A compound according to claim 1 of the formula $I_g$

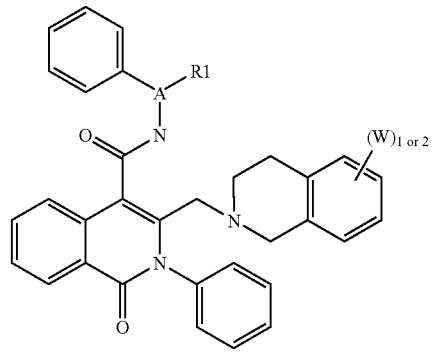

[Ig]

wherein A is N, CH or $CR^1$;

wherein each $R^1$ is independently hydrogen, $C_{1-6}$alkyl, —C(O)—$C_{1-6}$alkyl, C(O)—O—$C_{1-6}$alkyl, or phenyl, wherein said phenyl, or $C_{1-6}$alkyl is optionally substituted with one or more substituents selected from the group consisting of halogen, hydroxyl, halo$C_{1-6}$alkyl, nitro, $C_{1-6}$alkoxy, and $NR^2R^3$;

wherein W is selected from the group consisting of hydrogen, hydroxy, halogen, cyano, (=O), —O—$(CH_2)_c$—O—, wherein c is 2 or 3 (spiro), $(CH_2)_d$, wherein d is 5 or 6 (spiro), $C_{1-6}$alkyl, $C_{1-6}$alkoxy, —C(O)—$C_{1-6}$alkyl, —C(O)—O—$C_{1-6}$alkyl, —O—C(O)—$C_{1-6}$alkyl, —N($R^2$)—C(O)—$R^3$, —C(O)H, COOH; or wherein W is a moiety of the formula —$(CH_2)_a$—Y—$(CH_2)_b$—Z;

each of wherein a and b is independently an integer selected from 0, 1, 2 and 3;

wherein Y represents a bond, C(O), O, S, —O—C(O), —C(O)—O—, $NR^2$, —$NR^2$—C(O)—, —C(O)—NH—, o $S(O)_2$;

wherein Z is hydrogen, $C_{1-6}$alkyl, $NR^2R^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, pyrazinyl, phenyl, pyridyl, and halogen substituted phenyl;

wherein each of $R^2$ and $R^3$ is independently hydrogen, $C_{1-6}$alkyl, hydroxy$C_{1-6}$alkyl, halo$C_{1-6}$alkyl or phenyl;

or a pharmaceutically acceptable salt thereof.

23. A compound according to claim 22, wherein A is CH, and $R^1$ is $C_{1-6}$alkyl.

24. A compound according to claim 1 of formula $I_h$

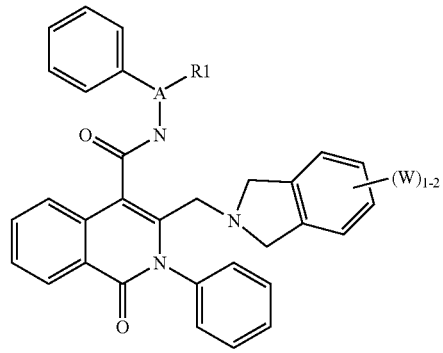

[Ih]

wherein A is N, CH or CR$^1$;
wherein each R$^1$ is independently hydrogen, C$_{1-6}$alkyl, —C(O)—C$_{1-6}$alkyl, C(O)—O—C$_{1-6}$alkyl, or phenyl, wherein said phenyl, or C$_{1-6}$alkyl is optionally substituted with one or more substituents selected from the group consisting of halogen, hydroxyl, haloC$_{1-6}$alkyl, nitro, C$_{1-6}$alkoxy, and NR$^2$R$^3$;
wherein W is selected from the group consisting of hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{1-6}$alkoxy, —C(O)—C$_{1-6}$alkyl, —C(O)—O—C$_{1-6}$alkyl, —O—C(O)—C$_{1-6}$alkyl, —C(O)H, COOH; or wherein W is a moiety of the formula —(CH$_2$)$_a$—Y—(CH$_2$)$_b$—Z;
wherein each of a and b is independently an integer selected from 0, 1, 2 and 3;
wherein Y represents a bond, C(O), O, S, —O—C(O), —C(O)—O—, NR$^2$, —NR$^2$—C(O)—, —C(O)—NH—, or S(O)$_2$;
wherein Z is hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;
wherein each of R$^2$ and R$^3$ is independently hydrogen, C$_{1-6}$alkyl, hydroxyC$_{1-6}$alkyl, haloC$_{1-6}$alkyl or phenyl;
or a pharmaceutically acceptable salt thereof.

25. A compound according to claim 24, wherein A is CH, and R$^1$ is C$_{1-6}$alkyl.

26. A compound according to claim 1 of formula I$_i$

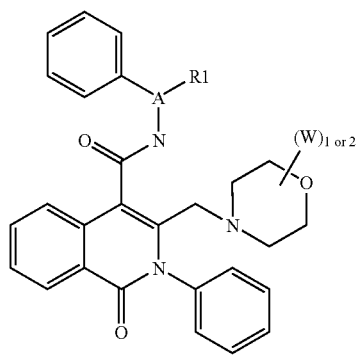

[Ii]

wherein A is N, CH or CR$^1$;
wherein each R$^1$ is independently represents hydrogen, C$_{1-6}$alkyl, —C(O)—C$_{1-6}$alkyl, C(O)—O—C$_{1-6}$alkyl, or phenyl, wherein said phenyl, or C$_{1-6}$alkyl is optionally substituted with one or more substituents selected from the group consisting of halogen, hydroxyl, haloC$_{1-6}$alkyl, nitro, C$_{1-6}$alkoxy, and NR$^2$R$^3$;
wherein W is selected from the group consisting of hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{1-6}$alkoxy, —C(O)—C$_{1-6}$alkyl, —C(O)—O—C$_{1-6}$alkyl, —O—C(O)—C$_{1-6}$alkyl, —C(O)H, COOH; or wherein X is a moiety of the formula —(CH$_2$)$_a$—Y—(CH$_2$)$_b$—Z;
wherein each of a and b is independently an integer selected from 0, 1, 2 and 3;
wherein Y is a bond, C(O), O, S, —O—C(O), —C(O)—O—, NR$^2$, —NR$^2$—C(O)—, —C(O)—NH—, or S(O)$_2$;
wherein Z is hydrogen, C$_{1-6}$alkyl, NR$^2$R$^3$, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, C$_{1-6}$alkyl, hydroxyl, and C$_{1-6}$alkoxy, pyrazinyl, phenyl, pyridyl, and halogen substituted phenyl;
wherein each of R$^2$ and R$^3$ is independently hydrogen, C$_{1-6}$alkyl, hydroxyC$_{1-6}$alkyl, haloC$_{1-6}$alkyl or phenyl;
or a pharmaceutically acceptable salt thereof.

27. A compound according to claim 26, wherein A is CH, and R$^1$ is C$_{1-6}$alkyl.

28. A compound according to claim 1 of formula Ij

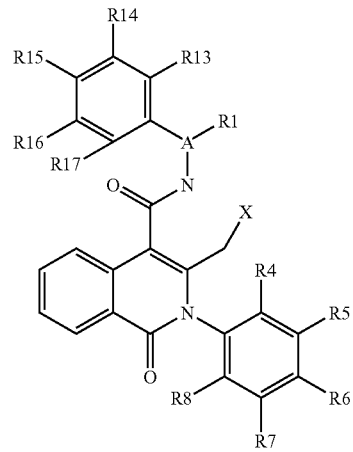

[Ij]

wherein A is N, CH or CR$^1$;
wherein each R$^1$ is independently hydrogen, C$_{1-6}$alkyl, —C(O)—C$_{1-6}$alkyl, —C(O)—O—C$_{1-6}$alkyl, or phenyl, wherein said phenyl or C$_{1-6}$alkyl is optionally substituted with one or more substituents selected from the group consisting of halogen, hydroxyl, haloC$_{1-6}$alkyl, nitro, C$_{1-6}$alkoxy, and NR$^2$R$^3$;
wherein X is hydrogen, C$_{1-6}$alkyl, cyano, —OR$^2$, —O—C(O)R$^2$, —OC(O)NR$^2$R$^3$, —C(O)—NR$^2$R$^3$, —N(R$^2$)C(O)R$^3$, —N(R$^2$)—C(O)NR$^2$R$^3$ or NR$^2$R$^3$, or X is a mono-cyclic, bicyclic or tri-cyclic moiety having 4-16 ring atoms one of which is nitrogen, and wherein one, two or three additional ring atoms may be a hetero atom selected from N, O and S, and wherein said mono-cyclic, bi-cyclic or tri-cyclic moiety may optionally be substituted with one or more substituents W, wherein W is selected from the group consisting of hydrogen, hydroxy, halogen, cyano, (=O), —O—(CH$_2$)$_c$—O—, wherein c is 2 or 3 (spiro), (CH$_2$)$_d$, wherein d is 5 or 6 (spiro), C$_{1-6}$alkyl, C$_{1-6}$alkoxy, —C(O)—C$_{1-6}$alkyl, —C(O)—O—C$_{1-6}$alkyl, —O—C(O)—C$_{1-6}$alkyl, —C(O)H, COOH; or
wherein W is a moiety of the formula —(CH$_2$)$_a$—Y—(CH$_2$)$_b$—Z;
wherein each of a and b is independently an integer selected from 0, 1, 2 and 3;

wherein Y is a bond, C(O), O, S, —O—C(O), —C(O)—O—, —NR², —NR²—C(O)—, —C(O)—NH—, or S(O)₂;

wherein Z is hydrogen, $C_{1-6}$alkyl, NR²R³, cyano or a mono-cyclic or fused bi-cyclic moiety comprising 4 to 12 ring atoms of which optionally one, two or three are hetero atoms selected from amongst N, O, and S, and wherein said mono-cyclic or fused bi-cyclic moiety is optionally substituted with one or more substituents selected from the group consisting of halogen, cyano, $C_{1-6}$alkyl, hydroxyl, and $C_{1-6}$alkoxy, phenyl, pyridyl, and halogen substituted phenyl;

wherein one of $R^4$-$R^8$ is halogen and the other is hydrogen; wherein one of $R^{13}$-$R^{17}$ is halogen and the other represent hydrogen;

wherein each of $R^2$ and $R^3$ is independently hydrogen, $C_{1-6}$alkyl, hydroxy$C_{1-6}$alkyl, halo$C_{1-6}$alkyl or phenyl;

or a pharmaceutically acceptable salt thereof.

29. A compound according to claim 28 wherein A is CH; $R^1$ represents is ethyl or cyclopropyl; $R^{14}$ represents is halogen; and $R^5$ or $R^8$ is halogen.

30. The compound according claim 1 of the formula Ik

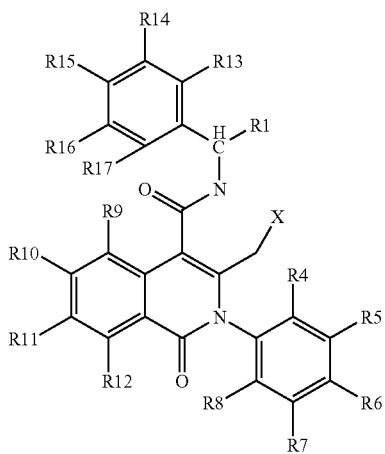

[Ik]

wherein $R^1$ is hydrogen, $C_{1-6}$alkyl, $C_{2-6}$alkenyl or $C_{2-6}$alkynyl;

wherein X is hydrogen, $C_{1-6}$alkyl, $C_{2-6}$alkenyl, $C_{2-6}$alkynyl or NR²R³, or X is a mono-cyclic or bi-cyclic moiety having 5-9 ring atoms one of which is nitrogen, and wherein one, two or three additional ring atoms may be a hetero atom selected from N, O and S, and wherein said mono-cyclic or bi-cyclic moiety may optionally be substituted with one or more substituents W, wherein W is selected from the group consisting of hydrogen, halogen, hydroxy, (=O), $C_{1-6}$alkyl, $C_{2-6}$alkenyl, $C_{2-6}$alkynyl, $C_{1-6}$alkoxy, or wherein W is a moiety of the formula —(CH₂)ₐ—Y—(CH₂)ᵦ—Z;

wherein each of a and b is independently an integer selected from 0, 1, 2 and 3;

wherein Y is a bond, and wherein Z is a mono-cyclic moiety comprising 5 to 6 ring atoms of which optionally one, two or three are hetero atoms selected from amongst N, O, and S, and wherein said mono-cyclic moiety is optionally substituted with one or more substituents selected from the group consisting of halogen, $C_{1-6}$alkyl, hydroxyl, and $C_{1-6}$alkoxy;

wherein each of $R^4$-$R^8$ is independently hydrogen or halogen;

wherein each of $R^9$-$R^{12}$ is independently hydrogen or halogen provided that at least one of $R^9$-$R^{12}$ is halogen;

wherein each of $R^{13}$-$R^{17}$ is independently hydrogen or halogen;

wherein each of $R^2$ and $R^3$ is independently hydrogen, $C_{1-6}$alkyl, $C_{2-6}$alkenyl, $C_{2-6}$alkynyl; and pharmaceutically acceptable salts thereof.

31. The compound according to claim 30 of formula Ik'

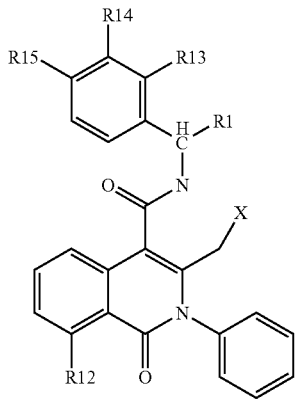

[Ik']

wherein $R^1$ is selected from $C_{1-6}$alkyl;

wherein X is selected from the group consisting of hydrogen, $C_{1-6}$alkyl or NR²R³, or X is a mono-cyclic or bi-cyclic moiety having 5-9 ring atoms one of which is nitrogen, and wherein one additional ring atoms may be a hetero atom selected from N, and wherein said mono-cyclic or bi-cyclic moiety may optionally be substituted with one or more substituents W, wherein W is selected from the group consisting of hydrogen, hydroxy, (=O), $C_{1-6}$alkyl or wherein W is a moiety of the formula —(CH₂)ₐ—Y—(CH₂)ᵦ—Z;

wherein each of a and b is independently an integer selected from 0, 1, 2 and 3;

wherein Y is a bond, and wherein Z is a mono-cyclic moiety comprising 5 to 6 ring atoms of which optionally one is a hetero atom selected from amongst N, O, and S, and wherein said mono-cyclic moiety is optionally substituted with one or more substituents selected from the group consisting of halogen, $C_{1-6}$alkyl, hydroxyl, and $C_{1-6}$alkoxy;

wherein $R^{12}$ is halogen;

each of $R^{13}$-$R^{15}$ is independently hydrogen or halogen;

or a pharmaceutically acceptable salt thereof.

32. A compound according to claim 1 of the formula Id'

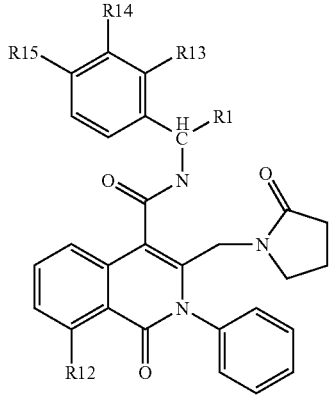

[Id']

wherein R$^1$ is ethyl or cyclopropyl;
R$^{12}$ is halogen;
each of R$^{13}$, R$^{14}$ and R15 is independently hydrogen, or halogen;
or a pharmaceutically acceptable salt thereof.

33. A compound according to claim 1 of the formula Id"

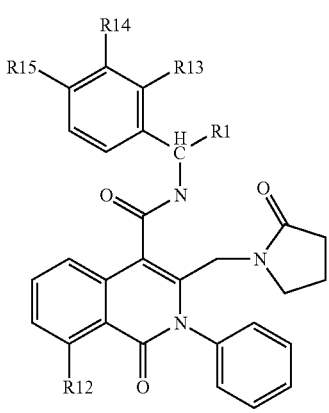

[Id"]

wherein R$^1$ is ethyl or cyclopropyl;
R$^{12}$ is chloro or fluoro;
each of R$^{12}$, R$^{14}$ and R$^{15}$ is independently hydrogen, chloro or fluoro, wherein two of R$^{12}$, R$^{14}$ and R$^{15}$ is hydrogen;
or a pharmaceutically acceptable salt thereof.

34. A compound according to claim 1 selected from
3-Methyl-1-oxo-2-phenyl-1,2-dihydro-isoquinoline-4-carboxylic acid ((S)-1-phenyl-propyl)-amide;
3,6-Dimethyl-1-oxo-2-phenyl-1,2-dihydro-isoquinoline-4-carboxylic acid ((S)-1-phenyl-propyl)-amide;
7-Chloro-3-methyl-1-oxo-2-phenyl-1,2-dihydro-isoquinoline-4-carboxylic acid ((S)-1-phenyl-propyl)-amide;
7-Bromo-3-methyl-1-oxo-2-phenyl-1,2-dihydro-isoquinoline-4-carboxylic acid ((S)-1-phenyl-propyl)-amide;
6-Fluoro-3-methyl-1-oxo-2-phenyl-1,2-dihydro-isoquinoline-4-carboxylic acid ((S)-1-phenyl-propyl)-amide;
3,5-Dimethyl-1-oxo-2-phenyl-1,2-dihydro-isoquinoline-4-carboxylic acid ((S)-1-phenyl-propyl)-amide;
7-Fluoro-3-methyl-1-oxo-2-phenyl-1,2-dihydro-isoquinoline-4-carboxylic acid ((S)-1-phenyl-propyl)-amide;
3,7-Dimethyl-1-oxo-2-phenyl-1,2-dihydro-isoquinoline-4-carboxylic acid ((S)-1-phenyl-propyl)-amide;
8-Chloro-3-methyl-1-oxo-2-phenyl-1,2-dihydro-isoquinoline-4-carboxylic acid ((S)-1-phenyl-propyl)-amide;
3-Methyl-1-oxo-2-phenyl-1,2-dihydro-isoquinoline-4-carboxylic acid ((S)-cyclopropyl-phenyl-methyl)-amide;
3-Methyl-1-oxo-2-phenyl-1,2-dihydro-isoquinoline-4-carboxylic acid [(S)-cyclopropyl-(3-fluoro-phenyl)-methyl]-amide;
3,8-Dimethyl-1-oxo-2-phenyl-1,2-dihydro-isoquinoline-4-carboxylic acid ((S)-1-phenyl-propyl)-amide;
2-(2-Fluoro-phenyl)-3-methyl-1-oxo-1,2-dihydro-isoquinoline-4-carboxylic acid ((S)-1-phenyl-propyl)-amide;
3-Methyl-1-oxo-2-o-tolyl-1,2-dihydro-isoquinoline-4-carboxylic acid ((S)-1-phenyl-propyl)-amide;
2-(2-Chloro-phenyl)-3-methyl-1-oxo-1,2-dihydro-isoquinoline-4-carboxylic acid ((S)-1-phenyl-propyl)-amide;
2-(2,6-Difluoro-phenyl)-3-methyl-1-oxo-1,2-dihydro-isoquinoline-4-carboxylic acid ((S)-1-phenyl-propyl)-amide;
2-(3-Fluoro-phenyl)-3-methyl-1-oxo-1,2-dihydro-isoquinoline-4-carboxylic acid ((S)-1-phenyl-propyl)-amide;
3-Methyl-1-oxo-2-m-tolyl-1,2-dihydro-isoquinoline-4-carboxylic acid ((S)-1-phenyl-propyl)-amide;
2-(3-Chloro-phenyl)-3-methyl-1-oxo-1,2-dihydro-isoquinoline-4-carboxylic acid ((S)-1-phenyl-propyl)-amide;
8-Chloro-3-methyl-1-oxo-2-phenyl-1,2-dihydro-isoquinoline-4-carboxylic acid [(S)-cyclopropyl-(3-fluoro-phenyl)-methyl]-amide;
3-Dimethylaminomethyl-1-oxo-2-phenyl-1,2-dihydro-isoquinoline-4-carboxylic acid ((S)-1-phenyl-propyl)-amide;
3-Methylaminomethyl-1-oxo-2-phenyl-1,2-dihydro-isoquinoline-4-carboxylic acid ((S)-1-phenyl-propyl)-amide;
3-Ethylaminomethyl-1-oxo-2-phenyl-1,2-dihydro-isoquinoline-4-carboxylic acid ((S)-1-phenyl-propyl)-amide;
3-Cyclopropylaminomethyl-1-oxo-2-phenyl-1,2-dihydro-isoquinoline-4-carboxylic acid ((S)-1-phenyl-propyl)-amide;
3-[(Cyclopropylmethyl-amino)-methyl]-1-oxo-2-phenyl-1,2-dihydro-isoquinoline-4-carboxylic acid ((S)-1-phenyl-propyl)-amide;
3-(3,6-Dihydro-2H-pyridin-1-ylmethyl)-1-oxo-2-phenyl-1,2-dihydro-isoquinoline-4-carboxylic acid ((S)-1-phenyl-propyl)-amide;
3-[4-(2-Methoxy-phenyl)-piperazin-1-ylmethyl]-1-oxo-2-phenyl-1,2-dihydro-isoquinoline-4-carboxylic acid ((S)-1-phenyl-propyl)-amide;
3-[4-(4-Fluoro-phenyl)-piperazin-1-ylmethyl]-1-oxo-2-phenyl-1,2-dihydro-isoquinoline-4-carboxylic acid ((S)-1-phenyl-propyl)-amide;
3-(4-Formyl-piperazin-1-ylmethyl)-1-oxo-2-phenyl-1,2-dihydro-isoquinoline-4-carboxylic acid ((S)-1-phenyl-propyl)-amide;
4-[1-Oxo-2-phenyl-4-(1-phenyl-propylcarbamoyl)-1,2-dihydro-isoquinolin-3-ylmethyl]-piperazine-1-carboxylic acid ethyl ester;
3-(4-Methyl-piperazin-1-ylmethyl)-1-oxo-2-phenyl-1,2-dihydro-isoquinoline-4-carboxylic acid ((S)-1-phenyl-propyl)-amide;
1-Oxo-2-phenyl-3-(1,3,4,9-tetrahydro-beta-carbolin-2-ylmethyl)-1,2-dihydro-isoquinoline-4-carboxylic acid ((S)-1-phenyl-propyl)-amide;
1-Oxo-2-phenyl-3-piperazin-1-ylmethyl-1,2-dihydro-isoquinoline-4-carboxylic acid ((S)-1-phenyl-propyl)-amide;
3-(3-Methyl-piperazin-1-ylmethyl)-1-oxo-2-phenyl-1,2-dihydro-isoquinoline-4-carboxylic acid ((S)-1-phenyl-propyl)-amide;
3-(3,5-Dimethyl-piperazin-1-ylmethyl)-1-oxo-2-phenyl-1,2-dihydro-isoquinoline-4-carboxylic acid ((S)-1-phenyl-propyl)-amide;
3-(4-Benzyl-piperazin-1-ylmethyl)-1-oxo-2-phenyl-1,2-dihydro-isoquinoline-4-carboxylic acid ((S)-1-phenyl-propyl)-amide;

1-Oxo-3-[4-(2-oxo-2-pyrrolidin-1-yl-ethyl)-piperazin-1-ylmethyl]-2-phenyl-1,2-dihydro-isoquinoline-4-carboxylic acid ((S)-1-phenyl-propyl)-amide;
3-Morpholin-4-ylmethyl-1-oxo-2-phenyl-1,2-dihydro-isoquinoline-4-carboxylic acid ((S)-1-phenyl-propyl)-amide;
3-(2,6-Dimethyl-morpholin-4-ylmethyl)-1-oxo-2-phenyl-1,2-dihydro-isoquinoline-4-carboxylic acid ((S)-1-phenyl-propyl)-amide;
1-Oxo-2-phenyl-3-thiomorpholin-4-ylmethyl-1,2-dihydro-isoquinoline-4-carboxylic acid ((S)-1-phenyl-propyl)-amide;
3-(1,4-Dioxa-8-aza-spiro[4.5]dec-8-ylmethyl)-1-oxo-2-phenyl-1,2-dihydro-isoquinoline-4-carboxylic acid ((S)-1-phenyl-propyl)-amide;
1-Oxo-2-phenyl-3-piperidin-1-ylmethyl-1,2-dihydro-isoquinoline-4-carboxylic acid ((S)-1-phenyl-propyl)-amide;
3-(2-Methyl-piperidin-1-ylmethyl)-1-oxo-2-phenyl-1,2-dihydro-isoquinoline-4-carboxylic acid ((S)-1-phenyl-propyl)-amide;
3-(2,6-Dimethyl-piperidin-1-ylmethyl)-1-oxo-2-phenyl-1,2-dihydro-isoquinoline-4-carboxylic acid ((S)-1-phenyl-propyl)-amide;
3-(2-Hydroxymethyl-piperidin-1-ylmethyl)-1-oxo-2-phenyl-1,2-dihydro-isoquinoline-4-carboxylic acid ((S)-1-phenyl-propyl)-amide;
1-[1-Oxo-2-phenyl-4-(1-phenyl-propylcarbamoyl)-1,2-dihydro-isoquinolin-3-ylmethyl]-piperidine-3-carboxylic acid ethyl ester;
3-(3-Methyl-piperidin-1-ylmethyl)-1-oxo-2-phenyl-1,2-dihydro-isoquinoline-4-carboxylic acid ((S)-1-phenyl-propyl)-amide;
3-(4-Hydroxy-piperidin-1-ylmethyl)-1-oxo-2-phenyl-1,2-dihydro-isoquinoline-4-carboxylic acid ((S)-1-phenyl-propyl)-amide;
1-Oxo-2-phenyl-3-(4-phenyl-piperidin-1-ylmethyl)-1,2-dihydro-isoquinoline-4-carboxylic acid ((S)-1-phenyl-propyl)-amide;
1-[1-Oxo-2-phenyl-4-(1-phenyl-propylcarbamoyl)-1,2-dihydro-isoquinolin-3-ylmethyl]-piperidine-4-carboxylic acid ethyl ester;
3-(4-Methyl-piperidin-1-ylmethyl)-1-oxo-2-phenyl-1,2-dihydro-isoquinoline-4-carboxylic acid ((S)-1-phenyl-propyl)-amide;
1-Oxo-2-phenyl-3-(4-pyridin-2-yl-piperazin-1-ylmethyl)-1,2-dihydro-isoquinoline-4-carboxylic acid ((S)-1-phenyl-propyl)-amide;
3-(Octahydro-quinolin-1-ylmethyl)-1-oxo-2-phenyl-1,2-dihydro-isoquinoline-4-carboxylic acid ((S)-1-phenyl-propyl)-amide;
3-Azepan-1-ylmethyl-1-oxo-2-phenyl-1,2-dihydro-isoquinoline-4-carboxylic acid ((S)-1-phenyl-propyl)-amide;
3-(3-Hydroxy-piperidin-1-ylmethyl)-1-oxo-2-phenyl-1,2-dihydro-isoquinoline-4-carboxylic acid ((S)-1-phenyl-propyl)-amide;
3-[4-(2,4-Dimethyl-phenyl)-piperazin-1-ylmethyl]-1-oxo-2-phenyl-1,2-dihydro-isoquinoline-4-carboxylic acid ((S)-1-phenyl-propyl)-amide;
3-[4-(3,4-Dimethyl-phenyl)-piperazin-1-ylmethyl]-1-oxo-2-phenyl-1,2-dihydro-isoquinoline-4-carboxylic acid ((S)-1-phenyl-propyl)-amide;
3-(4-Dimethylamino-piperidin-1-ylmethyl)-1-oxo-2-phenyl-1,2-dihydro-isoquinoline-4-carboxylic acid ((S)-1-phenyl-propyl)-amide;
3-[4-(2,5-Dimethyl-phenyl)-piperazin-1-ylmethyl]-1-oxo-2-phenyl-1,2-dihydro-isoquinoline-4-carboxylic acid ((S)-1-phenyl-propyl)-amide;
3-[4-(2-Fluoro-phenyl)-piperazin-1-ylmethyl]-1-oxo-2-phenyl-1,2-dihydro-isoquinoline-4-carboxylic acid ((S)-1-phenyl-propyl)-amide;
3-[4-(3-Methoxy-phenyl)-piperazin-1-ylmethyl]-1-oxo-2-phenyl-1,2-dihydro-isoquinoline-4-carboxylic acid ((S)-1-phenyl-propyl)-amide;
1-Oxo-2-phenyl-3-(4-m-tolyl-piperazin-1-ylmethyl)-1,2-dihydro-isoquinoline-4-carboxylic acid ((S)-1-phenyl-propyl)-amide;
3-[4-(4-Methoxy-phenyl)-piperazin-1-ylmethyl]-1-oxo-2-phenyl-1,2-dihydro-isoquinoline-4-carboxylic acid ((S)-1-phenyl-propyl)-amide;
1-Oxo-3-(4-phenethyl-piperazin-1-ylmethyl)-2-phenyl-1,2-dihydro-isoquinoline-4-carboxylic acid ((S)-1-phenyl-propyl)-amide;
1-Oxo-2-phenyl-3-(4-pyrimidin-2-yl-piperazin-1-ylmethyl)-1,2-dihydro-isoquinoline-4-carboxylic acid ((S)-1-phenyl-propyl)-amide;
3-[4-(2-Cyano-phenyl)-piperazin-1-ylmethyl]-1-oxo-2-phenyl-1,2-dihydro-isoquinoline-4-carboxylic acid ((S)-1-phenyl-propyl)-amide;
3-[4-(4-Chloro-phenyl)-piperazin-1-ylmethyl]-1-oxo-2-phenyl-1,2-dihydro-isoquinoline-4-carboxylic acid ((S)-1-phenyl-propyl)-amide;
3-((1S,3R,5R)-3-Hydroxy-8-aza-bicyclo[3.2.1]oct-8-ylmethyl)-1-oxo-2-phenyl-1,2-dihydro-isoquinoline-4-carboxylic acid ((S)-1-phenyl-propyl)-amide;
3-(4-Acetyl-piperazin-1-ylmethyl)-1-oxo-2-phenyl-1,2-dihydro-isoquinoline-4-carboxylic acid ((S)-1-phenyl-propyl)-amide;
3-(4-Methyl-[1,4]diazepan-1-ylmethyl)-1-oxo-2-phenyl-1,2-dihydro-isoquinoline-4-carboxylic acid ((S)-1-phenyl-propyl)-amide;
3-(4-Ethyl-piperazin-1-ylmethyl)-1-oxo-2-phenyl-1,2-dihydro-isoquinoline-4-carboxylic acid ((S)-1-phenyl-propyl)-amide;
3-((2S,6R)-2,6-Dimethyl-morpholin-4-ylmethyl)-1-oxo-2-phenyl-1,2-dihydro-isoquinoline-4-carboxylic acid ((S)-1-phenyl-propyl)-amide;
3-[4-(2,4-Difluoro-phenyl)-piperazin-1-ylmethyl]-1-oxo-2-phenyl-1,2-dihydro-isoquinoline-4-carboxylic acid ((S)-1-phenyl-propyl)-amide;
3-[4-(3-Dimethylamino-propyl)-piperazin-1-ylmethyl]-1-oxo-2-phenyl-1,2-dihydro-isoquinoline-4-carboxylic acid ((S)-1-phenyl-propyl)-amide;
3-(4-Isopropyl-piperazin-1-ylmethyl)-1-oxo-2-phenyl-1,2-dihydro-isoquinoline-4-carboxylic acid ((S)-1-phenyl-propyl)-amide;
3-(3-Aza-bicyclo[3.2.2]non-3-ylmethyl)-1-oxo-2-phenyl-1,2-dihydro-isoquinoline-4-carboxylic acid ((S)-1-phenyl-propyl)-amide;
3-(4-Cyclopentyl-piperazin-1-ylmethyl)-1-oxo-2-phenyl-1,2-dihydro-isoquinoline-4-carboxylic acid ((S)-1-phenyl-propyl)-amide;
3-[1,4']Bipiperidinyl-1'-ylmethyl-1-oxo-2-phenyl-1,2-dihydro-isoquinoline-4-carboxylic acid ((S)-1-phenyl-propyl)-amide;
3-(3,4-Dihydro-1H-isoquinolin-2-ylmethyl)-1-oxo-2-phenyl-1,2-dihydro-isoquinoline-4-carboxylic acid ((S)-1-phenyl-propyl)-amide;
3-[4-(2-Dimethylamino-ethyl)-piperazin-1-ylmethyl]-1-oxo-2-phenyl-1,2-dihydro-isoquinoline-4-carboxylic acid ((S)-1-phenyl-propyl)-amide;

3-(4-Hydroxymethyl-piperidin-1-ylmethyl)-1-oxo-2-phenyl-1,2-dihydro-isoquinoline-4-carboxylic acid ((S)-1-phenyl-propyl)-amide;

1-Oxo-2-phenyl-3-[4-(tetrahydro-furan-2-carbonyl)-piperazin-1-ylmethyl]-1,2-dihydro-isoquinoline-4-carboxylic acid ((S)-1-phenyl-propyl)-amide;

3-(4-Isobutyl-piperazin-1-ylmethyl)-1-oxo-2-phenyl-1,2-dihydro-isoquinoline-4-carboxylic acid ((S)-1-phenyl-propyl)-amide;

3-[4-(2-Methoxy-ethyl)-piperazin-1-ylmethyl]-1-oxo-2-phenyl-1,2-dihydro-isoquinoline-4-carboxylic acid ((S)-1-phenyl-propyl)-amide;

3-[4-(2-Morpholin-4-yl-ethyl)-piperazin-1-ylmethyl]-1-oxo-2-phenyl-1,2-dihydro-isoquinoline-4-carboxylic acid ((S)-1-phenyl-propyl)-amide;

3-(1,3-Dihydro-isoindol-2-ylmethyl)-1-oxo-2-phenyl-1,2-dihydro-isoquinoline-4-carboxylic acid ((S)-1-phenyl-propyl)-amide;

3-[4-(1-Methyl-piperidin-4-yl)-piperazin-1-ylmethyl]-1-oxo-2-phenyl-1,2-dihydro-isoquinoline-4-carboxylic acid ((S)-1-phenyl-propyl)-amide;

1-Oxo-2-phenyl-3-[4-(2-piperidin-1-yl-ethyl)-piperazin-1-ylmethyl]-1,2-dihydro-isoquinoline-4-carboxylic acid ((S)-1-phenyl-propyl)-amide;

1-Oxo-2-phenyl-3-[4-(2-pyrrolidin-1-yl-ethyl)-piperazin-1-ylmethyl]-1,2-dihydro-isoquinoline-4-carboxylic acid ((S)-1-phenyl-propyl)-amide;

3-(4-Dimethylcarbamoylmethyl-piperazin-1-ylmethyl)-1-oxo-2-phenyl-1,2-dihydro-isoquinoline-4-carboxylic acid ((S)-1-phenyl-propyl)-amide;

3-(Octahydro-pyrido[1,2-a]pyrazin-2-ylmethyl)-1-oxo-2-phenyl-1,2-dihydro-isoquinoline-4-carboxylic acid ((S)-1-phenyl-propyl)-amide;

3-(4-Formyl-[1,4]diazepan-1-ylmethyl)-1-oxo-2-phenyl-1,2-dihydro-isoquinoline-4-carboxylic acid ((S)-1-phenyl-propyl)-amide;

3-[4-(4-Cyano-phenyl)-piperazin-1-ylmethyl]-1-oxo-2-phenyl-1,2-dihydro-isoquinoline-4-carboxylic acid ((S)-1-phenyl-propyl)-amide;

1-Oxo-2-phenyl-3-(4-pyridin-4-ylmethyl-piperazin-1-ylmethyl)-1,2-dihydro-isoquinoline-4-carboxylic acid ((S)-1-phenyl-propyl)-amide;

1-Oxo-2-phenyl-3-[4-(3-pyrrolidin-1-yl-propyl)-piperazin-1-ylmethyl]-1,2-dihydro-isoquinoline-4-carboxylic acid ((S)-1-phenyl-propyl)-amide;

1-Oxo-2-phenyl-3-(4-pyridin-2-ylmethyl-piperazin-1-ylmethyl)-1,2-dihydro-isoquinoline-4-carboxylic acid ((S)-1-phenyl-propyl)-amide;

3-(4-Ethanesulfonyl-piperazin-1-ylmethyl)-1-oxo-2-phenyl-1,2-dihydro-isoquinoline-4-carboxylic acid ((S)-1-phenyl-propyl)-amide;

3-(4-sec-Butyl-piperazin-1-ylmethyl)-1-oxo-2-phenyl-1,2-dihydro-isoquinoline-4-carboxylic acid ((S)-1-phenyl-propyl)-amide;

3-[4-(1-Ethyl-propyl)-piperazin-1-ylmethyl]-1-oxo-2-phenyl-1,2-dihydro-isoquinoline-4-carboxylic acid ((S)-1-phenyl-propyl)-amide;

3-[4-(2-Cyano-ethyl)-piperazin-1-ylmethyl]-1-oxo-2-phenyl-1,2-dihydro-isoquinoline-4-carboxylic acid ((S)-1-phenyl-propyl)-amide;

3-(4-Methanesulfonyl-piperazin-1-ylmethyl)-1-oxo-2-phenyl-1,2-dihydro-isoquinoline-4-carboxylic acid ((S)-1-phenyl-propyl)-amide;

{1-[1-Oxo-2-phenyl-4-(1-phenyl-propylcarbamoyl)-1,2-dihydro-isoquinolin-3-ylmethyl]-piperidin-4-yl}-acetic acid ethyl ester;

3-[4-(3-Fluoro-phenyl)-piperazin-1-ylmethyl]-1-oxo-2-phenyl-1,2-dihydro-isoquinoline-4-carboxylic acid ((S)-1-phenyl-propyl)-amide;

1-Oxo-2-phenyl-3-((S)-3-phenyl-piperidin-1-ylmethyl)-1,2-dihydro-isoquinoline-4-carboxylic acid ((S)-1-phenyl-propyl)-amide;

1-Oxo-2-phenyl-3-[4-(pyrrolidine-1-carbonyl)-piperazin-1-ylmethyl]-1,2-dihydro-isoquinoline-4-carboxylic acid ((S)-1-phenyl-propyl)-amide;

3-[4-(Morpholine-4-carbonyl)-piperazin-1-ylmethyl]-1-oxo-2-phenyl-1,2-dihydro-isoquinoline-4-carboxylic acid ((S)-1-phenyl-propyl)-amide;

3-(4-Methoxy-piperidin-1-ylmethyl)-1-oxo-2-phenyl-1,2-dihydro-isoquinoline-4-carboxylic acid ((S)-1-phenyl-propyl)-amide;

3-(4'-Hydroxy-3',4',5',6'-tetrahydro-2'H-[3,4']bipyridinyl-1'-ylmethyl)-1-oxo-2-phenyl-1,2-dihydro-isoquinoline-4-carboxylic acid ((S)-1-phenyl-propyl)-amide;

3-(4-Hydroxy-3,4,5,6-tetrahydro-2H-[4,4']bipyridinyl-1-ylmethyl)-1-oxo-2-phenyl-1,2-dihydro-isoquinoline-4-carboxylic acid ((S)-1-phenyl-propyl)-amide;

3-(3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide;

3-(4-Hydroxy-4-methyl-piperidin-1-ylmethyl)-1-oxo-2-phenyl-1,2-dihydro-isoquinoline-4-carboxylic acid ((S)-1-phenyl-propyl)-amide;

3-(hexahydro-spiro[benzo[1,3]dioxole-2,4'-piperidin]-1'-ylmethyl)-1-oxo-2-phenyl-1,2-dihydro-isoquinoline-4-carboxylic acid ((S)-1-phenyl-propyl)-amide;

1-Oxo-2-phenyl-3-(3,4,5,6-tetrahydro-2H-[4,4']bipyridinyl-1-ylmethyl)-1,2-dihydro-isoquinoline-4-carboxylic acid ((S)-1-phenyl-propyl)-amide;

3-[4-(2-Dimethylamino-ethyl)-piperidin-1-ylmethyl]-1-oxo-2-phenyl-1,2-dihydro-isoquinoline-4-carboxylic acid ((S)-1-phenyl-propyl)-amide;

3-(4-Dimethylsulfamoyl-piperazin-1-ylmethyl)-1-oxo-2-phenyl-1,2-dihydro-isoquinoline-4-carboxylic acid ((S)-1-phenyl-propyl)-amide;

3-(1,1-Dioxo-thiomorpholin-4-ylmethyl)-1-oxo-2-phenyl-1,2-dihydro-isoquinoline-4-carboxylic acid ((S)-1-phenyl-propyl)-amide;

1-Oxo-2-phenyl-3-(2-pyridin-2-ylmethyl-piperidin-1-ylmethyl)-1,2-dihydro-isoquinoline-4-carboxylic acid ((S)-1-phenyl-propyl)-amide;

3-(2-Morpholin-4-ylmethyl-piperidin-1-ylmethyl)-1-oxo-2-phenyl-1,2-dihydro-isoquinoline-4-carboxylic acid ((S)-1-phenyl-propyl)-amide;

3-(4-Furo[3,2-c]pyridin-4-yl-piperazin-1-ylmethyl)-1-oxo-2-phenyl-1,2-dihydro-isoquinoline-4-carboxylic acid ((S)-1-phenyl-propyl)-amide;

3-(4-Cyclopropylmethyl-piperazin-1-ylmethyl)-1-oxo-2-phenyl-1,2-dihydro-isoquinoline-4-carboxylic acid ((S)-1-phenyl-propyl)-amide;

3-[4-(2-Morpholin-4-yl-ethyl)-piperidin-1-ylmethyl]-1-oxo-2-phenyl-1,2-dihydro-isoquinoline-4-carboxylic acid ((S)-1-phenyl-propyl)-amide;

1-Oxo-2-phenyl-3-(4-pyrimidin-2-yl-[1,4]diazepan-1-ylmethyl)-1,2-dihydro-isoquinoline-4-carboxylic acid ((S)-1-phenyl-propyl)-amide;

3-(4-Methyl-6,7-dihydro-4H-thieno[3,2-c]pyridin-5-ylmethyl)-1-oxo-2-phenyl-1,2-dihydro-isoquinoline-4-carboxylic acid ((S)-1-phenyl-propyl)-amide;

3-[1,4]Diazepan-1-ylmethyl-1-oxo-2-phenyl-1,2-dihydro-isoquinoline-4-carboxylic acid ((S)-1-phenyl-propyl)-amide;

3-((2S,5R)-2,5-Dimethyl-piperazin-1-ylmethyl)-1-oxo-2-phenyl-1,2-dihydro-isoquinoline-4-carboxylic acid ((S)-1-phenyl-propyl)-amide;

3-((S)-3-Methyl-piperazin-1-ylmethyl)-1-oxo-2-phenyl-1,2-dihydro-isoquinoline-4-carboxylic acid ((S)-1-phenyl-propyl)-amide;

3-((R)-3-Methyl-piperazin-1-ylmethyl)-1-oxo-2-phenyl-1,2-dihydro-isoquinoline-4-carboxylic acid ((S)-1-phenyl-propyl)-amide;

3-[3-(3-Chloro-phenyl)-piperazin-1-ylmethyl]-1-oxo-2-phenyl-1,2-dihydro-isoquinoline-4-carboxylic acid ((S)-1-phenyl-propyl)-amide;

3-[4-(1H-Indol-4-yl)-piperazin-1-ylmethyl]-1-oxo-2-phenyl-1,2-dihydro-isoquinoline-4-carboxylic acid ((S)-1-phenyl-propyl)-amide;

1-Oxo-3-(3-oxo-piperazin-1-ylmethyl)-2-phenyl-1,2-dihydro-isoquinoline-4-carboxylic acid ((S)-1-phenyl-propyl)-amide;

3-[4-(1H-Indol-5-yl)-piperazin-1-ylmethyl]-1-oxo-2-phenyl-1,2-dihydro-isoquinoline-4-carboxylic acid ((S)-1-phenyl-propyl)-amide;

3-(6,9-Diaza-spiro[4.5]dec-9-ylmethyl)-1-oxo-2-phenyl-1,2-dihydro-isoquinoline-4-carboxylic acid ((S)-1-phenyl-propyl)-amide;

3-(1,4-Diaza-spiro[5.5]undec-4-ylmethyl)-1-oxo-2-phenyl-1,2-dihydro-isoquinoline-4-carboxylic acid ((S)-1-phenyl-propyl)-amide;

3-(3-Isopropyl-piperazin-1-ylmethyl)-1-oxo-2-phenyl-1,2-dihydro-isoquinoline-4-carboxylic acid ((S)-1-phenyl-propyl)-amide;

3-(3,3-Dimethyl-piperazin-1-ylmethyl)-1-oxo-2-phenyl-1,2-dihydro-isoquinoline-4-carboxylic acid ((S)-1-phenyl-propyl)-amide;

3-[3-(4-Fluoro-phenyl)-piperazin-1-ylmethyl]-1-oxo-2-phenyl-1,2-dihydro-isoquinoline-4-carboxylic acid ((S)-1-phenyl-propyl)-amide;

1-Oxo-2-phenyl-3-(3-p-tolyl-piperazin-1-ylmethyl)-1,2-dihydro-isoquinoline-4-carboxylic acid ((S)-1-phenyl-propyl)-amide;

4-[1-Oxo-2-phenyl-4-(1-phenyl-propylcarbamoyl)-1,2-dihydro-isoquinolin-3-ylmethyl]-piperazine-1-carboxylic acid tert-butyl ester;

3-(4-Methylcarbamoylmethyl-piperazin-1-ylmethyl)-1-oxo-2-phenyl-1,2-dihydro-isoquinoline-4-carboxylic acid ((S)-1-phenyl-propyl)-amide;

8-Chloro-3-dimethylaminomethyl-1-oxo-2-phenyl-1,2-dihydro-isoquinoline-4-carboxylic acid ((S)-1-phenyl-propyl)-amide;

3-Cyclopentylaminomethyl-1-oxo-2-phenyl-1,2-dihydro-isoquinoline-4-carboxylic acid ((S)-1-phenyl-propyl)-amide;

3-Cyclohexylaminomethyl-1-oxo-2-phenyl-1,2-dihydro-isoquinoline-4-carboxylic acid ((S)-1-phenyl-propyl)-amide;

3-{[(2-Hydroxy-ethyl)-methyl-amino]-methyl}-1-oxo-2-phenyl-1,2-dihydro-isoquinoline-4-carboxylic acid ((S)-1-phenyl-propyl)-amide;

3-Imidazol-1-ylmethyl-1-oxo-2-phenyl-1,2-dihydro-isoquinoline-4-carboxylic acid ((S)-1-phenyl-propyl)-amide;

3-(2-Methyl-imidazol-1-ylmethyl)-1-oxo-2-phenyl-1,2-dihydro-isoquinoline-4-carboxylic acid ((S)-1-phenyl-propyl)-amide;

3-(4-Methyl-imidazol-1-ylmethyl)-1-oxo-2-phenyl-1,2-dihydro-isoquinoline-4-carboxylic acid ((S)-1-phenyl-propyl)-amide;

3-(2,5-Dihydro-pyrrol-1-ylmethyl)-1-oxo-2-phenyl-1,2-dihydro-isoquinoline-4-carboxylic acid ((S)-1-phenyl-propyl)-amide;

3-(2,5-Dimethyl-2,5-dihydro-pyrrol-1-ylmethyl)-1-oxo-2-phenyl-1,2-dihydro-isoquinoline-4-carboxylic acid ((S)-1-phenyl-propyl)-amide;

1-Oxo-2-phenyl-3-pyrrolidin-1-ylmethyl-1,2-dihydro-isoquinoline-4-carboxylic acid ((S)-1-phenyl-propyl)-amide;

1-Oxo-2-phenyl-3-(thiazol-2-ylaminomethyl)-1,2-dihydro-isoquinoline-4-carboxylic acid ((S)-1-phenyl-propyl)-amide;

1-Oxo-2-phenyl-3-(pyrimidin-4-ylaminomethyl)-1,2-dihydro-isoquinoline-4-carboxylic acid ((S)-1-phenyl-propyl)-amide;

3-(tert-Butylamino-methyl)-1-oxo-2-phenyl-1,2-dihydro-isoquinoline-4-carboxylic acid ((S)-1-phenyl-propyl)-amide;

3-[(2-Hydroxy-1,1-dimethyl-ethylamino)-methyl]-1-oxo-2-phenyl-1,2-dihydro-isoquinoline-4-carboxylic acid ((S)-1-phenyl-propyl)-amide;

3-(Isopropylamino-methyl)-1-oxo-2-phenyl-1,2-dihydro-isoquinoline-4-carboxylic acid ((S)-1-phenyl-propyl)-amide;

3-[(2-Hydroxy-1-methyl-ethylamino)-methyl]-1-oxo-2-phenyl-1,2-dihydro-isoquinoline-4-carboxylic acid ((S)-1-phenyl-propyl)-amide;

3-[(1-Hydroxymethyl-propylamino)-methyl]-1-oxo-2-phenyl-1,2-dihydro-isoquinoline-4-carboxylic acid ((S)-1-phenyl-propyl)-amide;

3-[(2,2-Dimethyl-propylamino)-methyl]-1-oxo-2-phenyl-1,2-dihydro-isoquinoline-4-carboxylic acid ((S)-1-phenyl-propyl)-amide;

1-Oxo-2-phenyl-3-prop-2-ynylaminomethyl-1,2-dihydro-isoquinoline-4-carboxylic acid ((S)-1-phenyl-propyl)-amide;

3-Allylaminomethyl-1-oxo-2-phenyl-1,2-dihydro-isoquinoline-4-carboxylic acid ((S)-1-phenyl-propyl)-amide;

3-[(Methyl-prop-2-ynyl-amino)-methyl]-1-oxo-2-phenyl-1,2-dihydro-isoquinoline-4-carboxylic acid ((S)-1-phenyl-propyl)-amide;

3-Diallylaminomethyl-1-oxo-2-phenyl-1,2-dihydro-isoquinoline-4-carboxylic acid ((S)-1-phenyl-propyl)-amide;

3-Diethylaminomethyl-1-oxo-2-phenyl-1,2-dihydro-isoquinoline-4-carboxylic acid ((S)-1-phenyl-propyl)-amide;

3-[(Isopropyl-methyl-amino)-methyl]-1-oxo-2-phenyl-1,2-dihydro-isoquinoline-4-carboxylic acid ((S)-1-phenyl-propyl)-amide;

3-[((S)-2-Hydroxy-1-methyl-ethylamino)-methyl]-1-oxo-2-phenyl-1,2-dihydro-isoquinoline-4-carboxylic acid ((S)-1-phenyl-propyl)-amide;

3-[((R)-2-Hydroxy-1-methyl-ethylamino)-methyl]-1-oxo-2-phenyl-1,2-dihydro-isoquinoline-4-carboxylic acid ((S)-1-phenyl-propyl)-amide;

3-{[(2-Methoxy-ethyl)-methyl-amino]-methyl}-1-oxo-2-phenyl-1,2-dihydro-isoquinoline-4-carboxylic acid ((S)-1-phenyl-propyl)-amide;

3-((R)-3-Hydroxy-pyrrolidin-1-ylmethyl)-1-oxo-2-phenyl-1,2-dihydro-isoquinoline-4-carboxylic acid ((S)-1-phenyl-propyl)-amide;

3-((S)-3-Hydroxy-pyrrolidin-1-ylmethyl)-1-oxo-2-phenyl-1,2-dihydro-isoquinoline-4-carboxylic acid ((S)-1-phenyl-propyl)-amide;

3-[(Cyclopentyl-methyl-amino)-methyl]-1-oxo-2-phenyl-1,2-dihydro-isoquinoline-4-carboxylic acid ((S)-1-phenyl-propyl)-amide;

3-{[(2-Hydroxy-1-methyl-ethyl)-methyl-amino]-methyl}-1-oxo-2-phenyl-1,2-dihydro-isoquinoline-4-carboxylic acid ((S)-1-phenyl-propyl)-amide;

3-{[Ethyl-(2-hydroxy-ethyl)-amino]-methyl}-1-oxo-2-phenyl-1,2-dihydro-isoquinoline-4-carboxylic acid ((S)-1-phenyl-propyl)-amide;

3-[(Ethyl-methyl-amino)-methyl]-1-oxo-2-phenyl-1,2-dihydro-isoquinoline-4-carboxylic acid ((S)-1-phenyl-propyl)-amide;

3-Cyclobutylaminomethyl-1-oxo-2-phenyl-1,2-dihydro-isoquinoline-4-carboxylic acid ((S)-1-phenyl-propyl)-amide;

3-Azetidin-1-ylmethyl-1-oxo-2-phenyl-1,2-dihydro-isoquinoline-4-carboxylic acid ((S)-1-phenyl-propyl)-amide;

3-(4-tert-Butyl-piperazin-1-ylmethyl)-1-oxo-2-phenyl-1,2-dihydro-isoquinoline-4-carboxylic acid ((S)-1-phenyl-propyl)-amide;

3-[4-(2-Hydroxy-ethyl)-piperazin-1-ylmethyl]-1-oxo-2-phenyl-1,2-dihydro-isoquinoline-4-carboxylic acid ((S)-1-phenyl-propyl)-amide;

3-{4-[2-(2-Hydroxy-ethoxy)-ethyl]-piperazin-1-ylmethyl}-1-oxo-2-phenyl-1,2-dihydro-isoquinoline-4-carboxylic acid ((S)-1-phenyl-propyl)-amide;

3-[4-(3-Chloro-5-trifluoromethyl-pyridin-2-yl)-piperazin-1-ylmethyl]-1-oxo-2-phenyl-1,2-dihydro-isoquinoline-4-carboxylic acid ((S)-1-phenyl-propyl)-amide;

3-[4-(3,5-Dichloro-pyridin-4-yl)-piperazin-1-ylmethyl]-1-oxo-2-phenyl-1,2-dihydro-isoquinoline-4-carboxylic acid ((S)-1-phenyl-propyl)-amide;

4-[1-Oxo-2-phenyl-4-((S)-1-phenyl-propylcarbamoyl)-1,2-dihydro-isoquinolin-3-ylmethyl]-piperazine-1-carboxylic acid benzyl ester;

3-[4-(3-Morpholin-4-yl-propyl)-piperazin-1-ylmethyl]-1-oxo-2-phenyl-1,2-dihydro-isoquinoline-4-carboxylic acid ((S)-1-phenyl-propyl)-amide;

1-Oxo-2-phenyl-3-[4-(3-piperidin-1-yl-propyl)-piperazin-1-ylmethyl]-1,2-dihydro-isoquinoline-4-carboxylic acid ((S)-1-phenyl-propyl)-amide;

3-[4-(4,6-Dimethoxy-pyrimidin-2-ylmethyl)-piperazin-1-ylmethyl]-1-oxo-2-phenyl-1,2-dihydro-isoquinoline-4-carboxylic acid ((S)-1-phenyl-propyl)-amide;

3-[4-(3-Hydroxy-propyl)-piperazin-1-ylmethyl]-1-oxo-2-phenyl-1,2-dihydro-isoquinoline-4-carboxylic acid ((S)-1-phenyl-propyl)-amide;

3-[4-(2,3-Dihydroxy-propyl)-piperazin-1-ylmethyl]-1-oxo-2-phenyl-1,2-dihydro-isoquinoline-4-carboxylic acid ((S)-1-phenyl-propyl)-amide;

(2-Oxo-2-{4-[1-oxo-2-phenyl-4-(1-phenyl-propylcarbamoyl)-1,2-dihydro-isoquinolin-3-ylmethyl]-piperazin-1-yl}-ethyl)-carbamic acid tert-butyl ester;

3-[4-(1H-Indazol-5-yl)-piperazin-1-ylmethyl]-1-oxo-2-phenyl-1,2-dihydro-isoquinoline-4-carboxylic acid ((S)-1-phenyl-propyl)-amide;

1-Oxo-2-phenyl-3-(4-quinolin-6-yl-piperazin-1-ylmethyl)-1,2-dihydro-isoquinoline-4-carboxylic acid ((S)-1-phenyl-propyl)-amide;

3-[4-(6,7-Dimethoxy-quinazolin-4-yl)-piperazin-1-ylmethyl]-1-oxo-2-phenyl-1,2-dihydro-isoquinoline-4-carboxylic acid ((S)-1-phenyl-propyl)-amide;

4-{4-[1-Oxo-2-phenyl-4-(1-phenyl-propylcarbamoyl)-1,2-dihydro-isoquinolin-3-ylmethyl]-piperazin-1-yl}-piperidine-1-carboxylic acid tert-butyl ester;

3-{4-[2-(4-Chloro-phenoxy)-ethyl]-piperazin-1-ylmethyl}-1-oxo-2-phenyl-1,2-dihydro-isoquinoline-4-carboxylic acid ((S)-1-phenyl-propyl)-amide;

{4-[1-Oxo-2-phenyl-4-(1-phenyl-propylcarbamoyl)-1,2-dihydro-isoquinolin-3-ylmethyl]-piperazin-1-yl}-acetic acid tert-butyl ester;

1-Oxo-2-phenyl-3-[4-(3,3,3-trifluoro-2-hydroxy-propyl)-piperazin-1-ylmethyl]-1,2-dihydro-isoquinoline-4-carboxylic acid ((S)-1-phenyl-propyl)-amide;

3-[4-(2-Hydroxy-propyl)-piperazin-1-ylmethyl]-1-oxo-2-phenyl-1,2-dihydro-isoquinoline-4-carboxylic acid ((S)-1-phenyl-propyl)-amide;

3-[4-(4-Amino-6,7-dimethoxy-quinazolin-2-yl)-piperazin-1-ylmethyl]-1-oxo-2-phenyl-1,2-dihydro-isoquinoline-4-carboxylic acid ((S)-1-phenyl-propyl)-amide;

(2-{4-[1-Oxo-2-phenyl-4-(1-phenyl-propylcarbamoyl)-1,2-dihydro-isoquinolin-3-ylmethyl]-piperazin-1-yl}-ethyl)-carbamic acid tert-butyl ester;

1-Oxo-3-{4-[2-(2-oxo-imidazolidin-1-yl)-ethyl]-piperazin-1-ylmethyl}-2-phenyl-1,2-dihydro-isoquinoline-4-carboxylic acid ((S)-1-phenyl-propyl)-amide;

3-{4-[(4,6-Dimethoxy-pyrimidin-2-yl)-phenyl-methyl]-piperazin-1-ylmethyl}-1-oxo-2-phenyl-1,2-dihydro-isoquinoline-4-carboxylic acid ((S)-1-phenyl-propyl)-amide;

3-(4-Benzo[1,2,5]thiadiazol-4-yl-piperazin-1-ylmethyl)-1-oxo-2-phenyl-1,2-dihydro-isoquinoline-4-carboxylic acid ((S)-1-phenyl-propyl)-amide;

3-[4-(2,3-Dihydro-benzo[1,4]dioxin-5-yl)-piperazin-1-ylmethyl]-1-oxo-2-phenyl-1,2-dihydro-isoquinoline-4-carboxylic acid ((S)-1-phenyl-propyl)-amide;

3-[4-(4-Methyl-quinolin-2-yl)-piperazin-1-ylmethyl]-1-oxo-2-phenyl-1,2-dihydro-isoquinoline-4-carboxylic acid ((S)-1-phenyl-propyl)-amide;

1-Oxo-2-phenyl-3-[4-(pyridin-2-ylcarbamoylmethyl)-piperazin-1-ylmethyl]-1,2-dihydro-isoquinoline-4-carboxylic acid ((S)-1-phenyl-propyl)-amide;

3-[4-(6-Chloro-3-oxo-3,4-dihydro-2H-benzo[1,4]oxazin-8-yl)-piperazin-1-ylmethyl]-1-oxo-2-phenyl-1,2-dihydro-isoquinoline-4-carboxylic acid ((S)-1-phenyl-propyl)-amide;

3-(4-Carbamoylmethyl-piperazin-1-ylmethyl)-1-oxo-2-phenyl-1,2-dihydro-isoquinoline-4-carboxylic acid ((S)-1-phenyl-propyl)-amide;

3-(4-Hydroxy-4-phenyl-piperidin-1-ylmethyl)-1-oxo-2-phenyl-1,2-dihydro-isoquinoline-4-carboxylic acid ((S)-1-phenyl-propyl)-amide;

3-[4-(4-Chloro-phenyl)-4-hydroxy-piperidin-1-ylmethyl]-1-oxo-2-phenyl-1,2-dihydro-isoquinoline-4-carboxylic acid ((S)-1-phenyl-propyl)-amide;

1-[1-Oxo-2-phenyl-4-(1-phenyl-propylcarbamoyl)-1,2-dihydro-isoquinolin-3-ylmethyl]-piperidine-4-carboxylic acid;

3-(4-Cyano-4-phenyl-piperidin-1-ylmethyl)-1-oxo-2-phenyl-1,2-dihydro-isoquinoline-4-carboxylic acid ((S)-1-phenyl-propyl)-amide;

3-(4-Benzyl-4-hydroxy-piperidin-1-ylmethyl)-1-oxo-2-phenyl-1,2-dihydro-isoquinoline-4-carboxylic acid ((S)-1-phenyl-propyl)-amide;

1-[1-Oxo-2-phenyl-4-(1-phenyl-propylcarbamoyl)-1,2-dihydro-isoquinolin-3-ylmethyl]-4-phenyl-piperidine-4-carboxylic acid ethyl ester;

1-Oxo-2-phenyl-3-[4-(phenyl-propionyl-amino)-piperidin-1-ylmethyl]-1,2-dihydro-isoquinoline-4-carboxylic acid ((S)-1-phenyl-propyl)-amide;

Methyl-{1-[1-oxo-2-phenyl-4-(1-phenyl-propylcarbamoyl)-1,2-dihydro-isoquinolin-3-ylmethyl]-piperidin-4-yl}-carbamic acid tert-butyl ester;

1-Oxo-2-phenyl-3-[4-(2-pyrrolidin-1-yl-ethyl)-piperidin-1-ylmethyl]-1,2-dihydro-isoquinoline-4-carboxylic acid ((S)-1-phenyl-propyl)-amide;

3-{4-[5-(4-Fluoro-phenyl)[1,3,4]oxadiazol-2-yl]-piperidin-1-ylmethyl}-1-oxo-2-phenyl-1,2-dihydro-isoquinoline-4-carboxylic acid ((S)-1-phenyl-propyl)-amide;

1-Oxo-2-phenyl-3-[4-(3-pyridin-4-yl-[1,2,4]oxadiazol-5-yl)-piperidin-1-ylmethyl]-1,2-dihydro-isoquinoline-4-carboxylic acid ((S)-1-phenyl-propyl)-amide;

1-Oxo-2-phenyl-3-[4-(3-pyrazin-2-yl-[1,2,4]oxadiazol-5-yl)-piperidin-1-ylmethyl]-1,2-dihydro-isoquinoline-4-carboxylic acid ((S)-1-phenyl-propyl)-amide;

1-Oxo-2-phenyl-3-[4-(3-pyridin-4-yl-[1,2,4]oxadiazol-5-yl)-piperidin-1-ylmethyl]-1,2-dihydro-isoquinoline-4-carboxylic acid ((S)-1-phenyl-propyl)-amide;

3-(4'-Hydroxy-3',4',5',6'-tetrahydro-2'H-[2,4]bipyridinyl-1'-ylmethyl)-1-oxo-2-phenyl-1,2-dihydro-isoquinoline-4-carboxylic acid ((S)-1-phenyl-propyl)-amide;

3-(spiro[isochroman-1,4'-piperidin]-1'-ylmethyl)-1-oxo-2-phenyl-1,2-dihydro-isoquinoline-4-carboxylic acid ((S)-1-phenyl-propyl)-amide;

3-[4-Hydroxy-4-(3-methoxy-phenyl)-piperidin-1-ylmethyl]-1-oxo-2-phenyl-1,2-dihydro-isoquinoline-4-carboxylic acid ((S)-1-phenyl-propyl)-amide;

3-[4-(3-Chloro-phenyl)-4-hydroxy-piperidin-1-ylmethyl]-1-oxo-2-phenyl-1,2-dihydro-isoquinoline-4-carboxylic acid ((S)-1-phenyl-propyl)-amide;

3-(6-chloro-3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide;

3-(4-{[4-Chloro-3-(4-fluoro-phenyl)-indan-1-yl]-methyl-amino}-piperidin-1-ylmethyl)-1-oxo-2-phenyl-1,2-dihydro-isoquinoline-4-carboxylic acid ((S)-1-phenyl-propyl)-amide;

3-(1-acetyl-spiro[indoline-3,4'-piperidin]-1'-ylmethyl)-1-oxo-2-phenyl-1,2-dihydro-isoquinoline-4-carboxylic acid ((S)-1-phenyl-propyl)-amide;

3-(1-acetyl-5-fluoro-spiro[indoline-3,4'-piperidin]-1'-ylmethyl)-1-oxo-2-phenyl-1,2-dihydro-isoquinoline-4-carboxylic acid ((S)-1-phenyl-propyl)-amide;

1-Oxo-3-(4-oxo-1-phenyl-1,3,8-triaza-spiro[4.5]dec-8-ylmethyl)-2-phenyl-1,2-dihydro-isoquinoline-4-carboxylic acid ((S)-1-phenyl-propyl)-amide;

3-(4-Acetylamino-piperidin-1-ylmethyl)-1-oxo-2-phenyl-1,2-dihydro-isoquinoline-4-carboxylic acid ((S)-1-phenyl-propyl)-amide;

1-Oxo-3-(1-oxo-2,8-diaza-spiro[4.5]dec-8-ylmethyl)-2-phenyl-1,2-dihydro-isoquinoline-4-carboxylic acid ((S)-1-phenyl-propyl)-amide;

3-[4-Hydroxy-4-(3-trifluoromethyl-phenyl)-piperidin-1-ylmethyl]-1-oxo-2-phenyl-1,2-dihydro-isoquinoline-4-carboxylic acid ((S)-1-phenyl-propyl)-amide;

1-Oxo-2-phenyl-3-(4-trifluoromethyl-piperidin-1-ylmethyl)-1,2-dihydro-isoquinoline-4-carboxylic acid ((S)-1-phenyl-propyl)-amide;

3-[4-(4-Methyl-piperazine-1-carbonyl)-piperidin-1-ylmethyl]-1-oxo-2-phenyl-1,2-dihydro-isoquinoline-4-carboxylic acid ((S)-1-phenyl-propyl)-amide;

3-(5-isopropyl-3H-spiro[isobenzofuran-1,4'-piperidin]-1'-ylmethyl)-1-oxo-2-phenyl-1,2-dihydro-isoquinoline-4-carboxylic acid ((S)-1-phenyl-propyl)-amide;

3-[4-(Acetyl-methyl-amino)-4-phenyl-piperidin-1-ylmethyl]-1-oxo-2-phenyl-1,2-dihydro-isoquinoline-4-carboxylic acid ((S)-1-phenyl-propyl)-amide;

4-{1-[1-Oxo-2-phenyl-4-(1-phenyl-propylcarbamoyl)-1,2-dihydro-isoquinolin-3-ylmethyl]-piperidin-4-yl}-piperazine-1-carboxylic acid tert-butyl ester;

(2-{1-[1-Oxo-2-phenyl-4-(1-phenyl-propylcarbamoyl)-1,2-dihydro-isoquinolin-3-ylmethyl]-piperidin-4-yl}-ethyl)-carbamic acid tert-butyl ester;

3-(4-Methylamino-4-phenyl-piperidin-1-ylmethyl)-1-oxo-2-phenyl-1,2-dihydro-isoquinoline-4-carboxylic acid ((S)-1-phenyl-propyl)-amide;

3-(4-Acetylamino-4-phenyl-piperidin-1-ylmethyl)-1-oxo-2-phenyl-1,2-dihydro-isoquinoline-4-carboxylic acid ((S)-1-phenyl-propyl)-amide;

3-[4-Acetylamino-4-(3-fluoro-phenyl)-piperidin-1-ylmethyl]-1-oxo-2-phenyl-1,2-dihydro-isoquinoline-4-carboxylic acid ((S)-1-phenyl-propyl)-amide;

1-Oxo-3-[4-(4-oxo-piperidine-1-carbonyl)-piperidin-1-ylmethyl]-2-phenyl-1,2-dihydro-isoquinoline-4-carboxylic acid ((S)-1-phenyl-propyl)-amide;

3-[4,4']Bipiperidinyl-1-ylmethyl-1-oxo-2-phenyl-1,2-dihydro-isoquinoline-4-carboxylic acid ((S)-1-phenyl-propyl)-amide;

{1-[1-Oxo-2-phenyl-4-(1-phenyl-propylcarbamoyl)-1,2-dihydro-isoquinolin-3-ylmethyl]-piperidin-4-yl}-carbamic acid tert-butyl ester;

3-[1,4]Bipiperidinyl-1'-ylmethyl-1-oxo-2-phenyl-1,2-dihydro-isoquinoline-4-carboxylic acid [cyclopropyl-(3-fluoro-phenyl)-methyl]-amide;

1-Oxo-3-(4-phenethyl-piperazin-1-ylmethyl)-2-phenyl-1,2-dihydro-isoquinoline-4-carboxylic acid [cyclopropyl-(3-fluoro-phenyl)-methyl]-amide;

3-(4-Isopropyl-piperazin-1-ylmethyl)-1-oxo-2-phenyl-1,2-dihydro-isoquinoline-4-carboxylic acid [cyclopropyl-(3-fluoro-phenyl)-methyl]-amide;

3-[4-(2-Morpholin-4-yl-ethyl)-piperazin-1-ylmethyl]-1-oxo-2-phenyl-1,2-dihydro-isoquinoline-4-carboxylic acid [cyclopropyl-(3-fluoro-phenyl)-methyl]-amide;

3-[4-(1-Methyl-piperidin-4-yl)-piperazin-1-ylmethyl]-1-oxo-2-phenyl-1,2-dihydro-isoquinoline-4-carboxylic acid [cyclopropyl-(3-fluoro-phenyl)-methyl]-amide;

1-Oxo-2-phenyl-3-[4-(2-piperidin-1-yl-ethyl)-piperazin-1-ylmethyl]-1,2-dihydro-isoquinoline-4-carboxylic acid [cyclopropyl-(3-fluoro-phenyl)-methyl]-amide;

1-Oxo-2-phenyl-3-[4-(2-pyrrolidin-1-yl-ethyl)-piperazin-1-ylmethyl]-1,2-dihydro-isoquinoline-4-carboxylic acid [cyclopropyl-(3-fluoro-phenyl)-methyl]-amide;

1-Oxo-2-phenyl-3-(4-pyridin-4-ylmethyl-piperazin-1-ylmethyl)-1,2-dihydro-isoquinoline-4-carboxylic acid [cyclopropyl-(3-fluoro-phenyl)-methyl]-amide;

3-(4-Hydroxy-3,4,5,6-tetrahydro-2H-[4,4']bipyridinyl-1-ylmethyl)-1-oxo-2-phenyl-1,2-dihydro-isoquinoline-4-carboxylic acid [cyclopropyl-(3-fluoro-phenyl)-methyl]-amide;

3-[4-(2-Morpholin-4-yl-ethyl)-piperidin-1-ylmethyl]-1-oxo-2-phenyl-1,2-dihydro-isoquinoline-4-carboxylic acid [cyclopropyl-(3-fluoro-phenyl)-methyl]-amide;

3-[4-Hydroxy-4-(3-methoxy-phenyl)-piperidin-1-ylmethyl]-1-oxo-2-phenyl-1,2-dihydro-isoquinoline-4-carboxylic acid [cyclopropyl-(3-fluoro-phenyl)-methyl]-amide;

3-[4-(Acetyl-methyl-amino)-4-phenyl-piperidin-1-ylmethyl]-1-oxo-2-phenyl-1,2-dihydro-isoquinoline-4-carboxylic acid [cyclopropyl-(3-fluoro-phenyl)-methyl]-amide;

2-(2-Fluoro-phenyl)-1-oxo-3-(4-phenethyl-piperazin-1-ylmethyl)-1,2-dihydro-isoquinoline-4-carboxylic acid ((S)-1-phenyl-propyl)-amide;
2-(2-Fluoro-phenyl)-3-(4-isopropyl-piperazin-1-ylmethyl)-1-oxo-1,2-dihydro-isoquinoline-4-carboxylic acid ((S)-1-phenyl-propyl)-amide;
3-[1,4]Bipiperidinyl-1'-ylmethyl-2-(2-fluoro-phenyl)-1-oxo-1,2-dihydro-isoquinoline-4-carboxylic acid ((S)-1-phenyl-propyl)-amide;
2-(2-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide;
2-(2-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide;
2-(2-Fluoro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide;
2-(2-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide;
2-(2-Fluoro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide;
2-(2-Fluoro-phenyl)-3-(4-hydroxy-3,4,5,6-tetrahydro-2H-[4,4']bipyridinyl-1-ylmethyl)-1-oxo-1,2-dihydro-isoquinoline-4-carboxylic acid ((S)-1-phenyl-propyl)-amide;
2-(2-Fluoro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide;
2-(2-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide;
3-[4-(2-Morpholin-4-yl-ethyl)-piperazin-1-ylmethyl]-1-oxo-2-o-tolyl-1,2-dihydro-isoquinoline-4-carboxylic acid ((S)-1-phenyl-propyl)-amide;
1-Oxo-3-[4-(2-piperidin-1-yl-ethyl)-piperazin-1-ylmethyl]-2-o-tolyl-1,2-dihydro-isoquinoline-4-carboxylic acid ((S)-1-phenyl-propyl)-amide;
1-Oxo-3-(4-pyridin-4-ylmethyl-piperazin-1-ylmethyl)-2-o-tolyl-1,2-dihydro-isoquinoline-4-carboxylic acid ((S)-1-phenyl-propyl)-amide;
2-(3-Fluoro-phenyl)-1-oxo-3-(4-phenethyl-piperazin-1-ylmethyl)-1,2-dihydro-isoquinoline-4-carboxylic acid ((S)-1-phenyl-propyl)-amide;
2-(3-Fluoro-phenyl)-3-(4-isopropyl-piperazin-1-ylmethyl)-1-oxo-1,2-dihydro-isoquinoline-4-carboxylic acid ((S)-1-phenyl-propyl)-amide;
3-[1,4]Bipiperidinyl-1'-ylmethyl-2-(3-fluoro-phenyl)-1-oxo-1,2-dihydro-isoquinoline-4-carboxylic acid ((S)-1-phenyl-propyl)-amide;
2-(3-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide;
2-(3-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide;
2-(3-Fluoro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide;
2-(3-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide;
2-(3-Fluoro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide;
2-(3-Fluoro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide;
2-(3-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide;
3-[4-(Acetyl-methyl-amino)-4-phenyl-piperidin-1-ylmethyl]-2-(3-fluoro-phenyl)-1-oxo-1,2-dihydro-isoquinoline-4-carboxylic acid ((S)-1-phenyl-propyl)-amide;
2-(3-Chloro-phenyl)-1-oxo-3-(4-phenethyl-piperazin-1-ylmethyl)-1,2-dihydro-isoquinoline-4-carboxylic acid ((S)-1-phenyl-propyl)-amide;
2-(3-Chloro-phenyl)-3-(4-isopropyl-piperazin-1-ylmethyl)-1-oxo-1,2-dihydro-isoquinoline-4-carboxylic acid ((S)-1-phenyl-propyl)-amide;
3-[1,4]Bipiperidinyl-1'-ylmethyl-2-(3-chloro-phenyl)-1-oxo-1,2-dihydro-isoquinoline-4-carboxylic acid ((S)-1-phenyl-propyl)-amide;
2-(3-Chloro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide;
2-(3-Chloro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide;
2-(3-Chloro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide;
2-(3-Chloro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide;
2-(3-Chloro-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide;
2-(3-Chloro-phenyl)-3-[4-(2-morpholin-4-yl-ethyl)-piperidin-1-ylmethyl]-1-oxo-1,2-dihydro-isoquinoline-4-carboxylic acid ((S)-1-phenyl-propyl)-amide;
2-(3-Chloro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide;
3-[4-(Acetyl-methyl-amino)-4-phenyl-piperidin-1-ylmethyl]-2-(3-chloro-phenyl)-1-oxo-1,2-dihydro-isoquinoline-4-carboxylic acid ((S)-1-phenyl-propyl)-amide;
1-Oxo-3-(4-phenethyl-piperazin-1-ylmethyl)-2-m-tolyl-1,2-dihydro-isoquinoline-4-carboxylic acid ((S)-1-phenyl-propyl)-amide;
3-[1,4]Bipiperidinyl-1'-ylmethyl-1-oxo-2-m-tolyl-1,2-dihydro-isoquinoline-4-carboxylic acid ((S)-1-phenyl-propyl)-amide;
3-[4-(2-Morpholin-4-yl-ethyl)-piperazin-1-ylmethyl]-1-oxo-2-m-tolyl-1,2-dihydro-isoquinoline-4-carboxylic acid ((S)-1-phenyl-propyl)-amide;
3-[4-(1-Methyl-piperidin-4-yl)-piperazin-1-ylmethyl]-1-oxo-2-m-tolyl-1,2-dihydro-isoquinoline-4-carboxylic acid ((S)-1-phenyl-propyl)-amide;
1-Oxo-3-[4-(2-piperidin-1-yl-ethyl)-piperazin-1-ylmethyl]-2-m-tolyl-1,2-dihydro-isoquinoline-4-carboxylic acid ((S)-1-phenyl-propyl)-amide;
1-Oxo-3-[4-(2-pyrrolidin-1-yl-ethyl)-piperazin-1-ylmethyl]-2-m-tolyl-1,2-dihydro-isoquinoline-4-carboxylic acid ((S)-1-phenyl-propyl)-amide;

1-Oxo-3-(4-pyridin-4-ylmethyl-piperazin-1-ylmethyl)-2-m-tolyl-1,2-dihydro-isoquinoline-4-carboxylic acid ((S)-1-phenyl-propyl)-amide;

3-[4-(2-Morpholin-4-yl-ethyl)-piperidin-1-ylmethyl]-1-oxo-2-m-tolyl-1,2-dihydro-isoquinoline-4-carboxylic acid ((S)-1-phenyl-propyl)-amide;

3-[4-Hydroxy-4-(3-methoxy-phenyl)-piperidin-1-ylmethyl]-1-oxo-2-m-tolyl-1,2-dihydro-isoquinoline-4-carboxylic acid ((S)-1-phenyl-propyl)-amide;

3-[4-(Acetyl-methyl-amino)-4-phenyl-piperidin-1-ylmethyl]-1-oxo-2-m-tolyl-1,2-dihydro-isoquinoline-4-carboxylic acid ((S)-1-phenyl-propyl)-amide;

1-Oxo-3-(2-oxo-pyrrolidin-1-ylmethyl)-2-phenyl-1,2-dihydro-isoquinoline-4-carboxylic acid ((S)-1-phenyl-propyl)-amide;

8-Chloro-1-oxo-3-(2-oxo-pyrrolidin-1-ylmethyl)-2-phenyl-1,2-dihydro-isoquinoline-4-carboxylic acid ((S)-1-phenyl-propyl)-amide;

3-Cyanomethyl-1-oxo-2-phenyl-1,2-dihydro-isoquinoline-4-carboxylic acid ((S)-1-phenyl-propyl)-amide;

3-Methyl-1-oxo-2-phenyl-1,2-dihydro-isoquinoline-4-carboxylic acid N,N-diphenyl-hydrazide;

N'-(3-Methyl-1-oxo-2-phenyl-1,2-dihydro-isoquinoline-4-carbonyl)-N-phenyl-hydrazine carboxylic acid methyl ester;

2-(3-Methoxy-phenyl)-3-methyl-1-oxo-1,2-dihydro-isoquinoline-4-carboxylic acid ((S)-1-phenyl-propyl)-amide;

2-(4-Methoxy-phenyl)-3-methyl-1-oxo-1,2-dihydro-isoquinoline-4-carboxylic acid ((S)-1-phenyl-propyl)-amide;

2-(4-Fluoro-phenyl)-3-methyl-1-oxo-1,2-dihydro-isoquinoline-4-carboxylic acid ((S)-1-phenyl-propyl)-amide;

2-(4-Chloro-phenyl)-3-methyl-1-oxo-1,2-dihydro-isoquinoline-4-carboxylic acid ((S)-1-phenyl-propyl)-amide;

3-Methyl-1-oxo-2-p-tolyl-1,2-dihydro-isoquinoline-4-carboxylic acid ((S)-1-phenyl-propyl)-amide;

2-(3-Methoxy-phenyl)-3-methyl-1-oxo-1,2-dihydro-isoquinoline-4-carboxylic acid [(S)-cyclopropyl-(3-fluoro-phenyl)-methyl]-amide;

2-(4-Methoxy-phenyl)-3-methyl-1-oxo-1,2-dihydro-isoquinoline-4-carboxylic acid [(S)-cyclopropyl-(3-fluoro-phenyl)-methyl]-amide;

2-(4-Fluoro-phenyl)-3-methyl-1-oxo-1,2-dihydro-isoquinoline-4-carboxylic acid [(S)-cyclopropyl-(3-fluoro-phenyl)-methyl]-amide;

2-(4-Chloro-phenyl)-3-methyl-1-oxo-1,2-dihydro-isoquinoline-4-carboxylic acid [(S)-cyclopropyl-(3-fluoro-phenyl)-methyl]-amide;

3-Methyl-1-oxo-2-p-tolyl-1,2-dihydro-isoquinoline-4-carboxylic acid [(S)-cyclopropyl-(3-fluoro-phenyl)-methyl]-amide;

2-(2-Methoxy-phenyl)-3-methyl-1-oxo-1,2-dihydro-isoquinoline-4-carboxylic acid ((S)-1-phenyl-propyl)-amide;

2-(2-Methoxy-phenyl)-3-methyl-1-oxo-1,2-dihydro-isoquinoline-4-carboxylic acid [(S)-cyclopropyl-(3-fluoro-phenyl)-methyl]-amide;

3-Methyl-8-nitro-1-oxo-2-phenyl-1,2-dihydro-isoquinoline-4-carboxylic acid ((S)-1-phenyl-propyl)-amide;

3-Methyl-8-nitro-1-oxo-2-phenyl-1,2-dihydro-isoquinoline-4-carboxylic acid [(S)-cyclopropyl-(3-fluoro-phenyl)-methyl]-amide;

8-Methoxy-3-methyl-1-oxo-2-phenyl-1,2-dihydro-isoquinoline-4-carboxylic acid ((S)-1-phenyl-propyl)-amide;

8-Methoxy-3-methyl-1-oxo-2-phenyl-1,2-dihydro-isoquinoline-4-carboxylic acid [(S)-cyclopropyl-(3-fluoro-phenyl)-methyl]-amide;

8-Amino-3-methyl-1-oxo-2-phenyl-1,2-dihydro-isoquinoline-4-carboxylic acid ((S)-1-phenyl-propyl)-amide;

8-Cyano-3-methyl-1-oxo-2-phenyl-1,2-dihydro-isoquinoline-4-carboxylic acid ((S)-1-phenyl-propyl)-amide;

8-Chloro-3-methyl-1-oxo-2-phenyl-1,2-dihydro-isoquinoline-4-carboxylic acid [(S)-1-(4-chloro-phenyl)-propyl]-amide;

8-Chloro-3-methyl-1-oxo-2-phenyl-1,2-dihydro-isoquinoline-4-carboxylic acid [(S)-1-(4-fluoro-phenyl)-propyl]-amide;

8-Chloro-3-methyl-1-oxo-2-phenyl-1,2-dihydro-isoquinoline-4-carboxylic acid [(S)-1-(2-fluoro-phenyl)-propyl]-amide;

8-Chloro-3-methyl-1-oxo-2-phenyl-1,2-dihydro-isoquinoline-4-carboxylic acid [(S)-1-(3-chloro-phenyl)-propyl]-amide;

8-Chloro-3-methyl-1-oxo-2-phenyl-1,2-dihydro-isoquinoline-4-carboxylic acid [(S)-(3-chloro-phenyl)-cyclopropyl-methyl]-amide;

8-Chloro-3-methyl-1-oxo-2-phenyl-1,2-dihydro-isoquinoline-4-carboxylic acid [(S)-(4-chloro-phenyl)-cyclopropyl-methyl]-amide;

8-Chloro-3-methyl-1-oxo-2-phenyl-1,2-dihydro-isoquinoline-4-carboxylic acid [(S)-1-(3-fluoro-phenyl)-propyl]-amide;

8-Chloro-3-methyl-1-oxo-2-phenyl-1,2-dihydro-isoquinoline-4-carboxylic acid ((S)-2-methyl-1-phenyl-propyl)-amide;

8-Chloro-3-methyl-1-oxo-2-phenyl-1,2-dihydro-isoquinoline-4-carboxylic acid [(S)-cyclopropyl-(4-fluoro-phenyl)-methyl]-amide;

8-Chloro-3-methyl-1-oxo-2-phenyl-1,2-dihydro-isoquinoline-4-carboxylic acid [(S)-1-(2-chloro-phenyl)-propyl]-amide;

8-Chloro-3-methyl-1-oxo-2-phenyl-1,2-dihydro-isoquinoline-4-carboxylic acid ((S)-cyclopentyl-phenyl-methyl)-amide;

8-Chloro-3-methyl-1-oxo-2-phenyl-1,2-dihydro-isoquinoline-4-carboxylic acid [(S)-(2-chloro-phenyl)-cyclopropyl-methyl]-amide;

8-Chloro-3-methyl-1-oxo-2-phenyl-1,2-dihydro-isoquinoline-4-carboxylic acid [(S)-cyclopropyl-(2-fluoro-phenyl)-methyl]-amide;

8-Chloro-3-methyl-1-oxo-2-phenyl-1,2-dihydro-isoquinoline-4-carboxylic acid ((S)-cyclohexyl-phenyl-methyl)-amide;

8-Chloro-3-methyl-1-oxo-2-phenyl-1,2-dihydro-isoquinoline-4-carboxylic acid ((S)-cyclopropyl-phenyl-methyl)-amide;

8-Chloro-3-methyl-1-oxo-2-phenyl-1,2-dihydro-isoquinoline-4-carboxylic acid [(S)-cyclobutyl-(3-fluoro-phenyl)-methyl]-amide;

8-Chloro-3-methyl-1-oxo-2-phenyl-1,2-dihydro-isoquinoline-4-carboxylic acid [(S)-cyclobutyl-(4-fluoro-phenyl)-methyl]-amide;

8-Chloro-3-methyl-1-oxo-2-phenyl-1,2-dihydro-isoquinoline-4-carboxylic acid [(R)-cyclopropyl-(3-fluoro-phenyl)-methyl]-amide;

8-Chloro-3-methyl-1-oxo-2-phenyl-1,2-dihydro-isoquinoline-4-carboxylic acid ((S)cyclobutyl-phenyl-methyl)-amide;

8-Chloro-3-methyl-1-oxo-2-phenyl-1,2-dihydro-isoquinoline-4-carboxylic acid[cyclobutyl-(2-fluoro-phenyl)-methyl]-amide;

3-(4-tert-Butyl-piperazin-1-ylmethyl)-8-chloro-1-oxo-2-phenyl-1,2-dihydro-isoquinoline-4-carboxylic acid [(S)-cyclopropyl-(3-fluoro-phenyl)-methyl]-amide;

8-Chloro-3-(4-isopropyl-piperazin-1-ylmethyl)-1-oxo-2-phenyl-1,2-dihydro-isoquinoline-4-carboxylic acid ((S)-1-phenyl-propyl)-amide;

8-Chloro-3-(4-isobutyl-piperazin-1-ylmethyl)-1-oxo-2-phenyl-1,2-dihydro-isoquinoline-4-carboxylic acid ((S)-1-phenyl-propyl)-amide;

8-Chloro-3-(octahydro-pyrido[1,2-a]pyrazin-2-ylmethyl)-1-oxo-2-phenyl-1,2-dihydro-isoquinoline-4-carboxylic acid ((S)-1-phenyl-propyl)-amide;

8-Chloro-3-(4-hydroxy-3,4,5,6-tetrahydro-2H-[4,4']bipyridinyl-1-ylmethyl)-1-oxo-2-phenyl-1,2-dihydro-isoquinoline-4-carboxylic acid ((S)-1-phenyl-propyl)-amide;

8-Chloro-3-(4-cyclopropylmethyl-piperazin-1-ylmethyl)-1-oxo-2-phenyl-1,2-dihydro-isoquinoline-4-carboxylic acid ((S)-1-phenyl-propyl)-amide;

8-Chloro-3-[4-(2-morpholin-4-yl-ethyl)-piperidin-1-ylmethyl]-1-oxo-2-phenyl-1,2-dihydro-isoquinoline-4-carboxylic acid ((S)-1-phenyl-propyl)-amide;

8-Chloro-3-[1,4]diazepan-1-ylmethyl-1-oxo-2-phenyl-1,2-dihydro-isoquinoline-4-carboxylic acid ((S)-1-phenyl-propyl)-amide;

8-Chloro-3-((S)-3-methyl-piperazin-1-ylmethyl)-1-oxo-2-phenyl-1,2-dihydro-isoquinoline-4-carboxylic acid ((S)-1-phenyl-propyl)-amide;

8-Chloro-3-imidazol-1-ylmethyl-1-oxo-2-phenyl-1,2-dihydro-isoquinoline-4-carboxylic acid ((S)-1-phenyl-propyl)-amide;

8-Chloro-3-(4-methyl-imidazol-1-ylmethyl)-1-oxo-2-phenyl-1,2-dihydro-isoquinoline-4-carboxylic acid ((S)-1-phenyl-propyl)-amide;

3-(tert-Butylamino-methyl)-8-chloro-1-oxo-2-phenyl-1,2-dihydro-isoquinoline-4-carboxylic acid ((S)-1-phenyl-propyl)-amide;

8-Chloro-3-(isopropylamino-methyl)-1-oxo-2-phenyl-1,2-dihydro-isoquinoline-4-carboxylic acid ((S)-1-phenyl-propyl)-amide;

8-Chloro-3-[4-hydroxy-4-(3-methoxy-phenyl)-piperidin-1-ylmethyl]-1-oxo-2-phenyl-1,2-dihydro-isoquinoline-4-carboxylic acid ((S)-1-phenyl-propyl)-amide;

3-(4-tert-Butyl-piperazin-1-ylmethyl)-8-chloro-1-oxo-2-phenyl-1,2-dihydro-isoquinoline-4-carboxylic acid ((S)-1-phenyl-propyl)-amide;

3-Benzoimidazol-1-ylmethyl-1-oxo-2-phenyl-1,2-dihydro-isoquinoline-4-carboxylic acid ((S)-1-phenyl-propyl)-amide;

1-Oxo-2-phenyl-3-pyrazol-1-ylmethyl-1,2-dihydro-isoquinoline-4-carboxylic acid ((S)-1-phenyl-propyl)-amide;

3-(4-Methyl-pyrazol-1-ylmethyl)-1-oxo-2-phenyl-1,2-dihydro-isoquinoline-4-carboxylic acid ((S)-1-phenyl-propyl)-amide;

1-Oxo-2-phenyl-3-[1,2,3]triazol-1-ylmethyl-1,2-dihydro-isoquinoline-4-carboxylic acid ((S)-1-phenyl-propyl)-amide;

2-(3-Methoxy-phenyl)-1-oxo-3-(4-pyridin-4-ylmethyl-piperazin-1-ylmethyl)-1,2-dihydro-isoquinoline-4-carboxylic acid ((S)-1-phenyl-propyl)-amide;

2-(4-Methoxy-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide;

2-(4-Fluoro-phenyl)-1-oxo-3-(4-phenethyl-piperazin-1-ylmethyl)-1,2-dihydro-isoquinoline-4-carboxylic acid ((S)-1-phenyl-propyl)-amide;

2-(4-Fluoro-phenyl)-3-(4-isopropyl-piperazin-1-ylmethyl)-1-oxo-1,2-dihydro-isoquinoline-4-carboxylic acid ((S)-1-phenyl-propyl)-amide;

3-[1,4]Bipiperidinyl-1'-ylmethyl-2-(4-fluoro-phenyl)-1-oxo-1,2-dihydro-isoquinoline-4-carboxylic acid ((S)-1-phenyl-propyl)-amide;

2-(4-Fluoro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide;

2-(4-Fluoro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide;

2-(4-Fluoro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide;

2-(4-Fluoro-phenyl)-3-[4-hydroxy-4-(3-methoxy-phenyl)-piperidin-1-ylmethyl]-1-oxo-1,2-dihydro-isoquinoline-4-carboxylic acid ((S)-1-phenyl-propyl)-amide;

2-(4-Chloro-phenyl)-1-oxo-3-(4-phenethyl-piperazin-1-ylmethyl)-1,2-dihydro-isoquinoline-4-carboxylic acid ((S)-1-phenyl-propyl)-amide;

2-(4-Chloro-phenyl)-3-(4-isopropyl-piperazin-1-ylmethyl)-1-oxo-1,2-dihydro-isoquinoline-4-carboxylic acid ((S)-1-phenyl-propyl)-amide;

3-[1,4]Bipiperidinyl-1'-ylmethyl-2-(4-chloro-phenyl)-1-oxo-1,2-dihydro-isoquinoline-4-carboxylic acid ((S)-1-phenyl-propyl)-amide;

2-(4-Chloro-phenyl)-3-[4-(2-morpholin-4-yl-ethyl)-piperazin-1-ylmethyl]-1-oxo-1,2-dihydro-isoquinoline-4-carboxylic acid ((S)-1-phenyl-propyl)-amide;

2-(4-Chloro-phenyl)-3-[4-(1-methyl-piperidin-4-yl)-piperazin-1-ylmethyl]-1-oxo-1,2-dihydro-isoquinoline-4-carboxylic acid ((S)-1-phenyl-propyl)-amide;

2-(4-Chloro-phenyl)-1-oxo-3-[4-(2-piperidin-1-yl-ethyl)-piperazin-1-ylmethyl]-1,2-dihydro-isoquinoline-4-carboxylic acid ((S)-1-phenyl-propyl)-amide;

2-(4-Chloro-phenyl)-1-oxo-3-[4-(2-pyrrolidin-1-yl-ethyl)-piperazin-1-ylmethyl]-1,2-dihydro-isoquinoline-4-carboxylic acid ((S)-1-phenyl-propyl)-amide;

3-(4-tert-Butyl-piperazin-1-ylmethyl)-8-fluoro-1-oxo-2-phenyl-1,2-dihydro-isoquinoline-4-carboxylic acid ((S)-1-phenyl-propyl)-amide;

8-Chloro-3-cyclopropylaminomethyl-1-oxo-2-phenyl-1,2-dihydro-isoquinoline-4-carboxylic acid ((S)-1-phenyl-propyl)-amide;

3-(4-tert-Butyl-piperazin-1-ylmethyl)-8-fluoro-1-oxo-2-phenyl-1,2-dihydro-isoquinoline-4-carboxylic acid [(S)-cyclopropyl-(3-fluoro-phenyl)-methyl]-amide;

8-Fluoro-1-oxo-2-phenyl-3-piperazin-1-ylmethyl-1,2-dihydro-isoquinoline-4-carboxylic acid [(S)-cyclopropyl-(3-fluoro-phenyl)-methyl]-amide;

8-Fluoro-1-oxo-3-(3-oxo-pyrazolidin-1-ylmethyl)-2-phenyl-1,2-dihydro-isoquinoline-4-carboxylic acid [(S)-cyclopropyl-(3-fluoro-phenyl)-methyl]-amide;

8-Fluoro-1-oxo-3-(3-oxo-piperazin-1-ylmethyl)-2-phenyl-1,2-dihydro-isoquinoline-4-carboxylic acid [(S)-cyclopropyl-(3-fluoro-phenyl)-methyl]-amide;

1-Oxo-2-phenyl-3-(1H-[1,2,4]triazol-3-ylsulfanylmethyl)-1,2-dihydro-isoquinoline-4-carboxylic acid ((S)-1-phenyl-propyl)-amide;

8-Chloro-1-oxo-3-(2-oxo-pyrrolidin-1-ylmethyl)-2-phenyl-1,2-dihydro-isoquinoline-4-carboxylic acid [(S)-cyclopropyl-(3-fluoro-phenyl)-methyl]-amide;

8-Fluoro-1-oxo-3-(2-oxo-pyrrolidin-1-ylmethyl)-2-phenyl-1,2-dihydro-isoquinoline-4-carboxylic acid ((S)-1-phenyl-propyl)-amide;

8-Fluoro-1-oxo-3-(2-oxo-pyrrolidin-1-ylmethyl)-2-phenyl-1,2-dihydro-isoquinoline-4-carboxylic acid [(S)-cyclopropyl-(3-fluoro-phenyl)-methyl]-amide;

8-Fluoro-1-oxo-3-(5-oxo-pyrazolidin-1-ylmethyl)-2-phenyl-1,2-dihydro-isoquinoline-4-carboxylic acid [(S)-cyclopropyl-(3-fluoro-phenyl)-methyl]-amide;

8-Fluoro-1-oxo-3-(2-oxo-piperazin-1-ylmethyl)-2-phenyl-1,2-dihydro-isoquinoline-4-carboxylic acid [(S)-cyclopropyl-(3-fluoro-phenyl)-methyl]-amide;

8-Fluoro-1-oxo-3-(2-oxo-piperidin-1-ylmethyl)-2-phenyl-1,2-dihydro-isoquinoline-4-carboxylic acid [(S)-cyclopropyl-(3-fluoro-phenyl)-methyl]-amide;

8-Chloro-3-cyanomethyl-1-oxo-2-phenyl-1,2-dihydro-isoquinoline-4-carboxylic acid [(S)-cyclopropyl-(3-fluoro-phenyl)-methyl]-amide;

2-(3,4-Dichloro-phenyl)-3-methyl-1-oxo-1,2-dihydro-isoquinoline-4-carboxylic acid ((S)-1-phenyl-propyl)-amide;

8-Fluoro-1-oxo-3-(2-oxo-pyrrolidin-1-ylmethyl)-2-phenyl-1,2-dihydro-isoquinoline-4-carboxylic acid ((S)-cyclopropyl-phenyl-methyl)-amide;

8-Fluoro-3-methyl-1-oxo-2-phenyl-1,2-dihydro-isoquinoline-4-carboxylic acid ((S)-cyclopropyl-phenyl-methyl)-amide 3-Ethyl-1-oxo-2-phenyl-1,2-dihydro-isoquinoline-4-carboxylic acid ((S)-1-phenyl-propyl)-amide;

8-Fluoro-3-methyl-1-oxo-2-phenyl-1,2-dihydro-isoquinoline-4-carboxylic acid ((S)-1-phenyl-propyl)-amide;

8-Fluoro-2-(3-fluoro-phenyl)-3-methyl-1-oxo-1,2-dihydro-isoquinoline-4-carboxylic acid ((S)-1-phenyl-propyl)-amide;

8-Fluoro-2-(4-fluoro-phenyl)-3-methyl-1-oxo-1,2-dihydro-isoquinoline-4-carboxylic acid ((S)-1-phenyl-propyl)-amide;

8-Fluoro-3-methyl-1-oxo-2-phenyl-1,2-dihydro-isoquinoline-4-carboxylic acid [(S)-cyclopropyl-(3-fluoro-phenyl)-methyl]-amide;

8-Fluoro-2-(3-fluoro-phenyl)-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide;

8-Fluoro-2-(4-fluoro-phenyl)-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide;

8-Fluoro-3-methyl-1-oxo-2-phenyl-1,2-dihydro-isoquinoline-4-carboxylic acid [(S)-cyclobutyl-(3-fluoro-phenyl)-methyl]-amide;

8-Fluoro-2-(2-fluoro-phenyl)-3-methyl-1-oxo-1,2-dihydro-isoquinoline-4-carboxylic acid[(S)-cyclopropyl-(3-fluoro-phenyl)-methyl]-amide;

8-Fluoro-2-(3-fluoro-phenyl)-3-methyl-1-oxo-1,2-dihydro-isoquinoline-4-carboxylic acid[(S)-cyclopropyl-(3-fluoro-phenyl)-methyl]-amide;

8-Fluoro-2-(4-fluoro-phenyl)-3-methyl-1-oxo-1,2-dihydro-isoquinoline-4-carboxylic acid[(S)-cyclopropyl-(3-fluoro-phenyl)-methyl]-amide;

6,8-Difluoro-3-methyl-1-oxo-2-phenyl-1,2-dihydro-isoquinoline-4-carboxylic acid [(S)-cyclopropyl-(3-fluoro-phenyl)-methyl]-amide;

5,8-Difluoro-3-methyl-1-oxo-2-phenyl-1,2-dihydro-isoquinoline-4-carboxylic acid [(S)-cyclopropyl-(3-fluoro-phenyl)-methyl]-amide;

3-Methyl-1-oxo-2-phenyl-8-trifluoromethyl-1,2-dihydro-isoquinoline-4-carboxylic acid ((S)-1-phenyl-propyl)-amide;

3-(1-tert-Butyl-piperidin-4-ylmethyl)-8-chloro-1-oxo-2-phenyl-1,2-dihydro-isoquinoline-4-carboxylic acid [(S)-cyclopropyl-(3-fluoro-phenyl)-methyl]-amide;

or a pharmaceutically acceptable salt of any of these compounds.

35. A method for the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder; schizoid personality disorder; schizoptypal personality disorder; psychosis or schizophrenia associated with major depression, bipolar disorder, Alzheimer's disease or Parkinson's disease; major depression; general anxiety disorder; bipolar disorder; mania; hypomania; cognitive impairment; ADHD attention deficit hyperactivity disorder; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome, which method comprises the administration of a therapeutically effective amount of a compound according to claim 1 to a patient in need thereof.

36. The method according to claim 35, wherein said disease is schizophrenia.

37. The method according to claim 36, wherein said treatment comprises the treatment of positive, negative and/or cognitive symptoms of schizophrenia.

38. The method according to claim 36 which additionally comprises a concomitant or sequential administration of a therapeutically effective amount of a compound selected from the list consisting of D2 antagonists, D2 partial agonists, PDE10 antagonists, 5-$HT_{2A}$ antagonists, 5-$HT_6$ antagonists and KCNQ4 antagonister.

39. A pharmaceutical composition comprising a compound according to any of claim 1-7, 8-11, 12, 13, 14, 15, 16, 17, 18, 19, 20, 21, 22, 23, 24, 25, 26, 27, 28, 29, 30, 31, 32, 33 or 34 and one or more pharmaceutically acceptable carrier or excipient.

40. A composition according to claim 39 which composition additionally comprises a compound selected from the list consisting of D2 antagonists, D2 partial agonists, PDE10 antagonists, 5-$HT_{2A}$ antagonists, 5-$HT_6$ antagonists and KCNQ4 antagonists.

41. A kit comprising a compound according to claim 1 together with a compound selected from the list consisting of D2 antagonists, D2 partial agonists, PDE10 antagonists, 5-$HT_{2A}$ antagonists, 5-$HT_6$ antagonists and KCNQ4 antagonists.

42. A method for the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder; schizoid personality disorder; schizoptypal personality disorder; psychosis or schizophrenia associated with major depression, bipolar disorder, Alzheimer's disease or Parkinson's disease; major depression; general anxiety disorder; bipolar disorder; mania; hypomania; cognitive impairment; ADHD attention deficit hyperactivity disorder;

obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome, which method comprises the administration of a therapeutically effective amount of a compound according to claim 34 to a patient in need thereof.

43. The method according to claim 42, wherein said disease is schizophrenia.

44. The method according to claim 43, wherein said treatment comprises the treatment of positive, negative and/or cognitive symptoms of schizophrenia.

45. The method according to claim 43 which additionally comprises a concomitant or sequential administration of a therapeutically effective amount of a compound selected from the list consisting of D2 antagonists, D2 partial agonists, PDE10 antagonists 5-$HT_{2A}$ antagonists, 5-$HT_6$ antagonists and KCNQ4 antagonister.

46. A pharmaceutical composition comprising a compound according to claim 34 and one or more pharmaceutically acceptable carrier or excipient.

47. A composition according to claim 46 which composition additionally comprises a compound selected from the list consisting of D2 antagonists, D2 partial agonists, PDE10 antagonists, 5-$HT_{2A}$ antagonists, 5-$HT_6$ antagonists and KCNQ4 antagonists.

48. A kit comprising a compound according to claim 34 together with a compound selected from the list consisting of D2 antagonists, D2 partial agonists, PDE10 antagonists, 5-$HT_{2A}$ antagonists, 5-$HT_6$ antagonists and KCNQ4 antagonists.

* * * * *